United States Patent
Santaguida et al.

(10) Patent No.: US 10,053,511 B2
(45) Date of Patent: *Aug. 21, 2018

(54) ANTI-CLAUDIN ANTIBODIES AND METHODS OF USE

(71) Applicant: AbbVie Stemcentrx LLC, North Chicago, IL (US)

(72) Inventors: Marianne Santaguida, Belmont, CA (US); Monette Aujay, San Francisco, CA (US); Laura Saunders, San Francisco, CA (US); David Liu, San Francisco, CA (US); Orit Foord, Foster City, CA (US); Robert A. Stull, Alameda, CA (US); Paul Anthony Escarpe, San Bruno, CA (US)

(73) Assignee: AbbVie Stemcentrx LLC, North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/034,992

(22) PCT Filed: Nov. 5, 2014

(86) PCT No.: PCT/US2014/064165
§ 371 (c)(1),
(2) Date: May 6, 2016

(87) PCT Pub. No.: WO2015/069794
PCT Pub. Date: May 14, 2015

(65) Prior Publication Data
US 2016/0289332 A1 Oct. 6, 2016

Related U.S. Application Data

(60) Provisional application No. 61/900,916, filed on Nov. 6, 2013.

(51) Int. Cl.
*C07K 16/30* (2006.01)
*C07K 16/28* (2006.01)
*C12N 5/00* (2006.01)
*A61K 47/68* (2017.01)

(52) U.S. Cl.
CPC .......... *C07K 16/30* (2013.01); *A61K 47/6851* (2017.08); *A61K 47/6857* (2017.08); *A61K 47/6869* (2017.08); *C07K 16/28* (2013.01); *C07K 16/3023* (2013.01); *C07K 16/3069* (2013.01); *C12N 5/0093* (2013.01); *C07K 2317/24* (2013.01); *C07K 2317/33* (2013.01); *C07K 2317/34* (2013.01); *C07K 2317/522* (2013.01); *C07K 2317/53* (2013.01); *C07K 2317/56* (2013.01); *C07K 2317/73* (2013.01); *C07K 2317/77* (2013.01); *C07K 2317/92* (2013.01)

(58) Field of Classification Search
CPC ..... C07K 16/28; C07K 16/30–16/3069; A61K 39/395–39/39558; A61K 47/6849–47/6869
See application file for complete search history.

(56) References Cited

U.S. PATENT DOCUMENTS

| 5,191,066 | A  | 3/1993  | Bieniarz et al. |
|-----------|----|---------|-----------------|
| 5,648,237 | A  | 7/1997  | Carter |
| 5,693,762 | A  | 12/1997 | Queen et al. |
| 5,714,350 | A  | 2/1998  | Co et al. |
| 6,180,370 | B1 | 1/2001  | Queen et al. |
| 6,350,861 | B1 | 2/2002  | Co et al. |
| 6,362,331 | B1 | 3/2002  | Kamal et al. |
| 6,376,217 | B1 | 4/2002  | Better |
| 6,723,700 | B1 | 4/2004  | Blaschuk et al. |
| 6,737,056 | B1 | 5/2004  | Presta |
| 6,753,165 | B1 | 6/2004  | Cox |
| 6,982,321 | B2 | 1/2006  | Winter |
| 7,049,311 | B1 | 5/2006  | Thurston et al. |
| 7,057,018 | B2 | 6/2006  | Desnoyers et al. |
| 7,087,409 | B2 | 8/2006  | Barbas, III et al. |
| 7,189,710 | B2 | 3/2007  | Kamal et al. |
| 7,407,951 | B2 | 8/2008  | Thurston et al. |
| 7,422,739 | B2 | 9/2008  | Anderson et al. |
| 7,429,658 | B2 | 9/2008  | Howard et al. |
| 7,557,099 | B2 | 7/2009  | Howard et al. |
| 7,608,429 | B2 | 10/2009 | Reilly |
| 7,619,068 | B2 | 11/2009 | Pilkington et al. |
| 7,632,678 | B2 | 12/2009 | Hansford et al. |
| 7,723,485 | B2 | 5/2010  | Junutula |
| 7,741,319 | B2 | 6/2010  | Howard et al. |

(Continued)

FOREIGN PATENT DOCUMENTS

| EP | 2241578 A1 | 10/2010 |
|----|------------|---------|
| EP | 2404936    | 1/2012 |

(Continued)

OTHER PUBLICATIONS

Communication pursuant to Rules 70(2) and 70(a(2) EPC dated Apr. 7, 2017, for responding to Extended European Search Report dated Mar. 22, 2017, issued in European application (14860725.2).
Abuzza et al., "Claudins 6, 9, and 13 are developmentally expressed renal tight junction proteins," Am J Physiol Renal Physiol. (Dec. 2006) 291(6):F1132-41.
Ban et al., "Tight junction-related protein expression and distribution in human corneal epithelium.," Exp. Eye Res. 76 (6): 663-9. doi:10.1016/S0014-4835(03)00054-X. PMID 12742348.(2003).
Boswell et al., "An integrated approach to identify normal tissue expression of targets for antibody-drug conjugates: case study of TENB2," British Journal of Pharmacology (2013) 168:445-457.
Chothia et al., "Canonical structures for the hypervariable regions of immunoglobulins," *J Mol Biol.* (Aug. 20, 1987) 196(4):901-17.

(Continued)

Primary Examiner — Jessica H Roark
(74) Attorney, Agent, or Firm — Womble Bond Dickinson (US) LLP

(57) ABSTRACT

Provided herein are anti-CLDN antibodies and antibody drug conjugates (ADC), including derivatives thereof, and methods of using the same to treat proliferative disorders.

55 Claims, 47 Drawing Sheets

(56) References Cited

U.S. PATENT DOCUMENTS

| | | |
|---|---|---|
| 7,767,403 B2 | 8/2010 | Frantz et al. |
| 7,825,267 B2 | 11/2010 | Koide et al. |
| 7,837,980 B2 | 11/2010 | Alley |
| 7,855,275 B2 | 12/2010 | Eigenbrot |
| 8,008,443 B2 | 8/2011 | Dall'Acqua |
| 8,034,808 B2 | 10/2011 | Delavault et al. |
| 8,053,562 B2 | 11/2011 | Humphreys |
| 8,076,458 B2 | 12/2011 | Ohta et al. |
| 8,163,736 B2 | 4/2012 | Gauzy et al. |
| 8,226,945 B2 | 7/2012 | Ebens |
| 8,507,654 B2 | 8/2013 | Baker |
| 8,865,875 B2 | 10/2014 | Liu |
| 9,274,119 B2 | 3/2016 | Aburatani et al. |
| 2002/0192209 A1 | 12/2002 | Baker et al. |
| 2003/0190311 A1 | 10/2003 | Dall'Acqua et al. |
| 2005/0152894 A1 | 7/2005 | Krummen |
| 2006/0120959 A1 | 6/2006 | De Haen et al. |
| 2007/0292414 A1 | 12/2007 | Duntsch et al. |
| 2008/0138313 A1 | 6/2008 | Frankel et al. |
| 2008/0175870 A1 | 7/2008 | Mather et al. |
| 2008/0220448 A1 | 9/2008 | Blincko et al. |
| 2008/0305044 A1 | 12/2008 | McDonagh et al. |
| 2009/0010945 A1 | 1/2009 | Alley et al. |
| 2009/0169547 A1 | 7/2009 | Sahin et al. |
| 2010/0162416 A1 | 6/2010 | Krtolica et al. |
| 2010/0275280 A1 | 10/2010 | Clevers et al. |
| 2011/0020221 A1 | 1/2011 | Berman et al. |
| 2011/0033378 A1 | 2/2011 | Dimasi |
| 2011/0059469 A1* | 3/2011 | Aburatani .............. C07K 16/28 435/7.23 |
| 2011/0256157 A1 | 10/2011 | Howard et al. |
| 2011/0300144 A1 | 12/2011 | Sahin et al. |
| 2011/0301334 A1 | 12/2011 | Bhakta |
| 2012/0071634 A1 | 3/2012 | Igawa et al. |
| 2012/0308478 A1 | 12/2012 | Sahin |
| 2013/0040362 A1 | 2/2013 | Vogel et al. |
| 2013/0061340 A1 | 3/2013 | Dylla et al. |
| 2013/0061342 A1 | 3/2013 | Dylla et al. |
| 2013/0101581 A1 | 4/2013 | Kuramochi et al. |
| 2013/0144041 A1 | 6/2013 | Dillon et al. |
| 2013/0183305 A1 | 7/2013 | Sahin et al. |
| 2013/0259806 A1 | 10/2013 | Light |
| 2013/0260385 A1 | 10/2013 | Dylla et al. |
| 2013/0330350 A1 | 12/2013 | Dimasi |
| 2014/0120581 A1 | 5/2014 | Niwa |
| 2014/0127219 A1 | 5/2014 | Sahin |
| 2014/0348839 A1 | 11/2014 | Chovvdhury et al. |
| 2015/0005477 A1 | 1/2015 | Lowman |
| 2015/0030636 A1 | 1/2015 | Dylla et al. |
| 2015/0320879 A1 | 11/2015 | Lyon |
| 2016/0159901 A1 | 6/2016 | Sahin et al. |

FOREIGN PATENT DOCUMENTS

| | | |
|---|---|---|
| WO | WO 97/34631 | 9/1997 |
| WO | WO 99/37779 | 1/1999 |
| WO | WO 00/42072 | 7/2000 |
| WO | WO 2004/029207 | 4/2004 |
| WO | WO 2005/003171 | 7/2004 |
| WO | WO 2006/034488 | 9/2005 |
| WO | WO 2010/094499 | 8/2010 |
| WO | WO 2011/057788 | 5/2011 |
| WO | WO 2011/128650 | 10/2011 |
| WO | WO 2011/130613 | 10/2011 |
| WO | WO 2011/130616 | 10/2011 |
| WO | WO 2012/064733 | 11/2011 |
| WO | WO 2012/003956 | 1/2012 |
| WO | WO 2012/031280 | 3/2012 |
| WO | WO 2012/117002 | 9/2012 |
| WO | WO 2012/156018 | 11/2012 |
| WO | WO 2013/093809 | 12/2012 |
| WO | WO 2013/119964 | 8/2013 |
| WO | WO 2014/057074 | 5/2014 |
| WO | WO 2014/075697 | 5/2014 |
| WO | WO 2014/075788 | 5/2014 |
| WO | WO 2014/124316 | 7/2014 |
| WO | WO 2014/146139 | 9/2014 |
| WO | WO 2015/014376 | 2/2015 |
| WO | WO 2015/123265 | 2/2015 |
| WO | WO 2015/031698 | 3/2015 |
| WO | WO 2015/150327 | 10/2015 |
| WO | WO 2016/064749 | 4/2016 |
| WO | WO2016073649 A1 * | 5/2016 |

OTHER PUBLICATIONS

Chothia et al., "Conformations of immunoglobulin hypervariable regions," Nature (Dec. 21-28, 1989) 342(6252):877-83.

Chothia et al., "Structural Repertoire of the Human VH Segments," J Mol Biol (1992) 227:799-817.

Cook et al., "The human immunoglobulin $V_H$ repertoire," Immunol Today (1995) 16:237-242.

Dylla et al., "Colorectal cancer stem cells are enriched in xenogeneic tumors following chemotherapy," PLoS One (Jun. 18, 2008) 3(6):e2428. doi: 10.1371/journal.pone.0002428.

Fazekas et al., "Are plant species inherently harder to discriminate than animal species using DNA barcoding markers?," Mol Ecol Resour. (May 2009) 9 Suppl s1:130-9. doi: 10.1111/0755-0998. 2009.02652.x.

Fuhrmann et al., "Poster Presentations—Immunomodulatory Agents and Interventions Abstract 5625: In vitro and in vivo pharmacology of MEDI-565 (MT111), a novel CEA/CD3-bispecific singlechain BiTE antibody in development for the treatment of gastrointestinal adenocarcinomas" Annual Meeting of AACR Abstract Cancer Research: (Apr. 15, 2010) vol. 70, Issue 8, Supplement 1 No. 5625 (2010).

Hoey et al., "DLL4 blockade inhibits tumor growth and reduces tumor-initiating cell frequency," Cell Stem Cell. (Aug. 7, 2009) 5(2):168-77. doi: 10.1016/j.stem.2009.05.019.

Kabat et al., Sequences of Proteins of Immunological Interest (5th Ed.), US Dept. of Health and Human Services, PHS, NIH, NIH Publication No. 91-3242 (1991).

Kitarjiri et al., "Expression patterns of claudins, tight junction adhesion molecules, in the inner ear," Hear. Res. (2004) 187 (1-2): 25-34. doi:10.1016/S0378-5955(03)00338-1. PMID 14698084.

Krause et al., "Structure and function of claudins," Biochim Biophys Acta. (Mar. 2008) 1778(3):631-45.

MacCallum et al., "Antibody-antigen interactions: contact analysis and binding site topography," J Mol Biol. (Oct. 11, 1996) 262(5):732-45.

Morin et al., "Claudin proteins in human cancer: promising new targets for diagnosis and therapy," Cancer Res. (Nov. 1, 2005) 65(21):9603-6.

Morita et al., "Claudin multigene family encoding four-transmembrane domain protein components of tight junction strands," Proc. Natl. Acad. Sci., Jan. 1999, vol. 96, pp. 511-516.

Morita et al., "Molecular architecture of tight junctions of periderm differs from that of the maculae occludentes of epidermis," J. Invest. Dermatol. (Jun. 6, 2002) 118 (6):1073-9. doi:10.1046/j.1523-1747. 2002.01774.x. PMID 12060405.

Nakano et al., "A claudin-9-based ion permeability barrier is essential for hearing," PLoS Genet (Aug. 2009) 5(8):e1000610. doi: 10.1371/journal.pgen.1000610.

Nichols et al., "Claudin 4 protein expression in primary and metastatic pancreatic cancer: support for use as a therapeutic target," Am J Clin Pathol. (Feb. 2004) 121(2):226-30.

Panowski, S., et al., "Site-specific Antibody Drug Conjugates for Cancer Therapy," MAbs (Jan.-Feb. 2014) 6(1):34-35.

Rahner et al., "Heterogeneity in expression and subcellular localization of claudins 2, 3, 4, and 5 in the rat liver, pancreas, and gut," Gastroenterology (Feb. 2001) 120(2):411-22.

Ravetch et al., "Fc receptors," Annu Rev Immunol. (1991) 9:457-92.

Retter et al., "VBASE2, an integrative V gene database," Nucl. Acids Res., (2005) 33 (Database issue): D671-D674.

Reyes et al., "The renal segmental distribution of claudins changes with development," Kidney Int. (2002) 62 (2):476-87. doi:10.1046/ 0523-1755.2002.00479.x. PMID 12110008.

(56) References Cited

OTHER PUBLICATIONS

Rodrigues, M. L., et al., "Engineering Fab' Fragments for Efficient F(ab)2 Formation in *Escherichia coli* and for Improved In Vivo Stability," The Journal of Immunology, Dec. 15, 1993, 151(12): 6954-6961.
Schulenberg et al., "Neoplastic stem cells: current concepts and clinical perspectives," *Crit Rev Oncol Hematol.* (Nov. 2010) 76(2):79-98. doi: 10.1016/j.critrevonc.2010.01.001.
Shields et al., "High Resolution Mapping of the Binding Site on Human IgG1 for FcγRi, FcγRII, FcγRIII, and FcRn and Design of IgG1 Variants with Improved Binding to the FcγR," *J. Biol. Chem.* (2001) 9(2):6591-6604.
Shields et al., "Lack of Fucose on Human IgG1 N-Linked Oligosaccharide Improves Binding to Human FcγRIII and Antibody-dependent Cellular Toxicity," *J. Biol. Chem.* (2002) 277:26733-26740.
Strop, P., et al., "Location Matters: Site of Conjugation Modulates Stability and Pharmacokinetics of Antibody Drug Conjugates," Chemistry & Biology, Feb. 21, 2013, 20:161-167.
Sun, M., et al., "Reduction-Alkylation Strategies for the Modification of Specific Monoclonal Antibody Disulfides," Bioconug. Chem. (2005) 16(5): 1282-1290.
Sussman, D., et al., Abstract 4634, "Engineered Cysteine Drug Conjugates Show Potency and Improved Safety," Cancer Research, Apr. 15, 2012, 72(8), Supp. 1.
Tamagawa et al., "Characteristics of claudin expression in follicle-associated epithelium of Peyer's patches: preferential localization of claudin-4 at the apex of the dome region," *Lab Invest.* (Jul. 2003) 83(7):1045-53.
Tomlinson et al., "The Repertoire of Human Germline $V_H$ Sequences Reveals About Fifty Groups of $V_H$ Segments with Different Hypervariable Loops," *J Mol Biol* (1992) 227:776-798.
Tomlinson et al., "The structural repertoire of the human $V_K$ domain," *EMBO J* 14:4628-4638 (1995).
Turksen et al., "Claudin-6: A Novel Tight Junction Molecule Is Developmentally Regulated in Mouse Embryonic Epithelium," *Dev Dyn.* (Oct. 2001) 222(2):292-300.
Turksen et al., "Barriers built on claudins," *J Cell Sci.* (May 15, 2004) 117(Pt 12):2435-47.
Turksen, "Claudins and Cancer Stem Cells," *Stem Cell Rev.* (Nov. 2011) 7(4):797-8. doi: 10.1007/s12015-011-9267-1.
Turksen et al., "Permeability barrier dysfunction in transgenic mice overexpressing claudin 6," *Development.* (Apr. 2002) 129(7):1775-84.
Umetsu, M., et al., "How Additives Influence the Refolding of Immunoglobulin-folded Proteins in a Stepwise Dialysis System: Spectroscopic Evidence for Highly Efficient Refolding of a Single-chain FV Fragment," J. Biol. Chem., Mar. 14, 2003, 278(11): 8979-8987.

Uri et al., "Immunologic and chemical targeting of the tight-junction protein Claudin-6 eliminates tumorigenic human pluripotent stem cells," Nature Communications, Jun. 18, 2013, pp. 1-8.
Van Itallie et al., "The density of small tight junction pores varies among cell types and is increased by expression of claudin-2," *J Cell Sci.* (Feb. 1, 2008) 121(Pt 3):298-305. doi: 10.1242/jcs.021485.
Visavader et al., "Cancer stem cells in solid tumours: accumulating evidence and unresolved questions," Nat Rev Cancer. (Oct. 2008) 8(10):755-68. doi: 10.1038/nrc2499.
Wang et al., "Heterogeneity of claudin expression by alveolar epithelial cells," *Am J Respir Cell Mol Biol.* (Jul. 2003) 29(1):62-70.
Zheng et al., "Claudin-6 and claudin-9 function as additional coreceptors for hepatitis C virus," *J Virol.* (2007) 81(22):12465-12471. PMID:17804490.
International Search Report dated Apr. 29, 2015 issued in PCT counterpart application (PCT/US2014/064165).
Written Opinion dated Apr. 29, 2015 issued in PCT counterpart application (PCT/US2014/064165).
International Preliminary Report on Patentability dated May 10, 2016 issued in PCT counterpart application (PCT/US2014/064165).
Extended European Search Report dated Mar. 22, 2017 issued in EP counterpart application (14860725.2).
NM_001305 *Homo sapiens* claudin 4 (CLDN4), mRNA, Sep. 5, 2016.
NM_020982 *Homo sapiens* claudin 9 (CLDN9), mRNA, Aug. 28, 2016.
NM_021195 *Homo sapiens* claudin 6 (CLDN6), mRNA, Sep. 9, 2016.
NP_001011889 claudin-9 [Rattus norvegicus], Aug. 25, 2016.
NP_001012022 claudin-4 [Rattus norvegicus], Aug. 25, 2016.
NP_001095834 claudin-6 precursor [Rattus norvegicus], Aug. 25, 2016.
NP_001180758 claudin-9 [Macaca mulatta], Apr. 1, 2016.
NP_001180762 claudin-6 precursor [Macaca mulatta], Apr. 1, 2016.
NP_001181493 claudin-4 [Macaca mulatta], Apr. 2, 2016.
NP_001296 claudin-4 [*Homo sapiens*], Sep. 5, 2016.
NP_034033 claudin-4 [Mus musculus], Aug. 25, 2016.
NP_061247 claudin-6 precursor [Mus musculus], Sep. 9, 2016.
NP_064689 claudin-9[Mus musculus], Aug. 26, 2016.
NP_066192 claudin-9 [*Homo sapiens*], Aug. 28, 2016.
NP_067018 claudin-6 precursor [*Homo sapiens*], Sep. 9, 2016.
XP_003314989 Predicted: claudin-9 [Pan troglodytes], Oct. 8, 2014.
XP_523276 Predicted; claudin-6 [Pan troglodytes], Jun. 2, 2016.
Official action dated Nov. 5, 2017, in Chilean application (No. 01102-2016).
Official action dated Dec. 6, 2017, in Russian application (No. 2016122041).

* cited by examiner

Percent Homology of ECDs for Various CLDN Ortholog Proteins

| ECD loop 1 | cynoCLDN6 | musCLDN6 NP_061247 | ratCLDN6 NP_001095834 |
|---|---|---|---|
| humCLDN6 NP_067018 | 100.0% | 98.00% | 98.00% |
| musCLDN6 NP_061247 | | | 99.00% |

| ECD loop 1 | cynoCLDN9 | musCLDN9 NP_064689 | ratCLDN9 NP_001011889 |
|---|---|---|---|
| humCLDN9 NP_006192 | 100.0% | 100.0% | 100.0% |
| musCLDN9 NP_064689 | | | 100.0% |

| ECD loop 1 | cynoCLDN4 | musCLDN4 NP_034033 | ratCLDN4 NP_001012022 |
|---|---|---|---|
| humCLDN4 NP_001296 | 100.0% | 92.31% | 92.31% |
| musCLDN4 NP_034033 | | | 100.0% |

| ECD loop 2 | cynoCLDN6 | musCLDN6 NP_061247 | ratCLDN6 NP_001095834 |
|---|---|---|---|
| humCLDN6 NP_067018 | 100.0% | 86.96% | 91.30% |
| musCLDN6 NP_061247 | | | 95.65% |

| ECD loop 2 | cynoCLDN9 | musCLDN9 NP_064689 | ratCLDN9 NP_001011889 |
|---|---|---|---|
| humCLDN9 NP_006192 | 100.0% | 100.0% | 100.0% |
| musCLDN9 NP_064689 | | | 100.0% |

| ECD loop 2 | cynoCLDN4 | musCLDN4 NP_034033 | ratCLDN4 NP_001012022 |
|---|---|---|---|
| humCLDN4 NP_001296 | 100.0% | 86.96% | 91.30% |
| musCLDN4 NP_034033 | | | 95.65% |

FIG. 4C

Anti-CLDN Mouse Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| SC27.1 | DIQMTQSSSSFSVSLGDRVTITC | KASEDIYNRLA | WYQQKPGNAPRLLIS | GATSLET | GTPSRFSGSGSGSGKDYTLSITSLRTEDAATYYC | QQYWSTPLT | FGTGTKLELK | 21 |
| SC27.22 | DIVLTQSPASLAVSLGQRATISC | RASQTVSTSSYSYMH | WFQQKPGQPPKLLIK | FASNVES | GVPARFSGSGSGTDFTLNIHPVEEEDISTYYC | QHSWEIPWT | FGGGTKLEIK | 25 |
| SC27.103 | QIVLTQSPAIMSASLGERVTMTC | TASSSVSSSYLH | WYQQKPGSSPTLWIY | RTSDLAS | GVPARFSGSGSGTSYSLTISSMEAEDAATYYC | HQYHRSPWT | FGGGTRLEIK | 29 |
| SC27.104 | DIQMTQSSSSFSVSLGDRVTITC | KASEDIYNRLA | WYQQKPGNAPRLLIS | GATSLET | GVPSRFSGSGSGKDYTLSITSLQTEDVATYYC | QQYWSNPPT | FGGGTKLEIK | 33 |
| SC27.105 | DVQMTQSPSSLSASLGERVSLTC | QASQSVSNNLN | WYQQTPGKAPRLLIY | GASKLED | GVSSRFSGTGYGTDFFTISSLEEEDVATYFC | LQHRYLWT | FGGGTKLEIK | 37 |
| SC27.106 | DIQMTQSSSSFSVSLGDRVTITC | KASEDIYNRLA | WYQQKPGNAPRLLIC | GATSLET | GVPSRFSGSGSGKDYTLSITSLQTEDVATYYC | QQYWSTPLT | FGAGTKLELK | 41 |
| SC27.108 | EIVLTQSPALMAASPGEKVTITC | SVSSSISSSNLH | WYQQKSGTSPKLWIY | GTSNLAS | GVPVRFSGSGSGTSYSLTISNMEAEDAATYYC | QQWSSYPHT | FGGGTKLEIK | 45 |
| SC27.201 | DIQMTQSSSSFSVSLGDRVTITC | KASEDIYNRLA | WYQQKPGNAPRLLIS | GATSLEA | GVPSGFSGSGSGKDYTLSITSLQTEDVATYYC | QQYWSTPPT | FGGGTKLEIK | 49 |
| SC27.203 | DIQMTQSSSSFSVSLGDRVTITC | KASEDIYNRLA | WYQQNPGNTPRLMS | GATSLET | GVPSRFSGSGSGKDYTLSITSLQIEDVSTYYC | QQYWSTPPT | FGGGTRLEIK | 53 |
| SC27.204 | DIVMTQSQKFMSTSVGDRVSVAC | KAGQNVGTSVA | WYQQKPGHSPKSLIY | SASYRYS | GVPNRFTGSGSGTDFTLTISNVQSEDLADYFC | QQYITYPYT | FGGGTKLEII | 57 |

FIG. 5A

Anti-CLDN Humanized Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| hSC27.1 | DIQMTQSPSSVSASVGDRVTITC | KASEDIYNRLA | WYQQKPGKAPKLLIY | GATSLET | GVPSRFSGSGSGTDYTLTISSLQPEDFATYYC | QQYWSTPLT | FGQGTKLEIK | 61 |
| hSC27.22 | DIVMTQSPDSLAVSLGERATINC | RASQTVSTSSYSYMH | WYQQKPGQPPKLLIY | FASNVES | GVPDRFSGSGSGTDFTLTISSLQAEDVAVYYC | QHSWEIPWT | FGQGTKLEIK | 65 |
| hSC27.108 | EIVLTQSPATLSLSPGERATLSC | SVSSSISSSNLH | WYQQKPGQAPRLLIY | GTSNLAS | GIPARFSGSGSGTDFTLTISSLEPEDFAVYYC | QQWSSYPHT | FGGGTKVEIK | 69 |
| hSC27.204 | DIQMTQSPSSLSASVGDRVTITC | KAGQNVGTSVA | WFQQKPGKAPKSLIY | SASYRYS | GVPSRFSGSGSGTDFTLTISSLQPEDFATYYC | QQYITYPYT | FGGGTKVEIK | 73 |
| hSC27.108v1 | EIVLTQSPDFQSVTPKEKVTITC | SVSSSISSSNLH | WYQQKPDQSPKLWIY | GTSNLAS | GVPSRFSGSGSGTDFTLTINSLEADAATYYC | QQWSSYPHT | FGGGTKVEIK | 77 |

FIG. 5A Cont.

Anti-CLDN Mouse Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| SC27.1 | EVQLQESRPELVKPGASVKISCKTSGYTFT | EYTLH | WVKQSHGKSLEWIG | GINPNNGDTIYNQKFKG | KATLTVDKSSSTAYMELRSLTSEYSAVYYCAR | RAITVYAMDY | WGQGTSVTVSS | 23 |
| SC27.22 | QVQLQQPGAELVRPGASVKLSCKASGYTFT | SYWMN | WVKQRPGQGLEWA | MIHPSDSEIRLNQKFKD | KATLTVDRSSSTAYMQLSSPTSEDSAVYYCAR | IDSYYGYLFYFDY | WGQGTTLTVSS | 27 |
| SC27.103 | EVHLQQSGPELVKPGGSMKISCKASGYSFT | GYTMN | WVKQSHGKNLEWIG | LFNPYNGGTSYNQKFKG | KATLTVDKSSSTAYMELLSLTSEDSAVYYCAR | CYRYDGLDY | WGQGTTLTVSS | 31 |
| SC27.104 | EVQLQQSGPELVKPGASVKISCKTSGYTFT | EYTVH | WVKQSHGKSLEWIG | GVYPKNGDTTYNQKFRG | KATLTVDKSSSTAYMELLSLTSEDSAVYYCTG | KDGYDGFAY | WGQGTLVTVSA | 35 |
| SC27.105 | EVQLQQSGPELVKPGASVKISCKASGYSFT | GYYMN | WVKQSPEKSLEWIG | EINPSTGSTTYNQKFKA | KATLTVDKSSSTAYMQLKSLTSEDSAVYYCAR | RDYYYGSGFYAMDY | WGQGTSVTVSS | 39 |
| SC27.106 | EVQLQQSGPELVKPGASVKISCKTSGYTFT | EYTMH | WVKQSHGKSLEWIG | GINPNNGGTNYNQKFKG | KATLTVDKSSSTAYMELRSLTSEDSAVYYCAR | RLITYYAMDY | WGQGTSVTVSS | 43 |
| SC27.108 | QVQMQQSGAELVRPCTSVKVSCKASGYAFT | NYLIE | WVKQRPGQGLEWIG | LINPGSGGTNYNEKFKG | KATLTADKSSTTAYMQLSSLTSDDSAVYFCAR | RSPLGSWIYYAYDGVAY | WGQGTLVTVSA | 47 |
| SC27.201 | EVQLQQSGPELVKPGASVKISCKTSGYTFT | ENIRH | WVKQSRGKSLEWIG | TINPNNGETRYNQKFKG | KATLTVDKSSSTAYMELRSLTSEDSAVYYCTR | GITKSPYGMDY | WGQGTSITVSS | 51 |
| SC27.203 | EVQLQQSGPELVKPGASVKISCKTSGYTFT | ENIIH | WVKQSHGKSLEWIG | GINPIPGGTSYNQKFKG | KATLTVDKSSSTAYMELRSLTSEDSAVYYCAR | GITTSPYAMDY | WGQGTSVTVSS | 55 |
| SC27.204 | EVKVLESGGGLVQPGGSLKLSCAASGFDFS | RYWMS | WVRQAPGKGLEWIG | EINPDSSTINYTPSLKA | KFIISRDNAKNTLYLQMSKVRSEDTALYYCTG | PAY | WGQGTLVTVSA | 59 |

FIG. 5B

Anti-CLDN Humanized Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| hSC27.1 | QVQLVQSGAEVKKPGASVKVSCKASGYTFT | EYTLH | WVRQAPGQRLEWMMG | GINPNNGDTTYNQKFKG | RVTITRDTSASTAYMELSSLRSEDTAVYYCAR | RAITVYAMDY | WGQGTLVTVSS | 63 |
| hSC27.22 | QVQLVQSGAEVKKPGASVKVSCKASGYTFT | SYWMN | WVRQAPGQRLEWMMG | MIHPSDSEIRLNQKFKD | RVTITRDTSASTAYMELSSLRSEDTAVYYCAR | IDSYYGYLFYFDY | WGQGTTVTVSS | 67 |
| hSC27.108 | QVQLVQSGAEVKKPGASVKVSCKASGYTFT | NYLIE | WVRQAPGQGLEWMMG | LINPGSGGTNYNEKFKD | RVTMTTDTSTSTAYMELRSLRSDDTAVYYCAR | RSPLGSWIYYAYDGVAY | WGQGTLVTVSS | 71 |
| hSC27.204 | EVQLLESGGGLVQPGGSLRLSCAASGFTFS | RYWMS | WVRQAPGKGLEWVS | EINPDSSTINYTPSLKA | RFTISRDNSKNTLYLQMNSLRAEDTAVYYCTG | PAY | WGQGTLVTVSS | 75 |
| hSC27.22 - VH1-8 | QVQLVQSGAEVKKPGASVKVSCKASGYTFT | SYWMN | WVRQATGQGLEWMMG | MIHPSDSEIRLNQKFKD | RVTMTRNTSISTAYMELSSLRSEDTAVYYCAR | IDSYYGYLFYFDY | WGQGTTVTVSS | 79 |
| hSC27.22 - VH1-46 | QVQLVQSGAEVKKPGASVKVSCKASGYTFT | SYWMN | WVRQAPGQGLEWMMG | MIHPSDSEIRLNQKFKD | RVTMTRDTSTSTVYMELSSLRSEDTAVYYCAR | IDSYYGYLFYFDY | WGQGTTVTVSS | 81 |
| hSC27.22 - VH1-69 | QVQLVQSGAEVKKPGSSVKVSCKASGGTFS | SYWMN | WVRQAPGQGLEWMMG | MIHPSDSEIRLNQKFKD | RVTITADESTSTAYMELSSLRSEDTAVYYCAR | IDSYYGYLFYFDY | WGQGTTVTVSS | 83 |
| hSC27.204v1 | EVQLLESGGGLVQPGGSLRLSCAASGFTFS | RYWMS | WVRQAPGKGLEWVS | EINPDSSTIKYTPSLKA | RFTISRDNSKNTLYLQMNSLRAEDTAVYYCTG | PAY | WGQGTLVTVSS | 85 |
| hSC27.204v2 | EVQLLESGGGLVQPGGSLRLSCAASGFTFS | RYWMS | WVRQAPGKGLEWVS | EINPDSSTIQYTPSLKA | RFTISRDNSKNTLYLQMNSLRAEDTAVYYCTG | PAY | WGQGTLVTVSS | 87 |
| hSC27.204v3 | EVQLLESGGGLVQPGGSLRLSCAASGFTFS | RYWMS | WVRQAPGKGLEWVS | EINPDSSTINYNPSLKA | RFTISRDNSKNTLYLQMNSLRAEDTAVYYCTG | PAY | WGQGTLVTVSS | 89 |
| hSC27.204v4 | EVQLLESGGGLVQPGGSLRLSCAASGFDFS | RYWMS | WVRQAPGKGLEWVS | EINPDSSTINYTPSLKA | RFTISRDNSKNTLYLQMNSLRAEDTAVYYCTG | PAY | WGQGTLVTVSS | 91 |

FIG. 5B Cont.

Anti-CLDN Humanized Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| hSC27.204v5 | EVQLLESGGGLVQPGGSLRLSCAASGFDFS | RYWMS | WVRQAPGKGLEWVS | EINPDSSTIKYTPSLKA | RFTISRDNSKNTLYLQMNSLRAEDTAVYYCTG | PAY | WGQGTLVTVSS | 93 |
| hSC27.204v6 | EVQLLESGGGLVQPGGSLRLSCAASGFDFS | RYWMS | WVRQAPGKGLEWVS | EINPDSSTIQYTPSLKA | RFTISRDNSKNTLYLQMNSLRAEDTAVYYCTG | PAY | WGQGTLVTVSS | 95 |
| hSC27.204v7 | EVQLLESGGGLVQPGGSLRLSCAASGFDFS | RYWMS | WVRQAPGKGLEWVS | EINPDSSTINYNPSLKA | RFTISRDNSKNTLYLQMNSLRAEDTAVYYCTG | PAY | WGQGTLVTVSS | 97 |
| hSC27.204v8 | EVQLLESGGGLVQPGGSLRLSCAASGFTFS | RYWMS | WVRQAPGKGLEWVS | EINPDSSTINYTPSLKA | RFTISRDNSKNTLYLQMNSLRAEDTAVYYCAG | PAY | WGQGTLVTVSS | 99 |
| hSC27.204v9 | EVQLLESGGGLVQPGGSLRLSCAASGFTFS | RYWMS | WVRQAPGKGLEWVS | EINPDSSTIKYTPSLKA | RFTISRDNSKNTLYLQMNSLRAEDTAVYYCAG | PAY | WGQGTLVTVSS | 101 |
| hSC27.204v10 | EVQLLESGGGLVQPGGSLRLSCAASGFTFS | RYWMS | WVRQAPGKGLEWVS | EINPDSSTIQYTPSLKA | RFTISRDNSKNTLYLQMNSLRAEDTAVYYCAG | PAY | WGQGTLVTVSS | 103 |
| hSC27.204v11 | EVQLLESGGGLVQPGGSLRLSCAASGFTFS | RYWMS | WVRQAPGKGLEWVS | EINPDSSTINYNPSLKA | RFTISRDNSKNTLYLQMNSLRAEDTAVYYCAG | PAY | WGQGTLVTVSS | 105 |
| hSC27.204v12 | EVQLLESGGGLVQPGGSLRLSCAASGFDFS | RYWMS | WVRQAPGKGLEWVS | EINPDSSTINYTPSLKA | RFTISRDNSKNTLYLQMNSLRAEDTAVYYCAG | PAY | WGQGTLVTVSS | 107 |
| hSC27.204v13 | EVQLLESGGGLVQPGGSLRLSCAASGFDFS | RYWMS | WVRQAPGKGLEWVS | EINPDSSTIKYTPSLKA | RFTISRDNSKNTLYLQMNSLRAEDTAVYYCAG | PAY | WGQGTLVTVSS | 109 |
| hSC27.204v14 | EVQLLESGGGLVQPGGSLRLSCAASGFDFS | RYWMS | WVRQAPGKGLEWVS | EINPDSSTIQYTPSLKA | RFTISRDNSKNTLYLQMNSLRAEDTAVYYCAG | PAY | WGQGTLVTVSS | 111 |
| hSC27.204v15 | EVQLLESGGGLVQPGGSLRLSCAASGFDFS | RYWMS | WVRQAPGKGLEWVS | EINPDSSTINYNPSLKA | RFTISRDNSKNTLYLQMNSLRAEDTAVYYCAG | PAY | WGQGTLVTVSS | 113 |

FIG. 5B Cont.

Anti-CLDN Mouse Antibody Variable Region Nucleic Acid Sequences

| Name | Chain | Nucleic Acid Sequence | SEQ ID NO |
|---|---|---|---|
| SC27.1 | Light Chain | GACATCCAGATGACACAATCTTCATCCTCCTTTTCTGTATCTCTAGGAGACAGAGTCACCATTACTTGCAAGGCAAGTGAAGACATATATAATCGGTTAGCCTGGTATCAGCAGAAACCAGGAAATGCTCCCAGGCTCTTAATATCTGGTGCAACCAGTTTGGAAACTGGGACTCCTTCAAGATTCAGTGGCAGTGGATCTGGAAAGGATTACACTCTCAGTATTACCAGTCTTCGGACTGAAGATGCTGCTACTTATTACTGTCAACAATATTGGAGTACTCCACTCACGTTCGGTTCGGAGGACCAAGCTGGAGCTGAAA | 20 |
| SC27.1 | Heavy Chain | GAGGTCCAGCTGCAAGAGTCTAGACCTGAGCTGGTGAAGCCTGGGGCTTCAGTGAAGATATCCTGCAAGACTTCTGGATACACATTCACTGAATACACCCTTGCACTGGGTGAAGCAGAGTCATGGAAAGAGCCTTGAGTGGATTGGAGGTATTAATCCTAACAATGGTGATACTATCTACAACCAGAAATTCAAGGGCAAGGCCACATTGACTGTAGACAAGTCCTCCAGCACAGCCTACATGGAGCTCCGCAGCCTGACATCTGAAATATTCTGCAGTCTATTACTGTGCAAGAAGGCGATTACGGTTCTATGGACTACTGGGGTCAAGGTACCTCAGTCACCGTCTCCTCA | 22 |
| SC27.22 | Light Chain | GACATTGTGCTGACACAGTCTCCTGCTTCCTTAGCTGTCTCTCTGGGCAGAGGGCCACCATCTCATGCAGGGCCAGCAGTGCATTAGTACATCTCAGTACATAGTTATGCACTGGTTCCAACAGAAACCAGGACAGCCACCCAAACTCCTCATCAAGTTTGCATCCAACCTAGAATCTGGGGTCCCTGCCAGATTCAGTGGCAGTGGGTCTGGGACAGACTTCACCCTCAACATCCATCCTGTGGAGGAGGAGGATATTTCAACATATTTCAACATATTACTGTCAGCAGAGTTCGGAGATTCCGTGGACGTTCGGTGGAGGCACCAAGCTGGAAATCAAA | 24 |
| SC27.22 | Heavy Chain | CAGGTCCAACTGCAGCAGCCTGGGGCTGAGCTGGTGAAGCCTGGGGCCTCAGTGAAGCTGTCCTGCAAGGCTTCAGTGAAGGCTACACACCTTCACCAGCTACTGGATGAACTGGGTGAAGCAGAGGCCTGGACAAGGCCTTGAATGGATTGCCATGATTCATCCTTCCGATAGTGAATCATCATGACTTTGGGAAGGACAAGGCCACACATTGACTGTAGACACATCCTCCAGCACAGCCTACATGGAGCTCCAGCAGCCTGACATCTGAGGACACTGCTGTCTATTACTGTGCAAGAATTGATAGTTATTATGGTTACCTGTTTTTACTTTGACTACTGGGGCCAAGGCACCACTCTCACAGTCTCCTCA | 26 |
| SC27.103 | Light Chain | CAAATTGTTCTCACCCAGTCTCCAGCAATCATGTCTGCATCTCTAGGGGAACGGGTCACCATGACCTGCAGCTCAAGTGTAAGTTCCAGTTACTTGCACTGGTACCAGCAGAAGCCAGGATCCTCCCCCACACTCTGGATTTATAGGACATCCAACCTGGCTTCTGGAGTCCCAGCTCGCTTCAGTGGCAGTGGATCTGGGACCTCTTACTCTCTCACAATCAGCAGGCTGAAGGCTGAAGATGCTGCCACTTATTACTGCCAGCAGTATCATCGTTCCCGTGGACGTTCGGTGGAGGCACCAAGCTGGAAATCAAA | 28 |
| SC27.103 | Heavy Chain | GAGGTCCACCTGCAACAGTCTGGACCTGAGCTGGTAGTGCCTGGAGCTTCAATGAAGATATCCTGCAAGGCTTCTGGTTACTCATTCACTGGCTACACCATGAACTGGGTGAAAGCAGAGCCATGGAAAGAACCTTGAGTGGATTGGACTTATTAATCCTTACAATGGTGGTACTAGTTATAACCAGAAGTTCAAGGGCAAGGCCACATTAACTGTAGACAAGTCATCCAGCACAGCCTACATGGAGCTCCTCAGTCTGACATCTGAGGACTCTGCAGTCTATTACTGTGCAAGATGCTGTAAGGTACCGGTCTTGACTACTGGGGCCAAGGCACCACTCTCACAGTCTCCTCA | 30 |

FIG. 5C

Anti-CLDN Mouse Antibody Variable Region Nucleic Acid Sequences

| Name | Chain | Nucleic Acid Sequence | SEQ ID NO |
|---|---|---|---|
| SC27.104 | Light Chain | GACATCCAGATGACACAATCTTCATCCTCCTTTCTGTATCTCTCAGGAGACAGAGTCACCATTACTTGCAAGGCAAGTGAGGACATATAATCGGTTAGCCTGGTATCAGCAGAAACCAGGAAA TGCTCCCAGGCTCTTAATATCGGTGCAACCAGTTTGGAAACTGGGGTTCCTTCAAGATTCAGTGGCAGTGGATCTGGAAAGGATTACACTCTCAGCATTACCAGTCTTCAGACTGAAGATGTTG CTACTTATTACTGTCAACAGTATTGGAGTACTCCGACGTTCGGTGGAGGCACCAAGCTGGAAATCAAA | 32 |
| SC27.104 | Heavy Chain | GAGGTCCAGCTGCAACAGTCTGAGCTGTGAAGCCTGGGCTTCAGTGAAGATATCCTGCAAGACTTCTGGATACACCTTCACTGAATACACCCTGGGTGAAGCAGAGCCATGG AAAGAGCCCTTGAGTGGATTGGAGGTGTTTATCTACACCTACACCAGAAGTTCAGGGGCAAGGCCACATTGACTGTAGACAAGTCCTCCAACACAGCCTATATGGAACTCC GCAGCCTGACATCTGAGGATCTGCAGTCTATTACTGTACAGGAAAGGATGGGTACGACGGGTTTGCTTACTGGGGCCAAGGGACTCTGGTCACTGTCTCTGCA | 34 |
| SC27.105 | Light Chain | GATGTTCAAATGACCCAGTCTCCATCCTCCCTGTCTGCATCTCTGGGAGAGAGAGTCTCCCTGACTTGCAGGGCAAGTCAGAGTGTTAGCAATAATTTAAACTGGTATCAGCAAACACCAGGGAA AGCTCCTAGGCTCTTGATCTATGCTGCAAGCAAATTGGAAGATGGGGTCTCTTCAAGGTTCAGTGGCACTGGATATGGGACACTGGAGGAAGAAGATGTGG CAACTTATTTTGTCTACAGCATAGGTATCGTGGACGTTCGGTTGGAGGCACCAAGCTGGAAATCAAA | 36 |
| SC27.105 | Heavy Chain | GAGGTCCAGCTGCAGCAGTCTGGACCTGAGTTGGTGAAGCCTGGGGCTTGAGTGGATATCCTGCAAGGCTTCACTGGCTACTATTCACTGGCTACTCAGTACATTCCTGAAGGCAAGTCCTGA AAAGAGCCCTGAGTGGATTGGAGAGATTAATCCTTACTACTGCAAGGAGTTCAAGGCCCAAGGTGTTAGAACAAATCCTCCAGCACAGCCTACATGCAGCTCA AGAGCCTGACATCTGAGGGACTCTGCAGTCTATGTGTTTCTATGCGTAGGGTCAAGGAACCTCAGTGACCGTCTCCTCA | 38 |
| SC27.106 | Light Chain | GACATCCAGATGACACAATCTTCATCCTCCTTTTCTGTATCTCTAGGAGACAGAGTCACCATTACTTGCAAGGCAAGTGAGGACATATATAATCGGTTAGCCTGGTATCAGCAGAAACCAGGAAA TGCTCCTAGGCTCTTAATATGTGTGCAACCAGTTTGGAAGTACTCCGCCTCACGTTCGGTGCTGGGACCAAACTGGAGCTGAAA CTACTTATTATCTGTCAACAGTATTGGAGTACTCCGCCTCACGTTCGGTGCTGGGACCAAACTGGAGCTGAAA | 40 |
| SC27.106 | Heavy Chain | GAGGTCCAGCTGCAACAGTCTGGACCTGAACCTGTGAAGCCTGGGGCTTCAGTGAAGATATCCTGCAAGACTTCTGGATACACCATTCACTGAATACACCATGGGTGAAGCAGAGCCATGG AAAGAGCCCTTGAGTGGATTGAGGTTGGAGGTATTAATCCTAACAATGGTGGCTACTAACTACAACCAGAAGTTCAAGGGCAAGGCCACATTGACTGTTGACAAGTCCTCCAGCACAGCCTACATGGAGCTCC GCAGCCTGACATCTGAGGATCTGCAGTCTATTACTGTGCAAGAAGGCTTATTACTGACTACTATGGCTACTATGGCTACTATGCCATGGGGTCAAGGAACCTCAGTCACCGTCTCCTCA | 42 |

FIG. 5C Cont.

Anti-CLDN Mouse Antibody Variable Region Nucleic Acid Sequences

| Name | Chain | Nucleic Acid Sequence | SEQ ID NO |
|---|---|---|---|
| SC27.108 | Light Chain | GAAATTGTGCTCACCCAGTCTCCAGCACTCATGGCTGCATCTCCAGGGGAGAAGGTCACCATCACCTGCAGCTCAAGTATAAGTTCCAGCAACTTGCACTGGTACCAGCAGAAGTCAGGAACCTCCCCCAAACTCTGGATTTATGCCACATCCAACCTGGCTTCTGGAGTCCCTGCTTCGCTTCAGTGGCAGTGGATCTGGGACCTCTTATTCTCTCACAATCAGCAACTGAAGCTGAAGATGCTGCCACTTATTACTGTCAACAGTGGAGTAGTTACCCACACAGTTCGGAGGGGGGACCAAGCTGGAAATAAAA | 44 |
| SC27.108 | Heavy Chain | CAGGTCCAAATGCAGCAGTCTGGAGCTGAGCTGGTAAGGCCTGGAGCTTCAGTGAAGGTGTCCTGCAAGGCTTCTGGATACGCCTTCACTAATTACTTGATAGAGTGGGTAAAGCAGAGGCCTGGACAGGGCCTTGAGTGGATTGGATCTGATTAATCCTGGAAGTGGTACTAATTACAATGAGAAGTTCAAGGGCAAGGCCAACATCACTGCAGACAAATCTCCACCACTGCCTACATGCAGCTCAGCAGCCTGACATCTGATGACTCTGCGGGTTTATTTCTGTGCAAGACGGTCTACTATGCTTACGACGGTTGCTTACTGGGGCCAAGGGACTCTGGTCACTGTCTCTGCA | 46 |
| SC27.201 | Light Chain | GACATCCAGATGACACAATCTTCATCCTCCTTTTCTGTCTCTCTGGGAGACAGAGTCACTATTACTTGCAAGGCAAGTCAGGACATCTATAATCGGTTAGCCTGGTATCAACAGAAACAGGAAATGCTCCTAGGCTCTTAATATCTGGTGCAACAGTTTGGAAGCTGGGGTTCCTTCAGGATTCAGTGGCAGTGGATCTGGAAAGGATTACACTTCAGCATTACCAGTGTCAGACTCTTCAGACTCTTCAGACTCTTCAGAAGTATTGCTACTTATTACTGTCAACAGTATTGGAGTACTCCTCCGACGTTCGGTGGAGGCACCAAGCTGGAACTCAAG | 48 |
| SC27.201 | Heavy Chain | GAGGTCCAGCTGCAACAGTCTGGACCTGAACTGGTGAAGCCTGGGGCTTCAGTGAAGATATCCTGCAAGGCTTCTGGATACACATTCACTGAAGATAGAAACATCAGACACTGGGTGAAGCAGAGCCGAGGAAGAGCCCTTGAGTGGATTGGATGGATTACTATGTTGAGACTCTTCAAGGGCAAGGCCACATTGACTGTAGACAAGTCCTCCAGCACAGCCTACATGGAGCTCCGCAGCCTGACATCTGAGGATTCTGCAGTCTATTACTGCACGGGGACTACTGGGTCAAGGAACGTCAATCACCGTCTCCTCA | 50 |
| SC27.203 | Light Chain | GACATCCAGATGACACAATCTTCATCCTCCTTTCTGTATCTCTAGGAGACAGAGTCACTTGCAAGGCAAGTCAGGATGTTAGCCTGGTATCAGCAGAAATCAGGAAATACTCCTAGGCTCTAATGTCTGGTGCAACAGTTTGGAAACTGGGGTTCCTCAAGATTCAGTGGCAGTGGATCTGGAAAGGATTACACTCTCAGCATTACCAGTGTCAGACTCTTCAGAGTGTTTCTACTTATTATTGTCAACAATATTGGAGTACTCCGCTCACGTTCGGTGGAGGCACCAAGCTGGAAATCAAA | 52 |
| SC27.203 | Heavy Chain | GAGGTCCAGCTGCAACAGTCTGGACCTGAGCTGGTGAAGCCTGGGGCTTCAGTGAAGATATCCTGCAAGACTTCACTGAAGACATTCACTGAAAACATCATACACTGGGTGAAGCAGAGCCATGGAAAGAGCCCTTGAGTGGATTGGATATTATTAATCCTAGCTACAACCAGAAGTTCAAGGGCAAGGCCACATTGACTGTAGACAAGTCCTCCAGCACAGCCTACATGGAGCTCCGTAGCCTGACATCTGAGGATTCTGCAGTCTATTACTGTGCAAGGGGGATTACTACGTCCCCTTATGCTATGGACTACTGGGGTCAAGGAACCTCAGTCACCGTCTCCTCA | 54 |
| SC27.204 | Light Chain | GACATTGTGATGACCCAGTCTCAAAAATTCATGTCCACATCAGTAGGAGACAGGGTCAGCGTCCCCTGCAAGGCCGGTCGGATTCAGAATGTGGGTACTAGTGTAGCCTGGTATCAACAGAAACCAGGACATTCTCTAAATCACTGATTTACTGGGCATCCACTAGGGAATCCGGGATCCCTGCTCGCTTCAGTGGCAGCTAGCTCCAGGGAGCATTTCACTCTCACCATCAGCAATGTGCAGCTCGAAGACTTGGCAGACTATTTCTGTCAGCAATATAGCAGCTATCCCTACACGTTCGGAGGGGGGACCAAGCTGGAAATAATA | 56 |
| SC27.204 | Heavy Chain | GAGGTGAAGGTTCTCGAGTCTGGAGGTGGCCTGGTGCAGCCTGGAGGATCCCTGAAACTCTCCTGTGCAGCCTCAGGATTCGATTTTAGTAGATACTGGATGAGTTGGGTCCGGCAGTCTCCAGGGAAAGGGCTAGAATGGATTGGAGAAATTAATCCAGATAGCAGTACAATTAACTATGCGCCATCTCTAAAGGCTAAATTCATCATCTCCAGAGACAACGCCAAAAATACGCTGTACCTGCAAATGAGCAAAGTGAGATCTGAGGACGCAGCCTTTTAATTACTGTACAGGGACCAGCTCCAGGCTCGGTCCGGCAGCCTCCAGGGTACTGCAAATGA | 58 |

FIG. 5C Cont.

Anti-CLDN Humanized Antibody Variable Region Nucleic Acid Sequences

| Name | Chain | Nucleic Acid Sequence | SEQ ID NO |
|---|---|---|---|
| hSC27.1 | Light Chain | GACATCCAGATGACCCAGTCTCCATCTTCCGTGTCTGCATCTGTAGGAGACAGAGTCACCATCACTTGTAAGGCGAGTGAGGATATTTACAACCGGTTAGCCTGGTATCAGGAAAACCAGGGAAAGCCCCTAAGCTCCTGATCTATGCTGCAACCAGTTTGGAAACTGGGGTCCCATCAAGGTTCAGCGGCAGTGGATCTGGGACAGATTCACTCTCACCATCAGCAGCCTGCAGCCTGAAGATTTTGCAACTTACTACTGTCAACAGAGTTACAGTTACCCTCACTCGGTCGGAGGGACCAAGGTGGAGATCAAA | 60 |
| hSC27.1 | Heavy Chain | CAGGTCCAGCTTGTGCAGTCTGGGGCTGAGGTGAAGAAGCCTGGGGCCTCAGTGAAGGTTTCCTGCAAGGCTTCTGGATACACCTTCACTGAGTATACTCTGCATTGGGTGCGCCAGGCCCCCGGACAAAGGCTTGAGTGGATGGGAGGGATCAACAATATAATACCAGAGTTCAACGGCAAGTTCACAATTAACCAGGGACACATCCGGGACACAGCCTACATGGAGCTGAGCAGCCTGAGATCTGAGGACACGGCTGTGTATTACTGTGCGAGAGGGCCATTACGGTCTATGCGGAGGTACCCTAGTGCACCGTCTCGAGC | 62 |
| hSC27.22 | Light Chain | GACATTGTCATGACCCAGTCCCCTGACAGTTTGGCCGTTAGCTTGGGGGAGCGGTGCCACCATCAACTGTAGGGCTAGTCAAACTGTTTCTACATCCTCTACTCTTACATGCATTGGTATCAGCAGAAACCTGGTCAGCCTCCCAAAACTCCTGATTTATTTGCATCTAAGGTCACTCGGGAGATCCCTGCTCGGTTCAGCGGATCAGGGGAGCGACTGGACCTTCACCCTCAGCAGCCTGAGCTGCAGCCCGTAGAAGCTGCCAGGAACAAGCTTGACACTTACACTTACACTCTCA | 64 |
| hSC27.22 | Heavy Chain | CAGGTGCAGTTGGTGCAGAGCGGCGCCGAAGTCAAGAAACCAGGAGCTCTGTCAAAGTCCTCTGTAAAGCCTCCGGATATACCTTCACCAGCTACTGAATTGGGTAAGACAGGCCCCCGGACAGAGCCTTGAGTGGATGGGAATGGACCATCCCTGACAGCGAGATTCGGCTCAACAGAAGTTTAAAGACCAGGTGACTATCACACGGATATCAGAGCCTACATGGAGTTGAGTTCTTCTTCGTAGCGAGCCATCGACTCATATATGGTATCTGTCTACTCTCGACTATTGGGGCCAGGGGACCACCGTGACTGTGTCTTCC | 66 |
| hSC27.108 | Light Chain | GAAATCGTGCTTACAACAATCCCCTGCCACTCTGAGCCTTTCCCAGGCGAGCGAGCAACCCTTCCTGCAGTGTTTCCTCTTCAACTCAGTTCCAGCAATTTGCACTGCTCCACTCAGCAGCAGAAGCCTGGTCAGGCACCGACCCCGATCGTTGATCTATGGCACATCTAAGCTGGCCAACATGGAGTTCCAACGCTGAATCGTCGGAACAGATTTCACTCTCACTATCAGCTCCCTTGAGCCTGAAGATTTTGCCGTGTACTACTGTCAGCAATGGAGTTCACCTCCCCACACCTTTGGCCGGGGGACCAAAGGTCAGAGATAAA | 68 |
| hSC27.108 | Heavy Chain | CAGGTACAGCTGGTGCAGTCCGGCGCTGAGGTTAAGAAGCCCGGTGCCTCCGTGAAGGTATCTGTAAGGCCTCAGGTTACACCTTTACAAATTATCTGATCGAATGGGTGAGACAGGCCCCAGGTCAGGGTCTGGAATGGATGGGATCGGAACAATCACCAACGAAAAGTTTAAGGAGAGTGACAATGACCACAGATGACCACAGATGACCACAGATACCACAAAATCGAGTATCACCTCCACGCATATATGGAGCTGAGCTCGAGCCTGAGATCGGTCGCATGAGGCCATGAGCTCTACTGCAAGGGCCAGGGCACCCTGGTCACCGTGTCCACATTGGCGCCACCGAGGGCACCCCTGGTCACCGTCTCAGCTCC | 70 |
| hSC27.204 | Light Chain | GACATCCAGATGACCCAGTCCCCTTCCCCTCAGCCTGTCTGCCTCTGTCGGTGACAGAGTGACCATCACATGCAGCGGGACAGAGTGCCCTCAGTTGCCCCTAGGAGATACCTGGGCTTGATCTACACCCTCGCCCCCTCGATCTACCCCCGGCGCTTACGCCACAAAGCGCAAAGGTAAATGGCGCAGATAGCCATGAGGGAGGTGCAGGGACCAAGGTGTACACCAAGGGCACCAAGGTGACCGTCTCCCACCGTCACCCTGAGGAGCACCCACAAGGTGAAATCAAG | 72 |
| hSC27.204 | Heavy Chain | GAAGTGCAGCTGCTGGAATCTGGCGGAGGGCTGGTGCAGCCTGGCAGGATCTCTGAGACTCGACTCGACCCGGACGCACCGACAGCCACAACAACCACAGCCCAAAAGCTGCCAACTGCAAAGGCCTCGCACCATCAAGCCGCATCGCCATCATCATCATCACCGCCACCTGTACAACCCACCACACACATCTCATTCATCTCCTCCGTGGCTGGACTCTGTTCCAGCAGAAGCCTGAGCAGCCGGCCACCTGCTGGCTGGCAGCTGGCTGGCGCTCCTGCTGCCGCTGCAGCTCCATCAGCATGGCTTCTGGACTCTCGGAGTCCTCGGGATCGCATGTCCGGTGCGGACAGGCTCCTGCAAGATGCCATCATCTCCGGGACAACACCCAAAGAACACCCTGTACACCGCTGACCGTGTCCTCT | 74 |

FIG. 5C Cont.

Anti-CLDN Humanized Antibody Variable Region Nucleic Acid Sequences

| Name | Chain | Nucleic Acid Sequence | SEQ ID NO |
|---|---|---|---|
| hSC27.108v1 | Light Chain | GAAATCGTGCTGACTCAGTCTCCCGATTTCCAGTCCGTCACACCCAAGGAGAAAGTCACCATCACTTGTTCTCTCCTCAAGCATCTCTTCTAGTAACCTGCACTGGTATCAGCAGAAGCCTGATCAGTCCCCTAAGCTTTGGATATACGGCACCTCAAACCTCGCCTCCGGAGTTCCTTCAAGGTTTTGCAGCTGGATCTGGAACCGATTTCACCCTTACAATAACAGTCTTGAGGCCGAGGACGCCGCCACTTACTACTGCCAGCAGTGGAGTTCTTACCCCACACATTTGGGGCGGCACCAAAGTGGAGATCAAA | 76 |
| hSC27.22 - VH1 - 8 | Heavy Chain | CAGGTGCAGCTGGTGCAGTCTGGCGCCGAAGTGAAGAAACCTGGCGCTCAGGCCTCCGTGAAGGTGTCCTGCAAGGCCTCCGGCTACACCTTTACCAGCTACTGGATGAACTGGGTGCGACAGGCTACCGGCCAGGGCCTGGAATGGATGGGCATGATCCACCCTTCCGACTCCGAGACTCGCTACAGCCCCAGCTTCCAGGGCAGAGTGACCATGACCCGGGACACCTCCATCTCCACCGCCTACATGGAACTGTCCTCCCTGCGGAGCGAGGACACCGCCGTGTACTACTGCGCCCGGGATCCCTACTACGGCTCTACTCTACGCCTACGGGCCAGGGCACCACCGTGACCGTGTCATCT | 78 |
| hSC27.22 - VH1 - 46 | Heavy Chain | CAGGTGCAGCTGGTGCAGTCTGGCGCCGAAGTGAAAAAGCCTGGCGCCTCCGTGAAGGTGTCCTGCAAGGCCTCCGGCTACACCTTTACCAGCTACTGGATGAACTGGGTGCGACAGGCCCCTGGACAGGGCCTGGAATGGATGGGCATGATCCACCCTTCCGACTCCGAAACCAGATACAGCCCCTCCTTCCAGGGCAGAGTGACCATGACCAGAGACACCTCCACCAGCACCGTGTACATGGAACTGTCCTCCCTGCGGAGCGAGGACACCGCCGTGTACTACTGCGCCCGGGATCCCTACTACGGCTCTACCCTACGGCCTACGGGCCAGGGCACCACCGTGACCGTGTCATCT | 80 |
| hSC27.22 - VH1 - 69 | Heavy Chain | CAGGTGCAGCTGGTGCAGTCTGGCGCCGAAGTGAAGAAACCCGGCTCCTCCGTGAAGGTGTCCTGCAAGGCCTCCGGCGGCACCTTCTCCAGCTACTGGATGAACTGGGTGCGACAGGCCCCTGGACAGGGCCTGGAATGGATGGGCATGATCAACCCCTCCGACTCCGAAACAGAGTGAACCATCAAGGACACAGAGTGAACGTCACGGCCGACGAGTCCACAAGCACCGTGTACATGGAACTGTCCTCCCTGCGGTCTGACGATCCGCCGGTGTACTACTGCGCCCGGGATCCCTACTACGGCTACTCTACCTACCTACGGCCTACGGGCCAGGGCACCACCGTGACCGTGTCATCT | 82 |
| hSC27.204v1 | Heavy Chain | GAAGTGCAGCTGCTGGAATCTGGCGCCGGACTGGTGCAGCCTGGCGGATCTCTGAGACTGTCTTGTGCCGCCTCTGGCTTCACCTTCTCCGGCTACTGGATGTCCTGGGTGCGACAGGCTCCTGGCAAGGGCCTGGAATGGGTTCCGAGATCAACCCCGACGGCGGCGGCACCAACTACAACCCCAGCCTGAAGGGCCGGTTCACCATCTCTCGGGACAACGCCAAGAACACCCTGTACCTGCAGATGAACTCCCTGCGGGCCGAGGACACCGCCGTGTACTACTGTGCTCGGGACTACGGCGACTACTACTGGGGCCAGGGCACCCTCGTGACCGTGTCCTCT | 84 |
| hSC27.204v2 | Heavy Chain | GAAGTGCAGCTGCTGGAATCTGGCGCCGGACTGGTGCAGCCTGGCGGATCTCTGAGACTGTCTTGTGCCGCCTCTGGCTTCACCTTCTCCGGCTACTGGATGTCCTGGGTGCGACAGGCTCCTGGCAAGGGCCTGGAATGGGTTCCGAGATCAACCCCGACGGCGGCGGCACCAACTACAACCCCAGCCTGAAGGGCCGGTTCACCATCTCTCGGGACAACGCCAAGAACACCCTGTACCTGCAGATGAACTCCCTGCGGGCCGAGGACACCGCCGTGTACTACTGTGCTCGGGACTACGGCGACTACTACTGGGGCCAGGGCACCCTCGTGACCGTGTCCTCT | 86 |
| hSC27.204v3 | Heavy Chain | GAAGTGCAGCTGCTGGAATCTGGCGCCGGACTGGTGCAGCCTGGCGGATCTCTGAGACTGTCTTGTGCCGCCTCTGGCTTCACCTTCTCCGGCTACTGGATGTCCTGGGTGCGACAGGCTCCTGGCAAGGGCCTGGAATGGGTTCCGAGATCAACCCCGACGGCGGCGGCACCAACTACAACCCCAGCCTGAAGGGCCGGTTCACCATCTCTCGGGACAACGCCAAGAACACCCTGTACCTGCAGATGAACTCCCTGCGGGCCGAGGACACCGCCGTGTACTACTGTGCTCGGGACTACGGCGACTACTACTGGGGCCAGGGCACCCTCGTGACCGTGTCCTCT | 88 |

FIG. 5C Cont.

Anti-CLDN Humanized Antibody Variable Region Nucleic Acid Sequences

| Name | Chain | Nucleic Acid Sequence | SEQ ID NO |
|---|---|---|---|
| hSC27.204v4 | Heavy Chain | GAAGTGCAGCTGCTGGAATCTGGCGGCGGACTGGTGCAGCCTGGCGGGTCTCTGAGACTGTCTTGTGCCGCCTCCGGCTTCGACTTCTCCGGGTACTGATGTCCTGGGTGCGACAGGCT CCTGGCAAGGGCCTGGAATGGGTGTCCGAGATCAACCCCGACTCCTCCACCATCAACTACAACCCCAGCCTGAAGGCCCGGGTTCACCATCTCTCGGGACAACATCTCCAAGAACACCCTGTAC CTGCAGATGAACTCCCTGCGGGCTGAGGACACCGCCGTGTACTACTGTGCCGGGCACCCTGTGACCGTGTCCTCT | 90 |
| hSC27.204v5 | Heavy Chain | GAAGTGCAGCTGCTGGAATCTGGCGGCGGACTGGTGCAGCCTGGCGGGTCTCTGAGACTGTCTTGTGCCGCCTCCGGCTTCGACTTCTCCGGGTACTGATGTCCTGGGTGCGACAGGCT CCTGGCAAGGGCCTGGAATGGGTGTCCGAGATCAACCCCGACTCCTCCACCATCAAGTACAACCCCAGCCTGAAGGCCCGGGTTCACCATCTCGGGACAACTCCAAGAACACCCTGTAC CTGCAGATGAACTCCCTGCGGGCTGAGGACACCGCCGTGTACTACTGTGCCGGGCACCCTGTGACCGTGTCCTCT | 92 |
| hSC27.204v6 | Heavy Chain | GAAGTGCAGCTGCTGGAATCTGGCGGCGGACTGGTGCAGCCTGGCGGGTCTCTGAGACTGTCTTGTGCCGCCTCCGGCTTCGACTTCTCCGGGTACTGATGTCCTGGGTGCGACAGGCT CCTGGCAAGGGCCTGGAATGGGTGTCCGAGATCAACCCCGACTCCTCCACCATCCAGTACAACCCCAGCCTGAAGGCCCGGGTTCACCATCTCTCGGGACAACTCCAAGAACACCCTGTAC CTGCAGATGAACTCCCTGCGGGCTGAGGACACCGCCGTGTACTACTGTGCCGGGCACCCTGTGACCGTGTCCTCT | 94 |
| hSC27.204v7 | Heavy Chain | GAAGTGCAGCTGCTGGAATCTGGCGGCGGACTGGTGCAGCCTGGCGGGTCTCTGAGACTGTCTTGTGCCGCCTCCGGCTTCGACTTCTCCGGGTACTGATGTCCTGGGTGCGACAGGCT CCTGGCAAGGGCCTGGAATGGGTGTCCGAGATCAACCCCGACTCCTCCACCATCAACTACAACCCCAGCCTGAAGGCCCGGGTTCACCATCTCTCGGGACAACTCCAAGAACACCCTGTAC CTGCAGATGAACTCCCTGCGGGCCCCCAGGGCACCCTGTGACCGTGTCCTCT | 96 |
| hSC27.204v8 | Heavy Chain | GAAGTGCAGCTGCTGGAATCTGGCGGCGGACTGGTGCAGCCTGGCGGGTCTCTGAGACTGTCTTGTGCCGCCTCCGGCTTCACCTTCTCCGGGTACTGATGTCCTGGGTGCGACAGGCT CCTGGCAAGGGCCTGGAATGGGTGTCCGAGATCAACCCCGACTCCTCCACCATCAACTACAACCCCAGCCTGAAGGCCCGGGTTCACCATCTCTCGGGACAACTCCAAGAACACCCTGTAC CTGCAGATGAACTCCCTGCGGGCTGAGGACACCGCCGTGTACTACTGTGCCGGGCCCCTATTGGGGCCAGGGCACCCTGTGACCGTGTCCTCT | 98 |
| hSC27.204v9 | Heavy Chain | GAAGTGCAGCTGCTGGAATCTGGCGGCGGACTGGTGCAGCCTGGCGGGTCTCTGAGACTGTCTTGTGCCGCCTCCGGCTTCACCTTCTCCGGGTACTGATGTCCTGGGTGCGACAGGCT CCTGGCAAGGGCCTGGAATGGGTGTCCGAGATCAACCCCGACTCCTCCACCATCAAGTACAACCCCAGCCTGAAGGCCCGGGTTCACCATCTCTCGGGACAACTCCAAGAACACCCTGTAC CTGCAGATGAACTCCCTGCGGGCTGAGGACACCGCCGTGTACTACTGTGCCGGGCCCCTATTGGGGCCAGGGCACCCTGTGACCGTGTCCTCT | 100 |
| hSC27.204v10 | Heavy Chain | GAAGTGCAGCTGCTGGAATCTGGCGGCGGACTGGTGCAGCCTGGCGGGTCTCTGAGACTGTCTTGTGCCGCCTCCGGCTTCACCTTCTCCGGGTACTGATGTCCTGGGTGCGACAGGCT CCTGGCAAGGGCCTGGAATGGGTGTCCGAGATCAACCCCGACTCCTCCACCATCCAGTACAACCCCAGCCTGAAGGCCCGGGTTCACCATCTCTCGGGACAACTCCAAGAACACCCTGTAC CTGCAGATGAACTCCCTGCGGGCTGAGGACACCGCCGTGTACTACTGTGCCGGGCCCCTATTGGGGCCAGGGCACCCTGTGACCGTGTCCTCT | 102 |

FIG. 5C Cont.

Anti-CLDN Humanized Antibody Variable Region Nucleic Acid Sequences

| Name | Chain | Nucleic Acid Sequence | SEQ ID NO |
|---|---|---|---|
| hSC27.204v11 | Heavy Chain | GAAGTGCAGCTGCTGGAATCTGGCGGCGGACTGGTGCAGCCTGGCGGATCTCTGAGACTGTCTTGTGCCGCCTCCGGCTTCACCTTCTCCCGGTACTGATGTCCTGGGTGCGACAGGCT CCTGGCAAGGGCCTGGAATGGGTGTCCGAGATCAACCCCGACTCCTCCACCATCAACTACAACCCCAGCCTGAAGGCCCGGTTCACCATCTCTCGGGACAACTCCAAGAACACCCTGTAC CTGCAGATGAACTCCCTGCGGGCCGAGGACACCGCCGTGTACTACTGTGCCGGCGCCCTGCTTATTGGGGCCCAGGGCACCCTGACCGTGTCCTCT | 104 |
| hSC27.204v12 | Heavy Chain | GAAGTGCAGCTGCTGGAATCTGGCGGCGGACTGGTGCAGCCTGGCGGATCTCTGAGACTGTCTTGTGCCGCCTCCGGCTTCGACTTCTCCCGGTACTGATGTCCTGGGTGCGACAGGCT CCTGGCAAGGGCCTGGAATGGGTGTCCGAGATCAACCCCGACTCCTCCACCATCAACTACAACCCCAGCCTGAAGGCCCGGTTCACCATCTCTCGGGACAACTCCAAGAACACCCTGTAC CTGCAGATGAACTCCCTGCGGGCCGAGGACACCGCCGTGTACTACTGTGCCGGCGCCCTGCTTATTGGGGCCCAGGGCACCCTGACCGTGTCCTCT | 106 |
| hSC27.204v13 | Heavy Chain | GAAGTGCAGCTGCTGGAATCTGGCGGCGGACTGGTGCAGCCTGGCGGATCTCTGAGACTGTCTTGTGCCGCCTCCGGCTTCGACTTCTCCCGGTACTGATGTCCTGGGTGCGACAGGCT CCTGGCAAGGGCCTGGAATGGGTGTCCGAGATCAACCCCGACTCCTCCACCATCAAGTACAACCCCAGCCTGAAGGCCCGGTTCACCATCTCTCGGGACAACTCCAAGAACACCCTGTAC CTGCAGATGAACTCCCTGCGGGCCGAGGACACCGCCGTGTACTACTGTGCCGGCGCCCTGCTTATTGGGGCCCAGGGCACCCTGACCGTGTCCTCT | 108 |
| hSC27.204v14 | Heavy Chain | GAAGTGCAGCTGCTGGAATCTGGCGGCGGACTGGTGCAGCCTGGCGGATCTCTGAGACTGTCTTGTGCCGCCTCCGGCTTCGACTTCTCCCGGTACTGATGTCCTGGGTGCGACAGGCT CCTGGCAAGGGCCTGGAATGGGTGTCCGAGATCAACCCCGACTACCTCCACCATCAAGTACAACCCCAGCCTGAAGGCCCGGTTCACCATCTCTCGGGACAACTCCAAGAACACCCTGTAC CTGCAGATGAACTCCCTGCGGGCCGAGGACACCGCCGTGTACTACTGTGCCGGCGCCCTGCTTATTGGGGCCCAGGGCACCCTGACCGTGTCCTCT | 110 |
| hSC27.204v15 | Heavy Chain | GAAGTGCAGCTGCTGGAATCTGGCGGCGGACTGGTGCAGCCTGGCGGATCTCTGAGACTGTCTTGTGCCGCCTCCGACTTCTCCCGGTACTGATGTCCTGGGTGCGACAGGCT CCTGGCAAGGGCCTGGAATGGGTGTCCGAGATCAACCCCGACTACCTCCACCATCAAGTACAACCCCAGCCTGAAGGCCCGGTTCACCATCTCTCGGGACAACTCCAAGAACACCCTGTAC CTGCAGATGAACTCCCTGCGGGCCGAGGACACCGCCGTGTACTACTGTGACTTCTCCGGTACTTCTCGGGACTTCTCCGGTACTGATGTCCGGGACAACTCCAAGAACACCCTGTAC | 112 |

FIG. 5C Cont.

Anti-CLDN Humanized Antibody Full Length Amino Acid Sequences

| Name | Chain | Full Sequence | SEQ ID NO |
|---|---|---|---|
| hSC27.1 | Light Chain | DIQMTQSPSSVSASVGDRVTITCKASEDIYNRLAWYQQKPGKAPKLLIYGATSLETGVPSRFSGSGSGTDYTLTISSLQPEDFATYYCQQYWSTPLTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 114 |
| hSC27.1 | Heavy Chain | QVQLVQSGAEVKKPGASVKVSCKASGYTFTEYTLHWVRQAPGQRLEWMGGINPNNGDTIYNQKFKGRVTITRDTSASTAYMELSSLRSEDTAVYYCARRAITVYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 115 |
| hSC27.22 | Light Chain | DIVMTQSPDSLAVSLGERATINCRASQTVSTSSYSYMHWYQQKPGQPPKLLIYFASNVESGVPDRFSGSGSGTDFTLTISSLQAEDVAVYYCQHSWEIPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 116 |
| hSC27.22 | Heavy Chain | QVQLVQSGAEVKKPGASVKVSCKASGYTFTSYWMNWRQAPGQRLEWMGMIHPSDSEIRLNQKFKDRVTITRDTSASTAYMELSSLRSEDTAVYYCARIDSYYGYLFYDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 117 |
| hSC27.108 | Light Chain | EIVLTQSPATLSLSPGERATLSCSVSSSISSSNLHWYQQKPGQAPRLLIYGTSNLASGIPARFSGSGSGTDFTLTISSLEPEDFAVYYCQQWSSYPHTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 118 |
| hSC27.108 | Heavy Chain | QVQLVQSGAEVKKPGASVKVSCKASGYTFTNYLIEWVRQAPGQGLEWMGLINPGSGGTNYNEKFKGRVTMTTDTSTSTAYMELRSLRSDDTAVYYCARRSPLGSWIYYAYDGVAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 119 |
| hSC27.204 | Light Chain | DIQMTQSPSSLSASVGDRVTITCKAGQNVGTSVAWFQQKPGKAPKSLIYSASYRYSGVPSRFSGSGSGTDFTLTISSLQPEDFATYYCQQYITYPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 120 |
| hSC27.204 | Heavy Chain | EVQLLESGGGLVQPGGSLRLSCAASGFTFSRYWMSWVRQAPGKGLEWVSEINPDSSTINYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 121 |

FIG. 5D

Anti-CLDN Humanized Antibody Full Length Amino Acid Sequences

| Name | Chain | Full Sequence | SEQ ID NO |
|---|---|---|---|
| hSC27.22ss1 | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 122 |
| hSC27.22 - VH1 - 8 | Heavy Chain | QVQLVQSGAEVKKPGASVKVSCKASGYTFTSYWMNWVRQATGQGLEWMGMIHPSDSEIRLNQKFKDRVTMTRNTSISTAYMELSSLRSEDTAVYYCARIDSYYGYLFYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 123 |
| hSC27.22 - VH1 - 46 | Heavy Chain | QVQLVQSGAEVKKPGASVKVSCKASGYTFTSYWMNWVRQAPGQGLEWMGMIHPSDSEIRLNQKFKDRVTMTRDTSTSTVYMELSSLRSEDTAVYYCARIDSYYGYLFYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 124 |
| hSC27.22 - VH1 - 69 | Heavy Chain | QVQLVQSGAEVKKPGSSVKVSCKASGGTFSSYWMNWVRQAPGQGLEWMGMIHPSDSEIRLNQKFKDRVTITADESTSTAYMELSSLRSEDTAVYYCARIDSYYGYLFYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 125 |
| hSC27.22 IgG2 | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG | 126 |

FIG. 5D Cont.

Anti-CLDN Humanized Antibody Full Length Amino Acid Sequences

| Name | Chain | Full Sequence | SEQ ID NO |
|---|---|---|---|
| hSC27.22 IgG4 R409K | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQ EGNVFSCSVMHEALHNHYTQKSLSLSLG | 127 |
| hSC27.22 IgG4 S228P | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQ EGNVFSCSVMHEALHNHYTQKSLSLSLG | 128 |
| hSC27.22 IgG4 S228P R409K | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQ EGNVFSCSVMHEALHNHYTQKSLSLSLG | 129 |
| hSC27.22 IgG4 K370E | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPENNYKTTPPVLDSDGSFFLYSRLTVDKSRWQ EGNVFSCSVMHEALHNHYTQKSLSLSLG | 130 |
| hSC27.22 IgG4 S228P K370E | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPENNYKTTPPVLDSDGSFFLYSRLTVDKSRWQ EGNVFSCSVMHEALHNHYTQKSLSLSLG | 131 |
| hSC27.22 IgG4 C127S S228P | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYFDYWGQGTTVTVSSASTKGPSVFPLAPSSRST SESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVD VSQEDPEVQFNWY VDGVEVHNAKTKPREEQFNSTYRVVSVLTVLHQDWLNGKEYKCKVSNKGLPSSIEKTISKAKGQPREPQVYTLPPSQEEMTKNQVSLTCLVEGFYPSDIAVEWESNGQPENNYKTTPPVLDSDGSFFLYSRLTVDKSRWQ EGNVFSCSVMHEALHNHYTQKSLSLSLG | 132 |

FIG. 5D Cont.

Anti-CLDN Humanized Antibody Full Length Amino Acid Sequences

| Name | Chain | Full Sequence | SEQ ID NO |
|---|---|---|---|
| hSC27.22 IgG4 C127S K370E | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYDYWGQGTTVTVSSASTKGPSVFPLAPSSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVEGFYPSDIAVEWESNGQPENNYKTTPPVLDSDGSFFLYSRLTVDKSRWQEGNVFSCSVMHEALHNHYTQKSLSLSLG | 133 |
| hSC27.22 IgG4 C127S S228P K370E | Heavy Chain | QVQLVQSGAEVKKPGASVKVSCKASGYTFTSYWMNWVRQAPGQRLEWMGMIHPSDSEIRLNQKFKDRVTITRDTSASTAYMELSSLRSEDTAVYYCARIDSYYGYLFYDYWGQGTTVTVSSASTKGPSVFPLAPSSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVEGFYPSDIAVEWESNGQPENNYKTTPPVLDSDGSFFLYSRLTVDKSRWQEGNVFSCSVMHEALHNHYTQKSLSLSLG | 134 |
| hSC27.108v1 | Light Chain | EIVLTQSPDFQSVTPKEKVTITCSVSSSSSSNLHWYQQKPDQSPKLWIYGTSNLASGVPSRFSGSGSGTDFTLTINSLEAEDAATYYCQQWSSYPHTFGGTGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 135 |
| hSC27.204v1 | Heavy Chain | EVQLLESGGGLVQPGGSLRLSCAASGFTFSRYVMMSWVRQAPGKGLEWVSEINPDSSTIKYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 136 |
| hSC27.204v2 | Heavy Chain | EVQLLESGGGLVQPGGSLRLSCAASGFTFSRYVMMSWVRQAPGKGLEWVSEINPDSSTIQYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 137 |
| hSC27.204v3 | Heavy Chain | EVQLLESGGGLVQPGGSLRLSCAASGFTFSRYVMMSWVRQAPGKGLEWVSEINPDSSTINYNPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 138 |

FIG. 5D Cont.

Anti-CLDN Humanized Antibody Full Length Amino Acid Sequences

| Name | Chain | Full Sequence | SEQ ID NO |
|---|---|---|---|
| hSC27.204v4 | Heavy Chain | EVQLLESGGGLVQPGGSLRLSCAASGFDFSRYWMSWVRQAPGKGLEWVSEINPDSSTINYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 139 |
| hSC27.204v5 | Heavy Chain | EVQLLESGGGLVQPGGSLRLSCAASGFDFSRYWMSWVRQAPGKGLEWVSEINPDSSTIKYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 140 |
| hSC27.204v6 | Heavy Chain | EVQLLESGGGLVQPGGSLRLSCAASGFDFSRYWMSWVRQAPGKGLEWVSEINPDSSTIQYTPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 141 |
| hSC27.204v7 | Heavy Chain | EVQLLESGGGLVQPGGSLRLSCAASGFDFSRYWMSWVRQAPGKGLEWVSEINPDSSTINYNPSLKARFTISRDNSKNTLYLQMNSLRAEDTAVYYCTGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 142 |
| hSC27.204v8 | Heavy Chain | EVQLLESGGGLVQPGGSLRLSCAASGFTFSRYWMSWVRQAPGKGLEWVSEINPDSSTINYTPSLKARFTISRDNSKNTLYLQMNSLRAEDTAVYYCAGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 143 |
| hSC27.204 v9 | Heavy Chain | EVQLLESGGGLVQPGGSLRLSCAASGFTFSRYWMSWVRQAPGKGLEWVSEINPDSSTIKYTPSLKARFTISRDNSKNTLYLQMNSLRAEDTAVYYCAGPAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 144 |

FIG. 5D Cont.

Anti-CLDN Humanized Antibody Full Length Amino Acid Sequences

| Name | Chain | Full Sequence | SEQ ID NO |
|---|---|---|---|
| hSC27.204v10 | Heavy Chain | EVQLLESGGGLVQPGGSLRLSCAASGFTFSRYWMSWVRQAPGKGLEWVSEINPDSSTIQYTPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 145 |
| hSC27.204v11 | Heavy Chain | EVQLLESGGGLVQPGGSLRLSCAASGFTFSRYWMSWVRQAPGKGLEWVSEINPDSSTINYNPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 146 |
| hSC27.204v12 | Heavy Chain | EVQLLESGGGLVQPGGSLRLSCAASGFDFSRYWMSWVRQAPGKGLEWVSEINPDSSTINYTPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 147 |
| hSC27.204v13 | Heavy Chain | EVQLLESGGGLVQPGGSLRLSCAASGFDFSRYWMSWVRQAPGKGLEWVSEINPDSSTIKYTPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 148 |
| hSC27.204v14 | Heavy Chain | EVQLLESGGGLVQPGGSLRLSCAASGFDFSRYWMSWVRQAPGKGLEWVSEINPDSSTINYNPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 149 |
| hSC27.204v15 | Heavy Chain | EVQLLESGGGLVQPGGSLRLSCAASGFDFSRYWMSWVRQAPGKGLEWVSEINPDSSTINYNPSLKARFTISRDNSKNTLYLQMNSLRAEDTAVYYCAGPAYWGQGTLVTVSSASTKGPSVFPLAPSSKSTSGGTAALGCL VKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPG | 150 |

CDRs of hSC27.108 Light and Heavy Chain Variable Regions

FIG. 5G

Anti-CLDN Antibodies Bind HEK-293T Cells Over-expressing
hCLDN6, CLDN4 and CLDN9

| Antibody | CLDN6 (MFI) | CLDN4 (MFI) | CLDN9 (MFI) |
|---|---|---|---|
| SC27.102 | 38709 | 818 | 265 |
| SC27.103 | 99568 | 75 | 12118 |
| SC27.104 | 39175 | 22618 | 7227 |
| SC27.105 | 82961 | 69 | 80 |
| SC27.106 | 55760 | 1987 | 595 |
| SC27.108 | 99745 | 88 | 86 |
| SC27.201 | 29895 | 23145 | 7101 |
| SC27.203 | 47431 | 2977 | 587 |
| SC27.204 | 106271 | 79 | 23048 |
| mIgG2b control | 84 | 73 | 81 |

FIG. 6B

Anti-CLDN Antibodies Kill HEK-293T Cells Over-expressing hCLDN6, hCLDN4 and hCLDN9

| Antibody | CLDN6 (IC$_{50}$) | CLDN4 (IC$_{50}$) | CLDN9 (IC$_{50}$) | HEK-T293T-naïve (IC$_{50}$) |
|---|---|---|---|---|
| SC27.103 | 57.7 | NK | 465.9 | NK |
| SC27.104 | 284.2 | 969.2 | NK | NK |
| SC27.105 | 234.9 | NK | NK | NK |
| SC27.108 | 101.9 | NK | NK | NK |
| SC27.201 | 48.2 | 69.7 | 155.1 | NK |
| SC27.204 | 25.2 | NK | 16.9 | NK |
| mIgG1 control | NK | NK | NK | NK |

IC$_{50}$ units – nM
NK = no killing

FIG. 9B

CLDN6 Protein Expression Determined by
Immunohistochemistry in PDX Tumor Cell Lines

| PDX Line | CLDN6 |
|---|---|
| LU123p1 | - |
| LU134p4 | ++, 90% |
| LU134p1 | +/++, 80% |
| LU135p3 | ++, 90% |
| LU123p2 | - |
| LU141p2 | - |
| BR36p3 | ++, 90% |
| BR36p4 | ++, 90% |
| OV25p3 | ++, 70% |
| OV25p4 | ++, 70% |
| OV39p2 | ++, 70% |
| OV39p6 | ++, 80% |
| OV46p3 | ++, 90% |
| OV46p4 | ++, 90% |
| OV79p1 | ++, 20% |
| OV79p3 | ++, 30% |
| OV27p2 | +/++, 10% |
| OV27p3MET | ++, 60% |
| OV27p6MET | ++, 30% |
| OV44p1 | +/++, 90% |
| OV54p1 | +, 1% |
| OV72p3MET | ++, 60% |
| OV78p3 | ++, 90% |
| OV87p2MET | ++/+++, 90% |
| OV89p3 | ++/+++, 20% |

FIG. 10A

ANTI-CLAUDIN ANTIBODIES AND METHODS OF USE

CROSS REFERENCED APPLICATIONS

This application claims the benefit of U.S. Provisional Application No. 61/900,916 filed on Nov. 6, 2013, which is incorporated herein by reference in its entirety.

SEQUENCE LISTING

This application contains a sequence listing which has been submitted in ASCII format via EFS-Web and is hereby incorporated by reference in its entirety. Said ASCII copy, created on May 31, 2017, is named SUBS_SEQL.txt and is 227,601 bytes in size.

FIELD OF THE INVENTION

This application generally relates to novel anti-CLDN antibodies or immunoreactive fragments thereof and compositions, including antibody drug conjugates, comprising the same for the treatment, diagnosis or prophylaxis of cancer and any recurrence or metastasis thereof. Selected embodiments of the invention provide for the use of such anti-CLDN antibodies or antibody drug conjugates for the treatment of cancer comprising a reduction in tumorigenic cell frequency.

BACKGROUND OF THE INVENTION

Differentiation and proliferation of stem cells and progenitor cells are normal ongoing processes that act in concert to support tissue growth during organogenesis, cell repair and cell replacement. The system is tightly regulated to ensure that only appropriate signals are generated based on the needs of the organism. Cell proliferation and differentiation normally occur only as necessary for the replacement of damaged or dying cells or for growth. However, disruption of these processes can be triggered by many factors including the under- or overabundance of various signaling chemicals, the presence of altered microenvironments, genetic mutations or a combination thereof. Disruption of normal cellular proliferation and/or differentiation can lead to various disorders including proliferative diseases such as cancer.

Conventional therapeutic treatments for cancer include chemotherapy, radiotherapy and immunotherapy. Often these treatments are ineffective and surgical resection may not provide a viable clinical alternative. Limitations in the current standard of care are particularly evident in those cases where patients undergo first line treatments and subsequently relapse. In such cases refractory tumors, often aggressive and incurable, frequently arise. The overall survival rates for many solid tumors have remained largely unchanged over the years due, at least in part, to the failure of existing therapies to prevent relapse, tumor recurrence and metastasis. There remains therefore a great need to develop more targeted and potent therapies for proliferative disorders. The current invention addresses this need.

SUMMARY OF THE INVENTION

The invention is broadly directed to antibodies and antibody drug conjugates (ADC) that bind to at least one member of the claudin (CLDN) family of proteins.

In selected embodiments the invention comprises an antibody that binds to cancer stem cells expressing at least one protein of the CLDN family. In another embodiment the antibodies of the invention bind specifically to CLND6 or specifically to CLDN6 and CLDN9. In another embodiment, the antibodies of the invention bind to CLDN6 and CLDN9 with substantially the same apparent binding affinity. Any of the anti-CLDN antibodies of the invention may be internalizing antibodies.

In one embodiment the antibody of the invention binds to at least one member of the CLDN family and competes for binding with an antibody comprising: a light chain variable region (VL) of SEQ ID NO: 21 and a heavy chain variable region (VH) of SEQ ID NO: 23; or a VL of SEQ ID NO: 25 and a VH of SEQ ID NO: 27; or a VL of SEQ ID NO: 29 and a VH of SEQ ID NO: 31; or a VL of SEQ ID NO: 33 and a VH of SEQ ID NO: 35; or a VL of SEQ ID NO: 37 and a VH of SEQ ID NO: 39; or a VL of SEQ ID NO: 41 and a VH of SEQ ID NO: 43; or a VL of SEQ ID NO: 45 and a VH of SEQ ID NO: 47; or a VL of SEQ ID NO: 49 and a VH of SEQ ID NO: 51; or a VL of SEQ ID NO: 53 and a VH of SEQ ID NO: 55; or a VL of SEQ ID NO: 57 and a VH of SEQ ID NO: 59.

In another embodiment the antibody of the invention binds specifically to CLND6; or binds specifically to CLDN6 and CLDN9 and competes for binding with an antibody comprising: a light chain variable region (VL) of SEQ ID NO: 21 and a heavy chain variable region (VH) of SEQ ID NO: 23; or a VL of SEQ ID NO: 25 and a VH of SEQ ID NO: 27; or a VL of SEQ ID NO: 29 and a VH of SEQ ID NO: 31; or a VL of SEQ ID NO: 33 and a VH of SEQ ID NO: 35; or a VL of SEQ ID NO: 37 and a VH of SEQ ID NO: 39; or a VL of SEQ ID NO: 41 and a VH of SEQ ID NO: 43; or a VL of SEQ ID NO: 45 and a VH of SEQ ID NO: 47; or a VL of SEQ ID NO: 49 and a VH of SEQ ID NO: 51; or a VL of SEQ ID NO: 53 and a VH of SEQ ID NO: 55; or a VL of SEQ ID NO: 57 and a VH of SEQ ID NO: 59.

Any of the anti-CLDN antibodies disclosed herein may be a chimeric, CDR grafted, humanized or recombinant antibody, or a fragment thereof.

In a particular embodiment the invention comprises a humanized antibody that binds to at least one protein of the CLDN family and competes for binding with an antibody comprising three variable light chain CDRs (CDRL) as set forth in SEQ ID NO: 61; and three variable heavy chain CDRs (CDRH) as set forth in SEQ ID NO: 63; or three CDRL as set forth in SEQ ID NO: 65 and three CDRH as set forth in SEQ ID NO: 67; or three CDRL as set forth in SEQ ID NO: 69 and three CDRH as set forth in SEQ ID NO: 71; three CDRL as set forth in SEQ ID NO: 73 and three CDRH as set forth in SEQ ID NO: 75.

In a further embodiment the invention comprises a humanized antibody that binds to at least one protein of the CLDN family and competes for binding with an antibody comprising a VH and VL, wherein the VL has three CDRL comprising a CDRL1 of SEQ ID NO: 151, a CDRL2 of SEQ ID NO: 152 and a CDRL3 of SEQ ID NO: 153; or a VL having three CDRLs comprising a CDRL1 of SEQ ID NO: 157, a CDRL2 of SEQ ID NO: 158 and a CDRL3 of SEQ ID NO: 159; or a VL having three CDRLs comprising a CDRL1 of SEQ ID NO: 163, a CDRL2 of SEQ ID NO: 164 and a CDRL3 of SEQ ID NO: 165; or a VL having three CDRLs comprising a CDRL1 of SEQ ID NO: 169, a CDRL2 of SEQ ID NO: 170 and a CDRL3 of SEQ ID NO: 171.

In a further embodiment the invention comprises a humanized antibody that binds to at least one protein of the CLDN family and competes for binding with an antibody comprising a VL and a VH, wherein the VH has three CDRs (CDRH) comprising a CDRH1 of SEQ ID NO: 154, a CDRH2 of SEQ ID NO: 155 and a CDRH3 of SEQ ID NO: 156; or the VH has three CDRHs comprising a CDRH1 of SEQ ID NO: 160, a CDRH2 of SEQ ID NO: 161 and a CDRH3 of SEQ ID NO: 162; or the VH has three CDRHs comprising a CDRH1 of SEQ ID NO: 166, a CDRH2 of SEQ ID NO: 167 and a CDRH3 of SEQ ID NO: 168; or the VH has three CDRHs comprising a CDRH1 of SEQ ID NO: 172, a CDRH2 of SEQ ID NO: 173 and a CDRH3 of SEQ ID NO: 174.

In a further embodiment the invention comprises a humanized antibody that binds to at least one protein of the CLDN family and competes for binding with an antibody comprising a VL and VH wherein the VL has three CDRLs comprising a CDRL1 of SEQ ID NO: 151, a CDRL2 of SEQ ID NO: 152 and a CDRL3 of SEQ ID NO: 153 and the VH has three CDRHs comprising a CDRH1 of SEQ ID NO: 154, a CDRH2 of SEQ ID NO: 155 and a CDRH3 of SEQ ID NO: 156; or an antibody comprising a VL and VH wherein the VL has three CDRLs comprising a CDRL1 of SEQ ID NO: 157, a CDRL2 of SEQ ID NO: 158 and a CDRL3 of SEQ ID NO: 159 and the VH has three CDRHs comprising a CDRH1 of SEQ ID NO: 160, a CDRH2 of SEQ ID NO: 161 and a CDRH3 of SEQ ID NO: 162; or an antibody comprising a VL and VH wherein the VL has three CDRLs comprising a CDRL1 of SEQ ID NO: 163, a CDRL2 of SEQ ID NO: 164 and a CDRL3 of SEQ ID NO: 165 and the VH has three CDRHs comprising a CDRH1 of SEQ ID NO: 166, a CDRH2 of SEQ ID NO: 167 and a CDRH3 of SEQ ID NO: 168; or an antibody comprising a VL and VH wherein the VL has three CDRLs comprising a CDRL1 of SEQ ID NO: 169, a CDRL2 of SEQ ID NO: 170 and a CDRL3 of SEQ ID NO: 171 and the VH has three CDRHs comprising a CDRH1 of SEQ ID NO: 172, a CDRH2 of SEQ ID NO: 173 and a CDRH3 of SEQ ID NO: 174.

In one embodiment the invention comprises a humanized antibody that binds to at least one protein of the CLDN family comprising a full length light chain set forth as SEQ ID NO: 114 and a full length heavy chain set forth as SEQ ID NO: 115; or a full length light chain set forth as SEQ ID NO: 116 and a full length heavy chain set forth as SEQ ID NO: 117; or a full length light chain set forth as SEQ ID NO: 118 and a full length heavy chain set forth as SEQ ID NO: 119; or a full length light chain set forth as SEQ ID NO: 120 and a full length heavy chain set forth as SEQ ID NO: 121.

In one embodiment the invention comprises an antibody drug conjugate (ADC) comprising any anti-CLDN antibody disclosed herein, wherein the antibody is conjugated to a payload. In another embodiment the invention comprises a pharmaceutical composition comprising an ADC, wherein the ADC comprises an anti-CLDN antibody of the invention conjugated to a payload.

In another embodiment the invention comprises a nucleic acid encoding the antibody of any of the anti-CLDN antibodies disclosed herein. In a related embodiment, the invention comprises a vector comprising one or more of the nucleic acids encoding an anti-CLDN antibody disclosed herein or a host cell comprising said vector.

In a preferred embodiment, the invention comprises an antibody drug conjugate (ADC) comprising a chimeric, CDR grafted, humanized or recombinant human antibody, or a fragment thereof, which binds to cancer stem cells expressing at least one protein of the CLDN family, wherein the antibody is conjugated to a cytotoxic agent.

In another embodiment the invention comprises an ADC of the formula Ab-[L-D]n, wherein Ab is any one of the anti-CLDN antibodies disclosed herein; L is an optional linker; D is a drug; and n is an integer from about 1 to about 20.

In one embodiment the invention comprises a method of treating cancer comprising administering to a subject in need thereof a pharmaceutical composition comprising an ADC, wherein the ADC comprises an anti-CLDN antibody of the invention conjugated to a payload.

In some embodiments the invention comprises a method of treating cancer comprising administering to a subject in need thereof a pharmaceutical composition comprising an anti-CLDN ADC, wherein the cancer is selected from ovarian cancer, lung cancer, e.g. lung adenocarcinoma, breast cancer and pancreatic cancer.

In one embodiment the invention comprises a method of treating cancer comprising administering to a subject in need thereof a pharmaceutical composition comprising an anti-CLDN ADC and at least one additional therapeutic moiety.

In one embodiment the invention comprises a method of reducing cancer stem cells in a tumor cell population, wherein the method comprises contacting a tumor cell population comprising cancer stem cells and tumor cells other than cancer stem cells with an anti-CLDN ADC; whereby the frequency of cancer stem cells is reduced, for example, such contacting can be performed in vivo or in vitro.

In one embodiment the invention comprises a method of delivering a cytotoxin to a cell comprising contacting the cell with an ADC comprising any anti-CLDN antibody disclosed herein.

BRIEF DESCRIPTION OF THE FIGURES

FIG. 4C shows a tabular representation of the percent identity of amino acid residues in the ECD1 and ECD2 loops amongst the 16 proteins comprising the set of human, rat, mouse and cynomolgus monkey orthologs of CLDN4, CLDN6 and CLDN9;

FIGS. 5A-5H provide amino acid and nucleic acid sequences of mouse and humanized anti-CLDN antibodies. FIGS. 5A and 5B show light chain (FIG. 5A) and heavy chain (FIG. 5B) variable region amino acid sequences of exemplary mouse and humanized anti-CLDN antibodies (SEQ ID NOS: 21-75, odd numbers) and variants of hSC27.22, hSC27.108 and hSC27.204. FIG. 5C shows the nucleic acid sequences of the same light and heavy chain variable regions of such exemplary mouse and humanized anti-CLDN antibodies (SEQ ID NOS: 20-74, even numbers) and variants of hSC27.22, hSC27.108 and hSC27.204. FIG. 5D shows the amino acid sequences of the full length light and heavy chains of humanized antibodies hSC27.1 and hSC27.22, thirteen variants of hSC27.22, one variant of hSC27.108 and fifteen variants of hSC27.204. FIGS. 5E-5H show annotated amino acid sequences (numbered as per Kabat et al.) of the light and heavy chain variable regions of the humanized anti-CLDN antibodies, hSC27.1 (FIG. 5E), hSC27.22 (FIG. 5F), hSC27.108 (FIG. 5G), and hSC27.204 (FIG. 5H), wherein the CDRs are derived using Kabat, Chothia, ABM and Contact methodology;

FIG. 6B shows the ability of anti-CLDN antibodies to bind HEK-293T cells overexpressing CLDN4, CLDN6 and CLDN9 as detected by flow cytometry, where the results are shown as mean fluorescence intensity (MFI) for each antibody binding to each cell line;

FIGS. 9A and 9B show that anti-CLDN antibodies SC27.1 and SC27.22 are able to internalize into cells overexpressing human CLDN4, CLDN6 and CLDN9 and mediate the delivery of saporin cytotoxin;

FIG. 10A shows expression of CLND6 in various PDX lung, breast and ovarian tumor cells using immunohistochemistry.

DETAILED DESCRIPTION OF THE INVENTION

Figure 1:
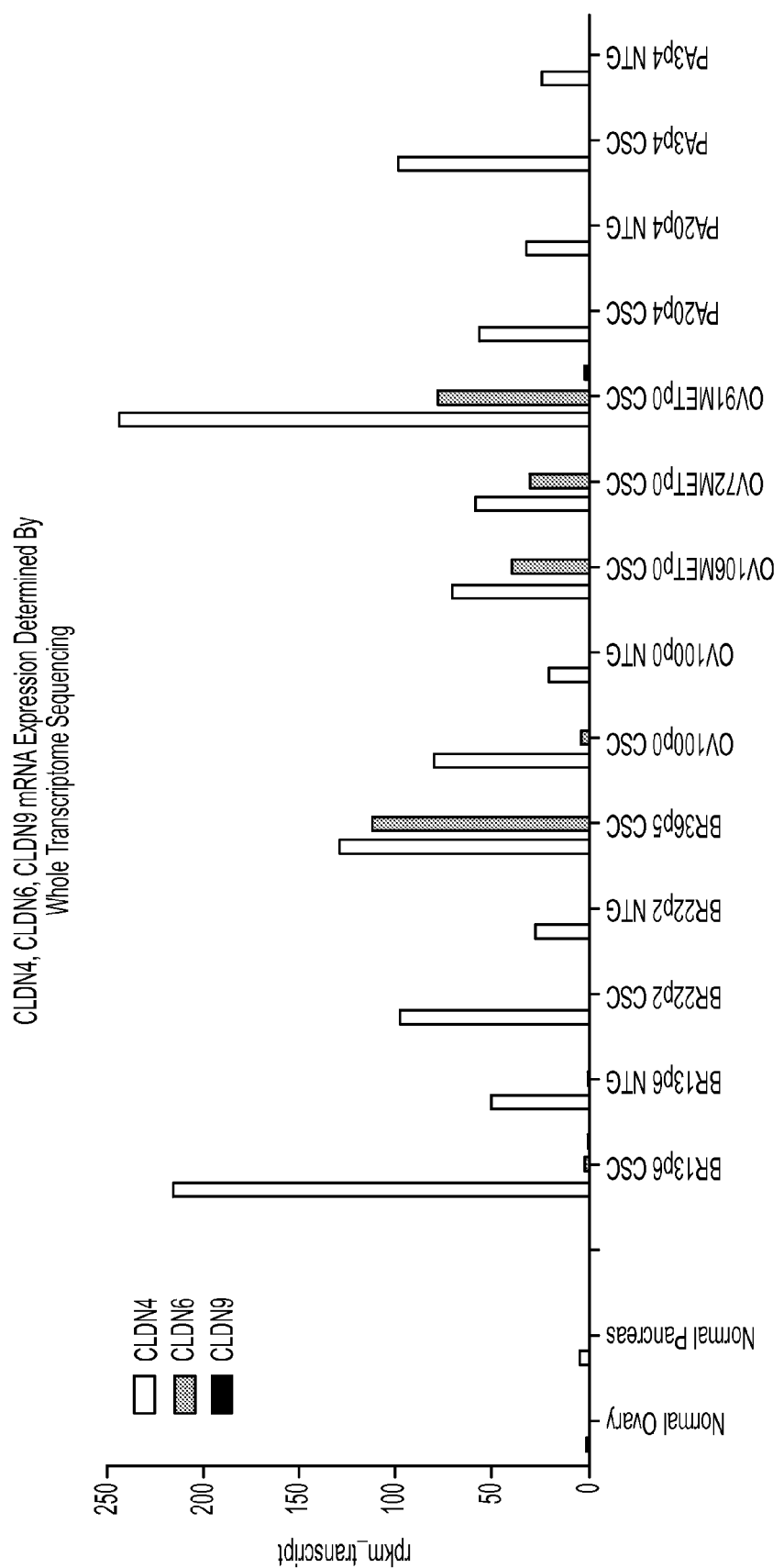
FIG. 1 shows the relative mRNA expression levels of CDLN4, CLDN6, and CLDN9 determined by whole transcriptome (SOLiD) sequencing in selected patient-derived xenograft (PDX) tumors. Tumor types are denoted according the abbreviations listed in Table 4.

The invention may be embodied in many different forms. Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

CLDN has surprisingly been found to be a biological marker of a number of tumor types and this association may be exploited for the treatment of such tumors. It has also unexpectedly been found that CLDN is associated with tumorigenic cells and may be effectively exploited to inhibit or eliminate them. Tumorigenic cells, which will be described in more detail below, are known to exhibit resistance to many conventional treatments. In contrast to the teachings of the prior art, the disclosed compounds and methods effectively overcome this inherent resistance.

The invention provides anti-CLDN antibodies (including antibody drug conjugates) and their use in the prognosis, diagnosis, theragnosis, treatment and/or prevention of a variety of CLDN-associated cancers regardless of any particular mechanism of action or specifically targeted cellular or molecular component.

I CLAUDIN (CLDN) PHYSIOLOGY

Claudins are integral membrane proteins comprising a major structural protein of tight junctions, the most apical cell-cell adhesion junction in polarized cell types such as those found in epithelial or endothelial cell sheets. Tight junctions are composed of strands of networked proteins that form continuous seals around cells to provide a physical but modulatable barrier to the transport of solutes and water in the paracellular space. The claudin family of proteins in humans is comprised of at least 23 members, ranging in size from 22-34 kDa. All claudins possess a tetraspanin topology in which both protein termini are located on the intracellular face of the membrane, resulting in the formation of two extracellular (EC) loops, EC1 and EC2. The EC loops mediate head-to-head homophilic, and for certain combinations of claudins, heterophilic interactions that lead to formation of tight junctions. The specific claudin-claudin interactions and claudin EC sequences are a key determinant of ion selectivity and tight junction strength (for example, see Nakano et al., 2009, PMID: 19696885). Typically, EC1 is about 50-60 amino acids in size, contains a conserved disulfide bond within a larger W—X(17-22)-W—X(2)-C—X(8-10)-C motif, and numerous charged residues that participate in ion channel formation (Turksen and Troy, 2004, PMID: 15159449). EC2 is smaller than EC1, being approximately 25 amino acids. Due to its helix-turn-helix conformation, it has been suggested that EC2 contributes to dimer or multimer formation of claudins on opposing cell membranes, although mutations in both loops may perturb complex formation. Claudin-claudin complexes in vitro may range in size from dimers to hexamers, depending upon the specific claudins involved (Krause et al., 2008, PMID: 18036336). Individual claudins show a range of tissue specific expression patterns, as well as developmentally regulated expression as determined by PCR analyses (Krause et al., 2008, PMID: 18036336; Turksen, 2011, PMID: 21526417).

Figure 4A:
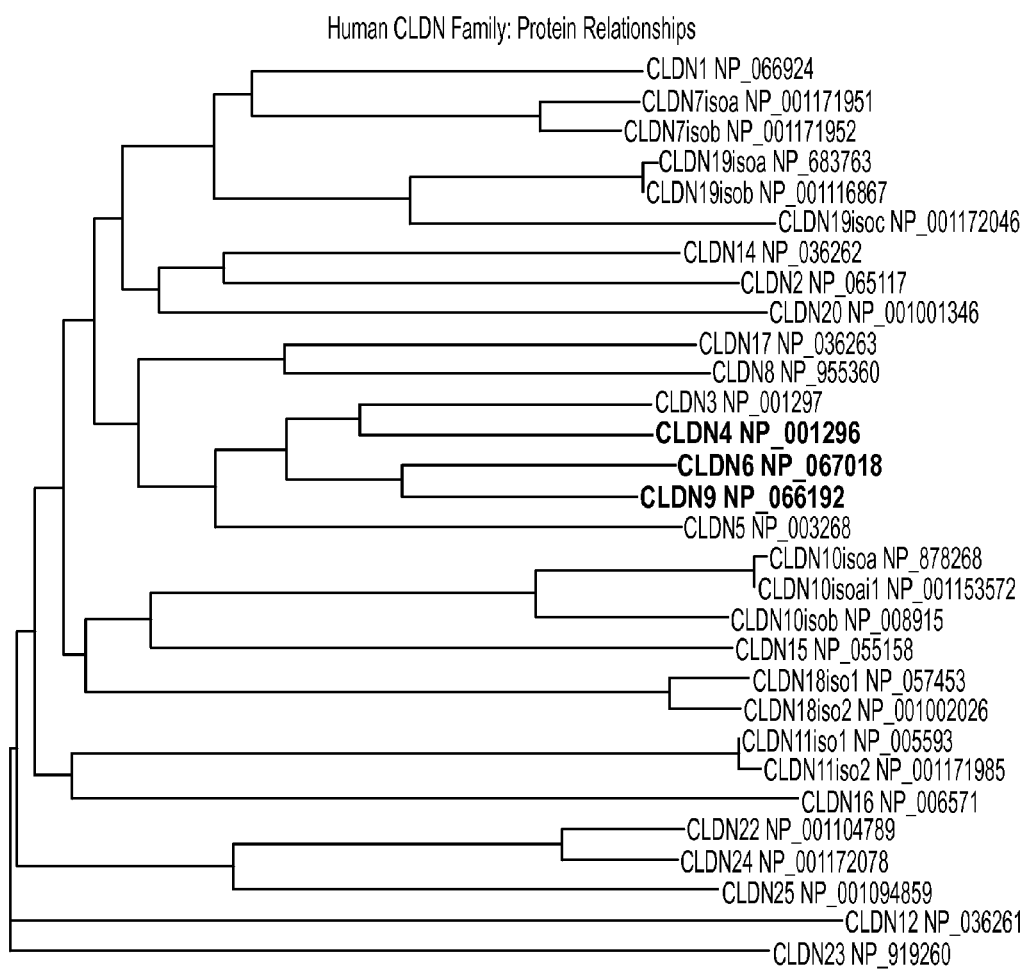
FIG. 4A is a dendrogram showing the relative degree of similarity between the 30 CLDN proteins encoded by the 23 human CLDN genes.

Sequence analysis can be used to construct phylogenetic trees for the claudin family members, indicating the relationship and degrees of relatedness of the protein sequences (FIG. 4A). For instance, it can be seen that the CLDN6 and CLDN9 proteins are closely related which, given the adjacent head-to-head location of their genes at the chromosomal location 16p3.3, is suggestive of an ancestral gene duplication. These similarities likely translate to an ability of these family members to interact heterotypically. Similarly, the CLDN3 and CLDN4 proteins are closely related by sequence analysis, and their genes can be found in tandem at the chromosomal location 7r11.23. High homology in the EC1 or EC2 loops between certain family members (e.g. FIG. 4B) provides opportunity to develop antibodies that are multi-reactive with various claudin family members.

CLDN6, also known as skullin, is a developmentally regulated claudin. Representative CLDN6 protein orthologs include, but are not limited to, human (NP_067018), chimpanzee (XP_523276), rhesus monkey (NP_001180762), mouse (NP_061247), and rat (NP_001095834). In humans, the CLDN6 gene consists of 2 exons spanning approximately 3.5 kBp at the chromosomal location 16p13.3. Transcription of the CLDN6 locus yields a mature 1.4 kB mRNA transcript (NM_021195), encoding a 219 amino acid protein (NP_061247). CLDN6 is expressed in ES cell derivatives committed to an epithelial fate (Turksen and Troy, 2001, PMID: 11668606), in the periderm (Morita et al., 2002, PMID: 12060405), and in the suprabasal level of the epidermis (Turkson and Troy, 2002, PMID: 11923212). It is also expressed in developing mouse kidney (Abuazza et al., 2006, PMID: 16774906), although expression is not detected in adult kidney (Reyes et al., 2002, PMID: 12110008). CLDN6 is also a coreceptor for hepatitis C virus, along with CLDN1 and CLDN9 (Zheng et al., 2007, PMID: 17804490).

CLDN9 is the most closely related family member to CLDN6. Representative CLDN9 protein orthologs include, but are not limited to, human (NP_066192), chimpanzee (XP_003314989), rhesus monkey (NP_001180758), mouse (NP_064689), and rat (NP_001011889). In humans, the CLDN9 gene consists of a single exon spanning approximately 2.1 kBp at the chromosomal locus 16p13.3. Transcription of the intronless CLDN9 locus yields a 2.1 kB mRNA transcript (NM_020982), encoding a 217 amino acid protein (NP_0066192). CLDN9 is expressed in various structures of the inner ear (Kitarjiri et al., 2004, PMID: 14698084; Nankano et al., 2009, PMID: 19696885), the cornea (Ban et al., 2003, PMID: 12742348), the liver (Zheng et al., 2007, PMID: 17804490) and developing kidney (Abuazza et al., 2006, PMID: 16774906). Consistent with its expression in the cochlea, animals expressing a CLDN9 protein with a missense mutation show defects in hearing likely due to altered paracellular $K^+$ permeability with consequent perturbation of ion currents critical for depolarization of hair cells involved in sound detection. Expression of CLDN9 in cells of the inner ear is specifically localized to a subdomain underneath more apical tight-junction strands formed by other claudins, indicating that not all claudins in normal tissues are found in the most apical and accessible tight junctions (Nankano et al., 2009, PMID: 19696885). In contrast to the results in the cochlea, mice expressing missense CLDN9 showed no signs of hepatic or renal defects (Nankano et al., 2009, PMID: 19696885).

CLDN4 is also known as the *Clostridium perfringens* enterotoxin receptor, due to its high affinity binding of this toxin responsible for food poisoning and other gastrointestinal illnesses. Representative CLDN4 protein orthologs include, but are not limited to, human (NP_001296), chimpanzee (XP_519142), rhesus monkey (NP_001181493), mouse (NP_034033), and rat (NP_001012022). In humans, the intronless CLDN4 gene spans approximately 1.82 kBp at the chromosomal location 17q11.23. Transcription of the CLDN4 locus yields a 1.82 kB mRNA transcript (NM_001305), encoding a 209 amino acid protein (NP_001296). Consistent with the ability of CLDN4 to bind a toxin produced by a gastrointestinal pathogen, CDLN4 expression can be detected throughout the GI tract as well as in prostate, bladder, breast, and lung (Rahner et al., 2001, PMID: 11159882; Tamagawa et al., 2003, PMID: 12861044; Wang et al., 2003, PMID: 12600828; Nichols et al., 2004, PMID: 14983936).

Although claudins are important in the function and homeostasis of normal tissues, tumor cells frequently exhibit abnormal tight junction function. This may be linked to disregulated expression and/or localization of claudins as a consequence of the dedifferentiation of tumor cells, or the requirement of rapidly growing cancerous tissues to efficiently absorb nutrients within a tumor mass with abnormal vascularization (Morin, 2005, PMID: 16266975). Individual claudin family members may be up-regulated in certain cancer types, yet down-regulated in others. For example, CLDN3 and CLDN4 expression is elevated in certain pancreatic, breast and ovarian cancers, yet may be lower in other breast (e.g., "claudin-low") carcinomas. Claudin proteins may be particularly good targets for antibody drug conjugates (ADCs) since it is known that claudins undergo endocytosis, turnover time of some claudins is short relative to other membrane proteins (Van Raffle et al., 2004, PMID: 15366421), claudin expression is disregulated in cancer cells and tight junctions structures among tumor cells are disrupted in cancer cells. These properties may afford more opportunities for antibodies to bind claudin proteins in neoplastic but not in normal tissues. Although antibodies specific to individual claudins may be useful, it is also possible that polyreactive claudin antibodies would be more likely to facilitate the delivery of payloads to a broader patient population. Specifically, polyreactive claudin antibodies may permit more efficient targeting of cells expressing multiple claudin proteins due to higher aggregate antigen density, reduce the likelihood of escape of tumor cells with low levels of antigen expression of any individual claudin, and as can be seen in the expression examples below, expand the number of therapeutic indications for a single ADC.

II CANCER STEM CELLS

According to the current models, a tumor comprises non-tumorigenic cells and tumorigenic cells. Non-tumorigenic cells do not have the capacity to self-renew and are incapable of reproducibly forming tumors, even when transplanted into immunocompromised mice in excess cell numbers. Tumorigenic cells, also referred to herein as "tumor initiating cells" (TICs), which make up 0.1-40% of a tumor's cell population, have the ability to form tumors. Tumorigenic cells encompass both tumor perpetuating cells (TPCs), referred to interchangeably as cancer stem cells (CSCs) and tumor progenitor cells (TProgs).

CSCs, like normal stem cells that support cellular hierarchies in normal tissue, are able to self-replicate indefinitely while maintaining the capacity for multilineage differentiation. CSCs are able to generate both tumorigenic progeny and non-tumorigenic progeny and are able to completely recapitulate the heterogeneous cellular composition of the parental tumor as demonstrated by serial isolation and transplantation of low numbers of isolated CSCs into immunocompromised mice.

TProgs, like CSCs have the ability to fuel tumor growth in a primary transplant. However, unlike CSCs, they are not able to recapitulate the cellular heterogeneity of the parental tumor and are less efficient at reinitiating tumorigenesis in subsequent transplants because TProgs are typically only capable of a finite number of cell divisions as demonstrated by serial transplantation of low numbers of highly purified TProg into immunocompromised mice. TProgs may further be divided into early TProgs and late TProgs, which may be distinguished by phenotype (e.g., cell surface markers) and their different capacities to recapitulate tumor cell architecture. While neither can recapitulate a tumor to the same extent as CSCs, early TProgs have a greater capacity to recapitulate the parental tumor's characteristics than late TProgs. Notwithstanding the foregoing distinctions, it has been shown that some TProg populations can, on rare occasion, gain self-renewal capabilities normally attributed to CSCs and can themselves become CSCs.

CSCs exhibit higher tumorigenicity and are relatively more quiescent than: (i) TProgs (both early and late TProgs); and (ii) non-tumorigenic cells such as tumor-infiltrating cells, for example, fibroblasts/stroma, endothelial and hematopoietic cells that may be derived from CSCs and typically comprise the bulk of a tumor. Given that conventional therapies and regimens have, in large part, been designed to debulk tumors and attack rapidly proliferating cells, CSCs are more resistant to conventional therapies and regimens than the faster proliferating TProgs and other bulk tumor cell populations such as non-tumorigenic cells. Other characteristics that may make CSCs relatively chemoresistant to conventional therapies are increased expression of multi-drug resistance transporters, enhanced DNA repair mechanisms and anti-apoptotic gene expression. These properties in CSCs constitute a key reason for the failure of standard oncology treatment regimens to ensure long-term benefit for most patients with advanced stage neoplasia because standard chemotherapy does not target the CSCs that actually fuel continued tumor growth and recurrence.

It has surprisingly been discovered that CLDN expression is associated with various tumorigenic cell subpopulations. The invention provides anti-CLDN antibodies that may be particularly useful for targeting tumorigenic cells and may be used to silence, sensitize, neutralize, reduce the frequency, block, abrogate, interfere with, decrease, hinder, restrain, control, deplete, moderate, mediate, diminish, reprogram, eliminate, or otherwise inhibit (collectively, "inhibit") tumorigenic cells, thereby facilitating the treatment, management and/or prevention of proliferative disorders (e.g. cancer). Advantageously, the novel anti-CLDN antibodies of the invention may be selected so they preferably reduce the frequency or tumorigenicity of tumorigenic cells upon administration to a subject regardless of the form of the CLDN determinant (e.g., phenotypic or genotypic). The reduction in tumorigenic cell frequency may occur as a result of (i) inhibition or eradication of tumorigenic cells; (ii) controlling the growth, expansion or recurrence of tumorigenic cells; (iii) interrupting the initiation, propagation, maintenance, or proliferation of tumorigenic cells; or (iv) by otherwise hindering the survival, regeneration and/or metastasis of the tumorigenic cells. In some embodiments, the inhibition of tumorigenic cells may occur as a result of a change in one or more physiological pathways. The change in the pathway, whether by inhibition of the tumorigenic cells, modification of their potential (for example, by induced differentiation or niche disruption) or otherwise interfering with the ability of tumorigenic cells to influence the tumor environment or other cells, allows for the more effective treatment of CLDN associated disorders by inhibiting tumorigenesis, tumor maintenance and/or metastasis and recurrence.

Methods that can be used to assess the reduction in the frequency of tumorigenic cells, include but are not limited to, cytometric or immunohistochemical analysis, preferably by in vitro or in vivo limiting dilution analysis (Dylla et al. 2008, PMID: PMC2413402 and Hoey et al. 2009, PMID: 19664991).

In vitro limiting dilution analysis may be performed by culturing fractionated or unfractionated tumor cells (e.g. from treated and untreated tumors, respectively) on solid medium that fosters colony formation and counting and characterizing the colonies that grow. Alternatively, the tumor cells can be serially diluted onto plates with wells containing liquid medium and each well can be scored as either positive or negative for colony formation at any time after inoculation but preferably more than 10 days after inoculation.

In vivo limiting dilution is performed by transplanting tumor cells, from either untreated controls or from tumors exposed to selected therapeutic agents, into immunocompromised mice in serial dilutions and subsequently scoring each mouse as either positive or negative for tumor formation. The scoring may occur at any time after the implanted tumors are detectable but is preferably done 60 or more days after the transplant. The analysis of the results of limiting dilution experiments to determine the frequency of tumorigenic cells is preferably done using Poisson distribution statistics or assessing the frequency of predefined definitive events such as the ability to generate tumors in vivo or not (Fazekas et al., 1982, PMID: 7040548).

Flow cytometry and immunohistochemistry may also be used to determine tumorigenic cell frequency. Both techniques employ one or more antibodies or reagents that bind art recognized cell surface proteins or markers known to enrich for tumorigenic cells (see WO 2012/031280). As known in the art, flow cytometry (e.g. florescence activated cell sorting (FACS)) can also be used to characterize, isolate, purify, enrich or sort for various cell populations including tumorigenic cells. Flow cytometry measures tumorigenic cell levels by passing a stream of fluid, in which a mixed population of cells is suspended, through an electronic detection apparatus which is able to measure the physical and/or chemical characteristics of up to thousands of particles per second. Immunohistochemistry provides additional information in that it enables visualization of tumorigenic cells in situ (e.g., in a tissue section) by staining the tissue sample with labeled antibodies or reagents which bind to tumorigenic cell markers.

The antibodies of the invention may be useful for identifying, characterizing, monitoring, isolating, sectioning or enriching populations or subpopulations of tumorigenic cells through methods such as, for example, flow cytometry, magnetic activated cell sorting (MACS), laser mediated sectioning or FACS. FACS is a reliable method used to isolate cell subpopulations at more than 99.5% purity based on specific cell surface markers. Other compatible techniques for the characterization and manipulation of tumorigenic cells including CSCs can be seen, for example, in U.S. Ser. Nos. 12/686,359, 12/669,136 and 12/757,649.

Listed below are markers that have been associated with CSC populations and have been used to isolate or characterize CSCs: ABCA1, ABCA3, ABCG2, ADAM9, ADCY9, ADORA2A, AFP, AXIN1, B7H3, BCL9, Bmi-1, BMP-4, C20orf52, C4.4A, carboxypeptidase M, CAV1, CAV2, CD105, CD133, CD14, CD16, CD166, CD16a, CD16b, CD2, CD20, CD24, CD29, CD3, CD31, CD324, CD325, CD34, CD38, CD44, CD45, CD46, CD49b, CD49f, CD56, CD64, CD74, CD9, CD90, CEACAM6, CELSR1, CPD, CRIM1, CX3CL1, CXCR4, DAF, decorin, easyh1, easyh2, EDG3, eed, EGFR, ENPP1, EPCAM, EPHA1, EPHA2, FLJ10052, FLVCR, FZD1, FZD10, FZD2, FZD3, FZD4, FZD6, FZD7, FZD8, FZD9, GD2, GJA1, GLI1, GLI2, GPNMB, GPR54, GPRC5B, IL1R1, IL1RAP, JAM3, Lgr5, Lgr6, LRP3, LY6E, MCP, mf2, mllt3, MPZL1, MUC1, MUC16, MYC, N33, Nanog, NB84, nestin, NID2, NMA, NPC1, oncostatin M, OCT4, OPN3, PCDH7, PCDHA10, PCDHB2, PPAP2C, PTPN3, PTS, RARRES1, SEMA4B, SLC19A2, SLC1A1, SLC39A1, SLC4A11, SLC6A14, SLC7A8, smarcA3, smarcD3, smarcE1, smarcA5, Sox1, STAT3, STEAP, TCF4, TEM8, TGFBR3, TMEPAI, TMPRSS4, transferrin receptor, TrkA, WNT10B, WNT16, WNT2, WNT2B, WNT3, WNT5A, YY1 and β-catenin. See, for example, Schulenburg et al., 2010, PMID: 20185329, U.S. Pat. No. 7,632,678 and U.S. Ser. Nos. 2007/0292414, 2008/0175870, 2010/0275280, 2010/0162416 and 2011/0020221.

Similarly, non-limiting examples of cell surface phenotypes associated with CSCs of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other CSC surface phenotypes that are known in the art. See, for example, Schulenburg et al., 2010, supra, Visvader et al., 2008, PMID: 18784658 and U.S. Ser. No. 2008/0138313. Of particular interest with respect to the instant invention are CSC preparations comprising $CD46^{hi}CD324^+$ phenotypes. "Positive," "low" and "negative" expression levels as they apply to markers or marker phenotypes are defined as follows. Cells with negative expression (i.e. "−") are herein defined as those cells expressing less than, or equal to, the 95th percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95th percentile of expression observed with an isotype control antibody using the FMO staining procedure described above are herein defined as "positive" (i.e. "+"). As defined herein there are various populations of cells broadly defined as "positive." A cell is defined as positive if the mean observed expression of the antigen is above the 95th percentile determined using FMO staining with an isotype control antibody as described above. The positive cells may be termed cells with low expression (i.e. "lo") if the mean observed expression is above the $95^{th}$ percentile determined by FMO staining and is within one standard deviation of the $95^{th}$ percentile. Alternatively, the positive cells may be termed cells with high expression (i.e. "hi") if the mean observed expression is above the $95^{th}$ percentile determined by FMO staining and greater than one standard deviation above the $95^{th}$ percentile. In other embodiments the 99th percentile may preferably be used as a demarcation point between negative and positive FMO staining and in particularly preferred embodiments the percentile may be greater than 99%.

The $CD46^{hi}CD324^+$ marker phenotype and those exemplified immediately above may be used in conjunction with standard flow cytometric analysis and cell sorting techniques to characterize, isolate, purify or enrich TIC and/or TPC cells or cell populations for further analysis.

The ability of the antibodies of the current invention to reduce the frequency of tumorigenic cells can therefore be determined using the techniques and markers described above. In some instances, the anti-CLDN antibodies may reduce the frequency of tumorigenic cells by 10%, 15%, 20%, 25%, 30% or even by 35%. In other embodiments, the reduction in frequency of tumorigenic cells may be in the order of 40%, 45%, 50%, 55%, 60% or 65%. In certain embodiments, the disclosed compounds my reduce the frequency of tumorigenic cells by 70%, 75%, 80%, 85%, 90% or even 95%. It will be appreciated that any reduction of the frequency of tumorigenic cells is likely to result in a corresponding reduction in the tumorigenicity, persistence, recurrence and aggressiveness of the neoplasia.

III ANTIBODIES

A. Antibody Structure

Antibodies and variants and derivatives thereof, including accepted nomenclature and numbering systems, have been extensively described, for example, in Abbas et al. (2010), *Cellular and Molecular Immunology* ($6^{th}$ Ed.), W.B. Saunders Company; or Murphey et al. (2011), *Janeway's Immunobiology* ($8^{th}$ Ed.), Garland Science.

As used herein an "antibody" or "intact antibody" typically refers to a Y-shaped tetrameric protein comprising two heavy (H) and two light (L) polypeptide chains held together by covalent disulfide bonds and non-covalent interactions. Human light chains are classified as kappa or lambda light chains. Each light chain is composed of one variable domain (VL) and one constant domain (CL). Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')$_2$, F(ab') fragments, single-chain fragments (e.g. ScFv and ScFvFc); and derivatives thereof including Fc fusions and other modifications, and any other immunoreactive molecule so long as it exhibits preferential association or binding with a determinant. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter α, β, ε, γ, and μ, respectively. Light chains of the antibodies from any vertebrate species can be assigned to one of two clearly distinct types, called kappa (κ) and lambda (λ), based on the amino acid sequences of their constant domains.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). $V_H$ and $V_L$ domains comprise three regions of extreme variability, which are termed hypervariable regions, or more commonly, complementarity-determining regions (CDRs), framed and separated by four less variable regions known as framework regions (FRs). The non-covalent association between the $V_H$ and the $V_L$ region forms the Fv fragment (for "fragment variable") which contains one of the two antigen-binding sites of the antibody. ScFv fragments (for single chain fragment variable), which can be obtained by genetic engineering, associates in a single polypeptide chain, the $V_H$ and the $V_L$ region of an antibody, separated by a peptide linker.

As used herein, the assignment of amino acids to each domain, framework region and CDR may be in accordance with one of the numbering schemes provided by Kabat et al. (1991) Sequences of Proteins of Immunological Interest ($5^{th}$ Ed.) US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, $3^{rd}$ Ed., Wily-VCH Verlag GmbH and Co. unless otherwise noted. The amino acid residues which comprise CDRs as defined by Kabat, Chothia and MacCallum (or "Contact") as obtained from the Abysis website database (infra.) are set out below.

TABLE 1

|        | Kabat  | Chothia | MacCallum |
|--------|--------|---------|-----------|
| VH CDR1 | 31-35  | 26-32   | 30-35     |
| VH CDR2 | 50-65  | 52-56   | 47-58     |
| VH CDR3 | 95-102 | 95-102  | 93-101    |
| VL CDR1 | 24-34  | 24-34   | 30-36     |
| VL CDR2 | 50-56  | 50-56   | 46-55     |
| VL CDR3 | 89-97  | 89-97   | 89-96     |

Variable regions and CDRs in an antibody sequence can be identified according to general rules that have been developed in the art (as set out above, such as, for example, the Kabat et al. numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably the sequences are analyzed using the Abysis database, which integrates sequence data from Kabat et al., IMGT and the Protein Data Bank (PDB) with structural data from the PDB. See Dr. Andrew C. R. Martin's book chapter Protein Sequence and Structure Analysis of Antibody Variable Domains. In: Antibody Engineering Lab Manual (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat et al.

For heavy chain constant region amino acid positions discussed in the invention, numbering is according to the Eu index first described in Edelman et al., 1969, Proc. Natl. Acad. Sci. USA 63(1): 78-85 describing the amino acid sequence of myeloma protein Eu, which reportedly was the first human IgG1 sequenced. The EU index of Edelman is also set forth in Kabat et al., 1991 (supra.). Thus, the terms "EU index as set forth in Kabat" or "EU index of Kabat" or "EU numbering" in the context of the heavy chain refers to the residue numbering system based on the human IgG1 Eu antibody of Edelman et al. as set forth in Kabat et al., 1991 (supra.) The numbering system used for the light chain constant region amino acid sequence is similarly set forth in Kabat et al., (supra.) An exemplary kappa light chain constant region amino acid sequence compatible with the present invention is set forth immediately below:

```
                                        (SEQ ID NO: 1)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

Similarly, an exemplary IgG1 heavy chain constant region amino acid sequence compatible with the present invention is set forth immediately below:

```
                                        (SEQ ID NO: 2)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG.
```

The disclosed constant region sequences, or variations or derivatives thereof, may be operably associated with the disclosed heavy and light chain variable regions using standard molecular biology techniques to provide full-length antibodies that may be used as such or incorporated in the anti-CLDN ADCs of the invention.

More generally the antibodies or immunoglobulins of the invention may be generated from any antibody that specifically recognizes or associates with the relevant determinant. As used herein "determinant" or "target" means any detectable trait, property, marker or factor that is identifiably associated with, or specifically found in or on a particular cell, cell population or tissue. Determinants or targets may be morphological, functional or biochemical in nature and are preferably phenotypic. In certain preferred embodiments a determinant is a protein that is differentially expressed (over- or under-expressed) by specific cell types or by cells under certain conditions (e.g., during specific points of the cell cycle or cells in a particular niche). For the purposes of the instant invention a determinant preferably is differentially expressed on aberrant cancer cells and may comprise a CLDN protein, or any of its splice variants, isoforms or family members, or specific domains, regions or epitopes thereof. An "antigen", "immunogenic determinant", "antigenic determinant" or "immunogen" means any protein or any fragment, region or domain thereof that can stimulate an immune response when introduced into an immunocompetent animal and is recognized by the antibodies produced from the immune response. The presence or absence of the determinants contemplated herein may be used to identify a cell, cell subpopulation or tissue (e.g., tumors, tumorigenic cells or CSCs).

There are two types of disulfide bridges or bonds in immunoglobulin molecules: interchain and intrachain disulfide bonds. As is well known in the art the location and number of interchain disulfide bonds vary according to the immunoglobulin class and species. While the invention is not limited to any particular class or subclass of antibody, the IgG1 immunoglobulin shall be used throughout the instant disclosure for illustrative purposes. In wild-type IgG1 molecules there are twelve intrachain disulfide bonds (four on each heavy chain and two on each light chain) and four interchain disulfide bonds. Intrachain disulfide bonds are generally somewhat protected and relatively less susceptible to reduction than interchain bonds. Conversely, interchain disulfide bonds are located on the surface of the immunoglobulin, are accessible to solvent and are usually relatively easy to reduce. Two interchain disulfide bonds exist between the heavy chains and one from each heavy chain to its respective light chain. It has been demonstrated that interchain disulfide bonds are not essential for chain association. The IgG1 hinge region contain the cysteines in the heavy chain that form the interchain disulfide bonds, which provide structural support along with the flexibility that facilitates Fab movement. The heavy/heavy IgG1 interchain disulfide bonds are located at residues C226 and C229 (Eu numbering) while the IgG1 interchain disulfide bond between the light and heavy chain of IgG1 (heavy/light) are formed between C214 of the kappa or lambda light chain and C220 in the upper hinge region of the heavy chain.

B. Antibody Generation and Production

Antibodies of the invention can be produced using a variety of methods known in the art.

1. Generation of Polyclonal Antibodies in Host Animals

The production of polyclonal antibodies in various host animals is well known in the art (see for example, Harlow and Lane (Eds.) (1988) Antibodies: A Laboratory Manual, CSH Press; and Harlow et al. (1989) Antibodies, NY, Cold Spring Harbor Press). In order to generate polyclonal antibodies, an immunocompetent animal is immunized with an antigenic protein or cells or preparations comprising an antigenic protein. After a period of time, polyclonal antibody-containing serum is obtained by bleeding or sacrificing the animal. The serum may be used in the form obtained from the animal or the antibodies may be partially or fully purified to provide immunoglobulin fractions or isolated antibody preparations.

Any form of antigen, or cells or preparations containing the antigen, can be used to generate an antibody that is specific for a determinant. The term "antigen" is used in a broad sense and may comprise any immunogenic fragment or determinant of the selected target including a single epitope, multiple epitopes, single or multiple domains or the entire extracellular domain (ECD). The antigen may be an isolated full-length protein, a cell surface protein (e.g., immunizing with cells expressing at least a portion of the antigen on their surface), or a soluble protein (e.g., immunizing with only the ECD portion of the protein). The antigen may be produced in a genetically modified cell. Any of the aforementioned antigens may be used alone or in combination with one or more immunogenicity enhancing adjuvants known in the art. The DNA encoding the antigen may be genomic or non-genomic (e.g., cDNA) and may encode at least a portion of the ECD, sufficient to elicit an immunogenic response. Any vectors may be employed to transform the cells in which the antigen is expressed, including but not limited to adenoviral vectors, lentiviral vectors, plasmids, and non-viral vectors, such as cationic lipids.

2. Monoclonal Antibodies

In selected embodiments, the invention contemplates use of monoclonal antibodies. The term "monoclonal antibody" or "mAb" refers to an antibody obtained from a population of substantially homogeneous antibodies, i.e., the individual antibodies comprising the population are identical except for possible mutations (e.g., naturally occurring mutations), that may be present in minor amounts.

Monoclonal antibodies can be prepared using a wide variety of techniques including hybridoma techniques, recombinant techniques, phage display technologies, transgenic animals (e.g., a XenoMouse®) or some combination thereof. For example, in preferred embodiments monoclonal antibodies can be produced using hybridoma and biochemical and genetic engineering techniques such as described in more detail in An, Zhigiang (ed.) *Therapeutic Monoclonal Antibodies: From Bench to Clinic*, John Wiley and Sons, $1^{st}$ ed. 2009; Shire et. al. (eds.) *Current Trends in Monoclonal Antibody Development and Manufacturing*, Springer Science+Business Media LLC, $1^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981). Following generation of a number of monoclonal antibodies that bind specifically to a determinant, particularly suitable antibodies may be selected through various screening processes, based on, for example, affinity for the determinant or rate of internalization. In particularly preferred embodiments monoclonal antibodies produced as described herein may be used as source antibodies and further modified to, for example, to improve affinity for the target, improve its production in cell culture, reduce immunogenicity in vivo, create multispecific constructs, etc. A more detailed description of monoclonal antibody production and screening is set out below and in the appended Examples.

3. Human Antibodies

The antibodies may comprise fully human antibodies. The term "human antibody" refers to an antibody (preferably a monoclonal antibody) which possesses an amino acid sequence that corresponds to that of an antibody produced by a human and/or has been made using any of the techniques for making human antibodies described below.

In one embodiment, recombinant human antibodies may be isolated by screening a recombinant combinatorial antibody library prepared using phage display. In one embodiment, the library is a scFv phage or yeast display library, generated using human VL and VH cDNAs prepared from mRNA isolated from B-cells.

Human antibodies can also be made by introducing human immunoglobulin loci into transgenic animals, e.g., mice in which the endogenous immunoglobulin genes have been partially or completely inactivated and human immunoglobulin genes have been introduced. Upon challenge antibody generation is observed which closely resembles that seen in humans in all respects, including gene rearrangement, assembly and fully human antibody repertoire. This approach is described, for example, in U.S. Pat. Nos. 5,545,807; 5,545,806; 5,569,825; 5,625,126; 5,633,425; 5,661,016, and U.S. Pat. Nos. 6,075,181 and 6,150,584 regarding XenoMouse® technology; and Lonberg and Huszar, 1995, PMID: 7494109). Alternatively, a human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., 1991, PMID: 2051030; and U.S. Pat. No. 5,750,373.

4. Derived Antibodies:

Once the source antibodies have been generated, selected and isolated as described above they may be further altered to provide anti-CLDN antibodies having improved pharmaceutical characteristics. Preferably the source antibodies are modified or altered using known molecular engineering techniques to provide derived antibodies having the desired therapeutic properties.

4.1 Chimeric and Humanized Antibodies

Selected embodiments of the invention comprise murine antibodies that immunospecifically bind to CLDN and, for the purposes of the instant disclosure, may be considered "source" antibodies. In selected embodiments, antibodies compatible with the invention can be derived from such "source" antibodies through optional modification of the constant region and/or the antigen binding amino acid sequences of the source antibody. In certain embodiments an antibody is "derived" from a source antibody if selected amino acids in the source antibody are altered through deletion, mutation, substitution, integration or combination. In another embodiment, a "derived" antibody is one in which fragments of the source antibody (e.g., one or more CDRs or the entire heavy and light chain variable regions) are combined with or incorporated into an acceptor antibody sequence to provide the derivative antibody (e.g. chimeric or humanized antibodies). These "derived" antibodies can be generated using standard molecular biological techniques as described below, such as, for example, to improve affinity for the determinant; to improve antibody stability; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification.

In one embodiment, the chimeric antibodies of the invention comprise chimeric antibodies that are derived from protein segments from at least two different species or class of antibodies that have been covalently joined. The term "chimeric" antibody is directed to constructs in which a portion of the heavy and/or light chain is identical or homologous to corresponding sequences in antibodies from a particular species or belonging to a particular antibody class or subclass, while the remainder of the chain(s) is identical or homologous to corresponding sequences in antibodies from another species or belonging to another antibody class or subclass, as well as fragments of such antibodies (U.S. Pat. No. 4,816,567; Morrison et al., 1984, PMID: 6436822). In some preferred embodiments chimeric antibodies of the instant invention may comprise all or most of the selected murine heavy and light chain variable regions operably linked to human light and heavy chain constant regions. In other particularly preferred embodiments, anti-CLDN antibodies may be "derived" from the mouse antibodies disclosed herein.

In other embodiments, the chimeric antibodies of the invention are "CDR grafted" antibodies, where the CDRs (as defined using Kabat, Chothia, McCallum, etc.) are derived from a particular species or belonging to a particular antibody class or subclass, while the remainder of the antibody is derived from an antibody from another species or belonging to another antibody class or subclass. For use in humans, one or more selected rodent CDRs (e.g., mouse CDRs) may be grafted into a human acceptor antibody, replacing one or more of the naturally occurring CDRs of the human antibody. These constructs generally have the advantages of providing full strength human antibody functions, e.g., complement dependent cytotoxicity (CDC) and antibody-dependent cell-mediated cytotoxicity (ADCC) while reducing unwanted immune responses to the antibody by the subject. In particularly preferred embodiments the CDR grafted antibodies will comprise one or more CDRs obtained from a mouse incorporated in a human framework sequence.

Similar to the CDR-grafted antibody is a "humanized" antibody. As used herein, a "humanized" antibody is a human antibody (acceptor antibody) comprising one or more amino acid sequences (e.g. CDR sequences) derived from one or more non-human antibodies (donor or source antibody). In certain embodiments, "back mutations" can be introduced into the humanized antibody, in which residues in one or more FRs of the variable region of the recipient human antibody are replaced by corresponding residues from the non-human species donor antibody. Such back mutations may to help maintain the appropriate three-dimensional configuration of the grafted CDR(s) and thereby improve affinity and antibody stability. Antibodies from various donor species may be used including, without limitation, mouse, rat, rabbit, or non-human primate. Furthermore, humanized antibodies may comprise new residues that are not found in the recipient antibody or in the donor antibody to, for example, further refine antibody performance. CDR grafted and humanized antibodies compatible with the instant invention are provided as set forth in Example 7 below.

Various art recognized techniques can be used to determine which human sequences to use as acceptor antibodies to provide humanized constructs in accordance with the instant invention. Compilations of compatible human germline sequences and methods of determining their suitability as acceptor sequences are disclosed, for example, in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638 each of which is incorporated herein in its entirety. The V-BASE directory (VBASE2—Retter et al., Nucleic Acid Res. 33;

671-674, 2005) which provides a comprehensive directory of human immunoglobulin variable region sequences (compiled by Tomlinson, I. A. et al. MRC Centre for Protein Engineering, Cambridge, UK) may also be used to identify compatible acceptor sequences. Additionally, consensus human framework sequences described, for example, in U.S. Pat. No. 6,300,064 may also prove to be compatible acceptor sequences are can be used in accordance with the instant teachings. In general, human framework acceptor sequences are selected based on homology with the murine source framework sequences along with an analysis of the CDR canonical structures of the source and acceptor antibodies. The derived sequences of the heavy and light chain variable regions of the derived antibody may then be synthesized using art recognized techniques.

By way of example CDR grafted and humanized antibodies, and associated methods, are described in U.S. Pat. Nos. 6,180,370 and 5,693,762. For further details, see, e.g., Jones et al., 1986, PMID: 3713831); and U.S. Pat. Nos. 6,982,321 and 7,087,409.

The sequence identity or homology of the CDR grafted or humanized antibody variable region to the human acceptor variable region may be determined as discussed herein and, when measured as such, will preferably share at least 60% or 65% sequence identity, more preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

It will be appreciated that the annotated CDRs and framework sequences as provided in the appended Figures are defined as per Kabat et al. using a proprietary Abysis database. However, as discussed herein one skilled in the art could readily identify the CDRs in accordance with the numbering schemes provided by Chothia et al. or MacCallum et al.

4.2 Site-Specific Antibodies

The antibodies of the instant invention may be engineered to facilitate conjugation to a cytotoxin or other anti-cancer agent (as discussed in more detail below). It is advantageous for the antibody drug conjugate (ADC) preparation to comprise a homogenous population of ADC molecules in terms of the position of the cytotoxin on the antibody and the drug to antibody ratio (DAR). Based on the instant disclosure one skilled in the art could readily fabricate site-specific engineered constructs as described herein. As used herein a "site-specific antibody" or "site-specific construct" means an antibody, or immunoreactive fragment thereof, wherein at least one amino acid in either the heavy or light chain is deleted, altered or substituted (preferably with another amino acid) to provide at least one free cysteine. Similarly, a "site-specific conjugate" shall be held to mean an ADC comprising a site-specific antibody and at least one cytotoxin or other compound conjugated to the unpaired cysteine (s). In certain embodiments the unpaired cysteine residue will comprise an unpaired intrachain residue. In other preferred embodiments the free cysteine residue will comprise an unpaired interchain cysteine residue. The engineered antibody can be of various isotypes, for example, IgG, IgE, IgA or IgD; and within those classes the antibody can be of various subclasses, for example, IgG1, IgG2, IgG3 or IgG4. For IgG constructs the light chain of the antibody can comprise either a kappa or lambda isotype each incorporating a C214 that, in preferred embodiments, may be unpaired due to a lack of a C220 residue in the IgG1 heavy chain.

In one embodiment the engineered antibody comprises at least one amino acid deletion or substitution of an intrachain or interchain cysteine residue. As used herein "interchain cysteine residue" means a cysteine residue that is involved in a native disulfide bond either between the light and heavy chain of an antibody or between the two heavy chains of an antibody while an "intrachain cysteine residue" is one naturally paired with another cysteine in the same heavy or light chain. In one embodiment the deleted or substituted interchain cysteine residue is involved in the formation of a disulfide bond between the light and heavy chain. In another embodiment the deleted or substituted cysteine residue is involved in a disulfide bond between the two heavy chains. In a typical embodiment, due to the complementary structure of an antibody, in which the light chain is paired with the VH and $C_H1$ domains of the heavy chain and wherein the CH2 and $C_H3$ domains of one heavy chain are paired with the CH2 and CH3 domains of the complementary heavy chain, a mutation or deletion of a single cysteine in either the light chain or in the heavy chain would result in two unpaired cysteine residues in the engineered antibody.

In some embodiments an interchain cysteine residue is deleted. In other embodiments an interchain cysteine is substituted for another amino acid (e.g., a naturally occurring amino acid). For example, the amino acid substitution can result in the replacement of an interchain cysteine with a neutral (e.g. serine, threonine or glycine) or hydrophilic (e.g. methionine, alanine, valine, leucine or isoleucine) residue. In one particularly preferred embodiment an interchain cysteine is replaced with a serine.

In some embodiments contemplated by the invention the deleted or substituted cysteine residue is on the light chain (either kappa or lambda) thereby leaving a free cysteine on the heavy chain. In other embodiments the deleted or substituted cysteine residue is on the heavy chain leaving the free cysteine on the light chain constant region. Upon assembly it will be appreciated that deletion or substitution of a single cysteine in either the light or heavy chain of an intact antibody results in a site-specific antibody having two unpaired cysteine residues.

In one particularly preferred embodiment the cysteine at position 214 (C214) of the IgG light chain (kappa or lambda) is deleted or substituted. In another preferred embodiment the cysteine at position 220 (C220) on the IgG heavy chain is deleted or substituted. In further embodiments the cysteine at position 226 or position 229 on the heavy chain is deleted or substituted. In one embodiment C220 on the heavy chain is substituted with serine (C220S) to provide the desired free cysteine in the light chain. In another embodiment C214 in the light chain is substituted with serine (C214S) to provide the desired free cysteine in the heavy chain. Such site-specific constructs provided in Example 8. A summary of these preferred constructs is shown in Table 2 immediately below where all numbering is according to the EU index as set forth in Kabat and WT stands for "wild-type" or native constant region sequences without alterations and delta (4) designates the deletion of an amino acid residue (e.g., C214Δ indicates that the cysteine at position 214 has been deleted).

TABLE 2

| Designation | Antibody Component | Alteration |
|---|---|---|
| ss1 | Heavy Chain | C220S |
| | Light Chain | WT |
| ss2 | Heavy Chain | C220Δ |
| | Light Chain | WT |
| ss3 | Heavy Chain | WT |
| | Light Chain | C214Δ |
| ss4 | Heavy Chain | WT |
| | Light Chain | C214S |

In an analogous manner preferred embodiments may comprise site-specific IgG4 antibodies where the C127 residue of the heavy chain is altered or eliminated to provide a free cysteine at the 220 position of the light chain. As set forth in the Examples below, such embodiments may exhibit improved stability and reduced toxicity.

The strategy for generating antibody-drug conjugates with defined sites and stoichiometries of drug loading, as disclosed herein, is broadly applicable to all anti-CLDN antibodies as it primarily involves engineering of the conserved constant domains of the antibody. As the amino acid sequences and native disulfide bridges of each class and subclass of antibody are well documented, one skilled in the art could readily fabricate engineered constructs of various antibodies without undue experimentation and, accordingly, such constructs are expressly contemplated as being within the scope of the instant invention.

4.3 Constant Region Modifications and Altered Glycosylation

Selected embodiments of the present invention may also comprise substitutions or modifications of the constant region (i.e. the Fc region), including without limitation, amino acid residue substitutions, mutations and/or modifications, which result in a compound with preferred characteristics including, but not limited to: altered pharmacokinetics, increased serum half-life, increase binding affinity, reduced immunogenicity, increased production, altered Fc ligand binding to an Fc receptor (FcR), enhanced or reduced ADCC or CDC, altered glycosylation and/or disulfide bonds and modified binding specificity.

Compounds with improved Fc effector functions can be generated, for example, through changes in amino acid residues involved in the interaction between the Fc domain and an Fc receptor (e.g., FcγRI, FcγRIIA and B, FcγRIII and FcRn), which may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311). With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

Still other embodiments comprise one or more engineered glycoforms, e.g., a site-specific antibody comprising an altered glycosylation pattern or altered carbohydrate composition that is covalently attached to the protein (e.g., in the Fc domain). See, for example, Shields, R. L. et al. (2002) J. Biol. Chem. 277:26733-26740. Engineered glycoforms may be useful for a variety of purposes, including but not limited to enhancing or reducing effector function, increasing the affinity of the antibody for a target or facilitating production of the antibody. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTIII)), by expressing a molecule comprising an Fc region in various organisms or cell lines from various organisms or by modifying carbohydrate(s) after the molecule comprising Fc region has been expressed (see, for example, WO 2012/117002).

4.4 Fragments

Regardless of which form of antibody (e.g. chimeric, humanized, etc.) is selected to practice the invention it will be appreciated that immunoreactive fragments, either by themselves or as part of an antibody drug conjugate, of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary site-specific fragments include: variable light chain fragments (VL), an variable heavy chain fragments (VH), scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active site-specific fragment comprises a portion of the antibody that retains its ability to interact with the antigen/substrates or receptors and modify them in a manner similar to that of an intact antibody (though maybe with somewhat less efficiency). Such antibody fragments may further be engineered to comprise one or more free cysteines.

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence comprising at least one free cysteine capable of conferring in vivo stability to the fragment.

As would be well recognized by those skilled in the art, fragments can be obtained by molecular engineering or via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

4.5 Multivalent Constructs

In other embodiments, the antibodies and conjugates of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S. Ser. No. 2009/0130105.

In one embodiment, the antibodies are bispecific antibodies in which the two chains have different specificities, as described in Millstein et al., 1983, *Nature*, 305:537-539. Other embodiments include antibodies with additional specificities such as trispecific antibodies. Other more sophisticated compatible multispecific constructs and methods of their fabrication are set forth in U.S. Ser. No. 2009/0155255, as well as WO 94/04690; Suresh et al., 1986, *Methods in Enzymology*, 121:210; and WO96/27011.

Multivalent antibodies may immunospecifically bind to different epitopes of the desired target molecule or may immunospecifically bind to both the target molecule as well as a heterologous epitope, such as a heterologous polypeptide or solid support material. While preferred embodiments only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

In certain preferred embodiments the antibodies of the invention may be utilized in adoptive immunity gene therapy to treat tumors. In one embodiment the antibodies of the invention (e.g. ScFv fragments) may be used to generate a chimeric antigen receptor (CAR). A "CAR" is a fused protein made up of an ECD comprising the anti-CLDN antibodies of the invention or immunoreactive fragments thereof (e.g. ScFv fragments), a transmembrane domain, and at least one intracellular domain. In one embodiment, T-cells, natural killer cells or dendritic cells that have been genetically engineered to express CARs can be introduced into a subject suffering from cancer in order to stimulate the immune system of the subject to specifically target tumor cells expressing CLDN. In preferred embodiments the CARs of the invention will comprise an intracellular domain that initiates a primary cytoplasmic signaling sequence, that is, a sequence for initiating antigen-dependent primary activation via a T-cell receptor complex, for example, intracellular domains derived from CD3ζ, FcRγ, FcRβ, CD3γ, CD3 δ, CD3ε, CD5, CD22, CD79a, CD79b, and CD66d. In other preferred embodiments, the CARs of the invention will comprise an intracellular domain that initiates a secondary or co-stimulating signal, for example, intracellular domains derived from CD2, CD4, CD5, CD8α, CD8β, CD28, CD134, CD137, ICOS, CD154, 4-1BB and glucocorticoid-induced tumor necrosis factor receptor (see U.S. Ser. No. US/2014/0242701).

In yet other embodiments, antibody variable domains with the desired binding specificities (antibody-antigen combining sites) are fused to immunoglobulin constant domain sequences, such as an immunoglobulin heavy chain constant domain comprising at least part of the hinge, CH2, and/or CH3 regions, using methods well known to those of ordinary skill in the art.

5. Recombinant Production of Antibodies

Antibodies and fragments thereof may be produced or modified using genetic material obtained from antibody producing cells and recombinant technology (see, for example, Berger and Kimmel, Guide to Molecular Cloning Techniques, *Methods in Enzymology* vol. 152 Academic Press, Inc., San Diego, Calif.; Sambrook and Russell (Eds.) (2000) *Molecular Cloning: A Laboratory Manual* (3$^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc.; and U.S. Pat. No. 7,709,611).

Another aspect of the invention pertains to nucleic acid molecules that encode the antibodies of the invention. The nucleic acids may be present in whole cells, in a cell lysate, or in a partially purified or substantially pure form. A nucleic acid is "isolated" or rendered substantially pure when separated from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA (e.g. genomic DNA, cDNA), RNA and artificial variants thereof (e.g., peptide nucleic acids), whether single-stranded or double-stranded or RNA, RNA and may or may not contain introns. In a preferred embodiment, the nucleic acid is a cDNA molecule.

Nucleic acids of the invention can be obtained using standard molecular biology techniques. For antibodies expressed by hybridomas (e.g., hybridomas prepared as set forth in the Examples below), cDNAs encoding the light and heavy chains of the antibody can be obtained by standard PCR amplification or cDNA cloning techniques. For antibodies obtained from an immunoglobulin gene library (e.g., using phage display techniques), nucleic acid encoding the antibody can be recovered from the library.

DNA fragments encoding VH and VL segments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, means that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, et al. (1991) (supra)) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. An exemplary IgG1 constant region is set forth in SEQ ID NO: 2. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, et al. (1991) (supra)) and DNA fragments encompassing these regions can be obtained by standard PCR amplification. The light chain constant region can be a kappa or lambda constant region, but most preferably is a kappa constant region. In this respect an exemplary compatible kappa light chain constant region is set forth in SEQ ID NO: 1.

Contemplated herein are certain polypeptides (e.g. antigens or antibodies) that exhibit "sequence identity", sequence similarity" or "sequence homology" to the polypeptides of the invention. A "homologous" polypeptide may exhibit 65%, 70%, 75%, 80%, 85%, or 90% sequence identity. In other embodiments a "homologous" polypeptides may exhibit 93%, 95% or 98% sequence identity. As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Residue positions which are not identical may differ by conservative amino acid substitutions or by non-conservative amino acid substitutions. A "conservative amino acid substitution" is one in which an amino acid residue is substituted by another amino acid residue having a side chain with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. In cases where there is a substitution with a non-conservative amino acid, in preferred embodiments the polypeptide exhibiting sequence identity will retain the desired function or activity of the polypeptide of the invention (e.g., antibody.)

Also contemplated herein are nucleic acids that that exhibit "sequence identity", sequence similarity" or "sequence homology" to the nucleic acids of the invention. A "homologous sequence" means a sequence of nucleic acid molecules exhibiting at least about 65%, 70%, 75%, 80%, 85%, or 90% sequence identity. In other embodiments, a "homologous sequence" of nucleic acids may exhibit 93%, 95% or 98% sequence identity to the reference nucleic acid.

The instant invention also provides vectors comprising such nucleic acids described above, which may be operably linked to a promoter (see, e.g., WO 86/05807; WO 89/01036; and U.S. Pat. No. 5,122,464); and other transcriptional regulatory and processing control elements of the eukaryotic secretory pathway. The invention also provides host cells harboring those vectors and host-expression systems.

As used herein, the term "host-expression system" includes any kind of cellular system that can be engineered to generate either the nucleic acids or the polypeptides and antibodies of the invention. Such host-expression systems include, but are not limited to microorganisms (e.g., E. coli or B. subtilis) transformed or transfected with recombinant bacteriophage DNA or plasmid DNA; yeast (e.g., Saccharomyces) transfected with recombinant yeast expression vectors; or mammalian cells (e.g., COS, CHO-S, HEK-293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or proteins having GnTIII activity).

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP 0 216 846, EP 0 256 055, EP 0 323 997 and EP 0 338 841 and U.S. Pat. Nos. 5,591,639 and 5,879,936. Another preferred expression system for the development of stable cell lines is the Freedom™ CHO-S Kit (Life Technologies).

Once an antibody of the invention has been produced by recombinant expression or any other of the disclosed techniques, it may be purified or isolated by methods known in the art, meaning that it is identified and separated and/or recovered from its natural environment and separated from contaminants that would interfere with diagnostic or therapeutic uses for the antibody. Isolated antibodies include antibodies in situ within recombinant cells.

These isolated preparations may be purified using various art recognized techniques, such as, for example, ion exchange and size exclusion chromatography, dialysis, diafiltration, and affinity chromatography, particularly Protein A or Protein G affinity chromatography.

6. Post-Production Selection

No matter how obtained, antibody-producing cells (e.g., hybridomas, yeast colonies, etc.) may be selected, cloned and further screened for desirable characteristics including, for example, robust growth, high antibody production and desirable antibody characteristics such as high affinity for the antigen of interest. Hybridomas can be expanded in vitro in cell culture or in vivo in syngeneic immunocompromised animals. Methods of selecting, cloning and expanding hybridomas and/or colonies are well known to those of ordinary skill in the art. Once the desired antibodies are identified the relevant genetic material may be isolated, manipulated and expressed using common, art-recognized molecular biology and biochemical techniques.

The antibodies produced by naïve libraries (either natural or synthetic) may be of moderate affinity ($K_a$ of about $10^6$ to $10^7$ $M^{-1}$). To enhance affinity, affinity maturation may be mimicked in vitro by constructing antibody libraries (e.g., by introducing random mutations in vitro by using error-prone polymerase) and reselecting antibodies with high affinity for the antigen from those secondary libraries (e.g. by using phage or yeast display). WO 9607754 describes a method for inducing mutagenesis in a CDR of an immunoglobulin light chain to create a library of light chain genes.

Various techniques can be used to select antibodies, including but not limited to, phage or yeast display in which a library of human combinatorial antibodies or scFv fragments is synthesized on phages or yeast, the library is screened with the antigen of interest or an antibody-binding portion thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206). Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies and provide for relatively easy manipulation of sequences (e.g., by recombinant shuffling).

IV CHARACTERISTICS OF ANTIBODIES

In selected embodiments, antibody-producing cells (e.g., hybridomas or yeast colonies) may be selected, cloned and further screened for favorable properties including, for example, robust growth, high antibody production and, as discussed in more detail below, desirable site-specific antibody characteristics. In other cases characteristics of the antibody may be imparted by selecting a particular antigen (e.g., a specific CLDN isoform) or immunoreactive fragment of the target antigen for inoculation of the animal. In still other embodiments the selected antibodies may be engineered as described above to enhance or refine immunochemical characteristics such as affinity or pharmacokinetics.

A. Neutralizing Antibodies

In selected embodiments the antibodies of the invention may be "antagonists" or "neutralizing" antibodies, meaning that the antibody may associate with a determinant and block or inhibit the activities of said determinant either directly or by preventing association of the determinant with a binding partner such as a ligand or a receptor, thereby interrupting the biological response that otherwise would result from the interaction of the molecules. A neutralizing or antagonist antibody will substantially inhibit binding of the determinant to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream (e.g., oncogenesis or cell survival).

B. Internalizing Antibodies

There is evidence that a substantial portion of expressed CLDN protein remains associated with the tumorigenic cell surface, thereby allowing for localization and internalization of the disclosed antibodies or ADCs. In preferred embodiments such antibodies will be associated with, or conjugated to, one or more drugs that kill the cell upon internalization. In particularly preferred embodiments the ADCs of the instant invention will comprise an internalizing site-specific ADC.

As used herein, an antibody that "internalizes" is one that is taken up (along with any cytotoxin) by the cell upon binding to an associated antigen or receptor. For therapeutic applications, internalization will preferably occur in vivo in a subject in need thereof. The number of ADCs internalized may be sufficient to kill an antigen-expressing cell, especially an antigen-expressing cancer stem cell. Depending on the potency of the cytotoxin or ADC as a whole, in some instances, the uptake of a single antibody molecule into the cell is sufficient to kill the target cell to which the antibody binds. For example, certain drugs are so highly potent that the internalization of a few molecules of the toxin conjugated to the antibody is sufficient to kill the tumor cell. Whether an antibody internalizes upon binding to a mammalian cell can be determined by various art-recognized assays including those described in the Examples below. Methods of detecting whether an antibody internalizes into a cell are also described in U.S. Pat. No. 7,619,068.

C. Depleting Antibodies

In other embodiments the antibodies of the invention are depleting antibodies. The term "depleting" antibody refers to an antibody that preferably binds to an antigen on or near the cell surface and induces, promotes or causes the death of the cell (e.g., by CDC, ADCC or introduction of a cytotoxic agent). In preferred embodiments, the selected depleting antibodies will be conjugated to a cytotoxin. Preferably a depleting antibody will be able to kill at least 20%, 30%, 40%, 50%, 60%, 70%, 80%, 85%, 90%, 95%, 97%, or 99% of CLDN-expressing cells in a defined cell population. The term "apparent 1050", as used herein, refers to the concentration at which a primary antibody linked to a toxin kills 50 percent of the cells expressing the antigen(s) recognized by the primary antibody. The toxin can be directly conjugated to the primary antibody, or can be associated with the primary antibody via a secondary antibody or antibody fragment that recognizes the primary antibody, and which secondary antibody or antibody fragment is directly conjugated to a toxin. Preferably a depleting antibody will have an IC50 of less than 5 µM, less than 1 µM, less than 100 nM, less than 50 nM, less than 30 nM, less than 20 nM, less than 10 nM, less than 5 nM, less than 2 nM or less than 1 nM. In some embodiments the cell population may comprise enriched, sectioned, purified or isolated tumorigenic cells, including cancer stem cells. In other embodiments the cell population may comprise whole tumor samples or heterogeneous tumor extracts that comprise cancer stem cells. Standard biochemical techniques may be used to monitor and quantify the depletion of tumorigenic cells in accordance with the teachings herein.

D. Binding Affinity

Disclosed herein are antibodies that have a high binding affinity for a specific determinant e.g. CLDN. The term "$K_D$" refers to the dissociation constant of a particular antibody-antigen interaction. An antibody of the invention can immunospecifically bind its target antigen when the dissociation constant $K_D$ ($k_{off}/k_{on}$) is $\leq 10^{-7}$ M. The antibody specifically binds antigen with high affinity when the $K_D$ is $\leq 5 \times 10^{-9}$ M, and with very high affinity when the $K_D$ is $\leq 5 \times 10^{-10}$ M. In one embodiment of the invention, the antibody has a $K_D$ of $\leq 10^{-9}$ M and an off-rate of about $1 \times 10^{-4}$/sec. In one embodiment of the invention, the off-rate is $<1 \times 10^{-5}$/sec. In other embodiments of the invention, the antibodies will bind to a determinant with a $K_D$ of between about $10^{-7}$ M and $10^{-10}$ M, and in yet another embodiment it will bind with a $K_D \leq 2 \times 10^{-10}$ M. Still other selected embodiments of the invention comprise antibodies that have a $K_D$ ($k_{off}/k_{on}$) of less than $10^{-6}$ M, less than $5 \times 10^{-6}$ M, less than $10^{-7}$ M, less than $5 \times 10^{-7}$ M, less than $10^{-8}$ M, less than $5 \times 10^{-9}$ M, less than $10^{-9}$ M, less than $5 \times 10^{-9}$ M, less than $10^{-10}$ M, less than $5 \times 10^{-10}$ M less than $10^{-11}$ M, less than $5 \times 10^{-11}$ M, less than $10^{-12}$ M less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M or less than $5 \times 10^{-15}$ M.

In certain embodiments, an antibody of the invention that immunospecifically binds to a determinant e.g. CLDN may have an association rate constant or $k_{on}$ (or $k_a$) rate (antibody+antigen $(Ag)^{k_{on}} \leftarrow$ antibody-Ag) of at least $10^5$ M$^{-1}$s$^{-1}$, at least $2 \times 10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, or at least $10^8$ M$^{-1}$ s$^{-1}$.

In another embodiment, an antibody of the invention that immunospecifically binds to a determinant e.g. CLDN may have a disassociation rate constant or $k_{off}$ (or $k_d$) rate (antibody+antigen $(Ag)^{k_{off}} \leftarrow$ antibody-Ag) of less than $10^{-1}$ s$^{-1}$, less than $5 \times 10^{-1}$s$^{-1}$, less than $10^{-2}$ s$^{-1}$, less than $5 \times 10^{-2}$ s$^{-1}$, less than $10^{-3}$ s$^{-1}$, less than $5 \times 10^{-3}$ s$^{-1}$, less than $10^{-4}$ s$^{-1}$, less than $5 \times 10^4$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$ less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$ or less than $10^{-10}$ s$^{-1}$.

Binding affinity may be determined using various techniques known in the art, for example, surface plasmon resonance, bio-layer interferometry, dual polarization interferometry, static light scattering, dynamic light scattering, isothermal titration calorimetry, ELISA, analytical ultracentrifugation, and flow cytometry.

The term "apparent binding affinity" as used herein, refers to the apparent binding of an antibody to its target antigen when the antigen is overexpressed on the surface of a cell. The apparent binding affinity of an antibody for an antigen is described herein as an "apparent EC50", which is the concentration of antibody at which 50% maximal binding to cells overexpressing the antigen occurs. In one embodiment, two antibodies can be said to have "substantially the same"

apparent binding affinity for an antigen, with >99% confidence, if they have apparent EC50 values that do not differ from one another by more than 45%, by more than 40%, by more than 35%, by more than 30%, by more than 25%, by more than 20%, by more than 10% or by more than 5%. In another embodiment an antibody that binds multiple target antigens, e.g. is multireactive towards one or more CLDN proteins, can be said to have "substantially the same" apparent binding affinity for the multiple antigens, with >99% confidence, if the apparent EC50 values of the antibody for each of the antigens do not differ from one another by more than 45%, by more than 40%, by more than 35%, by more than 30%, by more than 25%, by more than 20%, by more than 10% or by more than 5%. Since the assays used to determine the apparent binding affinity of an antibody for an antigen typically utilize cells overexpressing the antigen and which are exposed to antibodies under presumed equilibrium or near equilibrium conditions, the apparent EC50 value is reflective of the avidity, or combined or accumulated strength of multiple apparent binding affinities. Thus, in a related embodiment two antibodies will share substantially the same avidity for a target cell line expressing the antigen, with >99% confidence, if their apparent binding affinities for the cell line, expressed as apparent EC50 values, do not differ from one another by more than 45%, by more than 40%, by more than 35%, by more than 30%, by more than 25%, by more than 20%, by more than 10% or by more than 5%. Similarly an antibody that binds multiple target antigens, e.g. is multireactive towards one or more CLDN proteins, can be said to have substantially the same avidity for multiple antigens, with >99% confidence, if the apparent EC50 values for each of the antigens do not differ from one another by more than 45%, by more than 40%, by more than 35%, by more than 30%, by more than 25%, by more than 20%, by more than 10% or by more than 5%.

E. Binning and Epitope Mapping

As used herein, the term "binning" refers to methods used to group antibodies into "bins" based on their antigen binding characteristics and whether they compete with each other. The initial determination of bins may be further refined and confirmed by epitope mapping and other techniques as described herein. However it will be appreciated that empirical assignment of antibodies to individual bins provides information that may be indicative of the therapeutic potential of the disclosed antibodies.

More specifically, one can determine whether a selected reference antibody (or fragment thereof) competes for binding with a second test antibody (i.e., is in the same bin) by using methods known in the art and set forth in the Examples herein. In one embodiment, a reference antibody is associated with CLDN antigen under saturating conditions and then the ability of a secondary or test antibody to bind to CLDN is determined using standard immunochemical techniques. If the test antibody is able to substantially bind to CLDN at the same time as the reference anti-CLDN antibody, then the secondary or test antibody binds to a different epitope than the primary or reference antibody. However, if the test antibody is not able to substantially bind to CLDN at the same time, then the test antibody binds to the same epitope, an overlapping epitope, or an epitope that is in close proximity (at least sterically) to the epitope bound by the primary antibody. That is, the test antibody competes for antigen binding and is in the same bin as the reference antibody.

The term "compete" or "competing antibody" when used in the context of the disclosed antibodies means competition between antibodies as determined by an assay in which a test antibody or immunologically functional fragment being tested inhibits specific binding of a reference antibody to a common antigen. Typically, such an assay involves the use of purified antigen (e.g., CLDN or a domain or fragment thereof) bound to a solid surface or cells, an unlabeled test antibody and a labeled reference antibody. Competitive inhibition is measured by determining the amount of label bound to the solid surface or cells in the presence of the test antibody. Usually the test antibody is present in excess and/or allowed to bind first. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more.

Conversely, when the reference antibody is bound it will preferably inhibit binding of a subsequently added test antibody (i.e., an anti-CLDN antibody) by at least 30%, 40%, 45%, 50%, 55%, 60%, 65%, 70% or 75%. In some instance, binding of the test antibody is inhibited by at least 80%, 85%, 90%, 95%, or 97% or more.

Generally binning or competitive binding may be determined using various art-recognized techniques, such as, for example, immunoassays such as western blots, radioimmunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such immunoassays are routine and well known in the art (see, Ausubel et al, eds, (1994) *Current Protocols in Molecular Biology*, Vol. 1, John Wiley & Sons, Inc., New York). Additionally, cross-blocking assays may be used (see, for example, WO 2003/48731; and Harlow et al. (1988) *Antibodies, A Laboratory Manual*, Cold Spring Harbor Laboratory, Ed Harlow and David Lane).

Other technologies used to determine competitive inhibition (and hence "bins"), include: surface plasmon resonance using, for example, the BIAcore™ 2000 system (GE Healthcare); bio-layer interferometry using, for example, a Forte-Bio® Octet RED (ForteBio); or flow cytometry bead arrays using, for example, a FACSCanto II (BD Biosciences) or a multiplex LUMINEX™ detection assay (Luminex).

Luminex is a bead-based immunoassay platform that enables large scale multiplexed antibody pairing. The assay compares the simultaneous binding patterns of antibody pairs to the target antigen. One antibody of the pair (capture mAb) is bound to Luminex beads, wherein each capture mAb is bound to a bead of a different color. The other antibody (detector mAb) is bound to a fluorescent signal (e.g. phycoerythrin (PE)). The assay analyzes the simultaneous binding (pairing) of antibodies to an antigen and groups together antibodies with similar pairing profiles. Similar profiles of a detector mAb and a capture mAb indicates that the two antibodies bind to the same or closely related epitopes. In one embodiment, pairing profiles can be determined using Pearson correlation coefficients to identify the antibodies which most closely correlate to any particular antibody on the panel of antibodies that are tested. In preferred embodiments a test/detector mAb will be determined to be in the same bin as a reference/capture mAb if the Pearson's correlation coefficient of the antibody pair is at least 0.9. In other embodiments the Pearson's correlation coefficient is at least 0.8, 0.85, 0.87 or 0.89. In further embodiments, the Pearson's correlation coefficient is at least 0.91, 0.92, 0.93, 0.94, 0.95, 0.96, 0.97, 0.98, 0.99 or 1. Other methods of analyzing the data obtained from the Luminex assay are described in U.S. Pat. No. 8,568,992. The ability of Luminex to analyze 100 different types of beads (or more) simultaneously provides almost unlimited antigen and/or antibody surfaces, resulting in improved throughput and resolution in antibody epitope profiling over a biosensor assay (Miller, et al., 2011, PMID: 21223970).

"Surface plasmon resonance," refers to an optical phenomenon that allows for the analysis of real-time specific interactions by detection of alterations in protein concentrations within a biosensor matrix.

In other embodiments, a technique that can be used to determine whether a test antibody "competes" for binding with a reference antibody is "bio-layer interferometry", an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. Such biolayer interferometry assays may be conducted using a ForteBio® Octet RED machine as follows. A reference antibody (Ab1) is captured onto an anti-mouse capture chip, a high concentration of non-binding antibody is then used to block the chip and a baseline is collected. Monomeric, recombinant target protein is then captured by the specific antibody (Ab1) and the tip is dipped into a well with either the same antibody (Ab1) as a control or into a well with a different test antibody (Ab2). If no further binding occurs, as determined by comparing binding levels with the control Ab1, then Ab1 and Ab2 are determined to be "competing" antibodies. If additional binding is observed with Ab2, then Ab1 and Ab2 are determined not to compete with each other. This process can be expanded to screen large libraries of unique antibodies using a full row of antibodies in a 96-well plate representing unique bins. In preferred embodiments a test antibody will compete with a reference antibody if the reference antibody inhibits specific binding of the test antibody to a common antigen by at least 40%, 45%, 50%, 55%, 60%, 65%, 70% or 75%. In other embodiments, binding is inhibited by at least 80%, 85%, 90%, 95%, or 97% or more.

Once a bin, encompassing a group of competing antibodies, has been defined further characterization can be carried out to determine the specific domain or epitope on the antigen to which the antibodies in a bin bind. Domain-level epitope mapping may be performed using a modification of the protocol described by Cochran et al., 2004, PMID: 15099763. Fine epitope mapping is the process of determining the specific amino acids on the antigen that comprise the epitope of a determinant to which the antibody binds. The term "epitope" is used in its common biochemical sense and refers to that portion of the target antigen capable of being recognized and specifically bound by a particular antibody. In certain embodiments, epitopes or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. In certain embodiments, an antibody is said to specifically bind an antigen when it preferentially recognizes its target antigen in a complex mixture of proteins and/or macromolecules.

When the antigen is a polypeptide such as CLDN, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. An antibody epitope typically includes at least 3, and more usually, at least 5 or 8-10 amino acids in a unique spatial conformation. Methods of epitope determination or "epitope mapping" are well known in the art and may be used in conjunction with the instant disclosure to identify epitopes on CLDN bound by the disclosed antibodies.

Compatible epitope mapping techniques include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496). In other embodiments Modification-Assisted Profiling (MAP), also known as Antigen Structure-based Antibody Profiling (ASAP) provides a method that categorizes large numbers of monoclonal antibodies directed against the same antigen according to the similarities of the binding profile of each antibody to chemically or enzymatically modified antigen surfaces (U.S. Ser. No. 2004/0101920). This technology allows rapid filtering of genetically identical antibodies, such that characterization can be focused on genetically distinct antibodies. It will be appreciated that MAP may be used to sort the anti-CLDN antibodies of the invention into groups of antibodies binding different epitopes Once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

V ANTIBODY CONJUGATES

In certain preferred embodiments the antibodies of the invention may be conjugated with pharmaceutically active moiety or diagnostic moieties to form an "antibody drug conjugate" (ADC) or "antibody conjugate". The term "conjugate" is used broadly and means the covalent or non-covalent association of any pharmaceutically active moiety or diagnostic moiety with an antibody of the instant invention regardless of the method of association. In certain embodiments the association is effected through a lysine or cysteine residue of the antibody. In particularly preferred embodiments the pharmaceutically active or diagnostic moieties may be conjugated to the antibody via one or more site-specific free cysteine(s). The disclosed ADCs may be used for therapeutic and diagnostic purposes.

The ADCs of the instant invention may be used to deliver cytotoxins or other payloads to the target location (e.g., tumorigenic cells and/or cells expressing CLDN). As used herein the terms "drug" or "warhead" may be used interchangeably and will mean a biologically active or detectable molecule or compound, including anti-cancer agents as described below. A "payload" may comprise a drug or warhead in combination with an optional linker compound. The warhead on the conjugate may comprise peptides, proteins, prodrugs which are metabolized to an active agent in vivo, polymers, nucleic acid molecules, small molecules, binding agents, mimetic agents, synthetic drugs, inorganic molecules, organic molecules and radioisotopes. In an advantageous embodiment, the disclosed ADCs will direct the bound payload to the target site in a relatively unreactive, non-toxic state before releasing and activating the payload. This targeted release of the payload is preferably achieved through stable conjugation of the payloads via one or more cysteines or lysines and the relatively homogeneous composition of the ADC preparations which minimize over-conjugated toxic species. Coupled with drug linkers that are designed to largely release the drug once it has been delivered to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing an enhanced therapeutic index.

It will be appreciated that, while preferred embodiments of the invention comprise payloads of therapeutic moieties (e.g., cytotoxins), other payloads such as diagnostic agents and biocompatible modifiers may benefit from the targeted release provided by the disclosed conjugates. Accordingly, any disclosure directed to exemplary therapeutic payloads is also applicable to payloads comprising diagnostic agents or biocompatible modifiers as discussed herein unless otherwise dictated by context. The selected payload may be covalently or non-covalently linked to, the antibody and exhibit various stoichiometric molar ratios depending, at least in part, on the method used to effect the conjugation. The conjugates of the instant invention may be represented by the formula:

Ab-[L-D]n or a pharmaceutically acceptable salt thereof wherein
a) Ab comprises an anti-CLDN antibody;
b) L comprises an optional linker;
c) D comprises a drug; and
d) n is an integer from about 1 to about 20.

Those of skill in the art will appreciate that conjugates according to the aforementioned formula may be fabricated using a number of different linkers and drugs and that conjugation methodology will vary depending on the selection of components. As such, any drug or drug linker compound that associates with a reactive residue (e.g., cysteine or lysine) of the disclosed antibodies are compatible with the teachings herein. Similarly, any reaction conditions that allow for conjugation (e.g., site-specific conjugation) of the selected drug to an antibody are within the scope of the present invention. Notwithstanding the foregoing, particularly preferred embodiments of the instant invention comprise selective conjugation of the drug or drug linker to free cysteines using stabilization agents in combination with mild reducing agents as described herein. Such reaction conditions tend to provide more homogeneous preparations with less non-specific conjugation and contaminants and correspondingly less toxicity.

Exemplary payloads compatible with the teachings herein are set forth below:

A. Therapeutic Agents

The antibodies of the invention may be conjugated, linked or fused to or otherwise associated with a pharmaceutically active moiety which is a therapeutic moiety or a drug such as an anti-cancer agent including, but not limited to, cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

Preferred exemplary anti-cancer agents (including homologs and derivatives thereof) comprise 1-dehydrotestosterone, anthramycins, actinomycin D, bleomycin, calicheamicin, colchicin, cyclophosphamide, cytochalasin B, dactinomycin (formerly actinomycin), dihydroxy anthracin, dione, emetine, epirubicin, ethidium bromide, etoposide, glucocorticoids, gramicidin D, lidocaine, maytansinoids such as DM-1 and DM-4 (Immunogen), mithramycin, mitomycin, mitoxantrone, paclitaxel, procaine, propranolol, puromycin, tenoposide, tetracaine and pharmaceutically acceptable salts or solvates, acids or derivatives of any of the above.

Additional compatible cytotoxins comprise dolastatins and auristatins, including monomethyl auristatin E (MMAE) and monomethyl auristatin F (MMAF) (Seattle Genetics), amanitins such as alpha-amanitin, beta-amanitin, gamma-amanitin or epsilon-amanitin (Heidelberg Pharma), DNA minor groove binding agents such as duocarmycin derivatives (Syntarga), alkylating agents such as modified or dimeric pyrrolobenzodiazepines (PBD), mechlorethamine, thioepa, chlorambucil, melphalan, carmustine (BCNU), lomustine (CCNU), cyclothosphamide, busulfan, dibromomannitol, streptozotocin, mitomycin C and cisdichlorodiamine platinum (II) (DDP) cisplatin, splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins, antimetabolites such as methotrexate, 6-mercaptopurine, 6-thioguanine, cytarabine, and 5-fluorouracil decarbazine, antimitotic agents such as vinblastine and vincristine and anthracyclines such as daunorubicin (formerly daunomycin) and doxorubicin and pharmaceutically acceptable salts or solvates, acids or derivatives of any of the above.

In one embodiment the antibodies of the instant invention may be associated with anti-CD3 binding molecules to recruit cytotoxic T-cells and have them target tumorigenic cells (BiTE technology; see e.g., Fuhrmann et. al. (2010) Annual Meeting of AACR Abstract No. 5625).

In further embodiments ADCs of the invention may comprise therapeutic radioisotopes conjugated using appropriate linkers. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium ($^{193}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{225}$Ac, $^{76}$Br, and $^{211}$At. Other radionuclides are also available as diagnostic and therapeutic agents, especially those in the energy range of 60 to 4,000 keV.

In certain preferred embodiments, the ADCs of the invention may comprise pyrrolobenzodiazepines (PBDs) as a cytotoxic agent and pharmaceutically acceptable salts or solvates, acids or derivatives thereof. PBDs are alkylating agents that exert antitumor activity by covalently binding to DNA in the minor groove and inhibiting nucleic acid synthesis. PBDs have been shown to have potent antitumor properties while exhibiting minimal bone marrow depression. PBDs compatible with the invention may be linked to an antibody using several types of linkers (e.g., a peptidyl linker comprising a maleimido moiety with a free sulfhydryl), and in certain embodiments are dimeric in form (i.e., PBD dimers). Compatible PBDs (and optional linkers) that may be conjugated to the disclosed antibodies are described, for example, in U.S. Pat. Nos. 6,362,331, 7,049,311, 7,189,710, 7,429,658, 7,407,951, 7,741,319, 7,557,099, 8,034,808, 8,163,736, 2011/0256157, WO2011/130613, WO2011/128650, WO2011/130616 and WO2014/057074.

Antibodies of the present invention may also be conjugated to biological response modifiers. For example, in particularly preferred embodiments the drug moiety can be a polypeptide possessing a desired biological activity. Such proteins may include, for example, a toxin such as abrin, ricin A, Onconase (or another cytotoxic RNase), *pseudomonas* exotoxin, cholera toxin, diphtheria toxin; an apoptotic agent such as tumor necrosis factor e.g. TNF-α or TNF-β, α-interferon, β-interferon, nerve growth factor, platelet derived growth factor, tissue plasminogen activator, AIM I (WO 97/33899), AIM II (WO 97/34911), Fas Ligand (Takahashi et al., 1994, PMID: 7826947), and VEGI (WO 99/23105), a thrombotic agent, an anti-angiogenic agent, e.g., angiostatin or endostatin, a lymphokine, for example, interleukin-1 (IL-1), interleukin-2 (IL-2), interleukin-6 (IL-6), granulocyte macrophage colony stimulating factor (GM-CSF), and granulocyte colony stimulating factor (G-CSF), or a growth factor e.g., growth hormone (GH).

B. Diagnostic or Detection Agents

In other preferred embodiments, the antibodies of the invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled antibodies can be useful for monitoring the development or progression of a hyperproliferative disorder or as part of a clinical testing procedure to determine the efficacy of a particular therapy including the disclosed antibodies (i.e. theragnostics) or to determine a future course of treatment. Such markers or reporters may also be useful in purifying the selected antibody, for use in antibody analytics (e.g., epitope binding or antibody binning), separating or isolating tumorigenic cells or in preclinical procedures or toxicology studies.

Such diagnosis, analysis and/or detection can be accomplished by coupling the antibody to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabeled or conjugated to specific radioisotopes. In such embodiments appropriate detection methodology is well known in the art and readily available from numerous commercial sources.

In other embodiments the antibodies or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In preferred embodiments, the marker comprises a histidine tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

C. Biocompatible Modifiers

In selected embodiments the antibodies of the invention may be conjugated with biocompatible modifiers that may be used to adjust, alter, improve or moderate antibody characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weights and molecular configurations that can be selected to impart specific properties to the antibody (e.g. the half-life may be tailored). PEG can be attached to antibodies or antibody fragments or derivatives with or without a multifunctional linker either through conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed antibodies can be conjugated to albumin in order to make the antibody or antibody fragment more stable in vivo or have a longer half-life in vivo. The techniques are well known in the art, see e.g., WO 93/15199, WO 93/15200, and WO 01/77137; and EP 0 413, 622. Other biocompatible conjugates are evident to those of ordinary skill and may readily be identified in accordance with the teachings herein.

D. Linker Compounds

Numerous linker compounds can be used to conjugate the antibodies of the invention to the relevant drug. Preferably linkers will covalently bind with the reactive residue (preferably a cysteine or lysine) and the selected drug compound. Accordingly, any linker that reacts with the selected antibody residue and may be used to provide the relatively stable conjugates (site-specific or otherwise) of the instant invention is compatible with the teachings herein.

Numerous compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein, thiol-maleimide bioconjugation is one of the most widely used approaches due to its fast reaction rates and mild conjugation conditions. One issue with this approach is the possibility of the retro-Michael reaction and loss or transfer of the maleimido-linked payload from the antibody to other proteins in the plasma, such as, for example, human serum albumin. However, in preferred embodiments the use of selective reduction and site-specific antibodies as set forth herein in Example 15 may be used to stabilize the conjugate and reduce this undesired transfer. Thiol-acyl halide reactions provide bioconjugates that cannot undergo retro-Michael reaction and therefore are more stable. However, the thiol-halide reactions in general have slower reaction rates compared to maleimide-based conjugations and are thus not as efficient. Thiol-pyridyl disulfide reaction is another popular bioconjugation route. The pyridyl disulfide undergoes fast exchange with free thiol resulting in the mixed disulfide and release of pyridine-2-thione. Mixed disulfides can be cleaved in the reductive cell environment releasing the payload. Other approaches gaining more attention in bioconjugation are thiol-vinylsulfone and thiol-bisulfone reactions, each of which are compatible with the teachings herein and expressly included within the scope of the invention.

In preferred embodiments compatible linkers will confer stability on the ADCs in the extracellular environment, prevent aggregation of the ADC molecules and keep the ADC freely soluble in aqueous media and in a monomeric state. Before transport or delivery into a cell, the ADC is preferably stable and remains intact, i.e. the antibody remains linked to the drug moiety. While the linkers are stable outside the target cell they are designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety. The stability of the ADC may be measured by standard analytical techniques such as mass spectroscopy, hydrophobic interaction chromatography (HIC), HPLC, and the separation/analysis technique LC/MS. As set forth above covalent attachment of the antibody and the drug moiety requires the linker to have two reactive functional groups, i.e. bivalency in a reactive sense. Bivalent linker reagents which are useful to attach two or more functional or biologically active moieties, such as MMAE and site-specific antibodies are known, and methods have been described to provide their resulting conjugates.

Linkers compatible with the present invention may broadly be classified as cleavable and non-cleavable linkers. Cleavable linkers, which may include acid-labile linkers, protease cleavable linkers and disulfide linkers, are internalized into the target cell and are cleaved in the endosomal-lysosomal pathway inside the cell. Release and activation of the cytotoxin relies on endosome/lysosome acidic compartments that facilitate cleavage of acid-labile chemical linkages such as hydrazone or oxime. If a lysosomal-specific protease cleavage site is engineered into the linker the cytotoxins will be released in proximity to their intracellular targets. Alternatively, linkers containing mixed disulfides provide an approach by which cytotoxic payloads are released intracellularly as they are selectively cleaved in the reducing environment of the cell, but not in the oxygen-rich environment in the bloodstream. By way of contrast, compatible non-cleavable linkers containing amide linked polyethyleneglycol or alkyl spacers liberate toxic payloads during lysosomal degradation of the ADC within the target cell. In some respects the selection of linker will depend on the particular drug used in the conjugate.

Accordingly, certain embodiments of the invention comprise a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since cathepsin-B has been found to be highly expressed in cancerous tissue. Other examples of such linkers are described, for example, in U.S. Pat. No. 6,214,345. In a specific preferred embodiment, the peptidyl linker cleavable by an intracellular protease is a Val-Cit linker, a Val-Ala linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive. Typically, the pH-sensitive linker will be hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyl-dithio)-toluene). In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In particularly preferred embodiments (set forth in U.S.P.N. 2011/0256157) compatible peptidyl linkers will comprise:

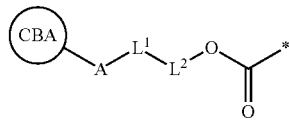

where the asterisk indicates the point of attachment to the drug, CBA is the anti-CLDN antibody, $L^1$ is a linker, A is a connecting group connecting $L^1$ to a reactive residue on the antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of the drug.

In one embodiment, $L^1$ is cleavable by the action of an enzyme. In one embodiment, the enzyme is an esterase or a peptidase.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg- and -Trp-Cit- where Cit is citrulline.

Preferably, the group —$X_1$—$X_2$— in dipeptide, —NH—$X_1$—$X_2$—CO—, is selected from: -Phe-Lys-, -Val-Ala-, -Val-Lys-, -Ala-Lys-, and -Val-Cit-.

Most preferably, the group —$X_1$—$X_2$— in dipeptide, —NH—$X_1$—$X_2$—CO—, is -Phe-Lys- or -Val-Ala-. In one embodiment, $L^2$ is present and together with —C(=O)O— forms a self-immolative linker. In one embodiment, $L^2$ is a substrate for enzymatic activity, thereby allowing release of the drug. In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

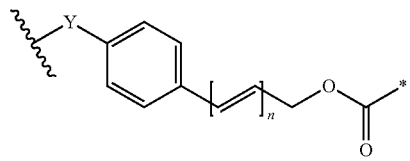

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

In another particularly preferred embodiments the linker may include a self-immolative linker and the dipeptide together form the group —NH-Val-Ala-CO—NH-PABC-, which is illustrated below:

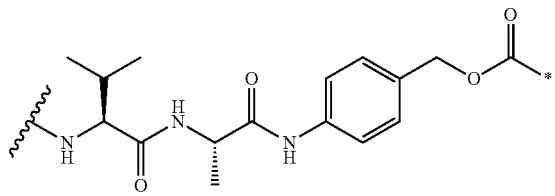 [SMILES: *N[C@H](C(=O)N[C@@H](C)C(=O)Nc1ccc(COC(*)=O)cc1)C(C)C]

where the asterisk indicates the point of attachment to the selected cytotoxic moiety, and the wavy line indicates the point of attachment to the remaining portion of the linker (e.g., the spacer-antibody binding segments) which may be conjugated to the antibody. Upon enzymatic cleavage of the dipeptide the self-immolative linker will allow for clean release of the protected compound (i.e., the cytotoxin) when a remote site is activated, proceeding along the lines shown below:

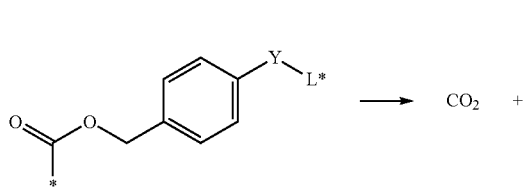

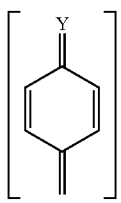 + L* where L* is the activated form of the remaining portion of the linker comprising the now cleaved peptidyl unit. The clean release of the drug ensures they will maintain the desired toxic activity.

In one embodiment, A is a covalent bond. Thus, $L^1$ and the antibody are directly connected. For example, where $L^1$ comprises a contiguous amino acid sequence, the N-terminus of the sequence may connect directly to the antibody residue.

In another embodiment, A is a spacer group. Thus, $L^1$ and the antibody are indirectly connected.

$L^1$ and A may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

As will be discussed in more detail below the drug linkers of the instant invention will preferably be linked to reactive thiol nucleophiles on cysteines, including free cysteines. To this end the cysteines of the antibodies may be made reactive for conjugation with linker reagents by treatment with various reducing agent such as DTT or TCEP or mild reducing agents as set forth herein. In other embodiments the drug linkers of the instant invention will preferably be linked to a lysine.

Preferably, the linker contains an electrophilic functional group for reaction with a nucleophilic functional group on the antibody. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, and carboxyl.

In particularly preferred embodiments the connection between a site-specific antibody and the drug-linker moiety is through a thiol residue of a free cysteine of the site specific antibody and a terminal maleimide group of present on the linker. In such embodiments, the connection between the antibody and the drug-linker is:

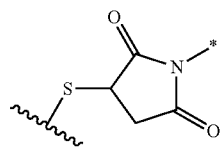 [SMILES: *SC1CC(=O)N(*)C1=O]

where the asterisk indicates the point of attachment to the remaining portion of drug-linker and the wavy line indicates the point of attachment to the remaining portion of the antibody. In this embodiment, the S atom is preferably derived from a site-specific free cysteine. With regard to other compatible linkers the binding moiety comprises a terminal iodoacetamide that may be reacted with activated residues to provide the desired conjugate. In any event one skilled in the art could readily conjugate each of the disclosed drug-linker compounds with a compatible anti-CLDN site-specific antibody in view of the instant disclosure.

E. Conjugation

It will be appreciated that a number of well known different reactions may be used to attach the drug moiety and/or linker to the selected antibody. For example, various reactions exploiting sulfhydryl groups of cysteines may be employed to conjugate the desired moiety. Particularly preferred embodiments will comprise conjugation of antibodies comprising one or more free cysteines as discussed in detail below. In other embodiments ADCs of the instant invention may be generated through conjugation of drugs to solvent-exposed amino groups of lysine residues present in the selected antibody. Still other embodiments comprise activation of the N-terminal threonine and serine residues which may then be used to attach the disclosed payloads to the antibody. The selected conjugation methodology will preferably be tailored to optimize the number of drugs attached to the antibody and provide a relatively high therapeutic index.

Various methods are known in the art for conjugating a therapeutic compound to a cysteine residue and will be apparent to the skilled artisan. Under basic conditions the cysteine residues will be deprotonated to generate a thiolate nucleophile which may be reacted with soft electrophiles, such as maleimides and iodoacetamides. Generally reagents for such conjugations may react directly with a cysteine thiol of a cysteine to form the conjugated protein or with a linker-drug to form a linker-drug intermediate. In the case of a linker, several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form a drug-linker intermediate, via a covalent bond, followed by reaction with a cysteine group of a protein of the invention. As will be apparent to the skilled artisan from the foregoing, bifunctional linkers are useful in the present invention. For example, the bifunctional linker may comprise a thiol modification group for covalent linkage to the cysteine residue(s) and at least one attachment moiety (e.g., a second thiol modification moiety) for covalent or non-covalent linkage to the compound.

Prior to conjugation, antibodies may be made reactive for conjugation with linker reagents by treatment with a reducing agent such as dithiothreitol (DTT) or (tris(2-carboxyethyl)phosphine (TCEP). In other embodiments additional nucleophilic groups can be introduced into antibodies through the reaction of lysines with reagents, including but not limited to, 2-iminothiolane (Traut's reagent), SATA, SATP or SAT(PEG)4, resulting in conversion of an amine into a thiol.

With regard to such conjugations cysteine thiol or lysine amino groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Preferred labelling reagents include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used. In certain embodiments methods include, for example, the use of maleimides, iodoacetimides or haloacetyl/alkyl halides, aziridne, acryloyl derivatives to react with the thiol of a cysteine to produce a thioether that is reactive with a compound. Disulphide exchange of a free thiol with an activated piridyldisulphide is also useful for producing a conjugate (e.g., use of 5-thio-2-nitrobenzoic (TNB) acid). Preferably, a maleimide is used.

As indicated above, lysine may also be used as a reactive residue to effect conjugation as set forth herein. The nucleophilic lysine residue is commonly targeted through amine-reactive succinimidylesters. To obtain an optimal number of deprotonated lysine residues, the pH of the aqueous solution must be below the pKa of the lysine ammonium group, which is around 10.5, so the typical pH of the reaction is about 8 and 9. The common reagent for the coupling reaction is NHS-ester which reacts with nucleophilic lysine through a lysine acylation mechanism. Other compatible reagents that undergo similar reactions comprise isocyanates and isothiocyanates which also may be used in conjunction with the teachings herein to provide ADCs. Once the lysines have been activated, many of the aforementioned linking groups may be used to covalently bind the warhead to the antibody.

Methods are also known in the art for conjugating a compound to a threonine or serine residue (preferably a N-terminal residue). For example methods have been described in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labelling proteins at N-terminal serine or threonine residues.

In particularly preferred embodiments reactive thiol groups may be introduced into the selected antibody (or fragment thereof) by introducing one, two, three, four, or more free cysteine residues (e.g., preparing antibodies comprising one or more free non-native cysteine amino acid residues). Such site-specific antibodies or engineered antibodies, allow for conjugate preparations that exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites (and is fully compatible with the instant invention), the present invention additionally provides for the selective reduction of certain prepared free cysteine sites and direction of the drug-linker to the same. The conjugation specificity promoted by the engineered sites and the selective reduction allows for a high percentage of site directed conjugation at the desired positions. Significantly some of these conjugation sites, such as those present in the terminal region of the light chain constant region, are typically difficult to conjugate effectively as they cross-react with other free cysteines. However, through molecular engineering and selective reduction of the resulting free cysteines efficient conjugation rates may be obtained which considerably reduces unwanted high-DAR contaminants and non-specific toxicity. More generally the engineered constructs and disclosed novel conjugation methods comprising selective reduction provide ADC preparations having improved pharmacokinetics and/or pharmacodynamics and, potentially, an improved therapeutic index.

The site-specific constructs present free cysteine(s), which when reduced comprise thiol groups that are nucleophilic and capable of reacting to form covalent bonds with electrophilic groups on linker moieties such as those disclosed above. Preferred antibodies of the instant invention will have reducible unpaired interchain or intrachain cysteines, i.e. cysteines providing such nucleophilic groups. Thus, in certain embodiments the reaction of free sulfhydryl groups of the reduced unpaired cysteines and the terminal maleimido or haloacetamide groups of the disclosed drug-linkers will provide the desired conjugation. In such cases the free cysteines of the antibodies may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile. While such reagents are compatible it will be appreciated that conjugation of the site-specific antibodies may be effected using various reactions, conditions and reagents known to those skilled in the art.

In addition it has been found that the free cysteines of engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this may be affected by certain reducing agents. In other preferred embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced with a cytotoxin as described herein. In this respect the use of such stabilizing agents in combination with reducing agents can markedly improve the efficiency of site-specific conjugation as determined by extent of conjugation on the heavy and light antibody chains and DAR distribution of the preparation.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site. Such agents (e.g., certain amino acids) are known to form salt bridges (via hydrogen bonding and electrostatic interactions) and may modulate protein-protein interactions in such a way as to impart a stabilizing effect that may cause favorable conformation changes and/or may reduce unfavorable protein-protein interactions. Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since the reaction conditions do not provide for the significant reduction of intact native disulfide bonds the conjugation reaction is naturally driven to the relatively few reactive thiols on the free cysteines (e.g., preferably 2 free thiols). As previously alluded to this considerably reduces the levels of non-specific conjugation and corresponding impurities in conjugate preparations fabricated as set forth herein.

In selected embodiments stabilizing agents compatible with the present invention will generally comprise compounds with at least one amine moiety having a basic pKa. In certain embodiments the amine moiety will comprise a primary amine while in other preferred embodiments the amine moiety will comprise a secondary amine. In still other preferred embodiments the amine moiety will comprise a tertiary amine. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In particularly preferred embodiments, compatible stabilizing agents may comprise arginine, lysine, proline and cysteine. In addition compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other preferred embodiments will comprise stabilizing agents where the amine moiety will have a pKa of greater than about 9.5 while certain other embodiments will comprise stabilizing agents exhibiting at least one amine moiety having a pKa of greater than about 10.0. In still other preferred embodiments the stabilizing agent will comprise a compound having the amine moiety with a pKa of greater than about 10.5, in other embodiments the stabilizing agent will comprise a compound having a amine moiety with a pKa greater than about 11.0, while in still other embodiments the stabilizing agent will comprise a amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the engineered antibody native disulfide bonds. Under such conditions, provided by the combination of selected stabilizing and reducing agents, the activated drug linker is largely limited to binding to the desired free site-specific cysteine site. Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In preferred embodiments mild reducing agents may comprise compounds having one or more free thiols while in particularly preferred embodiments mild reducing agents will comprise compounds having a single free thiol. Non-limiting examples of reducing agents compatible with the instant invention comprise glutathione, n-acetyl cysteine, cysteine, 2-aminoethane-1-thiol and 2-hydroxyethane-1-thiol.

It will be appreciated that selective reduction process set forth above is particularly effective at targeted conjugation to the free cysteine. In this respect the extent of conjugation to the desired target site (defined here as "conjugation efficiency") in site-specific antibodies may be determined by various art-accepted techniques. The efficiency of the site-specific conjugation of a drug to an antibody may be determined by assessing the percentage of conjugation on the target conjugation site (in this invention the free cysteine on the c-terminus of the light chain) relative to all other conjugated sites. In certain embodiments, the method herein provides for efficiently conjugating a drug to an antibody comprising free cysteines. In some embodiments, the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the percentage of target conjugation relative to all other conjugation sites.

It will further be appreciated that engineered antibodies capable of conjugation may contain free cysteine residues that comprise sulfhydryl groups that are blocked or capped as the antibody is produced or stored. Such caps include proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed herein such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

F. DAR Distribution and Purification

One of the advantages of conjugation with site specific antibodies of the present invention is the ability to generate relatively homogeneous ADC preparations comprising a narrow DAR distribution. In this regard the disclosed constructs and/or selective conjugation provides for homogeneity of the ADC species within a sample in terms of the stoichiometric ratio between the drug and the engineered antibody. As briefly discussed above the term "drug to antibody ratio" or "DAR" refers to the molar ratio of drug to antibody. In some embodiments a conjugate preparation may be substantially homogeneous with respect to its DAR distribution, meaning that within the preparation is a predominant species of site-specific ADC with a particular DAR (e.g., a DAR of 2 or 4) that is also uniform with respect to the site of loading (i.e., on the free cysteines). In certain embodiments of the invention it is possible to achieve the desired homogeneity through the use of site-specific antibodies or selective combination. In other preferred embodiments the desired homogeneity may be achieved through the use of site-specific constructs in combination with selective reduction. In yet other particularly preferred embodiments the preparations may be further purified using analytical or preparative chromatography techniques. In each of these embodiments the homogeneity of the ADC sample can be analyzed using various techniques known in the art including but not limited to SDS-PAGE, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As discussed herein liquid chromatography methods such as reverse phase (RP) and hydrophobic interaction chromatography (HIC) may separate compounds in the mixture by drug loading value. In some cases, mixed-mode chromatography (MMC) may also be used to isolate species with a specific drug load. More generally, once insoluble contaminants are removed the antibody preparation may be further purified using standard techniques such as, for example, hydroxylapatite chromatography, gel electrophoresis, dialysis, and affinity chromatography, with affinity chromatography of particular interest. In this regard protein A can be used to purify antibodies that are based on human IgG1, IgG2 or IgG4 heavy chains while protein G is recommended for all mouse isotypes and for human IgG3. Other techniques for protein purification such as fractionation on an ion-exchange column, ethanol precipitation, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody or conjugate to be recovered.

The disclosed ADCs and preparations thereof may comprise drug and antibody moieties in various stoichiometric molar ratios depending on the configuration of the antibody (e.g., an engineered construct) and, at least in part, on the method used to effect conjugation. In certain embodiments the drug loading per ADC may comprise from 1-20 warheads (i.e., n is 1-20). Other selected embodiments may comprise ADCs with a drug loading of from 1 to 15 warheads. In still other embodiments the ADCs may comprise from 1-12 warheads or, more preferably, from 1-10 warheads. In certain preferred embodiments the ADCs will comprise from 1 to 8 warheads.

With regard to site-specific conjugates. depending on how many and which interchain and intrachain disulfide bonds are disrupted theoretical drug loading may be relatively high though practical limitations such as free cysteine cross reactivity would limit the generation of homogeneous preparations comprising such DAR due to aggregates and other contaminants. That is, higher drug loading, e.g. >6, may cause aggregation, insolubility, toxicity, or loss of cellular permeability of certain antibody-drug conjugates. In view of such concerns practical drug loading provided by the instant invention preferably ranges from 1 to 8 drugs per conjugate, i.e. where 1, 2, 3, 4, 5, 6, 7, or 8 drugs are covalently attached to each antibody (e.g., for IgG1, other antibodies may have different loading capacity depending the number of disulfide bonds). Preferably the DAR of compositions of the instant invention will be approximately 2, 4 or 6 and in particularly preferred embodiments the DAR will comprise approximately 2.

Despite the relatively high level of homogeneity provided by the instant invention the disclosed compositions actually comprise a mixture of conjugates with a range of drug loads (e.g., from 1 to 8 drugs per IgG1 antibody) at various concentrations (along with certain reaction contaminants primarily caused by free cysteine cross reactivity); and which comprise drug moieties that are attached to the antibody by various thiol groups. Using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Due to inherent uncertainty in the quantification methodology employed and the difficulty in completely removing the non-predominant ADC species in a commercial setting, acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in certain preferred embodiments the present invention will comprise compositions having an average DAR of 1, 2, 3, 4, 5, 6, 7 or 8 each +/−0.5. In other preferred embodiments the present invention will comprise an average DAR of 2, 4, 6 or 8+/−0.5. Finally, in selected preferred embodiments the present invention will comprise an average DAR of 2+/−0.5. It will be appreciated that the range or deviation may be less than 0.4 in certain preferred embodiments. Thus, in other embodiments the compositions will comprise an average DAR of 1, 2, 3, 4, 5, 6, 7 or 8 each +/−0.3, an average DAR of 2, 4, 6 or 8+/−0.3, even more preferably an average DAR of 2 or 4+/−0.3 or even an average DAR of 2+/−0.3. In other embodiments IgG1 conjugate compositions will preferably comprise a composition with an average DAR of 1, 2, 3, 4, 5, 6, 7 or 8 each +/−0.4 and relatively low levels (i.e., less than 30%) of non-predominant ADC species. In other preferred embodiments the ADC composition will comprise an average DAR of 2, 4, 6 or 8 each +/−0.4 with relatively low levels (<30%) of non-predominant ADC species. In particularly preferred embodiments the ADC composition will comprise an average DAR of 2+/−0.4 with relatively low levels (<30%) of non-predominant ADC species. In yet other embodiments the predominant ADC species (e.g., DAR of 2) will be present at a concentration of greater than 70%, a concentration of greater than 75%, a concentration of greater that 80%, a concentration of greater than 85%, a concentration of greater than 90%, a concentration of greater than 93%, a concentration of greater than 95% or even a concentration of greater than 97% when measured against other DAR species.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined. By ELISA, the averaged value of the drugs per antibody in a particular preparation of ADC may be determined. However, the distribution of drug per antibody values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues.

VI DIAGNOSTICS AND SCREENING

A. Diagnostics

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc.

In a particularly preferred embodiment the antibodies of the instant invention may be used to detect and quantify levels of a particular determinant (e.g., CLDN) in a patient sample (e.g., plasma or blood) which may, in turn, be used to detect, diagnose or monitor proliferative disorders that are associated with the relevant determinant. In related embodiments the antibodies of the instant invention may be used to detect, monitor and/or quantify circulating tumor cells either in vivo or in vitro (WO 2012/0128801). In still other embodiments the circulating tumor cells may comprise tumorigenic cells.

In certain embodiments of the invention, the tumorigenic cells in a subject or a sample from a subject may be assessed or characterized using the disclosed antibodies prior to therapy or regimen to establish a baseline. In other examples, the tumorigenic cells can be assessed from a sample that is derived from a subject that was treated.

B. Screening

In certain embodiments, the antibodies can be used to screen samples in order to identify compounds or agents (e.g., antibodies or ADCs) that alter a function or activity of tumor cells by interacting with a determinant. In one embodiment, tumor cells are put in contact with an antibody or ADC and the antibody or ADC can be used to screen the tumor for cells expressing a certain target (e.g. CLDN) in order to identify such cells for purposes, including but not limited to, diagnostic purposes, to monitor such cells to determine treatment efficacy or to enrich a cell population for such target-expressing cells.

In yet another embodiment, a method includes contacting, directly or indirectly, tumor cells with a test agent or compound and determining if the test agent or compound modulates an activity or function of the determinant-associated tumor cells for example, changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

Screening methods include high throughput screening, which can include arrays of cells (e.g., microarrays) positioned or placed, optionally at pre-determined locations, for example, on a culture dish, tube, flask, roller bottle or plate. High-throughput robotic or manual handling methods can probe chemical interactions and determine levels of expression of many genes in a short period of time. Techniques have been developed that utilize molecular signals, for example via fluorophores or microarrays (Mocellin and Rossi, 2007, PMID: 17265713) and automated analyses that process information at a very rapid rate (see, e.g., Pinhasov et al., 2004, PMID: 15032660). Libraries that can be screened include, for example, small molecule libraries, phage display libraries, fully human antibody yeast display libraries (Adimab), siRNA libraries, and adenoviral transfection vectors.

VII PHARMACEUTICAL PREPARATIONS AND THERAPEUTIC USES

A. Formulations and Routes of Administration

The antibodies or ADCs of the invention can be formulated in various ways using art recognized techniques. In some embodiments, the therapeutic compositions of the invention can be administered neat or with a minimum of additional components while others may optionally be formulated to contain suitable pharmaceutically acceptable carriers. As used herein, "pharmaceutically acceptable carriers" comprise excipients, vehicles, adjuvants and diluents that are well known in the art and can be available from commercial sources for use in pharmaceutical preparation (see, e.g., Gennaro (2003) *Remington: The Science and Practice of Pharmacy with Facts and Comparisons: Drugfacts Plus,* 20th ed., Mack Publishing; Ansel et al. (2004) *Pharmaceutical Dosage Forms and Drug Delivery Systems,* $7^{th}$ ed., Lippencott Williams and Wilkins; Kibbe et al. (2000) *Handbook of Pharmaceutical Excipients,* $3^{rd}$ ed., Pharmaceutical Press.)

Suitable pharmaceutically acceptable carriers comprise substances that are relatively inert and can facilitate administration of the antibody or can aid processing of the active compounds into preparations that are pharmaceutically optimized for delivery to the site of action.

Such pharmaceutically acceptable carriers include agents that can alter the form, consistency, viscosity, pH, tonicity, stability, osmolarity, pharmacokinetics, protein aggregation or solubility of the formulation and include buffering agents, wetting agents, emulsifying agents, diluents, encapsulating agents and skin penetration enhancers. Certain non-limiting examples of carriers include saline, buffered saline, dextrose, arginine, sucrose, water, glycerol, ethanol, sorbitol, dextran, sodium carboxymethyl cellulose and combinations thereof. Antibodies for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington: The Science and Practice of Pharmacy* (2000) 20th Ed. Mack Publishing.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable carriers, such as anti-oxidants, buffers, preservatives, stabilizers, bacteriostats, suspending agents, thickening agents, and solutes that render the formulation isotonic with the blood (or other relevant bodily fluid) of the intended recipient. Examples of excipients include, for example, water, alcohols, polyols, glycerol, vegetable oils, and the like. Examples of suitable isotonic pharmaceutically acceptable carriers for use in such formulations include Sodium Chloride Injection, Ringer's Solution, or Lactated Ringer's Injection.

Compatible formulations for parenteral administration (e.g., intravenous injection) may comprise ADC or antibody concentrations of from about 10 µg/mL to about 100 mg/mL. In certain selected embodiments antibody or ADC concentrations will comprise 20 µg/mL, 40 µg/mL, 60 µg/mL, 80 µg/mL, 100 µg/mL, 200 µg/mL, 300, µg/mL, 400 µg/mL, 500 µg/mL, 600 µg/mL, 700 µg/mL, 800 µg/mL, 900 µg/mL or 1 mg/mL. In other preferred embodiments ADC concentrations will comprise 2 mg/mL, 3 mg/mL, 4 mg/mL, 5 mg/mL, 6 mg/mL, 8 mg/mL, 10 mg/mL, 12 mg/mL, 14 mg/mL, 16 mg/mL, 18 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL or 100 mg/mL.

The compounds and compositions of the invention may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

The particular dosage regimen, i.e., dose, timing and repetition, will depend on the particular individual, as well as empirical considerations such as pharmacokinetics (e.g., half-life, clearance rate, etc.). Determination of the frequency of administration may be made by persons skilled in the art, such as an attending physician based on considerations of the condition and severity of the condition being treated, age and general state of health of the subject being treated and the like. Frequency of administration may be adjusted over the course of therapy based on assessment of the efficacy of the selected composition and the dosing regimen. Such assessment can be made on the basis of markers of the specific disease, disorder or condition. In embodiments where the individual has cancer, these include direct measurements of tumor size via palpation or visual observation; indirect measurement of tumor size by x-ray or other imaging techniques; an improvement as assessed by direct tumor biopsy and microscopic examination of a tumor sample; the measurement of an indirect tumor marker (e.g., PSA for prostate cancer) or an antigen identified according to the methods described herein; reduction in the number of proliferative or tumorigenic cells, maintenance of the reduction of such neoplastic cells; reduction of the proliferation of neoplastic cells; or delay in the development of metastasis.

The CLDN antibodies or ADCs of the invention may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the CLDN antibodies or ADCs will be administered (preferably intravenously) at approximately 10, 20, 30, 40, 50, 60, 70, 80, 90 or 100 µg/kg body weight per dose. Other embodiments may comprise the administration of ADCs at about 200, 300, 400, 500, 600, 700, 800, 900, 1000, 1100, 1200, 1300, 1400, 1500, 1600, 1700, 1800, 1900 or 2000 µg/kg body weight per dose. In other preferred embodiments the disclosed conjugates will be administered at 2.5, 3, 3.5, 4, 4.5, 5, 5.5, 6, 6.5, 7, 7.58, 9 or 10 mg/kg. In still other embodiments the conjugates may be administered at 12, 14, 16, 18 or 20 mg/kg body weight per dose. In yet other embodiments the conjugates may be administered at 25, 30, 35, 40, 45, 50, 55, 60, 65, 70, 75, 80, 90 or 100 mg/kg body weight per dose. With the teachings herein one of skill in the art could readily determine appropriate dosages for various CLDN antibodies or ADCs based on preclinical animal studies, clinical observations and standard medical and biochemical techniques and measurements.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the conjugates may be administered in dosages from 1 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$. It will also be appreciated that art recognized and empirical techniques may be used to determine appropriate dosage.

Anti-CLDN antibodies or ADCs may be administered on a specific schedule. Generally, an effective dose of the CLDN conjugate is administered to a subject one or more times. More particularly, an effective dose of the ADC is administered to the subject once a month, more than once a month, or less than once a month. In certain embodiments, the effective dose of the CLDN antibody or ADC may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed antibodies or ADCs.

In certain preferred embodiments the course of treatment involving conjugated antibodies will comprise multiple doses of the selected drug product over a period of weeks or months. More specifically, antibodies or ADCs of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Combination Therapies

The CLDN proteins are expressed in the tight junctions of epithelial cells where they are thought to establish the paracellular barrier that controls the flow of molecules in the intercellular space between epithelial cells. The use of an anti-CLDN antibodies may result in the disruption of the tight junctions of epithelial cells and thus improve access of therapeutics that otherwise would not be able to penetrate cancer cells. Thus, the use of various therapies in combination with the anti-CLDN antibodies and ADCs of the invention may be useful in preventing or treating cancer and in preventing metastasis or recurrence of cancer. "Combination therapy", as used herein, means the administration of a combination comprising at least one anti-CLDN antibody or ADC and at least one therapeutic moiety (e.g., anti-cancer agent) wherein the combination preferably has therapeutic synergy or improves the measurable therapeutic effects in the treatment of cancer over (i) the anti-CLDN antibody or ADC used alone, or (ii) the therapeutic moiety used alone, or (iii) the use of the therapeutic moiety in combination with another therapeutic moiety without the addition of an anti-CLDN antibody or ADC. The term "therapeutic synergy", as used herein, means the combination of an anti-CLDN antibody or ADC and one or more therapeutic moiety(ies) having a therapeutic effect greater than the additive effect of the combination of the anti-CLDN antibody or ADC and the one or more therapeutic moiety(ies).

Desired outcomes of the disclosed combinations are quantified by comparison to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the anti-CLDN antibodies or ADCs described herein but in the presence of other therapeutic moiety(ies) such as standard of care treatment. A representative control individual is an individual afflicted with the same form of cancer as the individual being treated, who is about the same age as the individual being treated (to ensure that the stages of the disease in the treated individual and the control individual are comparable.)

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," a "p-value" can be calculated. P-values that fall below a user-defined cut-off point are regarded as significant. A p-value less than or equal to 0.1, less than 0.05, less than 0.01, less than 0.005, or less than 0.001 may be regarded as significant.

A synergistic therapeutic effect may be an effect of at least about two-fold greater than the therapeutic effect elicited by a single therapeutic moiety or anti-CLDN antibody or ADC, or the sum of the therapeutic effects elicited by the anti-CLDN antibody or ADC or the single therapeutic moiety (ies) of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single therapeutic moiety or anti-CLDN antibody or ADC, or the sum of the therapeutic effects elicited by the anti-CLDN antibody or ADC or the single therapeutic moiety(ies) of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

In practicing combination therapy, the anti-CLDN antibody or ADC and therapeutic moiety(ies) may be administered to the subject simultaneously, either in a single composition, or as two or more distinct compositions using the same or different administration routes. Alternatively, treatment with the anti-CLDN antibody or ADC may precede or follow the therapeutic moiety treatment by, e.g., intervals ranging from minutes to weeks. In one embodiment, both the therapeutic moiety and the antibody or ADC are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the antibody and the therapeutic moiety.

The combination therapy can be administered until the condition is treated, palliated or cured on various schedules such as once, twice or three times daily, once every two days, once every three days, once weekly, once every two weeks, once every month, once every two months, once every three months, once every six months, or may be administered continuously. The antibody and therapeutic moiety(ies) may be administered on alternate days or weeks; or a sequence of anti-CLDN antibody or ADC treatments may be given, followed by one or more treatments with the additional therapeutic moiety. In one embodiment an anti-CLDN antibody or ADC is administered in combination with one or more therapeutic moiety(ies) for short treatment cycles. In other embodiments the combination treatment is administered for long treatment cycles. The combination therapy can be administered via any route.

In some embodiments the anti-CLDN antibodies or ADCs may be used in combination with various first line cancer treatments. In one embodiment the combination therapy comprises the use of an anti-CLDN antibody or ADC and a platinum analog (e.g. ifosfamide, mytomycin C, vindesine, vinblastine, etoposide, ironitecan, gemcitabine, taxanes, vinorelbine, methotrexate, and pemetrexed) and optionally one or more other therapeutic moiety(ies).

In another embodiment the combination therapy comprises the use of an anti-CLDN antibody or ADC and a platinum-based drug (e.g. carboplatin or cisplatin) and optionally one or more other therapeutic moiety(ies) (e.g. vinorelbine; gemcitabine; a taxane such as, for example, docetaxel or paclitaxel; irinotican; or pemetrexed).

In another embodiment combination therapy for the treatment of EGFR-positive NSCLC comprises the use of an anti-CLDN antibody or ADC and afatinib and optionally one or more other therapeutic moiety(ies) (e.g. erlotinib and/or bevacizumab).

In another embodiment combination therapy for the treatment of EGFR-positive NSCLC comprises the use of an anti-CLDN antibody or ADC and erlotinib and optionally one or more other therapeutic moiety(ies) (e.g. bevacizumab).

In another embodiment combination therapy for the treatment of ALK-positive NSCLC comprises the use of an anti-CLDN antibody or ADC and ceritinib and optionally one or more other therapeutic moiety(ies).

In another embodiment combination therapy for the treatment of ALK-positive NSCLC comprises the use of an anti-CLDN antibody or ADC and crizotinib and optionally one or more other therapeutic moiety(ies).

In another embodiment the combination therapy comprises the use of an anti-CLDN antibody or ADC and bevacizumab and optionally one or more other therapeutic moiety(ies) (e.g. a taxane such as, for example, docetaxel or paclitaxel; and/or a platinum analog).

In another embodiment the combination therapy comprises the use of an anti-CLDN antibody or ADC and bevacizumab and optionally one or more other therapeutic moiety(ies) (e.g. gemcitabine and/or a platinum analog).

In one embodiment the combination therapy comprises the use of an anti-CLDN antibody or ADC and platinum-based drug (e.g. carboplatin or cisplatin) analog and optionally one or more other therapeutic moiety(ies) (e.g. a taxane such as, for example, docetaxel and paclitaxel).

In one embodiment the combination therapy comprises the use of an anti-CLDN antibody or ADC and platinum-based drug (e.g. carboplatin or cisplatin) analog and optionally one or more other therapeutic moiety(ies) (e.g. a taxane such, for example, docetaxel and paclitaxel and/or gemcitabine and/or doxorubicin).

In a particular embodiment the combination therapy for the treatment of platinum-resistant tumors comprises the use of an anti-CLDN antibody or ADC and doxorubicin and/or etoposide and/or gemcitabine and/or vinorelbine and/or ifosfamide and/or leucovorin-modulated 5-fluoroucil and/or bevacizumab and/or tamoxifen; and optionally one or more other therapeutic moiety(ies).

In another embodiment the combination therapy comprises the use of an anti-CLDN antibody or ADC and a PARP inhibitor and optionally one or more other therapeutic moiety(ies).

In another embodiment the combination therapy comprises the use of an anti-CLDN antibody or ADC and bevacizumab and optionally cyclophosphamide.

The invention also provides for the combination of anti-CLDN antibodies or ADCs with radiotherapy. The term "radiotherapy", as used herein, means, any mechanism for inducing DNA damage locally within tumor cells such as gamma-irradiation, X-rays, UV-irradiation, microwaves, electronic emissions and the like. Combination therapy using the directed delivery of radioisotopes to tumor cells is also contemplated, and may be used in combination or as a conjugate of the anti-CLDN antibodies disclosed herein. Typically, radiation therapy is administered in pulses over a period of time from about 1 to about 2 weeks. Optionally, the radiation therapy may be administered as a single dose or as multiple, sequential doses.

In other embodiments an anti-CLDN antibody or ADC may be used in combination with one or more of the anti-cancer agents described below.

D. Anti-Cancer Agents

The term "anti-cancer agent" or "chemotherapeutic agent" as used herein is one subset of "therapeutic moieties", which in turn is a subset of the agents described as "pharmaceutically active moieties". More particularly "anti-cancer agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, biological response modifiers, therapeutic antibodies, cancer vaccines, cytokines, hormone therapy, anti-metastatic agents and immunotherapeutic agents. It will be appreciated that in selected embodiments as discussed above, such anti-cancer agents may comprise conjugates and may be associated with antibodies prior to administration. In certain embodiments the disclosed anti-cancer agent will be linked to an antibody to provide an ADC as disclosed herein.

The term "cytotoxic agent", which can also be an anti-cancer agent means a substance that is toxic to the cells and decreases or inhibits the function of cells and/or causes destruction of cells. Typically, the substance is a naturally occurring molecule derived from a living organism (or a synthetically prepared natural product). Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca* mericana proteins (PAPI, PAPII, and PAP-S), *Momordica charantia* inhibitor, curcin, crotin, *saponaria officinalis* inhibitor, mitegellin, restrictocin, phenomycin, neomycin, and the tricothecenes) or animals, (e.g., cytotoxic RNases, such as extracellular pancreatic RNases; DNase I, including fragments and/or variants thereof).

An anti-cancer agent can include any chemical agent that inhibits, or is designed to inhibit, a cancerous cell or a cell likely to become cancerous or generate tumorigenic progeny (e.g., tumorigenic cells). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. Such agents are often administered, and are often most effective, in combination, e.g., in the formulation CHOP. Again, in selected embodiments such anti-cancer agents may be conjugated to the disclosed antibodies.

Examples of anti-cancer agents that may be used in combination with (or conjugated to) the antibodies of the invention include, but are not limited to, alkylating agents, alkyl sulfonates, anastrozole, amanitins, aziridines, ethylenimines and methylamelamines, acetogenins, a camptothecin, BEZ-235, bortezomib, bryostatin, callystatin, CC-1065, ceritinib, crizotinib, cryptophycins, dolastatin, duocarmycin, eleutherobin, erlotinib, pancratistatin, a sarcodictyin, spongistatin, nitrogen mustards, antibiotics, enediyne dynemicin, bisphosphonates, esperamicin, chromoprotein enediyne antiobiotic chromophores, aclacinomysins, actinomycin, authramycin, azaserine, bleomycins, cactinomycin, canfosfamide, carabicin, carminomycin, carzinophilin, chromomycinis, cyclosphosphamide, dactinomycin, daunorubicin, detorubicin, 6-diazo-5-oxo-L-norleucine, doxorubicin, epirubicin, esorubicin, exemestane, fluorouracil, fulvestrant, gefitinib, idarubicin, lapatinib, letrozole, lonafarnib, marcellomycin, megestrol acetate, mitomycins, mycophenolic acid, nogalamycin, olivomycins, pazopanib, peplomycin, potfiromycin, puromycin, quelamycin, rapamycin, rodorubicin, sorafenib, streptonigrin, streptozocin, tamoxifen, tamoxifen citrate, temozolomide, tepodina, tipifarnib, tubercidin, ubenimex, vandetanib, vorozole, XL-147, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, polysaccharide complex, razoxane; rhizoxin; SF-1126, sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside; cyclophosphamide; thiotepa; taxoids, chloranbucil; gemcitabine; 6-thioguanine; mercaptopurine; methotrexate; platinum analogs, vinblastine; platinum; etoposide; ifosfamide; mitoxantrone; vincristine; vinorelbine; novantrone; teniposide; edatrexate; daunomycin; aminopterin; xeloda; ibandronate; irinotecan, topoisomerase inhibitor RFS 2000; difluorometlhylornithine; retinoids; capecitabine; combretastatin; leucovorin; oxaliplatin; XL518, inhibitors of PKC-alpha, Raf, H-Ras, EGFR and VEGF-A that reduce cell proliferation and pharmaceutically acceptable salts or solvates, acids or derivatives of any of the above. Also included in this definition are anti-hormonal agents that act to regulate or inhibit hormone action on tumors such as anti-estrogens and selective estrogen receptor antibodies, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts or solvates, acids or derivatives of any of the above.

Particularly preferred anti-cancer agents comprise commercially or clinically available compounds such as erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7, 9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®). Additional commercially or clinically available anti-cancer agents comprise oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); vinorelbine (NAVELBINE®); capecitabine (XELODA®, Roche), tamoxifen (including NOLVADEX®; tamoxifen citrate, FARESTON® (toremifine citrate) MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

The term "pharmaceutically acceptable salt" or "salt" means organic or inorganic salts of a molecule or macromolecule. Acid addition salts can be formed with amino groups. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Where multiple charged atoms are part of the pharmaceutically acceptable salt, the salt can have multiple counter ions. Hence, a pharmaceutically acceptable salt can have one or more charged atoms and/or one or more counterion.

"Pharmaceutically acceptable solvate" or "solvate" refers to an association of one or more solvent molecules and a molecule or macromolecule. Examples of solvents that form pharmaceutically acceptable solvates include, but are not limited to, water, isopropanol, ethanol, methanol, DMSO, ethyl acetate, acetic acid, and ethanolamine.

In other embodiments the antibodies or ADCs of the instant invention may be used in combination with any one of a number of antibodies (or immunotherapeutic agents) presently in clinical trials or commercially available. The disclosed antibodies may be used in combination with an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lambrolizumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nivolumab, nofetumomabn, obinutuzumab, ocaratuzumab, ofatumumab, olaratumab, olaparib, onartuzumab, oportuzumab, oregovomab, panitumumab, parsatuzumab, patritumab, pemtumomab, pertuzumab, pidilizumab, pintumomab, pritumumab, racotumomab, radretumab, ramucirumab, rilotumumab, rituximab, robatumumab, satumomab, selumetinib, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8, MDX-1105 and MED14736 and combinations thereof.

Other particularly preferred embodiments comprise the use of antibodies approved for cancer therapy including, but not limited to, rituximab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of antibodies or ADCs with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed antibodies or ADCs may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VIII INDICATIONS

The invention provides for the use of antibodies and ADCs of the invention for the diagnosis, theragnosis, treatment and/or prophylaxis of various disorders including neoplastic, inflammatory, angiogenic and immunologic disorders and disorders caused by pathogens. Particularly, key targets for treatment are neoplastic conditions comprising solid tumors, although hematologic malignancies are within the scope of the invention. In certain embodiments the antibodies of the invention will be used to treat tumors or tumorigenic cells expressing a particular determinant (e.g. CLDN). Preferably the "subject" or "patient" to be treated will be human although, as used herein, the terms are expressly held to comprise any mammalian species.

Neoplastic conditions subject to treatment in accordance with the instant invention may be benign or malignant; solid tumors or other blood neoplasia; and may be selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In other preferred embodiments, the disclosed antibodies and ADCs are especially effective at treating lung cancer, including the following subtypes: small cell lung cancer and non-small cell lung cancer (e.g. squamous cell non-small cell lung cancer or squamous cell small cell lung cancer). In selected embodiments the antibodies and ADCs can be administered to patients exhibiting limited stage disease or extensive stage disease. In other preferred embodiments the disclosed conjugated antibodies will be administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g. carboplatin, cisplatin, oxaliplatin) and/or a taxane (e.g. docetaxel, paclitaxel, larotaxel or cabazitaxel).

The invention also provides for a preventative or prophylactic treatment of subjects who present with benign or precancerous tumors. No particular type of tumor or proliferative disorder is excluded from treatment using the antibodies of the invention.

IX ARTICLES OF MANUFACTURE

The invention includes pharmaceutical packs and kits comprising one or more containers, wherein a container can comprise one or more doses of an antibody or ADC of the invention. In certain embodiments, the pack or kit contains a unit dosage, meaning a predetermined amount of a composition comprising, for example, an antibody or ADC of the invention, with or without one or more additional agents and optionally, one or more anti-cancer agents.

The kit of the invention will generally contain in a suitable container a pharmaceutically acceptable formulation of the antibody or ADC of the invention and, optionally, one or more anti-cancer agents in the same or different containers. The kits may also contain other pharmaceutically acceptable formulations or devices, either for diagnosis or combination therapy. Examples of diagnostic devices or instruments include those that can be used to detect, monitor, quantify or profile cells or markers associated with proliferative disorders (for a full list of such markers, see above). In particularly preferred embodiments the devices may be used to detect, monitor and/or quantify circulating tumor cells either in vivo or in vitro (see, for example, WO 2012/0128801). In still other preferred embodiments the circulating tumor cells may comprise tumorigenic cells. The kits contemplated by the invention can also contain appropriate reagents to combine the antibody or ADC of the invention with an anti-cancer agent or diagnostic agent (e.g., see U.S. Pat. No. 7,422,739).

When the components of the kit are provided in one or more liquid solutions, the liquid solution can be non-aqueous, however, an aqueous solution is preferred, with a sterile aqueous solution being particularly preferred. The formulation in the kit can also be provided as dried powder(s) or in lyophilized form that can be reconstituted upon addition of an appropriate liquid. The liquid used for reconstitution can be contained in a separate container. Such liquids can comprise sterile, pharmaceutically acceptable buffer(s) or other diluent(s) such as bacteriostatic water for injection, phosphate-buffered saline, Ringer's solution or dextrose solution. Where the kit comprises the antibody or ADC of the invention in combination with additional therapeutics or agents, the solution may be pre-mixed, either in a molar equivalent combination, or with one component in excess of the other. Alternatively, the antibody or ADC of the invention and any optional anti-cancer agent or other agent can be maintained separately within distinct containers prior to administration to a patient.

The kit can comprise one or multiple containers and a label or package insert in, on or associated with the container(s), indicating that the enclosed composition is used for diagnosing or treating the disease condition of choice. Suitable containers include, for example, bottles, vials, syringes, etc. The containers can be formed from a variety of materials such as glass or plastic. The container(s) can comprise a sterile access port, for example, the container may be an intravenous solution bag or a vial having a stopper that can be pierced by a hypodermic injection needle.

In some embodiments the kit can contain a means by which to administer the antibody and any optional components to a patient, e.g., one or more needles or syringes (pre-filled or empty), an eye dropper, pipette, or other such like apparatus, from which the formulation may be injected or introduced into the subject or applied to a diseased area of the body. The kits of the invention will also typically include a means for containing the vials, or such like, and other components in close confinement for commercial sale, such as, e.g., blow-molded plastic containers into which the desired vials and other apparatus are placed and retained.

X MISCELLANEOUS

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. In addition, ranges provided in the specification and appended claims include both end points and all points between the end points. Therefore, a range of 2.0 to 3.0 includes 2.0, 3.0, and all points between 2.0 and 3.0.

Generally, techniques of cell and tissue culture, molecular biology, immunology, microbiology, genetics and chemistry described herein are those well known and commonly used in the art. The nomenclature used herein, in association with such techniques, is also commonly used in the art. The methods and techniques of the invention are generally performed according to conventional methods well known in the art and as described in various references that are cited throughout the present specification unless otherwise indicated.

XI REFERENCES

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

XII SEQUENCE LISTING SUMMARY

Appended to the instant application is a sequence listing comprising a number of nucleic acid and amino acid sequences. The following Table 3 provides a summary of the included sequences.

TABLE 3

| SEQ ID NO | Description |
|---|---|
| 1 | Kappa light chain (LC) constant region protein |
| 2 | IgGI heavy chain (HC) constant region protein |
| 3-19 | Reserved |
| 20 | SC27.1 VL DNA |
| 21 | SC27.1 VL protein |
| 22 | SC27.1 VH DNA |
| 23 | SC27.1 VH protein |
| 24-59 | Additional mouse clones as in SEQ ID NOs: 20-23 |
| 60 | hSC27.1 VL DNA |
| 61 | hSC27.1 VL protein |
| 62 | hSC27.1 VH DNA |
| 63 | hSC27.1 VH protein |
| 64-75 | Additional humanized clones as in SEQ ID NOs: 60-63 |
| 76-77 | hSC27.108v1 VL DNA and protein |
| 78-79 | hSC27.22-VH1-8 VH DNA and protein |
| 80-81 | hSC27.22-VH1-46 VH DNA and protein |
| 82-83 | hSC27.22-VH1-69 VH DNA and protein |
| 84-85 | hSC27.204v1 DNA and protein |
| 86-87 | hSC27.204v2 DNA and protein |
| 88-89 | hSC27.204v3 DNA and protein |
| 90-91 | hSC27.204v4 DNA and protein |
| 92-93 | hSC27.204v5 DNA and protein |
| 94-95 | hSC27.204v6 DNA and protein |
| 96-97 | hSC27.204v7 DNA and protein |
| 98-99 | hSC27.204v8 DNA and protein |
| 100-101 | hSC27.204v9 DNA and protein |
| 102-103 | hSC27.204v10 DNA and protein |
| 104-105 | hSC27.204v11 DNA and protein |
| 106-107 | hSC27.204v12 DNA and protein |
| 108-109 | hSC27.204v13 DNA and protein |
| 110-111 | hSC27.204v14 DNA and protein |
| 112-113 | hSC27.204v15 DNA and protein |
| 114-115 | hSC27.1 full length LC and HC protein |
| 116-117 | hSC27.22 full length LC and HC protein |
| 118-119 | hSC27.108 full length LC and HC protein |
| 120-121 | hSC27.204 full length LC and HC protein |
| 122 | hSC27.22ss1 full length HC protein |
| 123 | hSC27.22-VH1-8 full length HC protein |
| 124 | hSC27.22-VH1-46 full length HC protein |
| 125 | hSC27.22-VH1-69 full length HC protein |
| 126 | hSC27.22 IgG2 full length HC protein |
| 127 | hSC27.22 IgG4 R409K full length HC protein |
| 128 | hSC27.22 IgG4 S228P full length HC protein |
| 129 | hSC27.22 IgG4 S228P K370E R409K full length HC protein |
| 130 | hSC27.22 IgG4 K370E full length HC protein |
| 131 | hSC27.22 IgG4 S228P K370E full length HC protein |
| 132 | hSC27.22 IgG4 C127S S228P full length HC protein |
| 133 | hSC27.22 IgG4 C127S K370E full length HC protein |
| 134 | hSC27.22 IgG4 C127S S228P K370E full length HC protein |
| 135 | hSC27.108v1 full length LC protein |
| 136 | hSC27.204v1 full length HC protein |
| 137 | hSC27.204v2 full length HC protein |
| 138 | hSC27.204v3 full length HC protein |
| 139 | hSC27.204v4 full length HC protein |
| 140 | hSC27.204v5 full length HC protein |
| 141 | hSC27.204v6 full length HC protein |
| 142 | hSC27.204v7 full length HC protein |
| 143 | hSC27.204v8 full length HC protein |
| 144 | hSC27.204v9 full length HC protein |
| 145 | hSC27.204v10 full length HC protein |

TABLE 3-continued

| SEQ ID NO | Description |
|---|---|
| 146 | hSC27.204v11 full length HC protein |
| 147 | hSC27.204v12 full length HC protein |
| 148 | hSC27.204v13 full length HC protein |
| 149 | hSC27.204v14 full length HC protein |
| 150 | hSC27.204v15 full length HC protein |
| 151-156 | hSC27.1 CDRL1; CDRL2; CDRL3, CDRH1; CDRH2; CDRH3 |
| 157-162 | hSC27.22 CDRL1; CDRL2; CDRL3, CDRH1; CDRH2; CDRH3 |
| 163-168 | hSC27.108 CDRL1; CDRL2; CDRL3, CDRH1; CDRH2; CDRH3 |
| 169-174 | hSC27.204 CDRL1; CDRL2; CDRL3, CDRH1; CDRH2; CDRH3 |
| 175 | CDRH2 of hSC27.204v1; hSC27.204v5 and hSC27.405v13 |
| 176 | CDRH2 of hSC27.204v2; hSC27.204v6 and hSC27.405v14 |
| 177 | CDRH2 of hSC27.204v3; hSC27.204v7 and hSC27.405v15 |
| 178 | Codon optimized hSC27.22ss1 full length HC DNA |

XIII EXAMPLES

The invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

PDX tumor cell types are denoted by an abbreviation followed by a number, which indicates the particular tumor cell line. The passage number of the tested sample is indicated by p0-p# appended to the sample designation where p0 is indicative of an unpassaged sample obtained directly from a patient tumor and p# is indicative of the number of times the tumor has been passaged through a mouse prior to testing. As used herein, the abbreviations of the tumor types and subtypes are shown in Table 4 as follows:

TABLE 4

| Tumor Type | Abbreviation | Tumor subtype | Abbreviation |
|---|---|---|---|
| Bladder | BL | | |
| Breast | BR | basal-like | BR-Basal Like |
| | | estrogen receptor positive and/or progesterone receptor positive | BR-ERPR |
| | | ERBB2/Neu positive | BR-ERBB2/Neu |
| | | HER2 positive | BR-HER2 |
| | | triple-negative | TNBC |
| | | luminal A | BR-lumA |
| | | claudin subtype of triple-negative | TNBC-CL |
| | | claudin low | BR-CLDN-Low |
| Cervical | CER | | |
| Colorectal | CR | | |
| Endometrial | EM | | |
| Gastric | GA | diffuse adenocarcinoma | GA-Ad-Dif/Muc |
| | | intestinal adenocarcinoma | GA-Ad-Int |
| | | stromal tumors | GA-GIST |

TABLE 4-continued

| Tumor Type | Abbreviation | Tumor subtype | Abbreviation |
|---|---|---|---|
| Glioblastoma | GB | | |
| Head and neck | HN | | |
| Kidney | KDY | clear renal cell carcinoma | KDY-CC |
| | | papillary renal cell carcinoma | KDY-PAP |
| | | transitional cell or urothelial carcinoma | KDY-URO |
| | | unknown | KDY-UNK |
| Liver | LIV | hepatocellular carcinoma | LIV-HCC |
| | | cholangiocarcinoma | LIV-CHOL |
| Lymphoma | LN | | |
| Lung | LU | adenocarcinoma | LU-Ad |
| | | carcinoid | LU-CAR |
| | | large cell neuroendocrine | LU-LCC |
| | | non-small cell | NSCLC |
| | | squamous cell | LU-SCC |
| | | small cell | SCLC |
| | | spindle cell | LU-SPC |
| Ovarian | OV | clear cell | OV-CC |
| | | endometroid | OV-END |
| | | mixed subtype | OV-MIX |
| | | malignant mixed mesodermal | OV-MMMT |
| | | mucinous | OV-MUC |
| | | neuroendocrine | OV-NET |
| | | papillary serous | OV-PS |
| | | serous | OV-S |
| | | small cell | OV-SC |
| | | transitional cell carcinoma | OV-TCC |
| Pancreatic | PA | acinar cell carcinoma | PA-ACC |
| | | duodenal carcinoma | PA-DC |
| | | mucinous adenocarcinoma | PA-MAD |
| | | neuroendocrine | PA-NET |
| | | adenocarcinoma | PA-PAC |
| | | adenocarcinoma exocrine type | PA-PACe |
| | | ductal adenocarcinoma | PA-PDAC |
| | | ampullary adenocarcinoma | PA-AAC |
| Prostate | PR | | |
| Skin | SK | melanoma | MEL |
| | | squamous cell carcinomas | SK-SCC |
| | | uveal melanoma | UVM |
| Testicular | TES | | |
| Thyroid | THY | | |

Example 1

Identification of CLDN4, CLDN6 and CLDN9 Expression Using Whole Transcriptome Sequencing To characterize the cellular heterogeneity of solid tumors as they exist in cancer patients, aid in the identification of CSCs using particular phenotypic markers and identify clinically relevant therapeutic targets, a large PDX tumor bank was developed and maintained using art recognized techniques. The PDX tumor bank, comprising a large number of discrete tumor cell lines, was propagated in immunocompromised mice through multiple passages of heterogeneous tumor cells originally obtained from numerous cancer patients afflicted by a variety of solid tumor malignancies. The continued availability of a large number of discrete early passage PDX tumor cell lines having well defined lineages greatly facilitates the identification and isolation of CSCs as the PDX tumors allow for the reproducible and repeated characterization of CSCs. The use of minimally passaged PDX tumor cell lines simplifies in vivo experimentation and provides readily verifiable results. Moreover, early passage PDX tumors respond to therapeutic agents such as irinotecan (i.e. Camptosar®), which provides clinically relevant insight into underlying mechanisms driving tumor growth, resistance to current therapies and tumor recurrence.

To generate RNA from the PDX tumor cell lines, tumors were resected from mice after they reached 800-2,000 mm³ and the tumors were dissociated into single cell suspensions using art-recognized enzymatic digestion techniques (see, for example, U.S. Ser. No. 2007/0292414). Select dissociated PDX tumor cell preparations were depleted of mouse cells and sorted based on their expression of $CD46^{hi}$ and/or CD324, markers of CSC subpopulations (see U.S.P.N 2013/0260385 for the definition of $CD46^{hi}$). Cells that expressed human EpCAM, $CD46^{hi}$ and/or CD324 (i.e. CSC) or EpCAM but not $CD46^{hi}$ and/or CD324 (i.e. NTG cells), were isolated by FACS using a BD FACSAria cell sorter and lysed in RLTplus RNA lysis buffer (Qiagen) per the manufacturer's instructions. The lysates were then stored at −80° C. and thawed for RNA extraction. Upon thawing, total RNA was extracted using an RNeasy isolation kit (Qiagen, GmbH) following the vendor's instructions and then quantified using a Nanodrop spectrophotometer (Thermo Scientific) and/or a Bioanalyzer 2100 (Agilent Technologies), again using the manufacturer's protocols and recommended instrument settings. The resulting total RNA preparations were assessed by genetic sequencing and gene expression analyses.

Whole transcriptome sequencing of qualified, high quality RNA was performed using an Applied Biosystems (ABI) Sequencing by Oligo Ligation/Detection (SOLiD) 4.5 or SOLiD 5500xl next generation sequencing system (Life Technologies). cDNA was generated from 1 ng total RNA samples using either a modified whole transcriptome protocol from ABI designed for low input total RNA or the Ovation RNA-Seq System V2™ (NuGEN Technologies). The resulting cDNA library was fragmented and barcode adapters were added to allow pooling of fragment libraries from different samples during sequencing runs. Data generated by the SOLiD platform mapped to 34,609 genes as annotated by RefSeq version 47 using NCBI version hg19.2 of the published human genome and provided verifiable measurements of RNA levels in most samples. Sequencing data from the SOLiD platform is nominally represented as a transcript expression value using the metrics RPM (reads per million) or RPKM (read per kilobase per million) mapped to exon regions of genes, enabling basic gene expression analysis to be normalized and enumerated as RPM_Transcript or RPKM_Transcript.

The results of whole transcriptome sequencing using SOLiD showed elevated expression of CLDN4 mRNA in sorted CSC compared to NTG in the following PDX cell lines: BR13, BR22, OV100, PA20 and PA3, as well as high expression in additional CSC populations including BR36, OV106MET, OV72MET, and OV91MET (FIG. 1). CLDN6 mRNA was elevated in sorted CSC populations including BR36, OV106MET, OV72MET, and OV91MET (FIG. 1). Unlike the case for CLDN4 or CLDN6, the related family member, CLDN9, was observed to have low expression in all sorted tumor populations. In contrast to the tumor samples, normal ovary and pancreas tissues showed no or very low mRNA expression of all three family members, CLDN4, CLDN6 and CLDN9.

The identification of elevated CLDN4 and CLDN6 mRNA expression in different types of human tumor indicated these antigens merited further evaluation as a potential diagnostic and/or immunotherapeutic targets.

Example 2

Expression of CLDN4, CLDN6 and CLDN9 mRNA in Tumors Using qRT-PCR

To confirm expression of CLDN4, CLDN6 and further delineate CLDN9 expression in tumor cell subpopulations, qRT-PCR was run on RNA samples obtained from sorted CSC and NTG populations (as described in Example 1) from various PDX models. qRT-PCR was performed using the Fluidigm BioMark™ HD System according to industry standard protocols. 1 ng of RNA, prepared as described in Example 1, was converted to cDNA using the High Capacity cDNA Archive kit (Life Technologies) according to the manufacturer's instructions. cDNA material, pre-amplified using CLDN4, CLDN6 and CLDN9 specific Taqman assays, was then used for subsequent qRT-PCR experiments.

Figure 2A:
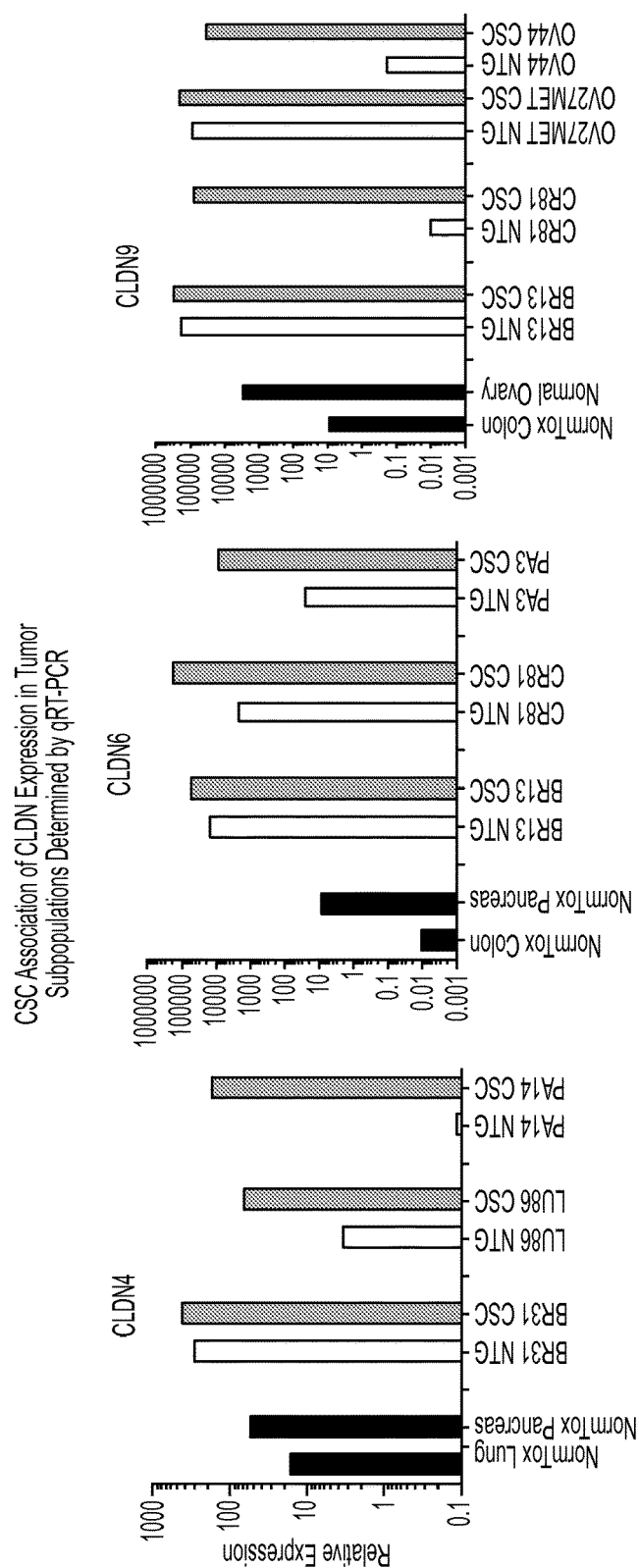
FIG. 2A shows the relative mRNA expression of CLDN4, CLDN6 and CLDN9 in cancer stem cells (CSCs; grey bar), compared to non-tumorigenic (NTG; white bar) cells and in matched normal tissue (black bar), as determined by qRT-PCR.

As shown in FIG. 2A, CLDN4 exhibited elevated expression in CSC subpopulations of BR31 (TNBC), LU86 (SCLC) and PA14 compared to NTG populations from the same PDX tumor lines. Compared to expression in normal lung and pancreas, sorted CSC populations showed 10-100 fold higher expression of CLDN4, suggesting a therapeutic window and potential benefit for targeting the CSC of these PDX models. CLDN6 was also found to exhibit elevated expression in CSC subpopulations of BR13 (TNBC), CR81 and PA3 when compared to NTG populations derived from the same PDX tumor lines, with CSC expression of CLDN6 approximately 10,000 fold greater than CLDN6 expression in normal pancreas and colon (FIG. 2A). Finally, CLDN9 was also found to show elevated expression in CSC populations of BR13 (TNBC), CR81, OV27MET (OV-S) and OV44 (OV-S) as compared with NTG populations obtained from the same PDX tumor lines, with expression of CLDN9 approximately 10,000 fold higher than that found in normal colon cells. These findings validate the results obtained from whole transcriptome sequencing of similar populations with regard to CLDN4 and CLDN6 and clearly show that, in various sorted CSC populations, CDLN4, CLDN6 and/or CLDN9 are highly overexpressed.

Figure 2B:
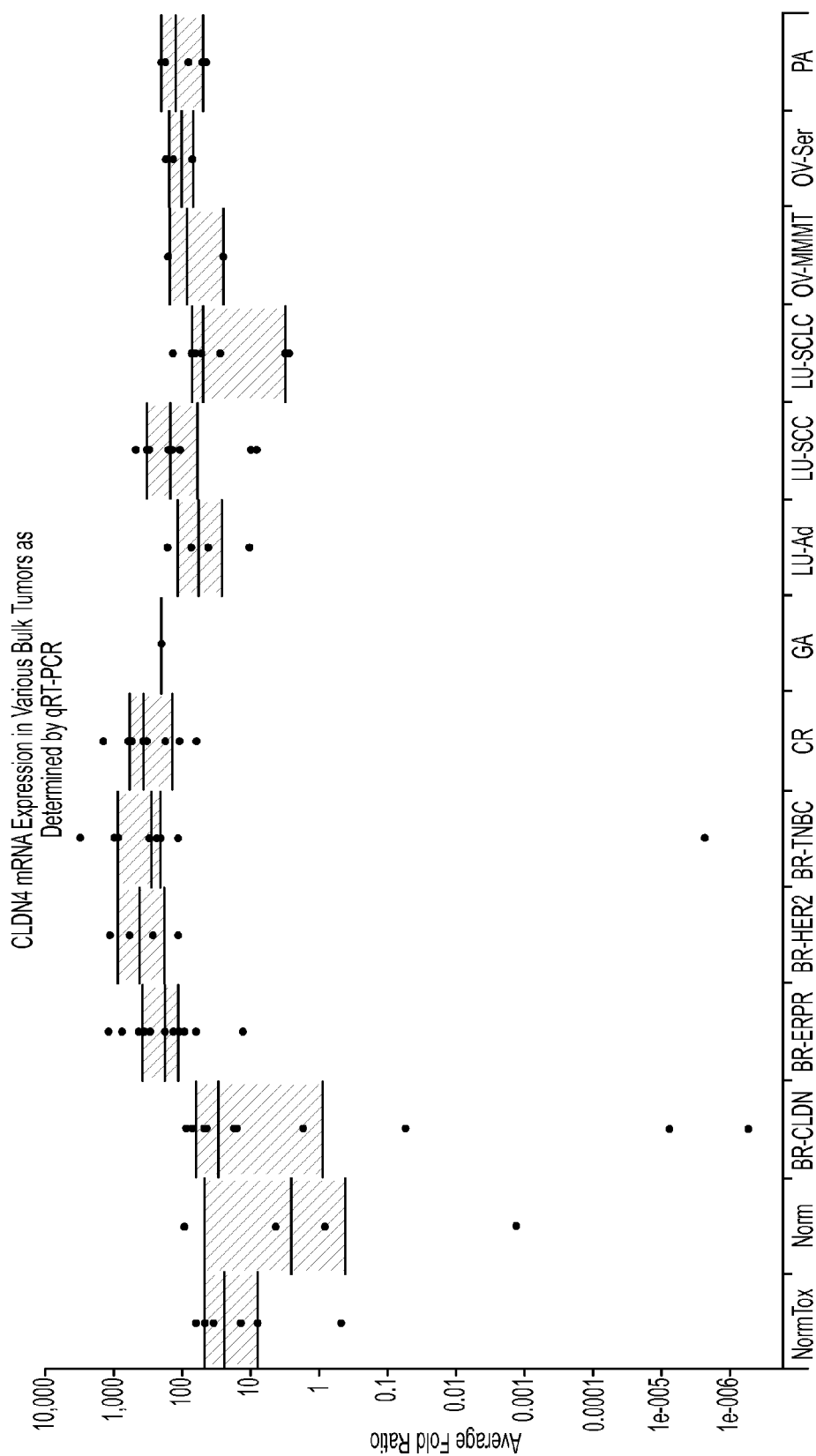
FIGS. 2B-2D show relative mRNA expression levels of CLDN4, CLDN6 and CLDN9, respectively, in PDX tumors determined by qRT-PCR.
Figure 2C:
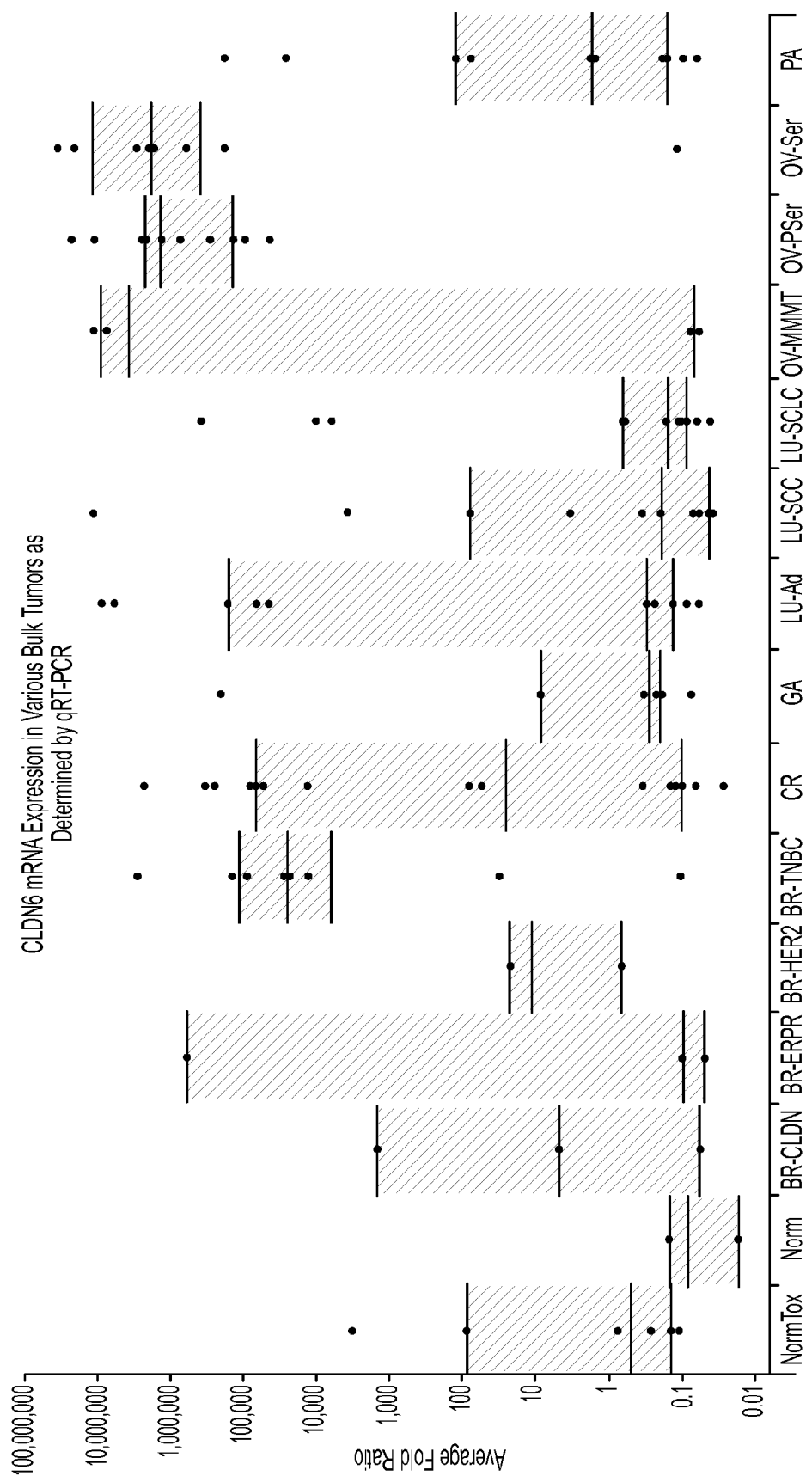
Figure 2D:
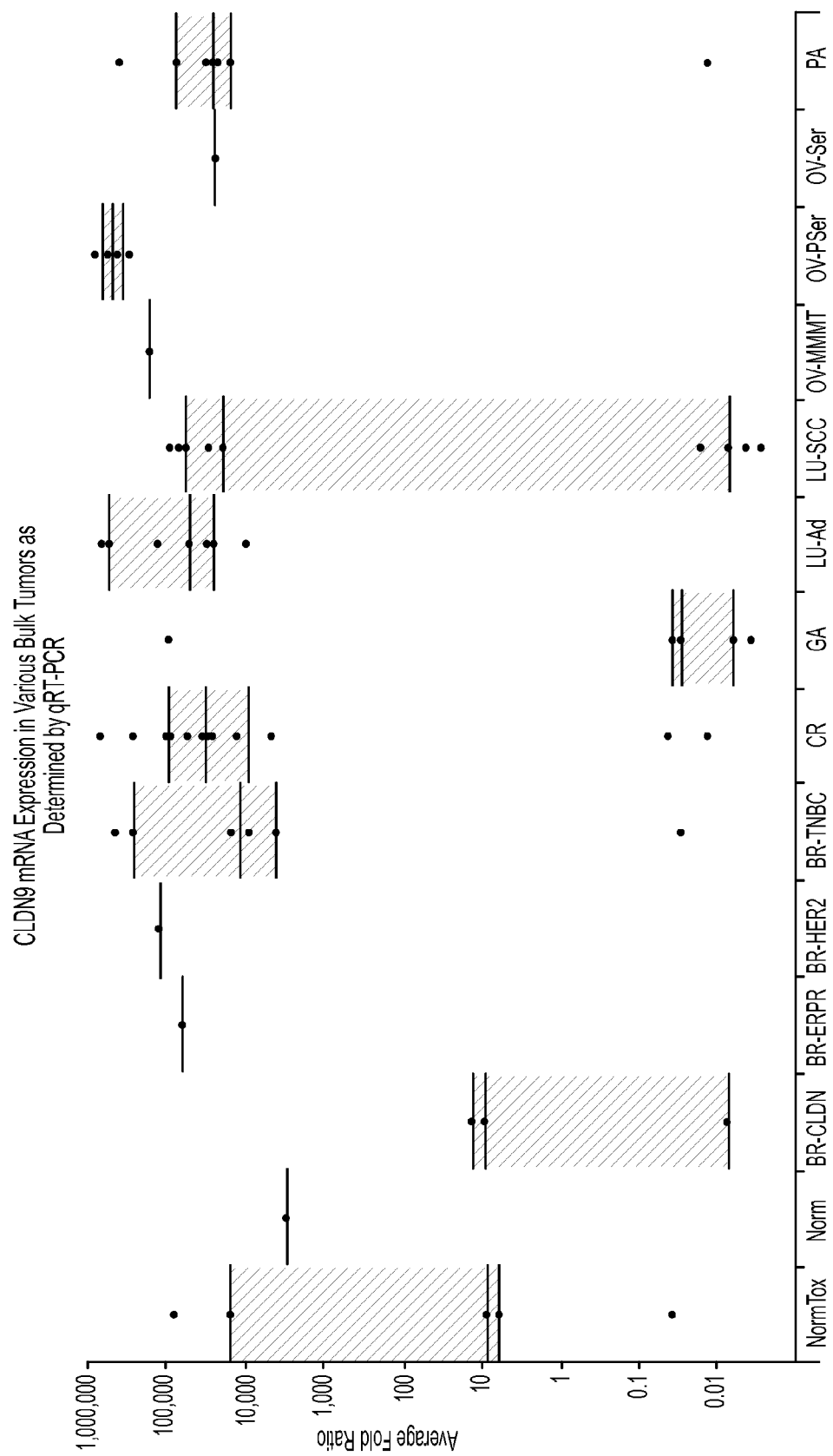

To further determine the expression levels of CLDN4, CLDN6 and CLDN9 in additional tumor specimens, mRNA expression of the relevant CLDN family members in various bulk (non-sorted) PDX tumor cell lines was compared to mRNA expression in normal tissues that might be of concern for intolerable toxicity when using ADC therapeutics (NormTox: colon, stomach, small intestine, lung and pancreas) and normal tissues of less concern in terms of toxicity (Norm: breast, ovary). CLDN4 mRNA expression was found to be elevated in many bulk BR, CR, LU-SCC and PA PDX lines, with highest expression seen in BR-TNBC, CR, LU-SCC, PA (FIG. 2B). CLDN6 mRNA was highly overexpressed in OV-S and OV-PS (FIG. 2C), while CLDN6 mRNA levels were also elevated in BR-TNBC and in subsets of LU-Ad and CR PDX lines (FIG. 2C). Finally, CLDN9 mRNA was found to be elevated in certain PDX cell lines including BR-TNBC, CR, LU-Ad, OV and PA PDX lines (FIG. 2D) when compared with the levels found in normal tissues. These results demonstrate that CLDN4, CLDN6 and CLDN9 expression is elevated across different PDX tumor models, indicating that antibodies against CLDN4, CLDN6 and CLDN9 will allow for comprehensive targeting of multiple cancer indications. These findings further suggest that, in certain selected embodiments multireactive antibodies (i.e. those that immunospecifically bind to more than one of the CLDN4, CLDN6 and CLDN9 antigens) may be particularly effective in reducing or eliminating tumorigenic cells.

Figure 2E:
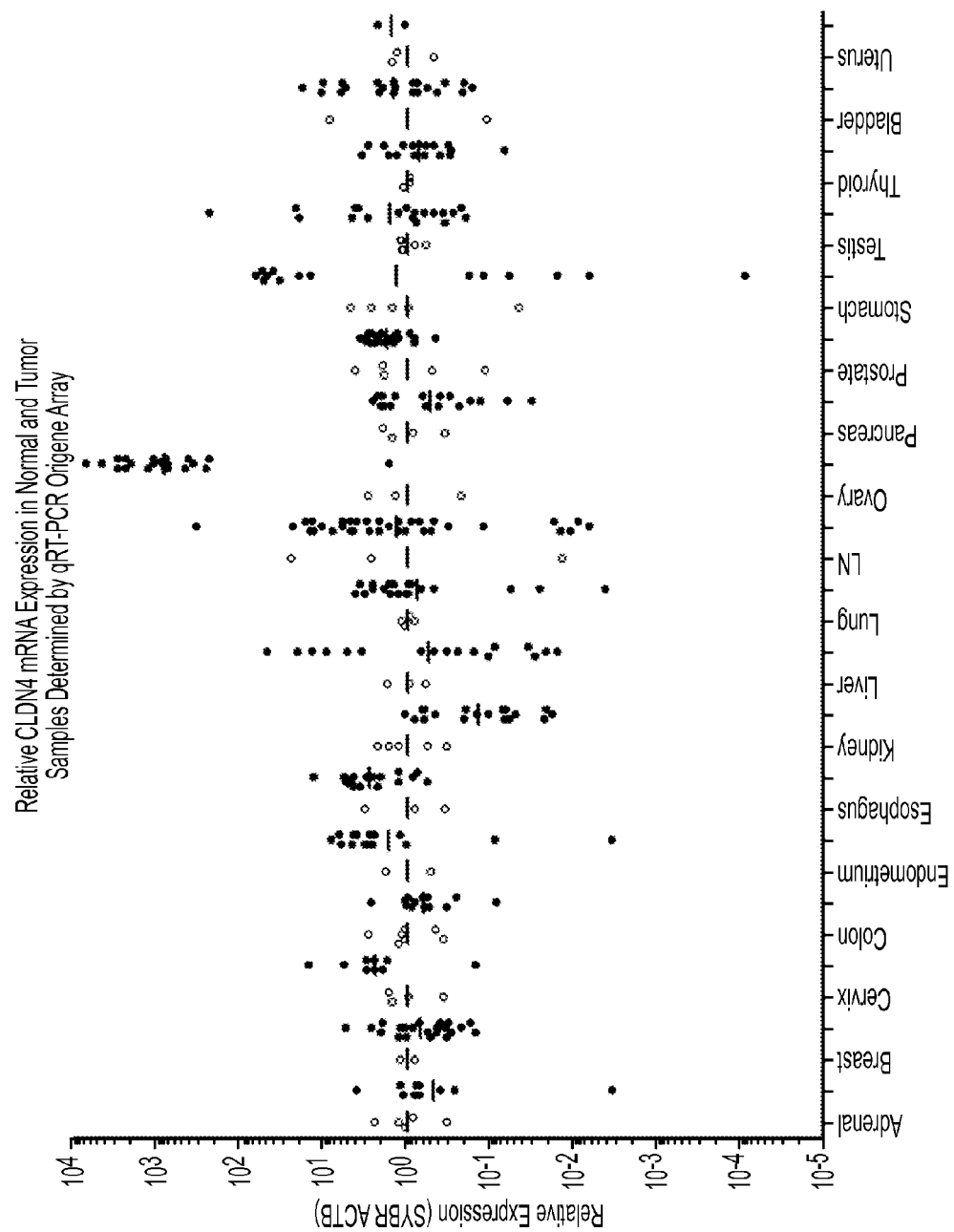
FIGS. 2E-2G show the relative levels of mRNA expression of CLDN4 (FIG. 2E), CLDN6 (FIG. 2F) or CLDN9 (FIG. 2G) as measured by qRT-PCR in whole tumor specimens (black dot) or matched normal adjacent tissue (white dot) from patients with one of eighteen different tumor types.
Figure 2F:
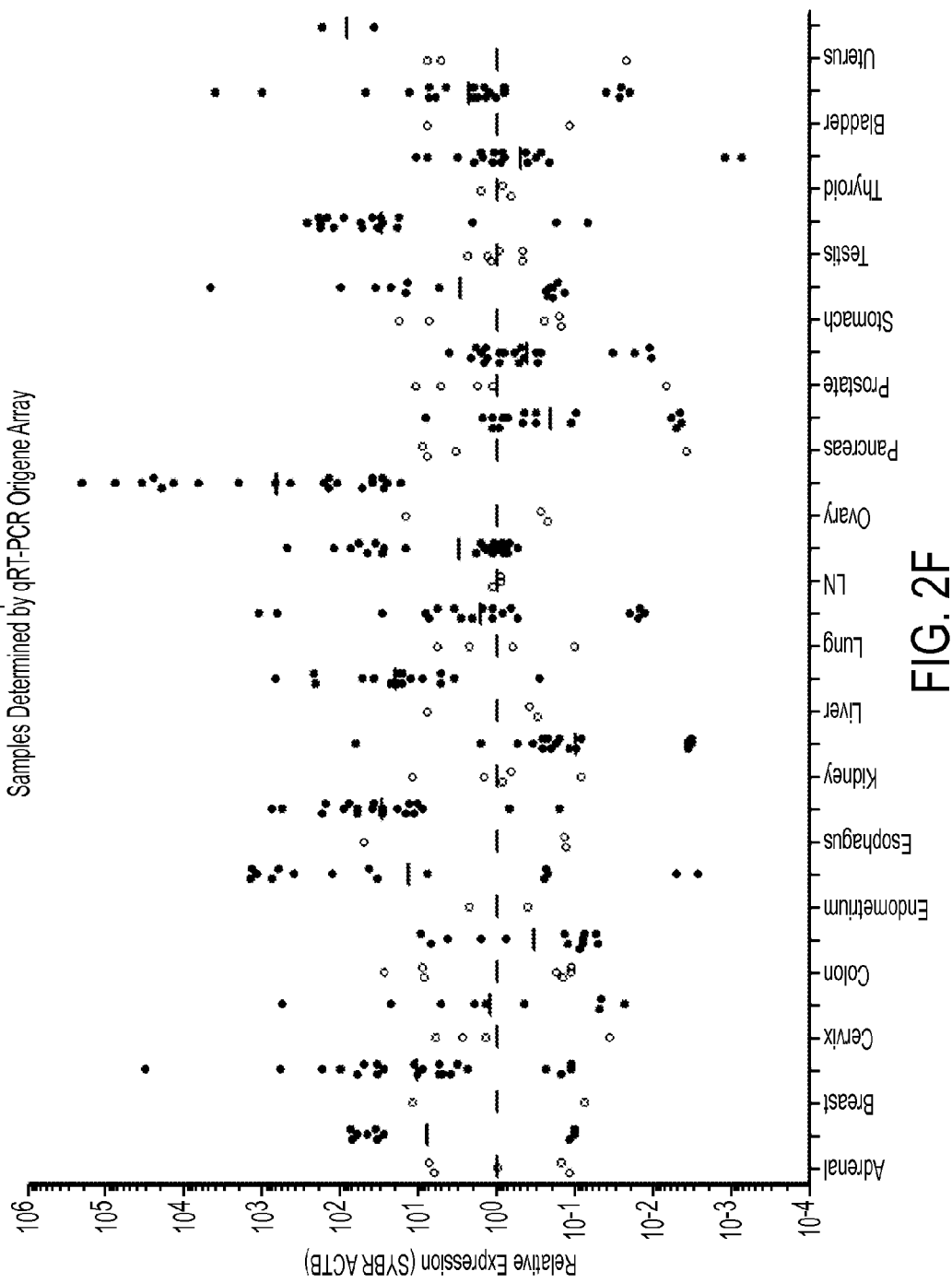
Figure 2G:
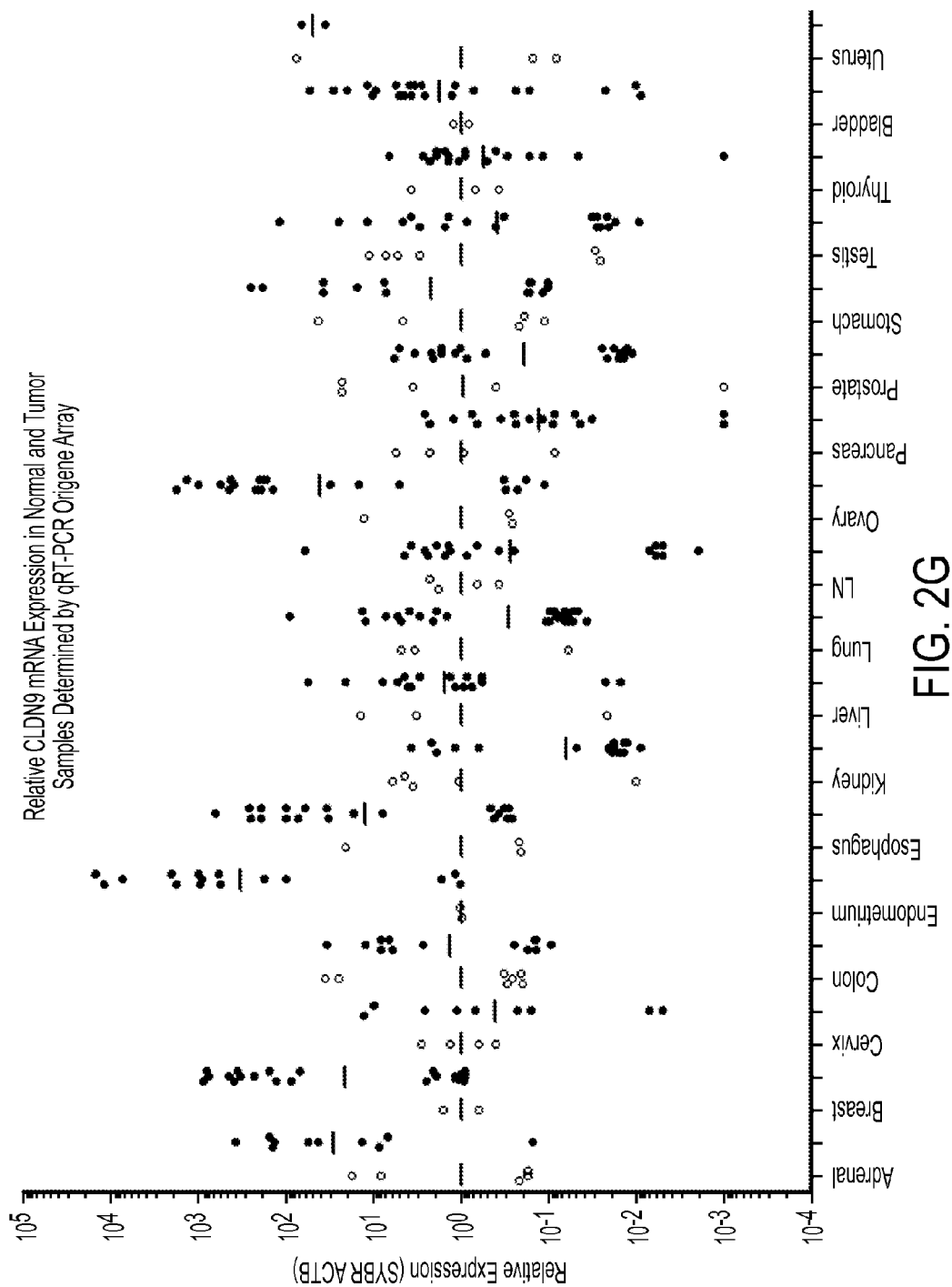

To further expand the analysis to a larger group of primary human tumor samples as well as normal tissue samples, a qRT-PCR assay was performed using CLDN4, CLDN6 or CLDN9-specific Taqman assays on a TissueScan™ qPCR (Origene Technologies) 384-well array according to the manufacturer's instructions. This array enables comparison of gene expression across 18 different tumor types, with multiple patient derived samples for each tumor type. Significantly, the Origene assay also enables the comparison of expression from normal tissue versus tumor tissue of the same tissue types. FIGS. 2E, 2F and 2G show the expression levels of CLDN4, CLDN6 and CLDN9, respectively, in various whole tumors specimens (black dots) normalized against β-actin and plotted relative to expression in the matched normal tissue (white dots) for each tumor type analyzed. Specimens not amplified were assigned a cycle count value (Ct) of 45, which represents the last cycle of amplification in the experimental protocol. Each dot represents a single tissue specimen, with the mean geometric value of the samples for an indicated tumor or matched normal tissue type represented as a black line.

Overexpression of CLDN4 relative to matched normal tissue was seen in cervical, endometrial, and ovarian tumors, and in a subset of esophageal, liver, gastric, lung, testicular and bladder tumors (FIG. 2E). This includes 2/2 cholangiocarcinomas of the liver, 1/3 adenomas of the liver and 3/12 hepatocellular carcinomas. The gastric tumor subsets with overexpression of CLDN4 included 7/7 adenocarcinomas and 1/1 villous adenomas (data not shown). Overexpression of CLDN6 relative to matched normal tissue was seen in endometrial, ovarian and testicular tumors, as well as subsets of adrenal, breast, esophageal, liver, lung, lymphoma and gastric tumors (FIG. 2F). This includes 2/2 cholangiocarcinomas of the liver, 2/3 adenomas of the liver and 7/12 hepatocellular carcinomas (data not shown). Overexpression of CLDN9 relative to matched normal tissue was seen in adrenal, endometrial, esophageal, and ovarian tumors, and a subset of breast, lung and bladder tumors (FIG. 2G). These data suggest that abnormal CLDN4, CLDN6 and CLDN9 expression may be indicative of and/or implicated in tumorigenesis and/or tumor progression in the above-mentioned tumors, and again demonstrate that antibodies directed to these claudin proteins may be used to effectively treat various tumors.

Example 3

CLDN Expression Profiles in Primary Tumors from the Cancer Genome Atlas

Figure 3A:
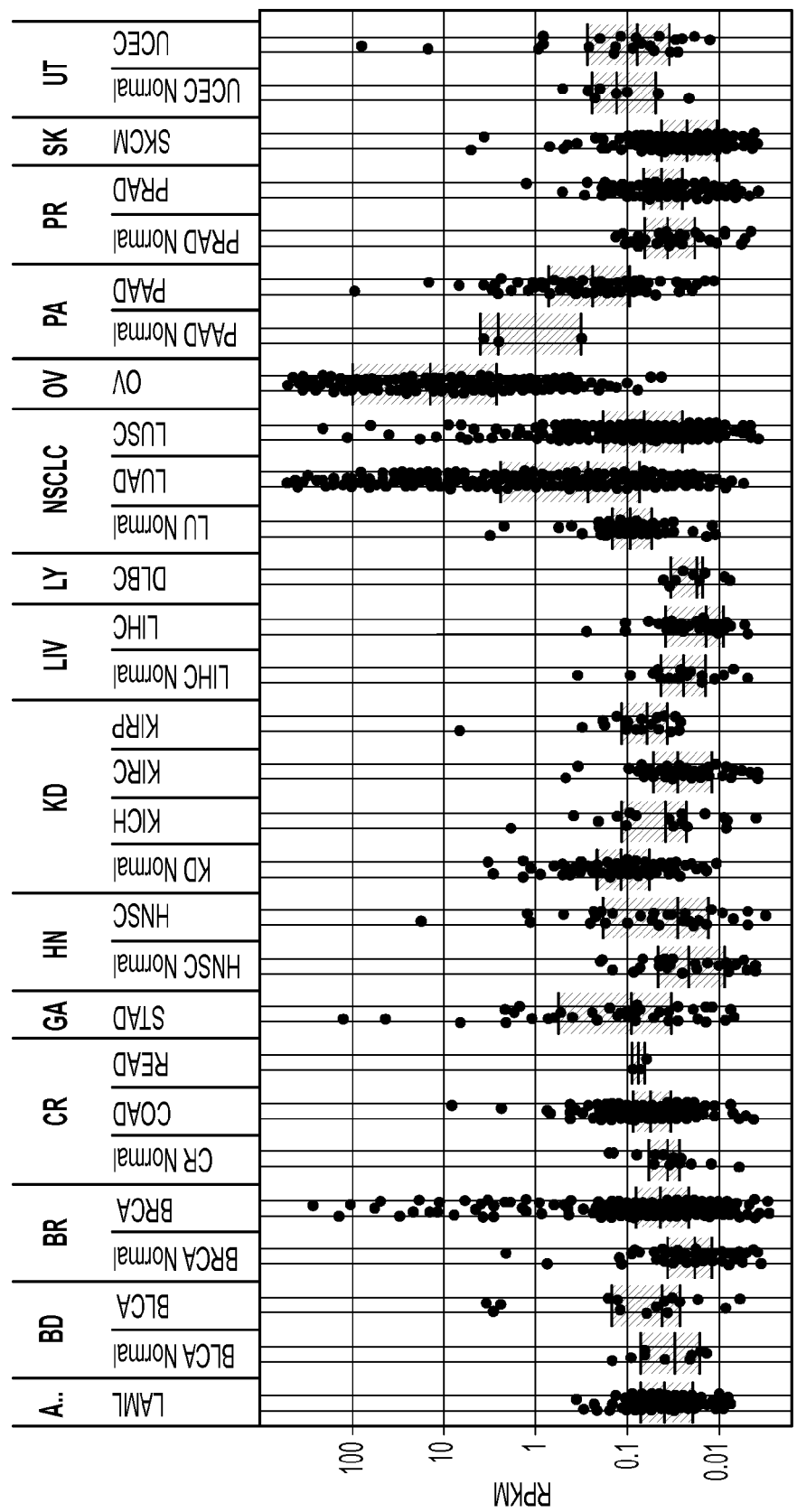
FIGS. 3A and 3B show relative mRNA expression of CLDN6 (FIG. 3A) and CLDN9 (FIG. 3B) across a large number of tumor and normal tissues derived from a public database.
Figure 3B:
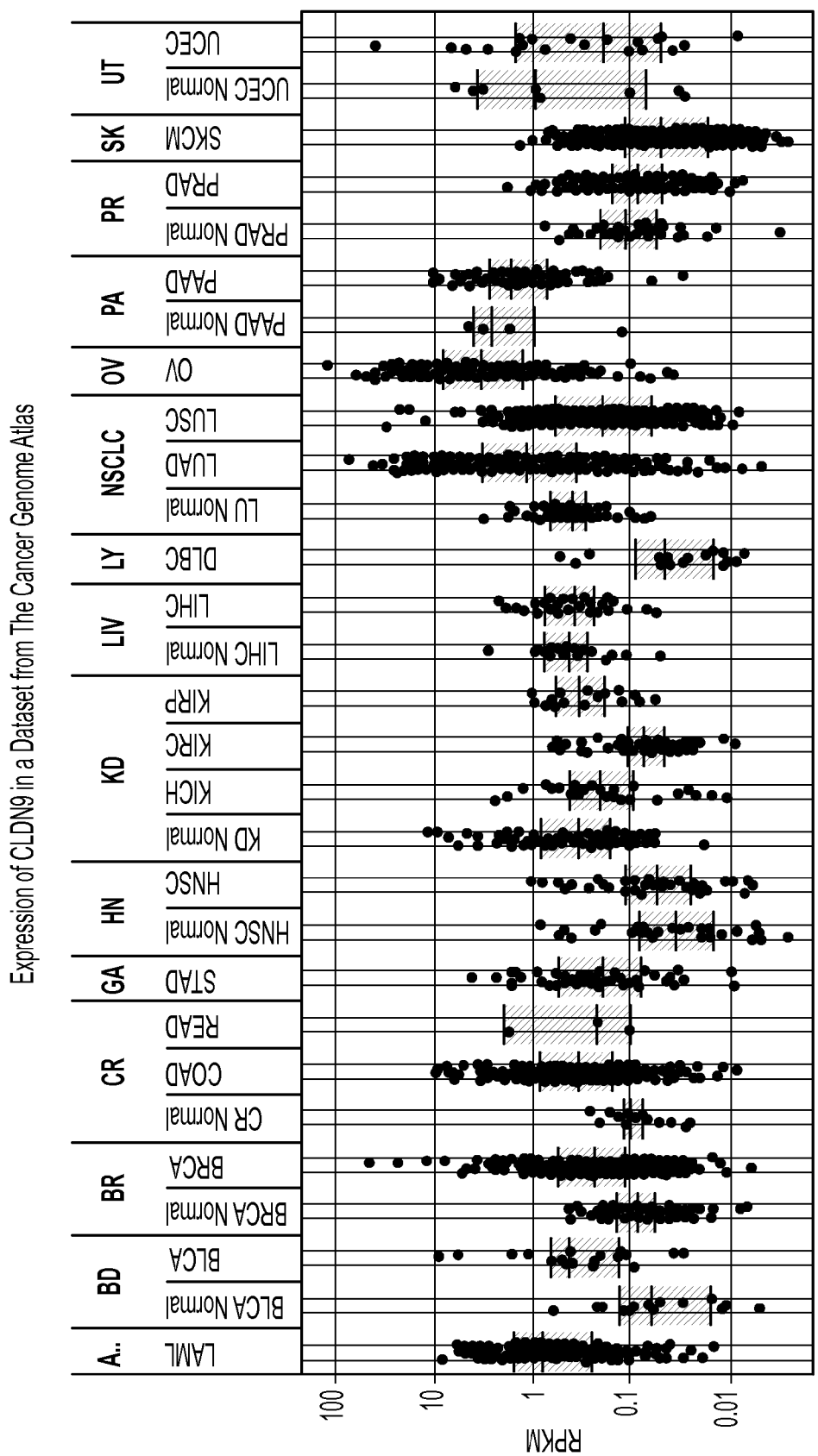

Overexpression of mRNA of CLDN6 and CLDN9 family members was confirmed in various tumors using a large, publically available dataset of tumors and normal samples known as The Cancer Genome Atlas (TCGA, National Cancer Institute). Exon level 3 expression data from the IlluminaHiSeq_RNASeqV2 platform was downloaded from the TCGA Data Portal (tcga-data.nci.nih.gov/tcga/tcgaDownload. isp) and parsed to aggregate the reads from the individual exons of each single gene to generate a single value read per kilobase of exon per million mapped reads (RPKM) for each gene in each sample. The rolled up data was then displayed using Tableau software. The parsed data for CLDN6 and CLDN9 are shown in FIGS. 3A and 3B, respectively, in which each sample is represented as a single dot, and the black horizontal lines represent the quartile boundaries for the setoff data points within a given normal tissue or tumor subtype. FIG. 3A shows that CLDN6 expression is elevated in OV tumors, which were subtyped as ovarian serous cystadenocarcinomas, compared to all other normal tissues. In addition, CLDN6 is elevated in a large number of LU-Ad samples compared to normal lung samples, and a substantial number of breast invasive carcinoma tumors (BRCA). Similar overexpression patterns can be see for CLDN9 as those observed for CLDN6 (FIG. 3B). Again, these data indicate that CLDN6 and CLDN9 expression levels are indicative of tumorigenesis in various tumors and reinforce their selection as potential therapeutic targets.

Figure 3C:
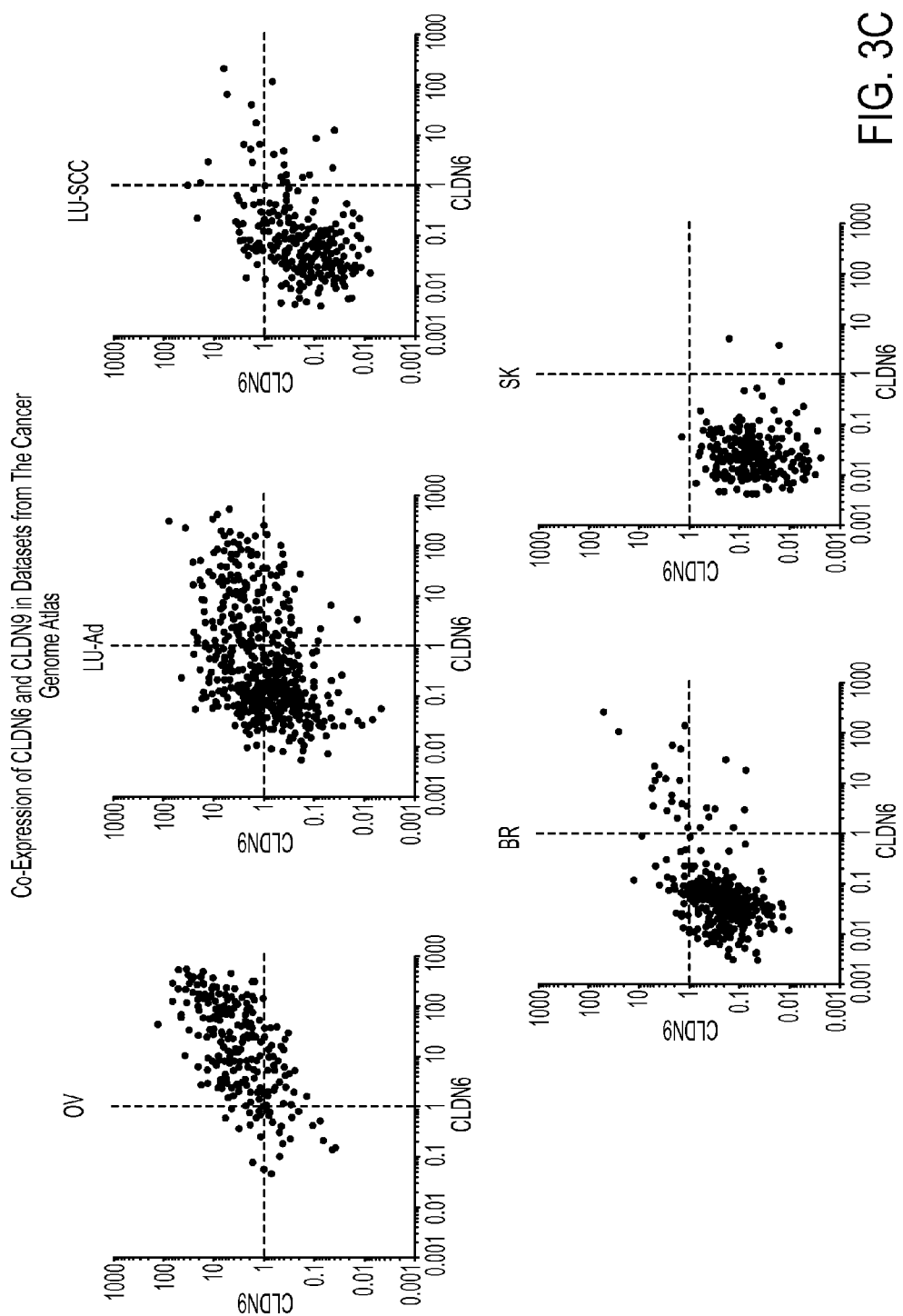
FIG. 3C shows the relative mRNA expression of CLDN6 (x-axis) versus that of CLDN9 (y-axis) for individual tumor samples for five tumor types derived from a public database.
Figure 3D:
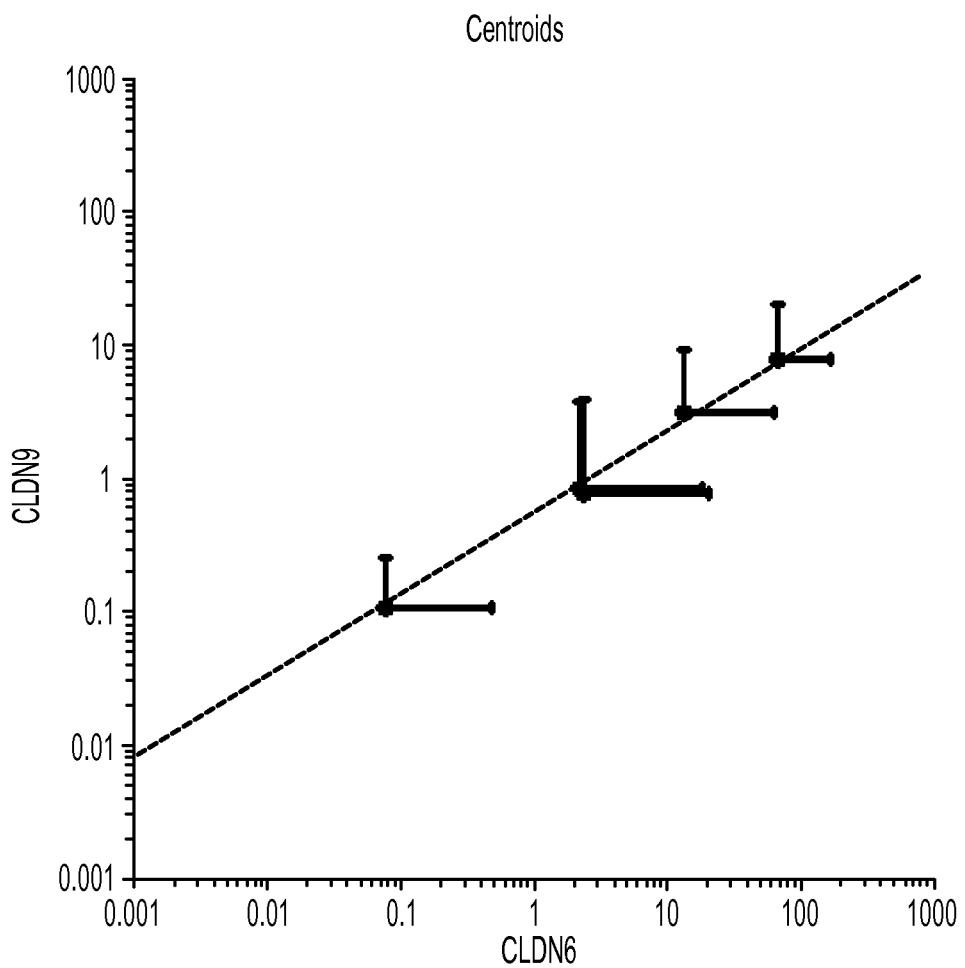
FIG. 3D shows a plot of the centroids (center of mass) of the scatter graphs for the five different tumor types shown in FIG. 3C, as well as a best fit regression line for the plotted centroids.

In five selected tumor types found in the TOGA data: OV, LU-Ad, LU-SC (squamous cell carcinoma), BR, and SK, the relative expression of CLDN6 versus CLDN9, for samples showing non-zero RPKM expression values for both genes, was plotted (FIG. 3C). These tumor types were selected to encompass a range of relative expression levels, from high (OV) to low (SK). FIG. 3C shows a progressive shift in the co-expression of both genes, from high (upper right quadrant in scatter plots) to low (lower left quadrant) across the indications, suggesting the expression of these genes may be linked. This can be more easily visualized by plotting the centroids (center of mass) from each of the scatterplots (FIG. 3D). The centroids show a very tight correlation of high significance for the CLDN6 and CLDN9 genes ($r^2=0.0996$; $p=0.0001$), which are proximal to one another (head to head on chromosome 16). In these same five indications, there was no significant correlation between: the expression of CLDN6 and a different claudin gene, CLDN1 ($r^2=0.14$); between CLDN6 and another tetraspanin, CD81 ($r^2=0.02$); or between CLDN6 and its other neighboring gene on chromosome 16, TNFRSF12A ($r^2=0.47$) (data not shown). A more modest yet significant correlation was seen in the co-expression of CLDN6 and CLDN4 genes ($r^2=0.80$; $p<0.05$) (data not shown). This rather surprisingly strong correlation between CLDN6 and CLDN9 is likely the result of the proximity of these two genes to one another, but is also suggestive of a functional link or functional co-disregulation of these genes. The tight co-expression pattern between CLDN6 and CLDN9 in several cancer indications provides a rationale for targeting multiple CLDN proteins as a therapeutic strategy.

Example 4

Figure 4B:
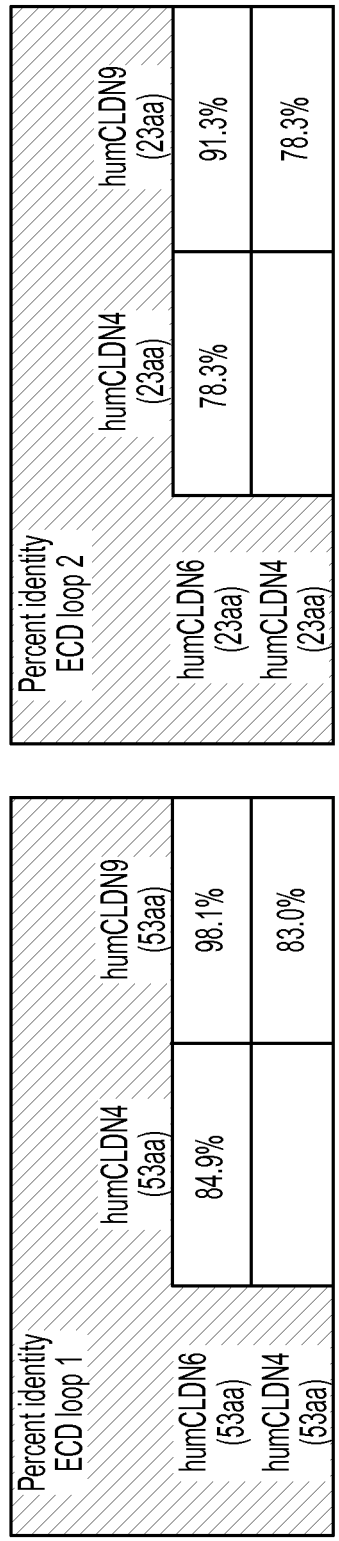
FIG. 4B shows a tabular representation of the percent identity of amino acid residues in extracellular domain (ECD) 1 or ECD2 in CLDN4, CLDN6 and CLDN9.

Cloning and Expression of Recombinant CLDN Proteins and Engineering of Cell Lines Overexpressing Cell Surface CLDN Proteins In order to deduce the relationship between claudin protein sequences, the AlignX program of the Vector NTI software package was used to align 30 claudin protein sequences from 23 human CLDN genes. The results of this alignment are depicted as a dendrogram in FIG. 4A. A review of the figure shows that CLDN6 and CLDN9 are very closely related in sequence, appearing adjacent to one another on the same branch of the dendrogram. FIG. 4A also shows that CLDN4 is the next most closely related family member to CLDN6. A more detailed review of the data shows that the human CLDN6 protein is very closely related to the human CLDN9 protein sequence in the extracellular domains (ECD), with >98% identity in ECD1 and >91% identity in ECD2 (FIG. 4B). Human CLDN4 was also found to be closely related to human CLDN6 in the ECD sequences, with >84% identity in ECD1 and >78% identity in ECD2 (FIG. 4B). Based upon these protein sequence relationships, it was hypothesized that immunization with a human CLDN6 antigen would yield antibodies recognizing human CLDN6 that will also be cross-reactive with human CLDN9, and perhaps also cross-reactive with human CLDN4.

In order to determine which species orthologs of CLDN6, CLDN9 and CLDN4 would be required for screening these multireactive claudin antibodies, ECD sequences of CLDN4, CLDN6 and CLDN9 were analyzed from each of the following species: human, cynomolgus monkey, mouse and rat. The analysis was performed using AlignX and NCBI database protein sequences when available (NP accession numbers of human, mouse and rat proteins are indicated in FIG. 4C). Alternatively, protein sequences were deduced from translation of the cynomolgus monkey CLDN genes assembled by BLAST of human CLDN open reading frame sequences versus cynomolgus monkey whole genome shotgun sequencing contigs. Inspection of these alignments reveals that: (1) deduced cynomolgus monkey protein ECD sequences for CLDN4, CLDN6, and CLDN9 proteins are 100% identical to the respective human ECD sequences; (2) mouse and rat CLDN9 ECD sequences are 100% identical to the human ortholog sequence; (3) and mouse and rat CLDN4 and CLDN6 ECD sequences differ from one another and from the respective human orthologs. Therefore, generation of a set of seven constructs comprising human CLDN4, human CLDN6, human CLDN9, mouse CLDN4, mouse CLDN6, rat CLDN4 and rat CLDN6 should enable determination of cross-reactivity for any antibody with all possible 12 orthologs.

DNA Fragments Encoding Human CLDN6, CLDN4, and CLDN9 Proteins.

To generate all molecular and cellular materials required in the present invention pertaining to the human CLDN6 (hCLDN6) protein, a codon-optimized DNA fragment encoding a protein identical to NCBI protein accession NP_067018 was synthesized (IDT). This DNA clone was used for all subsequent engineering of constructs expressing the mature hCLDN6 protein or fragments thereof. Similarly, codon-optimized DNA fragments encoding proteins identical to NCBI protein accession NP_001296 for human CLDN4 (hCLDN4), or NCBI protein accession NP_066192 for human CLDN9 (hCLDN9) were purchased and used for all subsequent engineering of constructs expressing the hCLDN4 or hCLDN9 proteins or fragments thereof.

DNA Fragments Encoding Mouse CLDN6 and CLDN4 Proteins.

To generate all molecular and cellular materials required in the present invention pertaining to the mouse CLDN6 (mCLDN6) protein, a codon-optimized DNA fragment encoding a protein identical to NCBI protein accession NP_061247 was synthesized (IDT). This DNA clone was used for all subsequent engineering of constructs expressing the mature mCLDN6 protein or fragments thereof. Similarly, a codon-optimized DNA fragment encoding a protein identical to NCBI protein accession NP_034033 for mouse CLDN4 (mCLDN4) was purchased and used for all subsequent engineering of constructs expressing the mature mCLDN4 protein or fragments thereof.

DNA Fragments Encoding Rat CLDN6 and CLDN4 Proteins.

To generate all molecular and cellular materials required in the present invention pertaining to the rat CLDN6 (rCLDN6) protein, a codon-optimized DNA fragment encoding a protein identical to NCBI protein accession NP_001095834 was synthesized (IDT). This DNA clone was used for all subsequent engineering of constructs expressing the mature rCLDN6 protein or fragments thereof. Similarly, a codon-optimized DNA fragment encoding a protein identical to NCBI protein accession NP_001012022 for rat CLDN4 (rCLDN4) was purchased and used for all subsequent engineering of constructs expressing the mature rCLDN4 protein or fragments thereof.

Cell Line Engineering

Engineered cell lines overexpressing the various CLDN proteins listed above were constructed using lentiviral vectors to transduce HEK-293T or 3T3 cell lines using art recognized techniques. First, PCR was used to amplify the DNA fragments encoding the protein of interest (e.g., hCLDN6, mCLDN6, rCLDN6, hCLDN9, hCLDN4, mCLDN4, or rCLDN4) using the commercially synthesized DNA fragments described above as templates. Then, the individual PCR products were subcloned into the multiple cloning site (MCS) of the lentiviral expression vector, pCDH-EF1-MCS-T2A-GFP (System Biosciences), to generate a suite of lentiviral vectors. The T2A sequence in resultant pCDH-EF1-CLDN-T2A-GFP vectors promotes ribosomal skipping of a peptide bond condensation, resulting in expression of two independent proteins: high level expression of the specific CLDN protein encoded upstream of the T2A peptide, with co-expression of the GFP marker protein encoded downstream of the T2A peptide. This suite of lentiviral vectors was used to create separate stable HEK-293T or 3T3 cell lines overexpressing individual CLDN proteins using standard lentiviral transduction techniques well known to those skilled in the art. CLDN-positive cells were selected with FACS using high-expressing HEK-293T subclones, which were also strongly positive for GFP.

Example 5

Generation of Anti-CLDN Antibodies

Because CLDN6 is most homologous to CLDN4 and CLDN9 (see FIG. 4A and analysis as described in Example 4, above), CLDN6 was used as the immunogen with which to generate multireactive anti-CLDN antibodies. Mice were inoculated with HEK-293T cells or 3T3 cells overexpressing hCLDN6 (generated as described in Example 4) in order to produce antibody-generating hybridomas. Six mice (two each of the following strains: Balb/c, CD-1, FVB) were inoculated with 1 million hCLDN6-HEK-293T cells emulsified with an equal volume of TiterMax® adjuvant. A second, separate inoculation of six mice (two each of the following strains: Balb/c, CD-1, FVB) was performed using 3T3 cells overexpressing CLDN6. Following the initial inoculation the mice were injected twice weekly for 4 weeks with cells overexpressing CLDN6 emulsified with an equal volume of alum adjuvant.

Mice were sacrificed and draining lymph nodes (popliteal, inguinal, and medial iliac) were dissected and used as a source for antibody producing cells. A single cell suspension of B cells ($305 \times 10^6$ cells) were fused with non-secreting P3x63Ag8.653 myeloma cells (ATCC #CRL-1580) at a ratio of 1:1 by electro cell fusion using a model BTX Hybrimmune System (BTX Harvard Apparatus). Cells were resuspended in hybridoma selection medium: DMEM medium (Cellgro) supplemented with azaserine (Sigma), 15% fetal clone I serum (Hyclone), 10% BM condimed (Roche Applied Sciences), 1 mM sodium pyruvate, 4 mM L-glutamine, 100 IU penicillin-streptomycin, 50 µM 2-mercaptoethanol, and 100 µM hypoxanthine, and cultured in three T225 flasks in 90 mL selection medium per flask. The flasks were placed in a humidified 37° C. incubator containing 5% $CO_2$ and 95% air for 6 days. The library was frozen down in 6 vials of CryoStor CS10 buffer (BioLife Solutions), with approximately $15 \times 10^6$ viable cells per vial, and stored in liquid nitrogen.

One vial from the library was thawed at 37° C. and the frozen hybridoma cells were added to 90 mL hybridoma selection medium, described above, and placed in a T150 flask. The cells were cultured overnight in a humidified 37° C. incubator with 5% $CO_2$ and 95% air. The following day hybridoma cells were collected from the flask and plated at one cell per well (using a FACSAria I cell sorter) in 200 µL of supplemented hybridoma selection medium into 48 Falcon 96-well U-bottom plates. The hybridomas were cultured for 10 days and the supernatants were screened for antibodies specific to hCLDN6, hCLDN4 or hCLDN9 proteins using flow cytometry. Flow cytometry was performed as follows: $1 \times 10^5$ per well of HEK-293T cells, stably transduced with lentiviral vectors encoding hCLDN6, hCLDN4 or hCLDN9, were incubated for 30 mins. with 100 µL hybridoma supernatent. Cells were washed with PBS/2% FCS and then incubated with 50 µL per sample DyeLight 649 labeled goat-anti-mouse IgG, Fc fragment specific secondary antibody diluted 1:200 in PBS/2% FCS. After a 15 min. incubation cells were washed twice with PBS/2% FCS and re-suspended in PBS/2% FCS with DAPI (to detect dead cells) and analyzed by flow cytometry for fluorescence exceeding that of cells stained with an isotype control antibody. Selected hybridomas that tested positive for antibodies directed to one or more of the CLDN antigens were set aside for further characterization. Remaining, unused hybridoma library cells were frozen in liquid nitrogen for future library testing and screening.

Example 6

Sequencing of Anti-CLDN Antibodies

Anti-CLDN antibodies were generated as described above and then sequenced as follows. Total RNA was purified from selected hybridoma cells using the RNeasy Miniprep Kit (Qiagen) according to the manufacturer's instructions. Between $10^4$ and $10^5$ cells were used per sample. Isolated RNA samples were stored at −80° C. until used. The variable region of the Ig heavy chain of each hybridoma was amplified using two 5' primer mixes comprising 86 mouse specific leader sequence primers designed to target the complete mouse VH repertoire in combination with a 3' mouse Cγ primer specific for all mouse Ig isotypes. Similarly, two primer mixes containing 64 5' VK leader sequences designed to amplify each of the VK mouse families was used in combination with a single reverse primer specific to the mouse kappa constant region in order to amplify and sequence the kappa light chain. The VH and VL transcripts were amplified from 100 ng total RNA using the Qiagen One Step RT-PCR kit as follows. A total of four RT-PCR reactions were run for each hybridoma, two for the VK light chain and two for the VH heavy chain. PCR reaction mixtures included 1.5 µL of RNA, 0.4 µL of 100 µM of either heavy chain or kappa light chain primers (custom synthesized by IDT), 5 µL of 5×RT-PCR buffer, 1 µL dNTPs, and 0.6 µL of enzyme mix containing reverse transcriptase and DNA polymerase. The thermal cycler program included the following steps: RT step 50° C. for 60 min., 95° C. for 15 min. followed by 35 cycles of (94.5° C. for 30 seconds, 57° C. for 30 seconds, 72° C. for 1 min.), and a final incubation at 72° C. for 10 min. The extracted PCR products were sequenced using the same specific variable region primers as described above. PCR products were sent to an external sequencing vendor (MCLAB) for PCR purification and sequencing services.

Figure 5E:
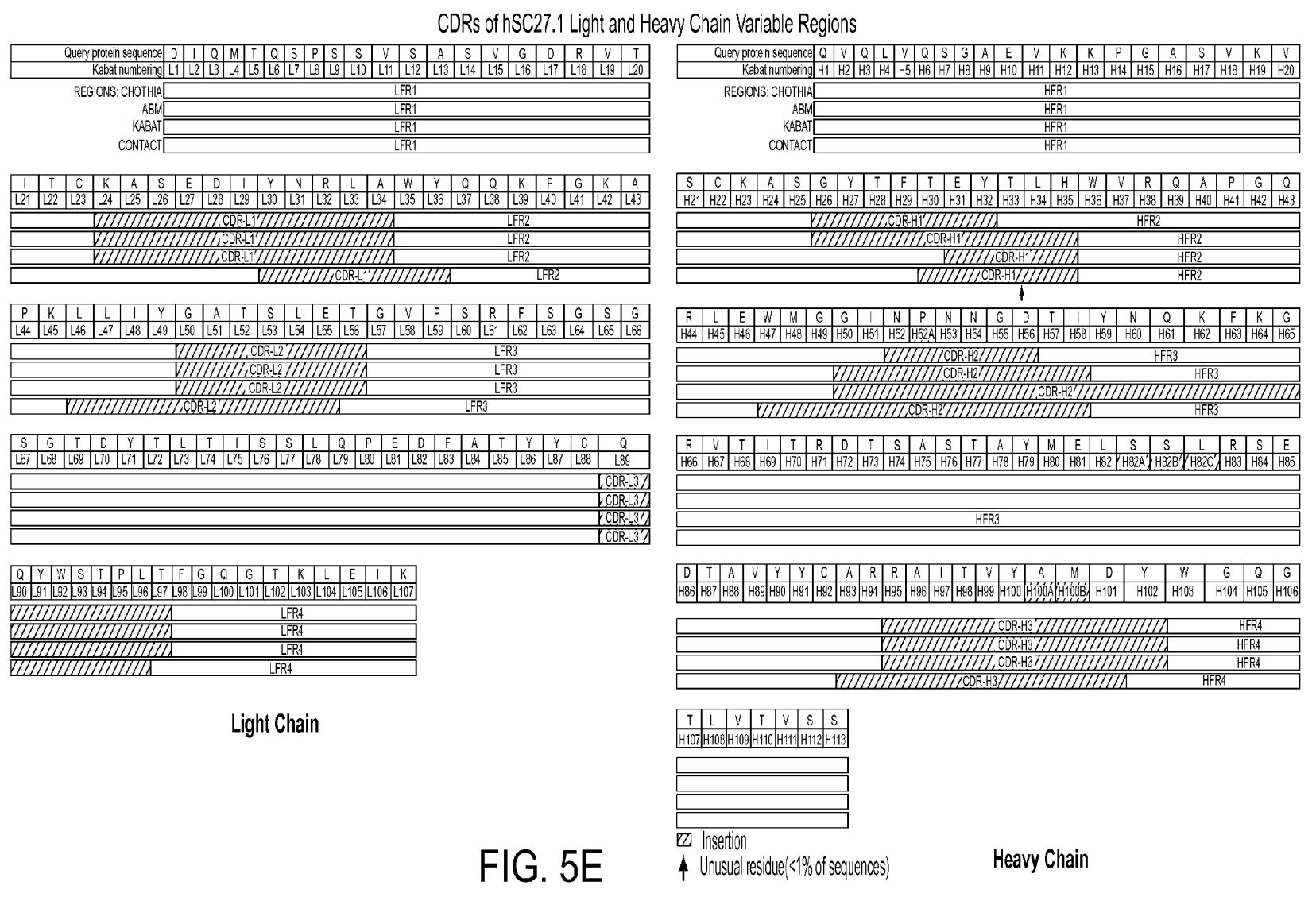
Figure 5F:
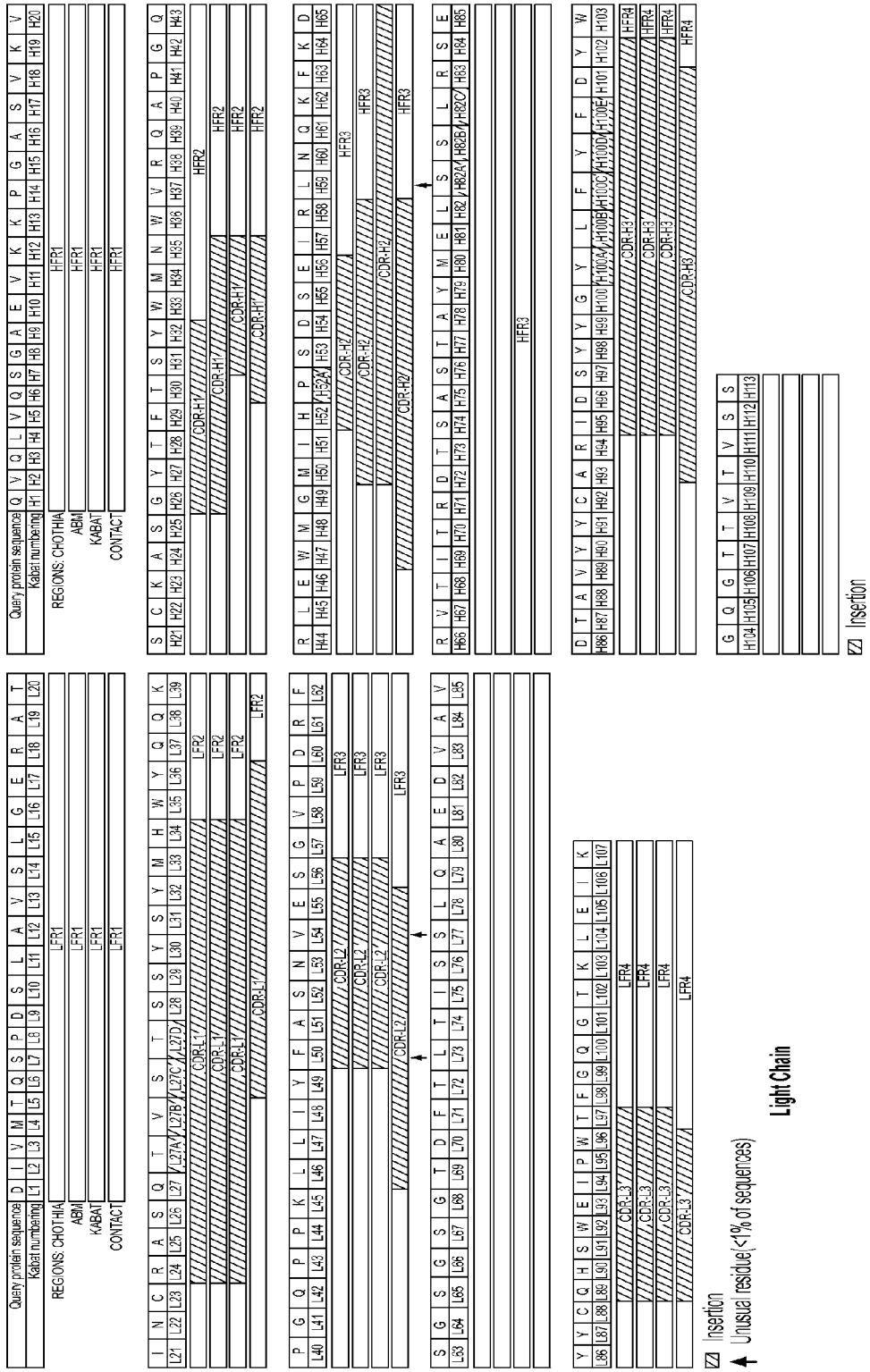
Figure 5H:

FIG. 5A depicts the contiguous amino acid sequences of numerous novel mouse light chain variable regions from anti-CLDN antibodies (SEQ ID NOS: 21-57, odd numbers).

FIG. 5B depicts the contiguous amino acid sequences of novel mouse heavy chain variable regions from the same anti-CLDN antibodies (SEQ ID NOS: 23-59, odd numbers). Mouse light and heavy chain variable region nucleic acid sequences are provided in FIG. 5C (SEQ ID NOS: 20-58, even numbers). Taken together FIGS. 5A and 5B provide the annotated sequences of 10 mouse anti-CLDN antibodies, termed SC27.1, SC27.22, SC27.103, SC27.104, SC27.105, SC27.106, SC27.108 (identical to SC27.109), SC27.201, SC27.203 and SC27.204. The amino acid sequences are annotated to identify the framework regions (i.e. FR1-FR4) and the complementarity determining regions (i.e. CDRL1-CDRL3 in FIG. 5A or CDRH1-CDRH3 in FIG. 5B) defined as per Kabat. The variable region sequences were analyzed using a proprietary version of the Abysis database to provide the CDR and FR designations. Though the CDRs are numbered according to Kabat those skilled in art will appreciate that the CDR and FR designations can also be defined according to Chothia, McCallum or any other accepted nomenclature system.

The SEQ ID NOS of each particular antibody are sequential odd numbers. Thus the monoclonal anti-CLDN antibody, SC27.1, comprises amino acid SEQ ID NOS: 21 and 23 for the VL and VH, respectively; and SC27.22 comprises SEQ ID NOS: 25 and 27 etc. The corresponding nucleic acid sequence for each antibody amino acid sequence is included in FIG. 5C and has the SEQ ID NO immediately preceding the corresponding amino acid SEQ ID NO. Thus, for example, the SEQ ID NOS of the nucleic acid sequences of the VL and VH of the SC27.1 antibody are SEQ ID NOS: 20 and 22, respectively.

Example 7

Generation of Chimeric and Humanized Anti-CLDN Antibodies

Chimeric anti-CLDN antibodies were generated using art-recognized techniques as follows. Total RNA was extracted from the anti-CLDN antibody-producing hybridomas using the method described in Example 6 and the RNA was PCR amplified. Data regarding V, D and J gene segments of the VH and VL chains of the mouse antibodies were obtained from the nucleic acid sequences of the anti-CLDN antibodies of the invention (see FIG. 5C for nucleic acid sequences). Primer sets specific to the framework sequence of the VH and VL chain of the antibodies were designed using the following restriction sites: AgeI and XhoI for the VH fragments, and XmaI and DraIII for the VL fragments. PCR products were purified with a Qiaquick PCR purification kit (Qiagen), followed by digestion with restriction enzymes AgeI and XhoI for the VH fragments and XmaI and DraIII for the VL fragments. The VH and VL digested PCR products were purified and ligated into IgH or IgK expression vectors, respectively. Ligation reactions were performed in a total volume of 10 μL with 200 U T4-DNA Ligase (New England Biolabs), 7.5 μL of digested and purified gene-specific PCR product and 25 ng linearized vector DNA. Competent E. coli DH10B bacteria (Life Technologies) were transformed via heat shock at 42° C. with 3 μL ligation product and plated onto ampicillin plates at a concentration of 100 μg/mL. Following purification and digestion of the amplified ligation products, the VH fragment was cloned into the AgeI-XhoI restriction sites of the pEE6.4 expression vector (Lonza) comprising HuIgG1 (pEE6.4HuIgG1) and the VL fragment was cloned into the XmaI-DraIII restriction sites of the pEE12.4 expression vector (Lonza) comprising a human kappa light constant region (pEE12.4Hu-Kappa).

Chimeric antibodies were expressed by co-transfection of either HEK-293T or CHO-S cells with pEE6.4HuIgG1 and pEE12.4Hu-Kappa expression vectors. Prior to transfection the HEK-293T cells were cultured in 150 mm plates under standard conditions in Dulbecco's Modified Eagle's Medium (DMEM) supplemented with 10% heat inactivated FCS, 100 μg/mL streptomycin and 100 U/mL penicillin G. For transient transfections cells were grown to 80% confluency. 2.5 μg each of pEE6.4HuIgG1 and pEE12.4Hu-Kappa vector DNA were added to 10 μL HEK-293T transfection reagent in 1.5 mL Opti-MEM. The mix was incubated for 30 min. at room temperature and added to cells. Supernatants were harvested three to six days after transfection. For CHO-S cells, 2.5 μg each of pEE6.4HuIgG1 and pEE12.4Hu-Kappa vector DNA were added to 15 μg PEI transfection reagent in 400 μL Opti-MEM. The mix was incubated for 10 min. at room temperature and added to cells. Supernatants were harvested three to six days after transfection. Culture supernatants containing recombinant chimeric antibodies were cleared from cell debris by centrifugation at 800×g for 10 min. and stored at 4° C. Recombinant chimeric antibodies were purified with Protein A beads Mouse anti-CLDN antibodies were humanized using a proprietary computer-aided CDR-grafting method (Abysis Database, UCL Business) and standard molecular engineering techniques as follows. Human framework regions of the variable regions were designed based on the highest homology between the framework sequences and CDR canonical structures of human germline antibody sequences, and the framework sequences and CDRs of the relevant mouse antibodies. For the purpose of the analysis the assignment of amino acids to each of the CDR domains was done in accordance with Kabat numbering. Once the variable regions were selected, they were generated from synthetic gene segments (Integrated DNA Technologies). Humanized antibodies were cloned and expressed using the molecular methods described above for chimeric antibodies.

The VL and VH amino acid sequences of the humanized antibodies were derived from the VL and VH sequences of the corresponding mouse antibody (e.g. hSC27.1 is derived from mouse SC27.1). There were no framework changes or back mutations made in the light or heavy chain variable regions of the four humanized antibodies generated: hSC27.1, hSC27.22, hSC17.108 and hSC27.204.

To address stability concerns, three variants of hSC27.22 were produced using different VH frameworks in the same VH1 family. The variants were termed hSC27.22-VH1-8; hSC27.22-VH1-46; hSC27.22-VH1-69. In addition, one variant of hSC27.108 was constructed, termed hSC27.108v1, which shares the same heavy chain as hSC27.108 (SEQ ID NO: 119) but differs in light chain compared to hSC27.108. In addition, several variants of hSC27.204 were generated, termed hSC27.204v1 through hSC27.204v15, all of which share the same light chain (SEQ ID NO: 120) but differ in the heavy chain. The heavy chains of hSC27.204 and hSC27.204v4 differ in a single framework region mutation, T28D. hSC27.204v1 through hSC27.204v3 and hSC27.204v5 through hSC27.204v7 incorporate conservative mutations in the CDRs to address stability concerns. Specifically, hSC27.204v1, hSC27.204v2, and hSC27.204v3 contain the modifications N58K, N58Q, and T60N, respectively, on the hSC27.204 heavy chain background. Similarly, hSC27.204v5, hSC27.204v6, and hSC27.204v7 contain the modifications N58K, N58Q, and T60N, respectively on the hSC27.204v4 background. Lastly, variants hSC27.204v8 and hSC27.204v9 do not include a back mutation at position 93 of the heavy chain in order to minimize immunogenicity. Specifically, variants hSC27.204v8, hSC27.204v9, hSC27.204v10, hSC27.204v11, hSC27.204v12, hSC27.204v13, hSC27.204v14, and hSC27.204v15 correspond to variants hSC27.204, hSC27.204v1, hSC27.204v2, hSC27.204v3, hSC27.204v4, hSC27.204v5, hSC27.204 6, and hSC27.204v7, respectively, except that variants 8-15 lack the A93T back mutation.

In addition, 9 variants of the hSC27.22 humanized antibody constant region were constructed. The first variant, hSC27.22ss1 is a site specific variant and is described in more detail in Example 8 below. The other variants were constructed by substituting the IgG isotype with either IgG2 (termed, "hSC27.22 IgG2") or mutated forms of IgG4 (termed, "hSC27.22 IgG4 R409K"; "hSC27.22 IgG4 S228P"; "hSC27.22 IgG4 S228P K370E R409K"; "hSC27.22 IgG4 K370E"; "hSC27.22 IgG4 S228P K370E"; "hSC27.22 IgG4 C127S S228P"; "hSC27.22 IgG4 C127S K370E"; and "hSC27.22 IgG4 C127S S228P K370E").

Table 5 below shows a summary of the humanized anti CLDN antibodies and their variants, numbered according to Kabat et al.

In each case, the binding affinity of the humanized antibody was checked to ensure that it was substantially equivalent to the corresponding mouse antibody. FIG. 5A depicts the contiguous amino acid sequences of the VL of exemplary humanized antibodies and their variants. FIG. 5B depicts the contiguous amino acid sequences of the VH of exemplary humanized antibodies and their variants. The nucleic acid sequences of the light and heavy chain variable regions of the anti-CLDN humanized antibodies are provided in FIG. 5C.

FIG. 5D shows the full length sequences of the light and heavy chains of exemplary humanized antibodies and their variants. hSC27.1 (SEQ ID NOS: 75 and 76) and hSC27.22 (SEQ ID NOS: 77 and 78).

FIGS. 5E to 5H comprise annotated amino acid sequences (numbered as per Kabat et al.) of the light and heavy chain variable regions of hSC27.1 (FIG. 5E); hSC27.22 (FIG. 5F); hSC27.108 (FIG. 5G); and hSC27.204 (FIG. 5H) humanized antibodies showing CDRs as determined using Kabat, Chothia, ABM and Contact methodology.

TABLE 5

| mAb | Isotype | human VH | human JH | VH FR changes | VH CDR Changes | human VK | human JK | VK FR changes | VK CDR Changes |
|---|---|---|---|---|---|---|---|---|---|
| hSC27.1 | IgG1 | IGHV1-3*01 | JH1 | None | None | IGKV1-12*01 | JK2 | None | None |
| hSC27.22 | IgG1 | IGHV1-3*01 | JH6 | None | None | IGKV4-1*01 | JK2 | None | None |
| hSC27.22ss1 | IgG1 C220S | IGHV1-3*01 | JH6 | None | None | IGKV4-1*01 | JK2 | None | None |
| hSC27.22-VH1-8 | IgG1 | IGHV1-8*01 | JH6 | None | None | IGKV4-1*01 | JK2 | None | None |
| hSC27.22 VH1-46 | IgG1 | IGHV1-46*01 | JH6 | None | None | IGKV4-1*01 | JK2 | None | None |
| hSC27.22 VH1-69 | IgG1 | IGHV1-69*01 | JH6 | None | None | IGKV4-1*01 | JK2 | None | None |
| hSC27.22 IgG2 | IgG2 | IGHV1-3*01 | JH6 | None | None | IGKV4-1*01 | JK2 | None | None |
| hSC27.22 IgG4 R409K | IgG4 R409K | IGHV1-3*01 | JH6 | None | None | IGKV4-1*01 | JK2 | None | None |
| hSC27.22 IgG4 S228P | IgG4 S228P | IGHV1-3*01 | JH6 | None | None | IGKV4-1*01 | JK2 | None | None |
| hSC27.22 IgG4 S228P K370E R409K | IgG4 S228P R409K K370E | IGHV1-3*01 | JH6 | None | None | IGKV4-1*01 | JK2 | None | None |
| hSC27.22 IgG4 K370E | IgG4 K370E | IGHV1-3*01 | JH6 | None | None | IGKV4-1*01 | JK2 | None | None |
| hSC27.22 IgG4 S228P K370E | IgG4 S228P K370E | IGHV1-3*01 | JH6 | None | None | IGKV4-1*01 | JK2 | None | None |
| hSC27.22 IgG4 C127S S228P | IgG4 C127S S228P | IGHV1-3*01 | JH6 | None | None | IGKV4-1*01 | JK2 | None | None |
| hSC27.22 IgG4 C127S K370E | IgG4 C127S K370E | IGHV1-3*01 | JH6 | None | None | IGKV4-1*01 | JK2 | None | None |
| hSC27.22 IgG4 C127S S228P K370E | IgG4 C127S S228P K370E | IGHV1-3*01 | JH6 | None | None | IGKV4-1*01 | JK2 | None | None |
| hSC27.108 | IgG1 | IGHV1-18*01 | JH1 | None | None | IGKV3-11*01 | JK4 | None | None |
| hSC27.108 v1 | IgG1 | IGHV1-18*01 | JH1 | None | None | IGKV6-21*01 | JK4 | L47W K49Y | None |
| hSC27.204 | IgG1 | IGHV3-23*01 | JH1 | A93T K94G | None | IGKV1-16*01 | JK4 | None | None |
| hSC27.204 v1 | IgG1 | IGHV3-23*01 | JH1 | A93T K94G | N58K | IGKV1-16*01 | JK4 | None | None |
| hSC27.204v2 | IgG1 | IGHV3-23*01 | JH1 | A93T K94G | N58Q | IGKV1-16*01 | JK4 | None | None |
| hSC27.204v3 | IgG1 | IGHV3-23*01 | JH1 | A93T K94G | T60N | IGKV1-16*01 | JK4 | None | None |
| hSC27.204v4 | IgG1 | IGHV3-23*01 | JH1 | T28D, A93T K94G | None | IGKV1-16*01 | JK4 | None | None |
| hSC27.204v5 | IgG1 | IGHV3-23*01 | JH1 | T28D, A93T K94G | N58K | IGKV1-16*01 | JK4 | None | None |
| hSC27.204v6 | IgG1 | IGHV3-23*01 | JH1 | T28D, A93T K94G | N58Q | IGKV1-16*01 | JK4 | None | None |
| hSC27.204v7 | IgG1 | IGHV3-23*01 | JH1 | T28D, A93T K94G | T60N | IGKV1-16*01 | JK4 | None | None |
| hSC27.204v8 | IgG1 | IGHV3-23*01 | JH1 | K94G | None | IGKV1-16*01 | JK4 | None | None |
| hSC27.204v9 | IgG1 | IGHV3-23*01 | JH1 | K94G | N58K | IGKV1-16*01 | JK4 | None | None |
| hSC27.204v10 | IgG1 | IGHV3-23*01 | JH1 | K94G | N58Q | IGKV1-16*01 | JK4 | None | None |
| hSC27.204v11 | IgG1 | IGHV3-23*01 | JH1 | K94G | T60N | IGKV1-16*01 | JK4 | None | None |
| hSC27.204v12 | IgG1 | IGHV3-23*01 | JH1 | T28D, K94G | None | IGKV1-16*01 | JK4 | None | None |
| hSC27.204v13 | IgG1 | IGHV3-23*01 | JH1 | T28D, K94G | N58K | IGKV1-16*01 | JK4 | None | None |

TABLE 5-continued

| mAb | Isotype | human VH | human JH | VH FR changes | VH CDR Changes | human VK | human JK | VK FR changes | VK CDR Changes |
|---|---|---|---|---|---|---|---|---|---|
| hSC27.204v14 | IgG1 | IGHV3-23*01 | JH1 | T28D, K94G | N58Q | IGKV1-16*01 | JK4 | None | None |
| hSC27.204v15 | IgG1 | IGHV3-23*01 | JH1 | T28D, K94G | T60N | IGKV1-16*01 | JK4 | None | None |

Example 8

Generation of Site-Specific Anti-CLDN Antibodies

An engineered human IgG1/kappa anti-CLDN site-specific antibody was constructed comprising a native light chain (LC) constant region and mutated heavy chain (HC) constant region, wherein cysteine 220 (C220) in the upper hinge region of the HC, which forms an interchain disulfide bond with cysteine 214 (C214) in the LC, was substituted with serine (C220S). When assembled, the HCs and LCs form an antibody comprising two free cysteines that are suitable for conjugation to a therapeutic agent. Unless otherwise noted, all numbering of constant region residues is in accordance with the EU numbering scheme as set forth in Kabat et al.

The engineered antibody was generated as follows. The nucleic acid sequence of the HC of the hSC27.22 antibody (SEQ ID NO: 67) was codon optimized by DNA2.0 (Menlo Park, Calif.) to generate the following nucleic acid sequence:

(SEQ ID NO: 178)
CAAGTGCAGCTCGTCCAGTCCGGTGCCGAAGTCAAGAAGCCGGGCGCATC

AGTGAAAGTGTCGTGCAAAGCCTCCGGGTACACCTTCACCTCATACTGGA

TGAACTGGGTCCGCCAAGCCCCGGGACAGAGACTGGAGTGGATGGGCATG

ATTCACCCATCCGATTCCGAGATCCGGCTGAACCAGAAGTTCAAGGACCG

CGTGACCATCACCCGGGACACCAGCGCCAGCACTGCCTACATGGAATTGA

GCTCGCTGCGGTCCGAGGATACCGCTGTGTACTATTGCGCGAGGATCGAC

TCCTACTACGGCTACCTTTTCTACTTCGACTACTGGGGACAAGGGACGAC

CGTGACTGTGTCGAGC.

The optimized nucleic acid was cloned onto an expression vector containing the C220S mutation in the constant region of the HC. The vector encoding the mutant C220S HC of hSC27.22 was co-transfected in CHO-S cells with a vector encoding the native IgG1 kappa LC of hSC27.22, and expressed using a mammalian transient expression system. The engineered anti-CLDN site-specific antibody containing the C220S mutant was termed hSC27.22ss1. The amino acid sequence of the full length HC of the hSC27.22ss1 site specific antibody is shown in FIG. 5D (SEQ ID NO: 122). The amino acid sequence of the LC of hSC27.22ss1 is identical to that of hSC27.22 (SEQ ID NO: 116).

Engineered human IgG4/kappa anti-CLDN site-specific antibodies were also constructed comprising a native LC constant region and mutated HC constant region, wherein cysteine 127 (C127) in the CH1 of the IgG4 heavy chain, which forms an interchain disulfide bond with cysteine 220 (C220) in the LC, was substituted with serine (C127S). When assembled, the HCs and LCs form an antibody comprising two free cysteines that are suitable for conjugation to a therapeutic agent. This modification was made using the Quikchange Site Directed Mutagenesis Kit (Agilent) according to the manufacturer's protocols using the IgG4 expression vector as a template.

The engineered antibodies were generated as follows. The codon optimized nucleic acid sequence of hSC27.22 (SEQ ID NO: 178), was cloned onto an expression vector containing the C127S mutation in the constant region of the HC. The vector encoding the mutant C127S HC of hSC27.22 was co-transfected in CHO-S cells with a vector encoding the native IgG1 kappa LC of hSC27.22, and expressed using a mammalian transient expression system. The C127S modification was applied to the various modified IgG4 constructs generated as described in Example 7 above. The resulting IgG4 site specific constructs are shown in Table 5 above and FIG. 5D and are termed: hSC27.22 IgG4 S228P; hSC27.22 IgG4 R409K; hSC27.22 IgG4 S228P K370E R409K; hSC27.22 IgG4 K370E; hSC27.22 IgG4 S228P K370E; hSC27.22 IgG4 C127S S228P; hSC27.22 IgG4 C127S K370E; and hSC27.22 IgG4 C127S S228P K370E.

The engineered anti-CLDN site specific antibodies were characterized by SDS-PAGE to confirm that the correct mutants had been generated. SDS-PAGE was conducted on a pre-cast 10% Tris-Glycine mini gel from Life Technologies in the presence and absence of a reducing agent such as DTT (dithiothreitol). Following electrophoresis, the gels were stained with a colloidal coomassie solution (data not shown). Under reducing conditions, two bands corresponding to the free LCs and free HCs, were observed. This pattern is typical of IgG molecules in reducing conditions. Under non-reducing conditions, the band patterns were different from native IgG molecules, indicative of the absence of a disulfide bond between the HC and LC. A band around 98 kD corresponding to the HC-HC dimer was observed. In addition, a faint band corresponding to the free LC and a predominant band around 48 kD that corresponded to a LC-LC dimer was observed. The formation of some amount of LC-LC species is expected due to the free cysteines on the c-terminus of each LC.

Example 9

Specificity of Anti-CLDN Antibodies

The mouse antibodies generated as described in Example 5, were characterized to determine whether they cross reacted with CLDN family members and orthologs of CLDN family members.

Flow cytometry analyses were performed as follows: HEK-293T cells were stably transduced with (i) lentiviral vectors encoding hCLDN6, mCLDN6, and rCLDN6; (ii) hCLDN9; or (iii) hCLDN4, mCLDN4 and rCLDN4, made as described in Example 4 above. 1×10$^5$ HEK-293T cells stably transduced with the aforementioned expression constructs were incubated at 4° C. for 30 mins. with either hSC27.1 or hSC27.22 antibodies, diluted to 10 μg/ml into a final volume of 50 μl PBS/2% FCS. Following incubation, cells were washed with 200 μL PBS/2% FCS, pelleted by centrifugation, supernatant was discarded, and cell pellets were resuspended in 50 μL per sample DyeLight 649 labeled goat-anti-mouse IgG, Fc fragment specific secondary antibody diluted 1:200 in PBS/2% FCS. After a 15 min. incubation at 4° C. cells were washed and pelleted twice with PBS/2% FCS as previously described and resuspended in 100 μL PBS/2% FCS with 2 μg/mL 4',6-diamidino-2-phenylindole dihydrochloride (DAPI). Samples were analyzed by flow cytometry and live cells were assessed with DyeLight 649 for fluorescence exceeding that of cells stained with an isotype control antibody.

Figure 6A:
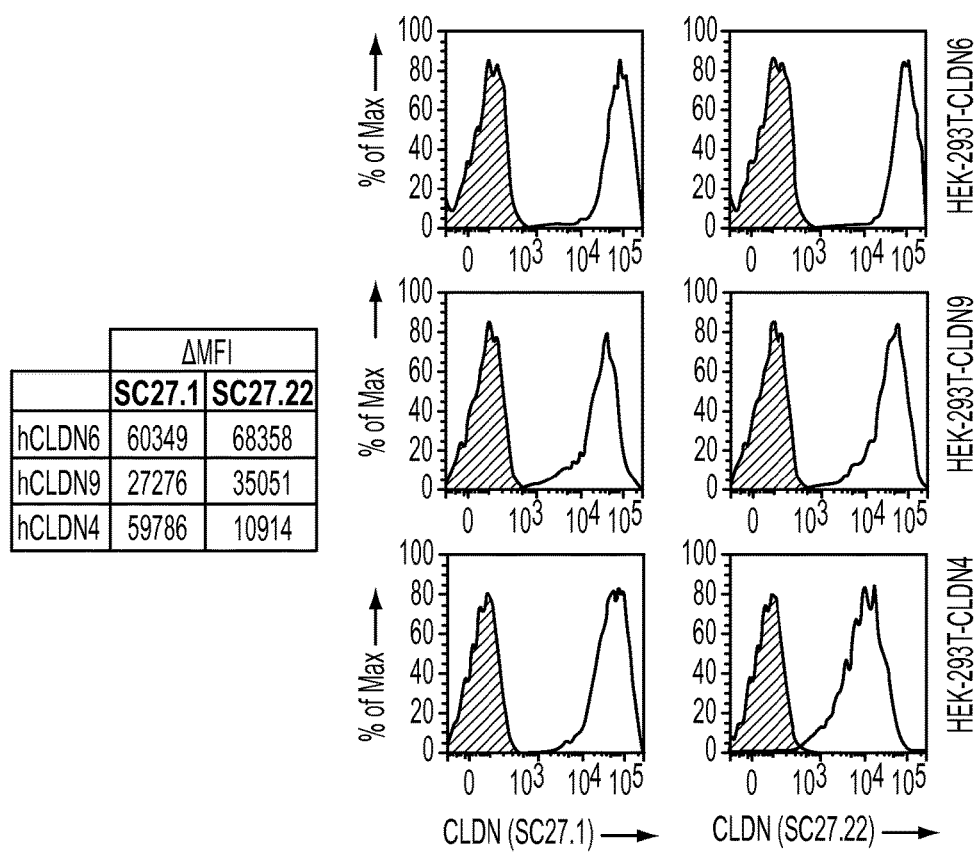
FIG. 6A shows the ability of anti-CLDN antibodies SC27.1 and SC27.22 to bind HEK-293T cells overexpressing human CLDN4, CLDN6 and CLDN9 as detected by flow cytometry, where results are shown as change in mean fluorescence intensity (ΔMFI) and a histogram, with the solid black line indicating the binding of the indicated antibody to cells overexpressing the indicated CLDN protein compared to fluorescence minus one (FMO) isotype-control (gray-fill)

The flow cytometry assay described above resulted in the identification of numerous anti-CLDN antibodies. Cross reactivity was determined based on the change in geometric mean fluorescence intensity (ΔMFI) for the binding of the antibody to the cell lines specifically overexpressing the indicated CLDN family member versus the signal determined using a fluorescence minus one (FMO) isotype-control (gray-fill) (FIG. 6A). Thus, the two hCLDN6-binding antibodies SC27.1 and SC27.22 can be described as claudin multireactive antibodies since they cross react in this assay with three members of the human CLDN family: hCLDN6, hCLDN4 and hCLDN9. SC27.1 and SC27.22 antibodies also bound to mouse and rat orthologs of CLDN4 and CLDN9 (data not shown).

To test the ability of various additional mouse antibodies to bind to CLDN family members, flow cytometry was performed using cell lines overexpressing human CLDN4, CLDN6 or CLND9 that had been incubated with 10 μg/mL of purified primary anti-CLDN antibody, or a mouse IgG2b control antibody, followed by incubation with an Alexa 647 anti-mouse secondary antibody. As shown in FIG. 6B, all the antibodies bound to CLDN6, whereas some were CLDN6-specific (e.g. SC27.102, SC27.105, and SC27.108), and others were multireactive and bound to both CLDN6 and CLDN9 (e.g., SC27.103 and SC27.204), or to CLDN6 and CLDN4 (e.g., SC27.104). Thus a wide range of multireactive binding profiles was obtained for the antibodies of the invention.

Figure 6C:
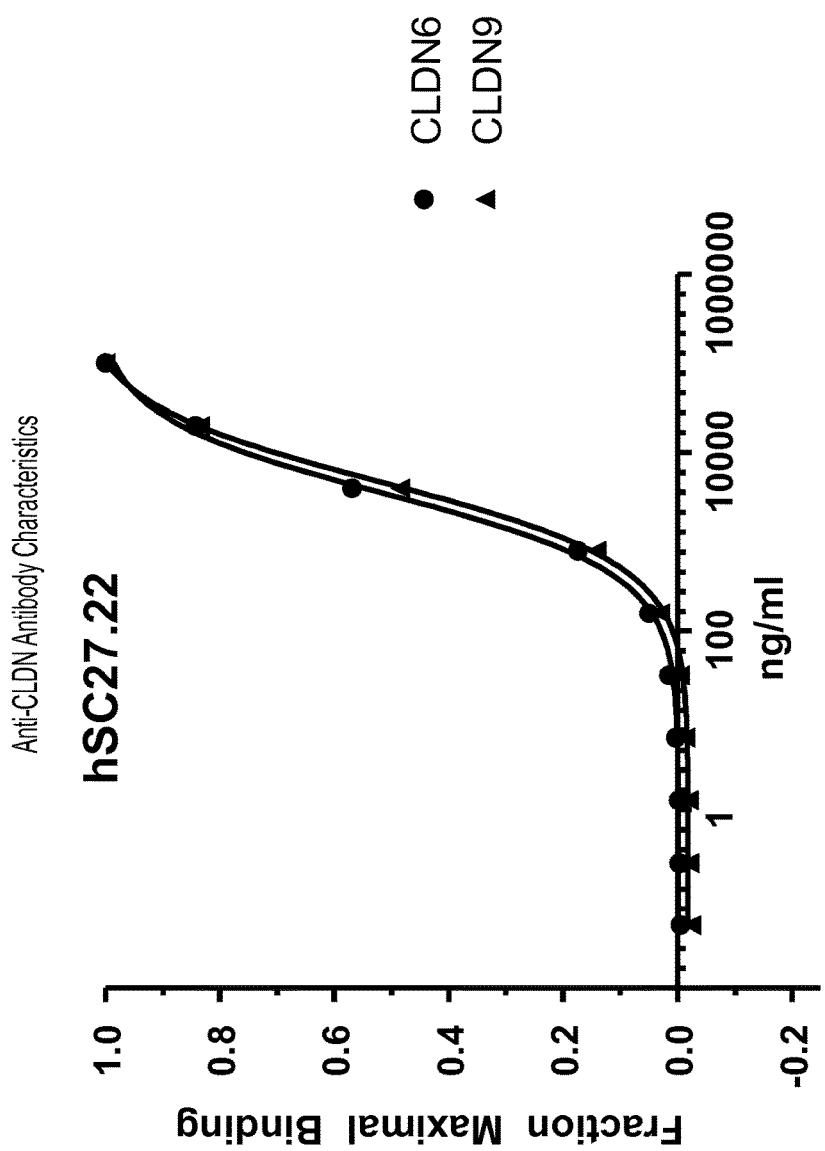
FIG. 6C shows the apparent binding affinity of an exemplary anti-CLDN antibody for CLDN6 and CLDN9 as determined by a titration of the amount of antibody versus a fixed number of cells expressing the antigen of interest.

To compare the apparent binding affinity of the multireactive anti-CLDN antibodies for CLDN6 and CLDN9, flow cytometry was performed with a serial dilution of humanized anti-CLDN antibody hSC27.22. The antibody was serially diluted to concentrations ranging from 50 μg/ml to 100 μg/ml and was added to a 96 well plate containing HEK-293T cells overexpressing CLDN6 or CLDN9, and kept on ice for one hour. A secondary anti-human antibody (Jackson ImmunoResearch Cat. #109-605-098) was added and incubated for one hour in the dark. The cells were washed twice in PBS after which Fixable Viability Dye (eBioscience Cat #65-0863-14) was added for 10 mins. Following additional washing with PBS, cells were fixed with paraformaldehyde (PFA) and read on a BD FACS Canto II flow cytometer in accordance with the manufacturer's instructions. MFI values were normalized using fluorescent microspheres (Bangs Laboratories) according to manufacturer's instructions. Normalized maximal MFI values observed for the binding of the antibody to either CLDN6 or CLDN9 expressing cells were used to transform the data into fraction maximal binding for each overexpressing cell, using the equation: fraction maximal binding= (observed normalized MFI/maximal normalized MFI). Apparent EC50 values for the binding of hSC27.22 to each cell line were then calculated using a four parameter variable slope curve fitting for a log (inhibitor) vs. response model supplied in the GraphPad Prism software package (La Jolla, Calif.). FIG. 6C shows that the humanized multireactive anti-CLDN6 antibody, hSC27.22, has an apparent EC50 for CLDN6 which is substantially the same as that for CLDN9. (apparent EC50 CLDN6—3.45 μg/mL ($r^2$ for goodness of fit=0.9987, 99% confidence bounds: 2.51-4.75 μg/mL); apparent EC50 CLDN9—4.66 μg/mL ($r^2$ for goodness of fit=0.9998, 99% confidence bounds: 4.09-5.31 μg/mL)).

Example 10

Detection of CLDN Protein Expression on PDX Tumors Using Flow Cytometry

Flow cytometry was used to assess the ability of the two representative hCLDN6-binding antibodies hSC27.1 and hSC27.22 to specifically detect the presence of hCLDN proteins on the surface of PDX tumor cells. Isotype-stained and fluorescence minus one (FMO) controls were employed to confirm staining specificity.

Figure 7:
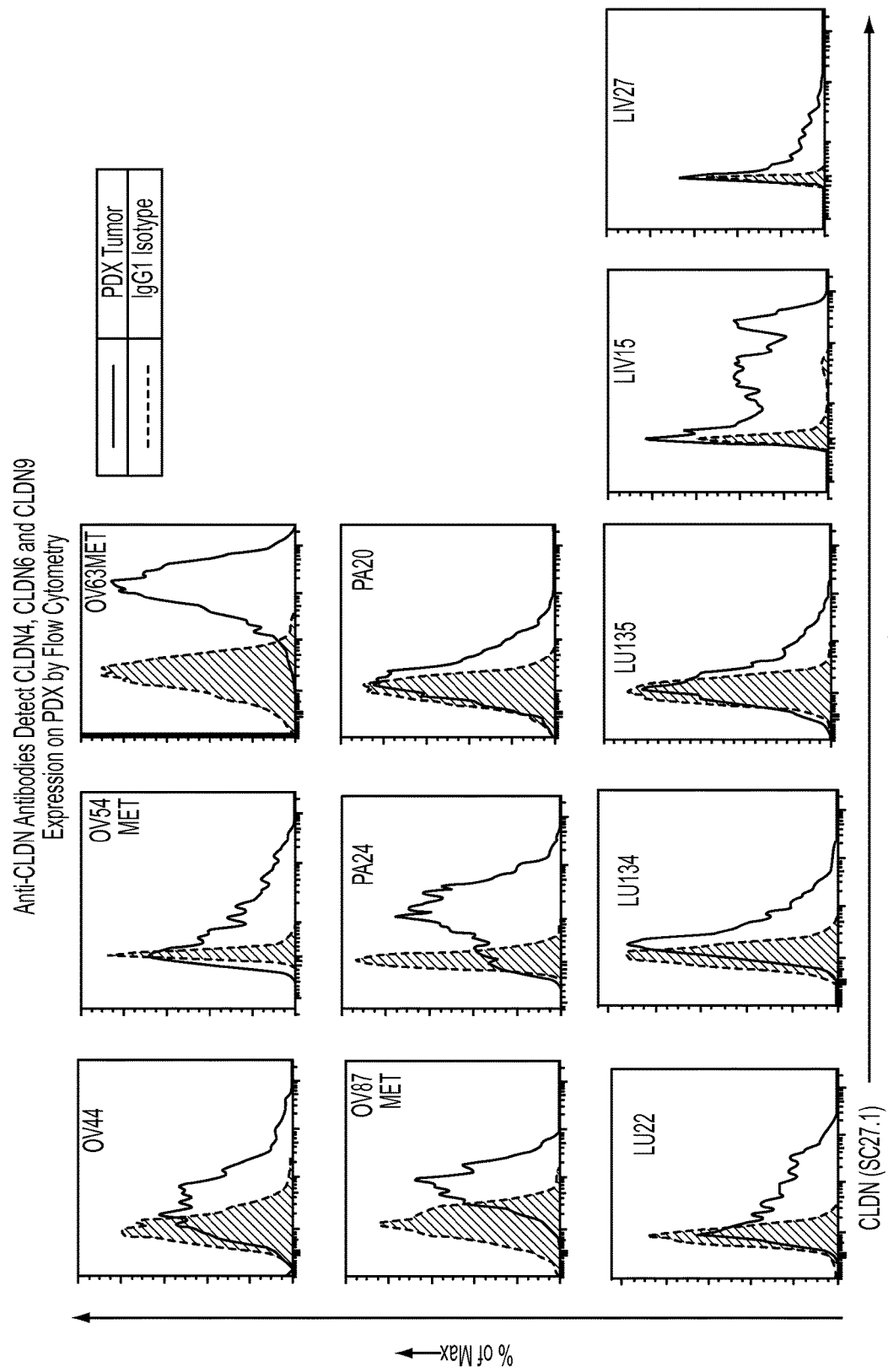
FIG. 7 shows expression of CLDN4, CLDN6, and CLDN9 proteins in cell populations derived from liver, lung, ovarian and pancreatic PDX tumors (solid black line) compared to fluorescence minus one (FMO) isotype-control (gray-fill)

Art-recognized enzymatic tissue digestion techniques were used to obtain single cell suspensions of PDX tumor cells (see, for example, U.S. Ser. No. 2007/0292414). PDX tumors were harvested, dissociated, and co-stained with commercially available anti-mouse CD45 and H-2kD antibodies (to demarcate mouse cells) and anti-human EpCAM and anti-CLDN antibodies. The anti-hCLDN antibody, hSC27.1, demonstrated positive staining on a subset of human (i.e. mCD45 and H-2kD negative) EpCAM-positive tumor cells, including OV-S (e.g., OV44, OV54), OV-PS (e.g. OV63MET), PA, LU-SCC (e.g., LU22), LU-Ad (e.g., LU134, LU135), and LIV (FIG. 7). Isotype control antibodies and FMO controls were employed to confirm staining specificity as is standard practice in the art. Flow cytometry was performed using a BD FACS Canto II flow cytometer in accordance with the manufacturer's instructions.

The levels of hCLDN staining varied across different PDX tumor cell lines, where some tumor cells did not stain at all (data not shown) while other tumor cell lines exhibited nearly uniformly positive staining of the human tumor cells (e.g. OV63MET) compared to isotype controls (FIG. 7). These data suggest that hCLDNs are expressed on the surface of a subpopulation of human tumor subtypes, which may be amenable to treatment using anti-CLDN antibodies or ADCs of the invention.

Example 11

Enrichment of CLDN Expression in Cancer Stem Cell Populations

Tumor cells can be divided broadly into two types of cell subpopulations: non-tumorigenic cells (NTG) and tumor initiating cells or tumorigenic cells. Tumorigenic cells have the ability to form tumors when implanted into immunocompromised mice, whereas non-tumorigenic cells do not. Cancer stem cells (CSCs) are a subset of tumorigenic cells and are able to self-replicate indefinitely while maintaining the capacity for multilineage differentiation.

To confirm the observations in Examples 1 and 2, which showed overexpression of CLDN4, CLDN6 and CLDN9 in CSC subpopulations of various tumors, and to determine whether the anti-CLDN antibodies of the invention are able to detect tumorigenic CSC populations, PDX tumors were dissociated into single cell suspensions as described in Example 10 above and selective markers, $CD46^{hi}CD324^+$, were used to enrich for CSC tumor cell subpopulations (see WO 2012/031280) as follows.

Figure 8A:
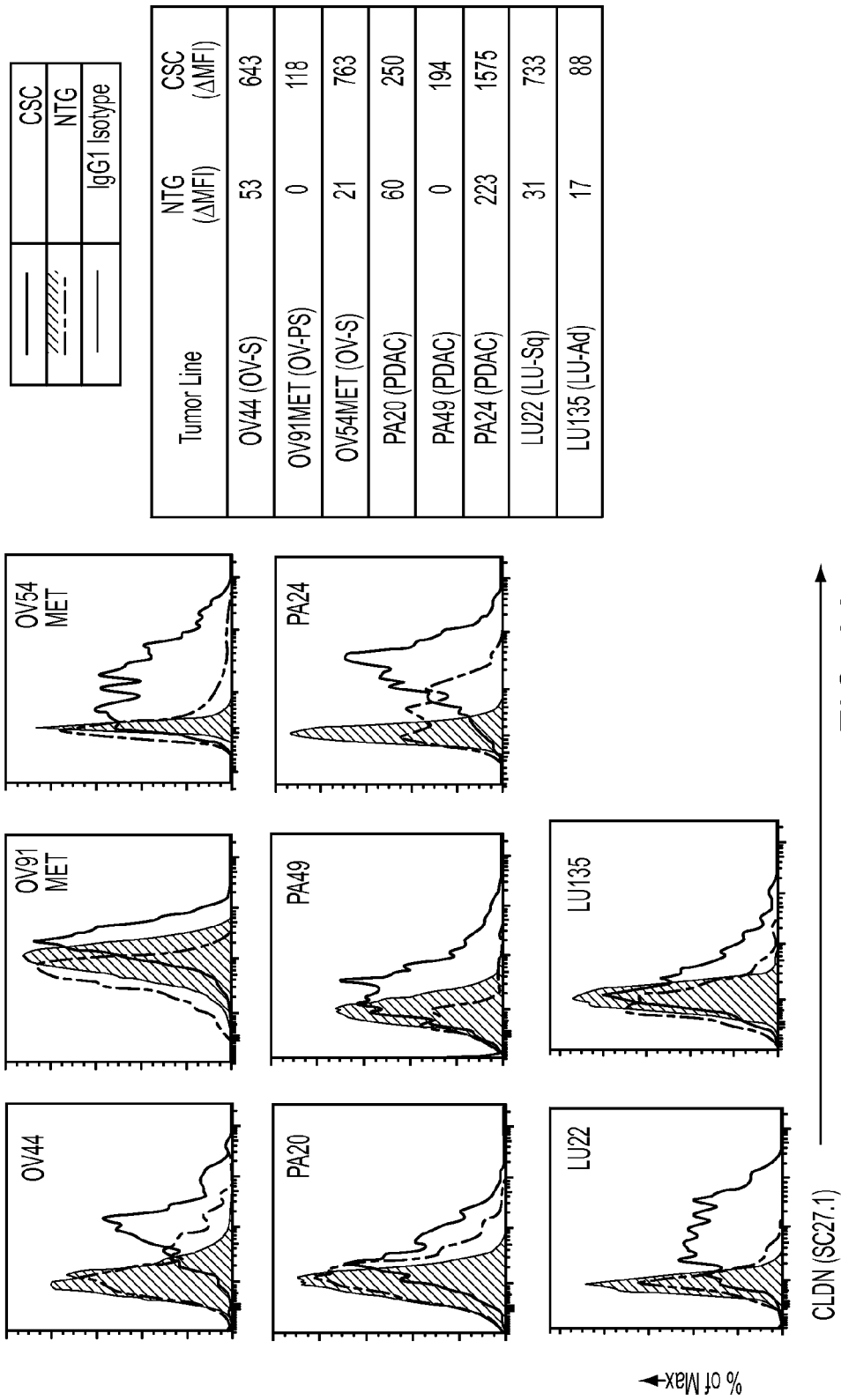
FIG. 8A shows expression of CLDN4, CLDN6, and CLDN9 proteins in human CSC (solid black line) compared to non-tumorigenic (dashed line) ovarian, pancreatic and lung tumor cell populations and FMO isotype controls (gray-fill)

PDX tumor single cell suspensions were incubated with the following antibodies: anti-CLDN SC27.1; anti-human EPCAM; anti-human CD46; anti-human CD324; and anti-mouse CD45 and H-2kD antibodies. The tumor cells were then assessed for staining by flow cytometry using a BD FACS Canto II flow cytometer. The human EPCAM$^+$ CD46$^{hi}$CD324$^+$ CSC tumor cell subpopulations of OV-S (e.g., OV44 and OV54MET), OV-PS (e.g. OV91MET), PA, LU-Ad (e.g., LU135), and LU-Sq (e.g., LU22) PDX tumors demonstrated positive staining with the anti-CLDN SC27.1 antibody, whereas NTG cells (CD46$^{lo/-}$ and/or CD324$^-$) demonstrated significantly less staining with anti-CLDN antibodies (FIG. 8A). Isotype control antibodies and FMO controls were employed to confirm staining specificity as is standard practice in the art. A table summarizing the differential staining of anti-CLDN antibodies observed on the surface of CSC and NTG cells is shown in FIG. 8A, with expression enumerated as the change in geometric mean fluorescence intensity (ΔMFI) between the indicated anti-CLDN antibody and the isotype control for the respective tumor cell subpopulations. These data confirm the expression of hCLDN proteins on CSCs and again suggest anti-CLDN antibodies may be effective for the treatment of cancer.

To determine whether CLDN expression in tumors could be correlated with enhanced tumorigenicity, the following study was conducted. Human OV PDX tumor samples (OV91 MET) were grown in immunocompromised mice and were resected after the tumor reached 800-2,000 mm$^3$. The tumors were dissociated into single cell suspensions using art-recognized enzymatic digestion techniques (see, for example, U.S. Ser. No. 2007/0292414). Human OV PDX tumor cells were stained with mouse anti-CD45 or anti-H2kD antibodies, and with anti-ESA antibodies to differentiate between human tumor cells and mouse cells. The tumors were also stained with anti-CLDN antibody (SC27.22) and then sorted using a FACSAria™ Flow Cytometer (BD Biosciences). The human OV PDX tumor cells were separated into CLDN$^+$ and CLDN$^-$ subpopulations. Five female NOD/SCID immunocompromised mice were injected subcutaneously with 200 CLDN$^+$ OV tumor cells; and five mice were injected with 200 CLDN$^-$ OV tumor cells. Tumor volumes were measured on a weekly basis for four months.

Figure 8B:
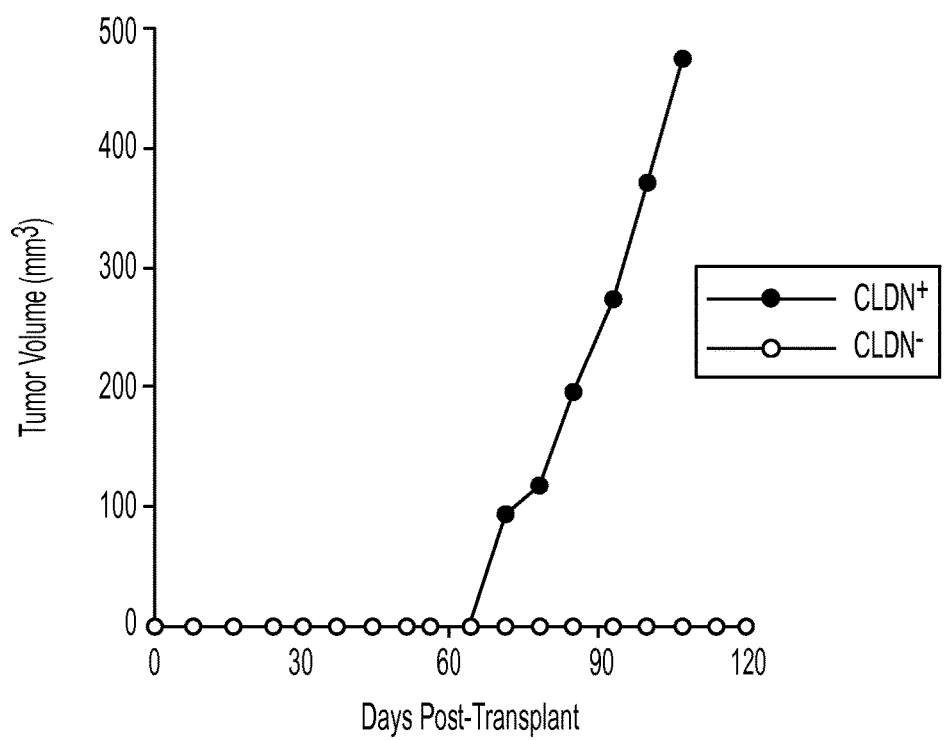
FIG. 8B shows the growth of tumors in mice transplanted with CLDN⁺ (closed circles) or CLDN⁻ (open circles) ovarian tumor cells where CLDN⁺ tumor cells exhibit enhanced tumorigenicity compared to CLDN⁻ ovarian tumor cells.

FIG. 8B shows that CLDN$^+$ (closed circles) tumor cells were able to functionally reconstitute tumors in vivo, whereas CLDN$^-$ tumors (open circles) were not. Thus, tumor cells expressing CLDN were much more tumorigenic than those tumor cells that did not express CLDN, suggesting that the CLDN protein can functionally define a tumorigenic subpopulation within human tumors, and supporting the concept that selected anti-CLDN ADCs can be used to target a tumorigenic subpopulation of tumor cells, which could result in significant tumor regression and prevention of tumor recurrence.

Example 12

Anti-CLDN Antibodies Facilitate Delivery of Cytotoxic Agents In Vitro

To determine whether anti-CLDN antibodies are able to internalize and mediate the delivery of cytotoxic agents to live tumor cells, an in vitro cell killing assay was performed using selected anti-CLDN antibodies and saporin linked to a secondary anti-mouse antibody FAB fragment. Saporin is a plant toxin that deactivates ribosomes, thereby inhibiting protein synthesis and resulting in the death of the cell. Saporin is only cytotoxic inside the cell where it has access to ribosomes, but is unable to internalize on its own. Therefore, saporin-mediated cellular cytotoxicity in these assays is indicative of the ability of the anti-mouse FAB-saporin conjugate to internalize into the target cell only upon binding and internalization of anti-CLDN antibodies.

Figure 9A:
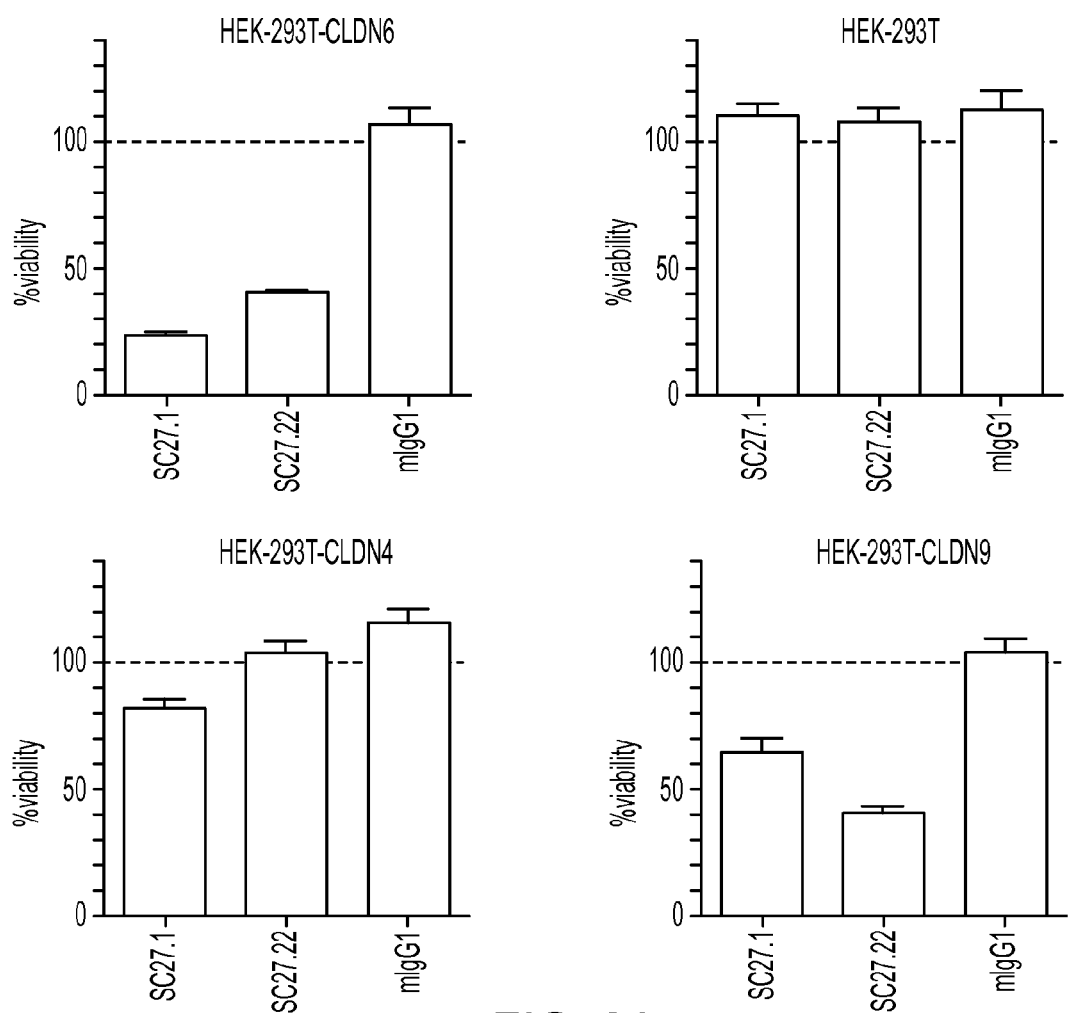

Single cell suspensions of HEK-293T cells and HEK-293T cells overexpressing hCLDN6, hCLDN4, or hCLDN9 were plated at 500 cells per well into BD Tissue Culture plates (BD Biosciences). One day later, 250 pM of purified SC27.1, SC27.22, or isotype control (mIgG1) antibodies and a fixed concentration of 2 nM anti-Mouse IgG FAB-saporin conjugate (Advanced Targeting Systems) were added to the culture. The HEK-293T cells were incubated for 72 hours post antibody treatment. After the incubation, viable cells were enumerated using CellTiter-Glo® (Promega) as per the manufacturer's instructions. Raw luminescence counts using cultures containing cells incubated only with the secondary FAB-saporin conjugate were set as 100% reference values and all other counts calculated accordingly. Both of the anti-CLDN antibodies, SC27.1 and SC27.22, at a concentration of 250 pM effectively killed HEK-293T cells overexpressing hCLDN6 and hCLDN9 (FIG. 9A), whereas the mouse IgG1 isotype control antibody (mIgG1) at the same concentration did not. Naïve HEK-293T cells were not effectively killed by the treatment whereas HEK-293T cells overexpressing hCLDN4 were effectively killed by SC27.1 but were not killed by SC27.22 treatment at the dose tested. The dashed horizontal line represents the level at which no cytotoxicity was observed.

In order to determine the apparent IC50 of additional antibodies for CLDN4, CLDN6 or CLDN9, the experiment described in the paragraph above was repeated with titrations of antibodies, across a concentration range of 0.15 nM to 1000 nM (FIG. 9B). The percentage of cell killing observed at each antibody concentration was enumerated by CellTiter-Glo® as described above, and a curve was fitted to the resulting data in order to calculate an apparent IC50 for the killing activity of antibody on each cell line. Antibodies which had an apparent IC50 of >2000 nM were deemed not to kill a particular cell line and are denoted as "NK" in FIG. 9B. A control mouse IgG1 antibody also did not kill any of the cell lines tested. Although this cytotoxicity assay measures the ability of various antibodies to mediate delivery of a cytotoxin via internalization of bound antigen rather than providing a direct measure of antibody binding affinity, the apparent IC50 of the antibodies shown in FIG. 9B in general correlates well with the single point flow cytometry data presented in FIG. 6B. For example, in both experiments SC27.108 is shown to be CLDN6-specific (apparent IC50=100 nM). Similarly, by flow cytometry SC27.103 shows strong binding to CLDN6 and moderate binding to CLDN9, which correlates with an apparent IC50 value of 58 nM for CLDN6 and 466 nM for CLDN9. However, it is also clear that detectable binding above background does not always result in detectable killing (e.g., SC27.104 binds to CLDN9 (see FIG. 6B) but is not able to effectively internalize and kill CLDN9-overexpressing cells (see FIG. 9B); whereas SC27.201 binds CLDN9 (see FIG. 6B) and is able to internalize into cells expressing CLDN9 and kill those cells (see FIG. 9B)).

Together, the above results demonstrate the ability of multireactive anti-CLDN antibodies to mediate internalization and their ability to deliver cytotoxic payloads, supporting the hypothesis that anti-CLDN antibodies may have therapeutic utility as the targeting moiety for an ADC.

Example 13

Detection of CLDN6 on the Surface of Tumors Using Immunohistochemistry

To assess the extent of CLDN6 protein expression in tumors, immunohistochemistry (IHC) was performed on formalin fixed paraffin embedded (FFPE) PDX tumors and tissue microarrays (TMAs) of primary ovarian tumors (Oklahoma University).

Planar sections of cell pellet blocks were cut and mounted on glass microscope slides. After xylene de-paraffinization 5 µm sections were pre-treated with Antigen Retrieval Solution (Dako) for 20 min. at 99° C., cooled to 75° C. and then treated with 0.3% hydrogen peroxide in PBS followed by treatment with Avidin/Biotin Blocking Solution (Vector Laboratories). FFPE slides were then blocked with 10% donkey serum in 3% BSA in PBS buffer and incubated with a primary anti-CLDN6 rabbit polyclonal antibody purchased from IBL America (Catalog #18865), diluted to 10 µg/ml in 3% BSA/PBS, for 30 min. at room temperature. FFPE slides were incubated with biotin-conjugated donkey anti-rabbit antibody (Vector Laboratories), diluted to 2.5 µg/ml in 3% BSA/PBS, for 30 min. at room temperature followed by incubation with streptavidin-HRP (ABC Elite Kit; Vector Laboratories). Chromogenic detection was developed with 3,3'-diaminobenzidine (Thermo Scientific) for 5 min. at room temperature and tissues were counterstained with Meyer's hematoxylin (IHC World), washed with alcohol and immersed in xylene.

To confirm the specificity of the primary anti-CLDN6 antibody, IHC was performed on FFPE slides of HEK-293T cells overexpressing hCLDN6, hCLDN4 or hCLND9. The anti-CLDN6 polyclonal antibody specifically stained hCLDN6-overexpressing HEK-293T cell pellets but did not stain overexpressing cell lines of hCLDN4 and hCLDN9 (data not shown).

FIG. 10A shows a summary overview of hCLDN6 expression in OV, BR, and LU PDX tumors, as determined by IHC. Staining intensity was scored from no staining (−) to high staining intensity (+++). The percentage of tumor cells that expressed CLDN6 is also noted. CLDN6 expression was observed in LU, BR and OV tumors with many PDX lines showing expression in 90% of the cells on the FFPE slide.

Figure 10B:
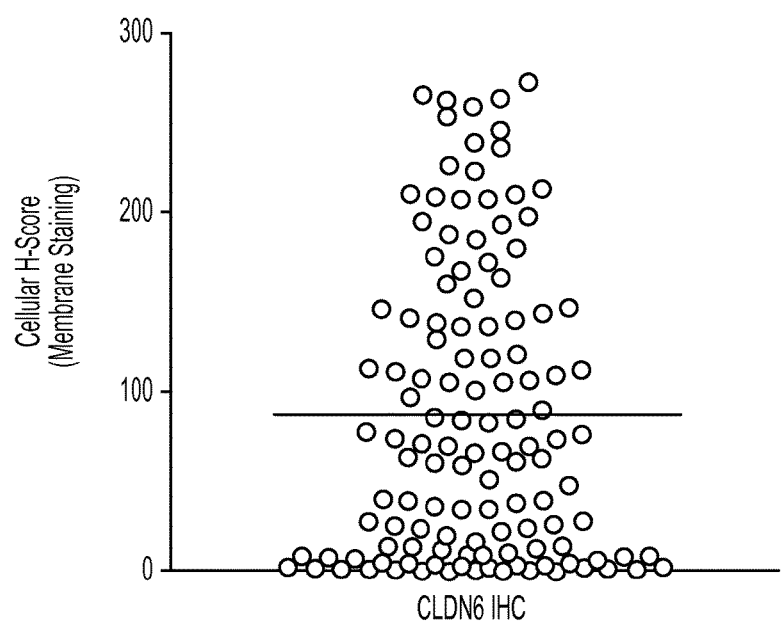
FIG. 10B shows expression of CLND6 in various primary ovarian tumors using immunohistochemistry.

To determine the penetrance of hCLDN6 expression in ovarian cancer patients, IHC was also performed on FFPE slides generated from TMAs made from 125 primary ovarian tumors resected from cancer patients (Oklahoma University). The H-Score was generated utilizing the Leica Biosystems Tissue IA software on digitally scanned images of the TMAs. Briefly, staining preferences specific to hCLDN6 were assigned in the Measure Stained Cells Algorithm under the Tissue IA Optimiser. TMA cores were then individually annotated so that the image analysis would only analyze tumor cells and not other tissue constituents such as stroma. The TMA was analyzed using the hCLDN6 Membrane Stain algorithm which produced an H-score. The H-score algorithm was calculated for membrane staining of tumor cells using the following formula; H-Score=(% staining intensity at 0)*0+(% staining intensity at 1+)*1+(% staining intensity at 2+)*2+(% staining intensity at 3+)*3. Thus, this score produces a continuous variable that ranges from 0 to 300. The results in the table in FIG. 10B show level of expression of CLDN6 in the 125 tumor samples of the TMA, with 70% of the tumors expressing some level of CLDN6.

Together, these IHC data demonstrate that CLDN6 is expressed on the cell surface of ovarian, breast and lung tumors as well as in primary human tumors, reconfirming that claudins are relevant targets for the development of antibody and ADC therapeutics for treatment of a significant number of cancer patients. Anti-CLDN6 may have diagnostic utility in these and possibly additional cancer indications.

Example 14

Preparation of Anti-CLDN6 Antibody-Drug Conjugates

Anti-CLDN antibody drug conjugates (ADCs) are prepared having the Ab-[L-D] structure, where Ab refers to the anti-CLDN antibody, L refers to an optional linker (e.g. a linker comprising a terminal maleimido moiety with a free sulfhydryl group) and D refers to a drug or cytotoxin (e.g. auristatins, calicheamicin etc.). Each ADC comprises an anti-CLDN antibody covalently linked to a linker-drug. ADCs are synthesized and purified using techniques known in the art, for example, essentially as follows. The cystine bonds of anti-CLDN antibodies are partially reduced with a pre-determined molar addition of mol tris(2-carboxyethyl)-phosphine (TCEP) per mol antibody for 90 min. at 20° C. in phosphate buffered saline (PBS) with 5 mM EDTA. The linker-drug, dissolved in dimethyl acetamide (DMA), is added at a ratio of 3 mol/mol anti-CLDN antibody. The reaction is allowed to proceed for 30 min. Using a 10 mM stock solution of N-acetyl cysteine (NAC) prepared in water, the reaction is quenched with the addition of excess NAC to linker-drug. After a minimum quench time of 20 mins., the pH is adjusted to 6.0 with the addition of 0.5 M acetic acid and buffer exchanged by diafiltration into diafiltration buffer using a 30 kDa membrane. The dialfiltered anti-CLDN ADC is then formulated with sucrose and polysorbate-20 to the target final concentration. The resulting anti-CLDN ADCs are analyzed for protein concentration (by measuring UV), aggregation (SEC), drug to antibody ratio (DAR) by reverse-phase HPLC (RP-HPLC) and in vitro cytotoxicity.

Example 15

Conjugation of Site Specific Anti-CLDN Antibodies Using a Selective Reduction Process Anti-CLDN antibody drug conjugates (ADCs) are prepared having the Ab-[L-D] structure as described in Example 14 above, wherein the Ab moiety is a site specific antibody, for example, hSC27.22ss1, generated as set forth in Example 8 above. The desired product is an ADC that is maximally conjugated on the unpaired cysteine (C214 in the case of IgG1 site specific antibodies or C127 on IgG4 site specific antibodies) on each LC constant region and that minimizes ADCs having a drug to antibody ratio (DAR) which is greater than 2 (DAR>2) or less than 2 (DAR<2) while maximizing ADCs having a DAR of 2 (DAR=2).

In order to further improve the specificity of the conjugation and homogeneity of the final site-specific ADC, the site specific antibody (e.g. "hSC27.22ss1" or "hSC27.22 IgG4 C127S S228P") is selectively reduced using, for example, a process comprising a stabilizing agent (e.g. L-arginine) and a mild reducing agent (e.g. glutathione) prior to conjugation with the linker-drug, followed by preparative hydrophobic interaction chromatography (HIC) that is used to separate the different DAR species. The above procedures are conducted, for example, essentially as described below.

A preparation of the site specific antibody is partially reduced in a buffer containing 1M L-arginine/5 mM glutathione, reduced (GSH)/5 mM EDTA, pH 8.0 for a minimum of one hour at room temperature. All preparations are then buffer exchanged into a 20 mM Tris/3.2 mM EDTA, pH 8.2 buffer using a 30 kDa membrane (Millipore Amicon Ultra) to remove the reducing buffer. The resulting partially reduced preparations are then conjugated to a cytotoxin (e.g. auristatin, calicheamicin etc.) via a linker (e.g. maleimide linker) for a minimum of 30 mins. at room temperature. The reaction is then quenched with the addition of excess NAC to linker-drug using a 10 mM stock solution of NAC prepared in water. After a minimum quench time of 20 mins., the pH is adjusted to 6.0 with the addition of 0.5 M acetic acid. The site specific ADC is buffer exchanged into diafiltration buffer using a 30 kDa membrane. The site specific ADC preparation is then diluted with a high salt buffer to increase the conductivity to promote binding onto the resin, and then loaded on a Butyl HP resin chromatography column (GE Life Sciences). A decreasing salt gradient is then employed to separate the different DAR species based on hydrophobicity, where DAR=0 species elute first, followed by DAR=1, DAR=2, and then higher DAR species.

The final ADC "HIC purified DAR=2" preparation is analyzed using RP-HPLC to determine the percent conjugation on the HCs and LCs and the DAR distribution. The samples are also analyzed using analytical HIC to determine the amount of DAR=2 species relative to the unwanted DAR>2 and DAR<2 species.

Example 16

Humanized Anti-CLDN Antibody Drug Conjugates Suppress Tumor Growth In Vivo

The anti-CLDN ADCs, generated, for example, as described in Examples 14 and 15 above, are tested using art-recognized techniques, essentially as described below, to demonstrate their ability to suppress ovarian tumor growth in immunodeficient mice.

PDX tumor lines expressing CLDN and control tumor lines which do not express CLDN are grown subcutaneously in the flanks of female NOD/SCID mice using art-recognized techniques. Tumor volumes and mouse weights are monitored once or twice per week. When tumor volumes reach 150-250 mm$^3$, mice are randomly assigned to treatment groups and injected intraperitoneally with a single dose of 1 or 2 mg/kg humanized anti-CLDN ADC, a single dose of 2 mg/kg anti-hapten control human IgG ADC or vehicle control, for example, 0.9% saline or 5% glucose. Following treatment, tumor volumes and mouse weights are monitored until tumors exceed 800 mm$^3$ or the mice become sick. Mice treated with humanized anti-CLDN ADC that do not exhibit any adverse health effects beyond those typically seen in immunodeficient, tumor-bearing NOD/SCID mice and that effectively reduce tumor volume compared to control IgG ADC and vehicle are selected for further analysis including toxicity studies.

Example 17

Reduction of Cancer Stem Cell Frequency by Anti-CLDN Antibody-Drug Conjugates

As demonstrated in Example 11 CLDN expression is associated with cancer stem cells. Accordingly, to demonstrate that treatment with anti-CLDN ADCs reduces the frequency of cancer stem cells (CSC) that are known to be drug resistant and to fuel tumor recurrence and metastasis, in vivo limiting dilution assays (LDA) are performed, for example, essentially as described below.

PDX tumors (e.g. melanoma or ovarian) are grown subcutaneously in immunodeficient mice. When tumor volumes average 150 mm$^3$-250 mm$^3$ in size, the mice are randomly segregated into two groups. One group is injected intraperitoneally with a human IgG1 conjugated to a drug as a negative control; and the other group is injected intraperitoneally with an anti-CLDN ADC (e.g., as prepared in Examples 14 and 15). One week following dosing, two representative mice from each group are euthanized and their tumors are harvested and dispersed to single-cell suspensions. The tumor cells from each treatment group are then harvested, pooled and disaggregated as previously described in Example 1. The cells are labeled with FITC conjugated anti-mouse H2kD and anti-mouse CD45 antibodies to detect mouse cells; EpCAM to detect human cells; and DAPI to detect dead cells. The resulting suspension is then sorted by FACS using a BD FACS Canto II flow cytometer and live human tumor cells are isolated and collected.

Four cohorts of mice are injected with either 1250, 375, 115 or 35 sorted live, human cells from tumors treated with anti-CLDN ADC. As a negative control four cohorts of mice are transplanted with either 1000, 300, 100 or 30 sorted live, human cells from tumors treated with the control IgG1 ADC. Tumors in recipient mice are measured weekly, and individual mice are euthanized before tumors reach 1500 mm$^3$. Recipient mice are scored as having positive or negative tumor growth. Positive tumor growth is defined as growth of a tumor exceeding 100 mm$^3$.

Poisson distribution statistics (L-Calc software, Stemcell Technologies) is used to calculate the frequency of CSCs in each population.

The invention claimed is:

1. An anti-Claudin 6 ("anti-CLDN6") antibody comprising:
    (a) three CDRs of a light chain variable region set forth as SEQ ID NO: 21 and three CDRs of a heavy chain variable region set forth as SEQ ID NO: 23; or
    (b) three CDRs of a light chain variable region set forth as SEQ ID NO: 25 and three CDRs of a heavy chain variable region set forth as SEQ ID NO: 27; or
    (c) three CDRs of a light chain variable region set forth as SEQ ID NO: 29 and three CDRs of a heavy chain variable region set forth as SEQ ID NO: 31; or
    (d) three CDRs of a light chain variable region set forth as SEQ ID NO: 33 and three CDRs of a heavy chain variable region set forth as SEQ ID NO: 35; or
    (e) three CDRs of a light chain variable region set forth as SEQ ID NO: 37 and three CDRs of a heavy chain variable region set forth as SEQ ID NO: 39; or
    (f) three CDRs of a light chain variable region set forth as SEQ ID NO: 41 and three CDRs of a heavy chain variable region set forth as SEQ ID NO: 43; or
    (g) three CDRs of a light chain variable region set forth as SEQ ID NO: 45 and three CDRs of a heavy chain variable region set forth as SEQ ID NO: 47; or
    (h) three CDRs of a light chain variable region set forth as SEQ ID NO: 49 and three CDRs of a heavy chain variable region set forth as SEQ ID NO: 51; or
    (i) three CDRs of a light chain variable region set forth as SEQ ID NO: 53 and three CDRs of a heavy chain variable region set forth as SEQ ID NO: 55; or
    (j) three CDRs of a light chain variable region set forth as SEQ ID NO: 57 and three CDRs of a heavy chain variable region set forth as SEQ ID NO: 59; or
    (k) three CDRs of a light chain variable region set forth as SEQ ID NO: 61 and three CDRs of a heavy chain variable region set forth as SEQ ID NO: 63; or
    (l) three CDRs of a light chain variable region set forth as SEQ ID NO: 65 and three CDRs of a heavy chain variable region set forth as SEQ ID NO: 67; or
    (m) three CDRs of a light chain variable region set forth as SEQ ID NO: 69 and three CDRs of a heavy chain variable region set forth as SEQ ID NO: 71; or
    (n) three CDRs of a light chain variable region set forth as SEQ ID NO: 73 and three CDRs of a heavy chain variable region set forth as SEQ ID NO: 87.

2. The anti-CLDN6 antibody of claim 1 comprising three CDRs of a light chain variable region set forth as SEQ ID NO: 73 and three CDRs of a heavy chain variable region set forth as SEQ ID NO: 87.

3. The anti-CLDN6 antibody of claim 1, wherein the antibody binds specifically to CLDN6 and CLDN9.

4. The anti-CLDN6 antibody of claim 1, wherein the antibody is an internalizing antibody.

5. The anti-CLDN6 antibody of claim 2, wherein the CDR residues are numbered according to Kabat.

6. The anti-CLDN6 antibody of claim 2, wherein the CDR residues are numbered according to Chothia.

7. The anti-CLDN6 antibody of claim 2, wherein the CDR residues are numbered according to MacCallum.

8. The anti-CLDN6 antibody of claim 1, comprising:
    (a) a light chain variable region set forth as SEQ ID NO: 21 and a heavy chain variable region set forth as SEQ ID NO: 23; or
    (b) a light chain variable region set forth as SEQ ID NO: 25 and a heavy chain variable region set forth as SEQ ID NO: 27; or
    (c) a light chain variable region set forth as SEQ ID NO: 29 and a heavy chain variable region set forth as SEQ ID NO: 31; or
    (d) a light chain variable region set forth as SEQ ID NO: 33 and a heavy chain variable region set forth as SEQ ID NO: 35; or
    (e) a light chain variable region set forth as SEQ ID NO: 37 and a heavy chain variable region set forth as SEQ ID NO: 39; or
    (f) a light chain variable region set forth as SEQ ID NO: 41 and a heavy chain variable region set forth as SEQ ID NO: 43; or
    (g) a light chain variable region set forth as SEQ ID NO: 45 and a heavy chain variable region set forth as SEQ ID NO: 47; or
    (h) a light chain variable region set forth as SEQ ID NO: 49 and a heavy chain variable region set forth as SEQ ID NO: 51; or
    (i) a light chain variable region set forth as SEQ ID NO: 53 and a heavy chain variable region set forth as SEQ ID NO: 55; or
    (j) a light chain variable region set forth as SEQ ID NO: 57 and a heavy chain variable region set forth as SEQ ID NO: 59; or
    (k) a light chain variable region set forth as SEQ ID NO: 61 and a heavy chain variable region set forth as SEQ ID NO: 63; or
    (l) a light chain variable region set forth as SEQ ID NO: 65 and a heavy chain variable region set forth as SEQ ID NO: 67; or
    (m) a light chain variable region set forth as SEQ ID NO: 69 and a heavy chain variable region set forth as SEQ ID NO: 71; or
    (n) a light chain variable region set forth as SEQ ID NO: 73 and heavy chain variable region set forth as SEQ ID NO: 87.

9. The anti-CLDN6 antibody of claim 8, comprising a light chain variable region set forth as SEQ ID NO: 73 and heavy chain variable region set forth as SEQ ID NO: 87.

10. The anti-CLDN6 antibody of claim 9, wherein the anti-CLDN6 antibody comprises two light chains and two heavy chains, and wherein the anti-CLDN6 antibody comprises two unpaired cysteine residues.

11. The anti-CLDN6 antibody of claim 10, wherein each of the two light chains comprises an unpaired cysteine residue.

12. The anti-CLDN6 antibody of claim 11, wherein each unpaired cysteine residue is at position C214.

13. The anti-CLDN6 antibody of claim 10, wherein each of the two heavy chains comprises an unpaired cysteine residue.

14. The anti-CLDN6 antibody of claim 13, wherein each of the two heavy chains is IgG1 and each unpaired cysteine residue is at position C220.

15. The anti-CLDN6 antibody of claim 1 comprising:
   (a) a full length light chain set forth as SEQ ID NO: 114 and a full length heavy chain set forth as SEQ ID NO: 115; or
   (b) a full length light chain set forth as SEQ ID NO: 116 and a full length heavy chain set forth as SEQ ID NO: 117; or
   (c) a full length light chain set forth as SEQ ID NO: 116 and a full length heavy chain set forth as SEQ ID NO: 122; or
   (d) a full length light chain set forth as SEQ ID NO: 118 and a full length heavy chain set forth as SEQ ID NO: 119; or
   (e) a full length light chain set forth as SEQ ID NO: 120 and a full length heavy chain set forth as SEQ ID NO: 121; or
   (f) a full length light chain set forth as SEQ ID NO: 120 and a full length heavy chain set forth as SEQ ID NO: 137.

16. The anti-CLDN6 antibody of claim 1, wherein the antibody is selected from the group consisting of monoclonal antibody, chimeric antibody, CDR-grafted antibody, humanized antibody, primatized antibody, multispecific antibody, bispecific antibody, monovalent antibody, multivalent antibody, Fab fragment, F(ab')$_2$ fragment, Fv fragment, and scFv fragment; or an immunoreactive fragment thereof that binds CLDN6.

17. The anti-CLDN6 antibody of claim 16, wherein the antibody is selected from the group consisting of chimeric antibody, CDR-grafted antibody, and humanized antibody.

18. The anti-CLDN6 antibody of claim 1, wherein the anti-CLDN6 antibody is conjugated to a cytotoxic agent.

19. The anti-CLDN6 antibody of claim 18, wherein the cytotoxic agent is a pyrrolobenzodiazepine (PBD), an auristatin, a maytansinoid, a calicheamicin or a radioisotope.

20. The anti-CLDN6 antibody of claim 19, wherein the cytotoxic agent is a pyrrolobenzodiazepine (PBD).

21. The anti-CLDN6 antibody of claim 10, wherein the anti-CLDN6 antibody is conjugated to a cytotoxic agent, and wherein the cytotoxic agent is conjugated to the two unpaired cysteine residues.

22. The anti-CLDN6 antibody of claim 21, wherein the cytotoxic agent is a pyrrolobenzodiazepine (PBD), an auristatin, a maytansinoid, a calicheamicin or a radioisotope.

23. The anti-CLDN6 antibody of claim 22, wherein the cytotoxic agent is a pyrrolobenzodiazepine (PBD).

24. An antibody drug conjugate comprising an anti-Claudin 6 ("anti-CLDN6") antibody conjugated to a cytotoxic agent, wherein the anti-CLDN6 antibody comprises:
   (a) three CDRs of a light chain variable region set forth as SEQ ID NO: 21 and three CDRs of a heavy chain variable region set forth as SEQ ID NO: 23; or
   (b) three CDRs of a light chain variable region set forth as SEQ ID NO: 25 and three CDRs of a heavy chain variable region set forth as SEQ ID NO: 27; or
   (c) three CDRs of a light chain variable region set forth as SEQ ID NO: 29 and three CDRs of a heavy chain variable region set forth as SEQ ID NO: 31; or
   (d) three CDRs of a light chain variable region set forth as SEQ ID NO: 33 and three CDRs of a heavy chain variable region set forth as SEQ ID NO: 35; or
   (e) three CDRs of a light chain variable region set forth as SEQ ID NO: 37 and three CDRs of a heavy chain variable region set forth as SEQ ID NO: 39; or
   (f) three CDRs of a light chain variable region set forth as SEQ ID NO: 41 and three CDRs of a heavy chain variable region set forth as SEQ ID NO: 43; or
   (g) three CDRs of a light chain variable region set forth as SEQ ID NO: 45 and three CDRs of a heavy chain variable region set forth as SEQ ID NO: 47; or
   (h) three CDRs of a light chain variable region set forth as SEQ ID NO: 49 and three CDRs of a heavy chain variable region set forth as SEQ ID NO: 51; or
   (i) three CDRs of a light chain variable region set forth as SEQ ID NO: 53 and three CDRs of a heavy chain variable region set forth as SEQ ID NO: 55; or
   (j) three CDRs of a light chain variable region set forth as SEQ ID NO: 57 and three CDRs of a heavy chain variable region set forth as SEQ ID NO: 59; or
   (k) three CDRs of a light chain variable region set forth as SEQ ID NO: 61 and three CDRs of a heavy chain variable region set forth as SEQ ID NO: 63; or
   (l) three CDRs of a light chain variable region set forth as SEQ ID NO: 65 and three CDRs of a heavy chain variable region set forth as SEQ ID NO: 67; or
   (m) three CDRs of a light chain variable region set forth as SEQ ID NO: 69 and three CDRs of a heavy chain variable region set forth as SEQ ID NO: 71; or
   (n) three CDRs of a light chain variable region set forth as SEQ ID NO: 73 and three CDRs of a heavy chain variable region set forth as SEQ ID NO: 87.

25. The antibody drug conjugate of claim 24 wherein the antibody drug conjugate has the formula Ab-[L-D]n, wherein:
   (a) Ab comprises the anti-CLDN6 antibody;
   (b) L comprises an optional linker;
   (c) D comprises a drug, which is the cytotoxic agent; and
   (d) n is an integer from 1 to 8.

26. The antibody drug conjugate of claim 25, wherein the cytotoxic agent is a pyrrolobenzodiazepine (PBD), an auristatin, a maytansinoid, a calicheamicin or a radioisotope.

27. The antibody drug conjugate of claim 26, wherein the cytotoxic agent is a pyrrolobenzodiazepine (PBD).

28. The antibody drug conjugate of claim 27, wherein Ab comprises a light chain variable region set forth as SEQ ID NO: 73 and a heavy chain variable region set forth as SEQ ID NO: 87 and wherein D is a pyrrolobenzodiazepine (PBD).

29. The antibody drug conjugate of claim 28, wherein n is 2.

30. A pharmaceutical composition comprising the antibody drug conjugate of claim 24 and a pharmaceutically acceptable carrier.

31. A pharmaceutical composition comprising the antibody drug conjugate of claim 28 and a pharmaceutically acceptable carrier.

32. A pharmaceutical composition comprising the antibody drug conjugate of claim 29 and a pharmaceutically acceptable carrier.

33. The pharmaceutical composition of claim 30 comprising an average drug to antibody ratio (DAR) of 1, 2, 3, 4, 5, 6, 7 or 8 each ±0.4.

34. The pharmaceutical composition of claim 33 comprising an average drug to antibody ratio (DAR) of 2±0.4.

35. The pharmaceutical composition of claim 34 comprising less than 30% of non-predominant ADC species.

36. The anti-CLDN6 antibody of claim 2, wherein the anti-CLDN6 antibody comprises two light chains and two heavy chains, and wherein the anti-CLDN6 antibody comprises two unpaired cysteine residues.

37. The anti-CLDN6 antibody of claim 36, wherein the anti-CLDN6 antibody is an IgG1 antibody comprising a deletion or substitution of a cysteine residue at light chain position 214 or heavy chain position 220.

38. The anti-CLDN6 antibody of claim 37 comprising native cysteine residues at heavy chain positions 226 and 229.

39. The antibody drug conjugate of claim 24, wherein the anti-CLDN6 antibody is an internalizing antibody.

40. The antibody drug conjugate of claim 24, wherein anti-CLDN6 antibody comprises three CDRs of a light chain variable region set forth as SEQ ID NO: 73 and three CDRs of a heavy chain variable region set forth as SEQ ID NO: 87.

41. The antibody drug conjugate of claim 40, wherein the CDR residues are numbered according to Kabat.

42. The antibody drug conjugate of claim 40, wherein the CDR residues are numbered according to Chothia.

43. The antibody drug conjugate of claim 40, wherein the CDR residues are numbered according to MacCallum.

44. The antibody drug conjugate of claim 24, comprising:
  (a) a light chain variable region set forth as SEQ ID NO: 21 and a heavy chain variable region set forth as SEQ ID NO: 23; or
  (b) a light chain variable region set forth as SEQ ID NO: 25 and a heavy chain variable region set forth as SEQ ID NO: 27; or
  (c) a light chain variable region set forth as SEQ ID NO: 29 and a heavy chain variable region set forth as SEQ ID NO: 31; or
  (d) a light chain variable region set forth as SEQ ID NO: 33 and a heavy chain variable region set forth as SEQ ID NO: 35; or
  (e) a light chain variable region set forth as SEQ ID NO: 37 and a heavy chain variable region set forth as SEQ ID NO: 39; or
  (f) a light chain variable region set forth as SEQ ID NO: 41 and a heavy chain variable region set forth as SEQ ID NO: 43; or
  (g) a light chain variable region set forth as SEQ ID NO: 45 and a heavy chain variable region set forth as SEQ ID NO: 47; or
  (h) a light chain variable region set forth as SEQ ID NO: 49 and a heavy chain variable region set forth as SEQ ID NO: 51; or
  (i) a light chain variable region set forth as SEQ ID NO: 53 and a heavy chain variable region set forth as SEQ ID NO: 55; or
  (j) a light chain variable region set forth as SEQ ID NO: 57 and a heavy chain variable region set forth as SEQ ID NO: 59; or
  (k) a light chain variable region set forth as SEQ ID NO: 61 and a heavy chain variable region set forth as SEQ ID NO: 63; or
  (l) a light chain variable region set forth as SEQ ID NO: 65 and a heavy chain variable region set forth as SEQ ID NO: 67; or
  (m) a light chain variable region set forth as SEQ ID NO: 69 and a heavy chain variable region set forth as SEQ ID NO: 71; or
  (n) a light chain variable region set forth as SEQ ID NO: 73 and heavy chain variable region set forth as SEQ ID NO: 87.

45. The antibody drug conjugate of claim 44, comprising a light chain variable region set forth as SEQ ID NO: 73 and heavy chain variable region set forth as SEQ ID NO: 87.

46. The antibody drug conjugate of claim 24, wherein the anti-CLDN6 antibody comprises two light chains and two heavy chains, and wherein the anti-CLDN6 antibody comprises two unpaired cysteine residues.

47. The antibody drug conjugate of claim 46, wherein each of the two light chains comprises an unpaired cysteine residue.

48. The antibody drug conjugate of claim 47, wherein each unpaired cysteine residue is at position C214.

49. The antibody drug conjugate of claim 46, wherein each of the two heavy chains comprises an unpaired cysteine residue.

50. The antibody drug conjugate of claim 49, wherein each of the two heavy chains is IgG1 and each unpaired cysteine residue is at position C220.

51. The antibody drug conjugate of claim 46, wherein the anti-CLDN6 antibody is an IgG1 antibody comprising a deletion or substitution of a cysteine residue at light chain position 214 or heavy chain position 220.

52. The antibody drug conjugate of claim 51, comprising native cysteine residues at heavy chain positions 226 and 229.

53. The antibody drug conjugate of claim 45, wherein the cytotoxic agent is a pyrrolobenzodiazepine (PBD).

54. The antibody drug conjugate of claim 53, wherein the antibody drug conjugate has a drug loading of 2.

55. The antibody drug conjugate of claim 46, wherein the anti-CLDN6 antibody comprises a light chain variable region set forth as SEQ ID NO: 73 and a heavy chain variable region set forth as SEQ ID NO: 87,
  wherein the anti-CLDN6 antibody is an IgG1 antibody that comprises (i) a deletion or substitution of a cysteine residue at light chain position 214 or heavy chain position 220 and (ii) native cysteine residues at heavy chain positions 226 and 229,
  and wherein the cytotoxic agent is a pyrrolobenzodiazepine (PBD).

* * * * *

SEQUENCE LISTING

```
<160> NUMBER OF SEQ ID NOS: 178

<210> SEQ ID NO 1
<211> LENGTH: 107
<212> TYPE: PRT
<213> ORGANISM: Homo sapiens
<220> FEATURE:
<221> NAME/KEY: MISC_FEATURE
<223> OTHER INFORMATION: Kappa light chain (LC) constant region protein

<400> SEQUENCE: 1
```

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
             85                  90                  95

Pro Val Thr Lys Ser Phe Asn Arg Gly Glu Cys
            100                 105

<210> SEQ ID NO 2
<211> LENGTH: 329
<212> TYPE: PRT
<213> ORGANISM: Homo sapiens
<220> FEATURE:
<221> NAME/KEY: MISC_FEATURE
<223> OTHER INFORMATION: IgG1 heavy chain (HC) constant region protein

<400> SEQUENCE: 2

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
             85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 321
<212> TYPE: DNA
<213> ORGANISM: Mus musculus
<220> FEATURE:
<221> NAME/KEY: misc_feature
<223> OTHER INFORMATION: SC27.1 Light Chain Variable Region

<400> SEQUENCE: 20

```
gacatccaga tgacacaatc ttcatcctcc ttttctgtat ctctaggaga cagagtcacc      60
attacttgca aggcaagtga agacatatat aatcggttag cctggtatca gcagaaacca     120
ggaaatgctc ccaggctctt aatatctggt gcaaccagtt tggaaactgg gactccttca     180
agattcagtg gcagtggatc tggaaaggat tacactctca gtattaccag tcttcggact     240
gaagatgctg ctacttatta ctgtcaacaa tattggagta ctccactcac gttcggtact     300
gggaccaagc tggagctgaa a                                                321
```

<210> SEQ ID NO 21
<211> LENGTH: 107
<212> TYPE: PRT
<213> ORGANISM: Mus musculus
<220> FEATURE:
<221> NAME/KEY: MISC_FEATURE
<223> OTHER INFORMATION: SC27.1 Light Chain Variable Region

<400> SEQUENCE: 21

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Thr Pro Ser Arg Phe Ser Gly
    50                  55                  60

Ser Gly Ser Gly Lys Asp Tyr Thr Leu Ser Ile Thr Ser Leu Arg Thr
65                  70                  75                  80

Glu Asp Ala Ala Thr Tyr Tyr Cys Gln Gln Tyr Trp Ser Thr Pro Leu
                85                  90                  95

Thr Phe Gly Thr Gly Thr Lys Leu Glu Leu Lys
            100                 105

<210> SEQ ID NO 22
<211> LENGTH: 357
<212> TYPE: DNA
<213> ORGANISM: Mus musculus
<220> FEATURE:
<221> NAME/KEY: misc_feature
<223> OTHER INFORMATION: SC27.1 Heavy Chain Variable Region

<400> SEQUENCE: 22
gaggtccagc tgcaagagtc tagacctgag ctggtgaagc ctggggcttc agtgaagata      60
tcctgcaaga cttctggata cacattcact gaatacacct tgcactgggt gaagcagagt    120
catggaaaga gccttgagtg gattggaggt attaatccta acaatggtga tactatctac    180
aaccagaaat tcaagggcaa ggccacattg actgtagaca gtcctccag cacagcctac    240 atggagctcc gcagcctgac atctgaatat tctgcagtct attactgtgc aagaagggcg    300
attacggtct atgctatgga ctactgggt caaggtacct cagtcaccgt ctcctca        357

<210> SEQ ID NO 23
<211> LENGTH: 119
<212> TYPE: PRT
<213> ORGANISM: Mus musculus
<220> FEATURE:
<221> NAME/KEY: MISC_FEATURE
<223> OTHER INFORMATION: SC27.1 Heavy Chain Variable Region

<400> SEQUENCE: 23

Glu Val Gln Leu Gln Glu Ser Arg Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Leu His Trp Val Lys Gln Ser His Gly Lys Ser Leu Glu Trp Ile
        35                  40                  45

Gly Gly Ile Asn Pro Asn Asn Gly Asp Thr Ile Tyr Asn Gln Lys Phe
    50                  55                  60

Lys Gly Lys Ala Thr Leu Thr Val Asp Lys Ser Ser Ser Thr Ala Tyr

```
                65                   70                   75                   80
Met Glu Leu Arg Ser Leu Thr Ser Glu Tyr Ser Ala Val Tyr Tyr Cys
                        85                   90                   95

Ala Arg Arg Ala Ile Thr Val Tyr Ala Met Asp Tyr Trp Gly Gln Gly
                100                 105                 110

Thr Ser Val Thr Val Ser Ser
        115

<210> SEQ ID NO 24
<211> LENGTH: 333
<212> TYPE: DNA
<213> ORGANISM: Mus musculus
<220> FEATURE:
<221> NAME/KEY: misc_feature
<223> OTHER INFORMATION: SC27.22 Light Chain Variable Region

<400> SEQUENCE: 24
gacattgtgc tgacacagtc tcctgcttcc ttagctgtat ctctggggca gagggccacc      60
atctcatgca gggccagcca gactgtcagt acatctagct atagttatat gcactggttc     120
caacagaaac caggacagcc acccaaactc ctcatcaagt ttgcatccaa cgtagaatct     180
ggggtccctg ccagattcag tggcagtggg tctgggacag acttcaccct caacatccat     240
cctgtggagg aggaggatat ttcaacatat tactgtcagc acagttggga gattccgtgg     300
acgttcggtg gaggcaccaa gctggaaatc aaa                                  333

<210> SEQ ID NO 25
<211> LENGTH: 111
<212> TYPE: PRT
<213> ORGANISM: Mus musculus
<220> FEATURE:
<221> NAME/KEY: MISC_FEATURE
<223> OTHER INFORMATION: SC27.22 Light Chain Variable Region

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Thr Val Ser Thr Ser
            20                  25                  30

Ser Tyr Ser Tyr Met His Trp Phe Gln Gln Lys Pro Gly Gln Pro Pro
        35                  40                  45

Lys Leu Leu Ile Lys Phe Ala Ser Asn Val Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ile Ser Thr Tyr Tyr Cys Gln His Ser Trp
                85                  90                  95

Glu Ile Pro Trp Thr Phe Gly Gly Gly Thr Lys Leu Glu Ile Lys
            100                 105                 110

<210> SEQ ID NO 26
<211> LENGTH: 366
<212> TYPE: DNA
<213> ORGANISM: Mus musculus
<220> FEATURE:
<221> NAME/KEY: misc_feature
<223> OTHER INFORMATION: SC27.22 Heavy Chain Variable Region

<400> SEQUENCE: 26
caggtccaac tgcagcagcc tggggctgag ctggtgaggc ctggagcttc agtgaagctg      60
```

```
tcctgcaagg cttctggcta ccttcacc agctactgga tgaactgggt gaagcagagg      120
cctggacaag gccttgaatg gattgccatg attcatcctt ccgatagtga aattaggtta      180
aatcagaagt tcaaggacaa ggccacattg actgtagaca gatcctccag cacagcctac      240
atgcaactca gcagcccgac atctgaggac tctgcggtct attactgtgc aagaattgat      300
agttattatg gttacctgtt ttactttgac tactggggcc aaggcaccac tctcacagtc      360
tcctca                                                                366
```

```
<210> SEQ ID NO 27
<211> LENGTH: 122
<212> TYPE: PRT
<213> ORGANISM: Mus musculus
<220> FEATURE:
<221> NAME/KEY: MISC_FEATURE
<223> OTHER INFORMATION: SC27.22 Heavy Chain Variable Region

<400> SEQUENCE: 27
```

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Ala Met Ile His Pro Ser Asp Ser Glu Ile Arg Leu Asn Gln Lys Phe
    50                  55                  60

Lys Asp Lys Ala Thr Leu Thr Val Asp Arg Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Leu Thr Val Ser Ser
        115                 120

```
<210> SEQ ID NO 28
<211> LENGTH: 324
<212> TYPE: DNA
<213> ORGANISM: Mus musculus
<220> FEATURE:
<221> NAME/KEY: misc_feature
<223> OTHER INFORMATION: SC27.103 Light Chain Variable Region

<400> SEQUENCE: 28
```

```
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccacact ctggatttat aggacatccg acctggcttc tggagtccca     180
gctcgcttca gtggcagtgg atctgggacc tcttactctc tcacaatcag cagcatggag     240
gctgaagatg ctgccactta ttactgccac cagtatcatc gttccccgtg gacgttcggt     300
ggaggcacca ggctggaaat caaa                                            324
```

```
<210> SEQ ID NO 29
<211> LENGTH: 108
<212> TYPE: PRT
<213> ORGANISM: Mus musculus
<220> FEATURE:
<221> NAME/KEY: MISC_FEATURE
<223> OTHER INFORMATION: SC27.103 Light Chain Variable Region
```

<400> SEQUENCE: 29

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Lys Pro Gly Ser Ser Pro Thr Leu Trp
        35                  40                  45

Ile Tyr Arg Thr Ser Asp Leu Ala Ser Gly Val Pro Ala Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Trp Thr Phe Gly Gly Gly Thr Arg Leu Glu Ile Lys
            100                 105

<210> SEQ ID NO 30
<211> LENGTH: 354
<212> TYPE: DNA
<213> ORGANISM: Mus musculus
<220> FEATURE:
<221> NAME/KEY: misc_feature
<223> OTHER INFORMATION: SC27.103 Heavy Chain Variable Region

<400> SEQUENCE: 30
gaggtccacc tgcaacagtc tggacctgag ctagtgaagc ctggaggttc aatgaagata      60
tcctgcaagg cttctggtta ctcattcact ggctacacca tgaactgggt gaagcagagc    120
catggaaaga accttgagtg gattggactt tttaatcctt acaatggtgg tactagttat    180
aaccagaagt tcaagggcaa ggccacatta actgtagaca gtcatccag cacagcctac     240 atggagctcc tcagtctgac atctgaggac tctgcagtct attactgtgc aagatgctat    300
aggtacgacg gtcttgacta ctggggccaa ggcaccactc tcacagtctc ctca          354

<210> SEQ ID NO 31
<211> LENGTH: 118
<212> TYPE: PRT
<213> ORGANISM: Mus musculus
<220> FEATURE:
<221> NAME/KEY: MISC_FEATURE
<223> OTHER INFORMATION: SC27.103 Heavy Chain Variable Region

<400> SEQUENCE: 31

Glu Val His Leu Gln Gln Ser Gly Pro Glu Leu Val Lys Pro Gly Gly
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Phe Asn Pro Tyr Asn Gly Gly Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Cys Tyr Arg Tyr Asp Gly Leu Asp Tyr Trp Gly Gln Gly Thr
            100                 105                 110

Thr Leu Thr Val Ser Ser

<210> SEQ ID NO 32
<211> LENGTH: 321
<212> TYPE: DNA
<213> ORGANISM: Mus musculus
<220> FEATURE:
<221> NAME/KEY: misc_feature
<223> OTHER INFORMATION: SC27.104 Light Chain Variable Region

<400> SEQUENCE: 32

```
gacatccaga tgacacaatc ttcatcctcc ttttctgtat ctctaggaga cagagtcacc     60
attacttgca aggcaagtga ggacatatat aatcggttag cctggtatca gcagaaacca    120
ggaaatgctc ccaggctctt aatatctggt gcaaccagtt tggaaactgg ggttccttca    180
agattcagtg gcagtggatc tggaaaggat tacactctca gcattaccag tcttcagact    240
gaagatgttg ctacttatta ctgtcaacag tattggagta atcctccgac gttcggtgga    300
ggcaccaagc tggaaatcaa a                                              321
```

<210> SEQ ID NO 33
<211> LENGTH: 107
<212> TYPE: PRT
<213> ORGANISM: Mus musculus
<220> FEATURE:
<221> NAME/KEY: MISC_FEATURE
<223> OTHER INFORMATION: SC27.104 Light Chain Variable Region

<400> SEQUENCE: 33

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Asn Pro Pro
                85                  90                  95

Thr Phe Gly Gly Gly Thr Lys Leu Glu Ile Lys
            100                 105

<210> SEQ ID NO 34
<211> LENGTH: 354
<212> TYPE: DNA
<213> ORGANISM: Mus musculus
<220> FEATURE:
<221> NAME/KEY: misc_feature
<223> OTHER INFORMATION: SC27.104 Heavy Chain Variable Region

<400> SEQUENCE: 34

```
gaggtccagc tgcaacagtc tggacctgag ctggtgaagc ctggggcttc agtgaagata     60
tcctgcaaga cttctggata cacattcact gaatacaccg tgcactgggt gaagcagagc    120
catggaaaga gccttgagtg gattggaggt gtttatccta agaatggtga atactaccta    180
catggaaaga gccttgagtg gattggaggt gtttatccta agaatggtga actacctac
aaccagaagt tcagggggcaa ggccacattg actgtagaca gtcctccaa cacagcctat    240
atggaactcc gcagcctgac atctgaggat tctgcagtct attactgtac aggaaaggat    300
gggtacgacg ggtttgctta ctggggccaa gggactctgg tcactgtctc tgca          354
```

```
<210> SEQ ID NO 35
<211> LENGTH: 118
<212> TYPE: PRT
<213> ORGANISM: Mus musculus
<220> FEATURE:
<221> NAME/KEY: MISC_FEATURE
<223> OTHER INFORMATION: SC27.104 Heavy Chain Variable Region

<400> SEQUENCE: 35

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Val His Trp Val Lys Gln Ser His Gly Lys Ser Leu Glu Trp Ile
        35                  40                  45

Gly Gly Val Tyr Pro Lys Asn Gly Asp Thr Thr Tyr Asn Gln Lys Phe
    50                  55                  60

Arg Gly Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Gly Lys Asp Gly Tyr Asp Gly Phe Ala Tyr Trp Gly Gln Gly Thr
            100                 105                 110

Leu Val Thr Val Ser Ala
        115

<210> SEQ ID NO 36
<211> LENGTH: 318
<212> TYPE: DNA
<213> ORGANISM: Mus musculus
<220> FEATURE:
<221> NAME/KEY: misc_feature
<223> OTHER INFORMATION: SC27.105 Light Chain Variable Region

<400> SEQUENCE: 36
gatgttcaaa tgacccagtc tccatcctcc ctgtctgcat ctttgggaga gagagtctcc      60
ctgacttgcc aggcaagtca gagtgttagc aataatttaa actggtatca gcaaacacca     120
gggaaagctc ctaggctctt gatctatggt gcaagcaaat tggaagatgg ggtctcttca     180
aggttcagtg gcactggata tgggacagat ttcactttca ccatcagcag cctggaggaa     240
gaagatgtgg caacttattt ttgtctacag cataggtatc tgtggacgtt cggtggaggc     300
accaagctgg aaatcaaa                                                   318

<210> SEQ ID NO 37
<211> LENGTH: 106
<212> TYPE: PRT
<213> ORGANISM: Mus musculus
<220> FEATURE:
<221> NAME/KEY: MISC_FEATURE
<223> OTHER INFORMATION: SC27.105 Light Chain Variable Region

<400> SEQUENCE: 37

Asp Val Gln Met Thr Gln Ser Pro Ser Ser Leu Ser Ala Ser Leu Gly
1               5                   10                  15

Glu Arg Val Ser Leu Thr Cys Gln Ala Ser Gln Ser Val Ser Asn Asn
            20                  25                  30

Leu Asn Trp Tyr Gln Gln Thr Pro Gly Lys Ala Pro Arg Leu Leu Ile
        35                  40                  45
```

Tyr Gly Ala Ser Lys Leu Glu Asp Gly Val Ser Ser Arg Phe Ser Gly
        50                  55                  60

Thr Gly Tyr Gly Thr Asp Phe Thr Phe Thr Ile Ser Ser Leu Glu Glu
65                  70                  75                  80

Glu Asp Val Ala Thr Tyr Phe Cys Leu Gln His Arg Tyr Leu Trp Thr
                85                  90                  95

Phe Gly Gly Gly Thr Lys Leu Glu Ile Lys
            100                 105

<210> SEQ ID NO 38
<211> LENGTH: 369
<212> TYPE: DNA
<213> ORGANISM: Mus musculus
<220> FEATURE:
<221> NAME/KEY: misc_feature
<223> OTHER INFORMATION: SC27.105 Heavy Chain Variable Region

<400> SEQUENCE: 38
gaggtccagc tgcagcagtc tggacctgag ttggtgaagc ctggggcttc agtgaagata    60
tcctgcaagg cttctggtta ctcattcact ggctactaca tgaactgggt gaagcaaagt   120
cctgaaaaga gccttgagtg gattggagag attaatccta gcactggtag tactacttac   180
aaccagaagt tcaaggccaa ggccacattg actgtagaca atcctccag cacagcctac    240 atgcagctca gagcctgac atctgaggac tctgcagtct attactgtgc aagaagggat    300
tattactacg gtagtggttt ctatgctatg gactactggg gtcaaggaac ctcagtcacc   360
gtctcctca                                                          369

<210> SEQ ID NO 39
<211> LENGTH: 123
<212> TYPE: PRT
<213> ORGANISM: Mus musculus
<220> FEATURE:
<221> NAME/KEY: MISC_FEATURE
<223> OTHER INFORMATION: SC27.105 Heavy Chain Variable Region

<400> SEQUENCE: 39

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met Asn Trp Val Lys Gln Ser Pro Glu Lys Ser Leu Glu Trp Ile
            35                  40                  45

Gly Glu Ile Asn Pro Ser Thr Gly Ser Thr Thr Tyr Asn Gln Lys Phe
        50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Arg Asp Tyr Tyr Tyr Gly Ser Gly Phe Tyr Ala Met Asp Tyr
            100                 105                 110

Trp Gly Gln Gly Thr Ser Val Thr Val Ser Ser
        115                 120

<210> SEQ ID NO 40
<211> LENGTH: 321
<212> TYPE: DNA
<213> ORGANISM: Mus musculus
<220> FEATURE:
<221> NAME/KEY: misc_feature
<223> OTHER INFORMATION: SC27.106 Light Chain Variable Region

<400> SEQUENCE: 40

```
gacatccaga tgacacaatc ttcatcctcc ttttctgtat ctctaggaga cagagtcacc    60
attacttgca aggcaagtga ggacatatat aatcggttag cctggtatca gcagaaacca   120
ggaaatgctc ctaggctctt aatatgtggt gcaaccagtt tggaaactgg ggttccttca   180
agattcagtg gcagtggatc tggaaaggat tacactctca gcattaccag tcttcagact   240
gaagatgttg ctacttatta ctgtcaacag tattggagta ctccgctcac gttcggtgct   300
gggaccaaac tggagctgaa a                                             321
```

<210> SEQ ID NO 41
<211> LENGTH: 107
<212> TYPE: PRT
<213> ORGANISM: Mus musculus
<220> FEATURE:
<221> NAME/KEY: MISC_FEATURE
<223> OTHER INFORMATION: SC27.106 Light Chain Variable Region

<400> SEQUENCE: 41

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Cys Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Leu
                85                  90                  95

Thr Phe Gly Ala Gly Thr Lys Leu Glu Leu Lys
            100                 105

<210> SEQ ID NO 42
<211> LENGTH: 357
<212> TYPE: DNA
<213> ORGANISM: Mus musculus
<220> FEATURE:
<221> NAME/KEY: misc_feature
<223> OTHER INFORMATION: SC27.106 Heavy Chain Variable Region

<400> SEQUENCE: 42

```
gaggtccagc tgcaacagtc tggacctgag ctggtgaagc ctggggcttc agtgaagata    60
tcctgcaaga cttctggata cacattcact gaatacacca tgcactgggt gaagcagagc   120
catggaaaga gccttgagtg gattggaggt attaatccta caatggtgg tactaactac   180 aaccagaagt tcaagggcaa ggccacattg actgttgaca gtcctccag cacagcctac   240 atggagctcc gcagcctgac atctgaggat tctgcagtct attactgtgc aagaaggctt   300
attacttact atgctatgga ctactggggt caaggaacct cagtcaccgt ctcctca     357
```

<210> SEQ ID NO 43
<211> LENGTH: 119
<212> TYPE: PRT
<213> ORGANISM: Mus musculus
<220> FEATURE:
<221> NAME/KEY: MISC_FEATURE
<223> OTHER INFORMATION: SC27.106 Heavy Chain Variable Region

<400> SEQUENCE: 43

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Arg Arg Leu Ile Thr Tyr Tyr Ala Met Asp Tyr Trp Gly Gln Gly
            100                 105                 110

Thr Ser Val Thr Val Ser Ser
        115
```

<210> SEQ ID NO 44
<211> LENGTH: 324
<212> TYPE: DNA
<213> ORGANISM: Mus musculus
<220> FEATURE:
<221> NAME/KEY: misc_feature
<223> OTHER INFORMATION: SC27.108 Light Chain Variable Region

<400> SEQUENCE: 44

```
gaaattgtgc tcacccagtc tccagcactc atggctgcat ctccagggga gaaggtcacc    60
atcacctgca gtgtcagctc aagtataagt tccagcaact tgcactggta ccagcagaag   120
tcaggaacct cccccaaact ctggatttat ggcacatcca acctggcttc tggagtccct   180
gttcgcttca gtggcagtgg atctgggacc tcttattctc tcacaatcag caacatggag   240
gctgaagatg ctgccactta ttactgtcaa cagtggagta gttacccaca cacgttcgga   300
ggggggacca agctggaaat aaaa                                          324
```

<210> SEQ ID NO 45
<211> LENGTH: 108
<212> TYPE: PRT
<213> ORGANISM: Mus musculus
<220> FEATURE:
<221> NAME/KEY: MISC_FEATURE
<223> OTHER INFORMATION: SC27.108 Light Chain Variable Region

<400> SEQUENCE: 45

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Asn Met Glu
65                  70                  75                  80

Ala Glu Asp Ala Ala Thr Tyr Tyr Cys Gln Gln Trp Ser Ser Tyr Pro
            85                  90                  95
```

His Thr Phe Gly Gly Gly Thr Lys Leu Glu Ile Lys
            100                 105

<210> SEQ ID NO 46
<211> LENGTH: 378
<212> TYPE: DNA
<213> ORGANISM: Mus musculus
<220> FEATURE:
<221> NAME/KEY: misc_feature
<223> OTHER INFORMATION: SC27.108 Heavy Chain Variable Region

<400> SEQUENCE: 46
caggtccaaa tgcagcagtc tggagctgag ctggtaaggc ctgggacttc agtgaaggtg    60
tcctgcaagg cttctggata cgccttcact aattacttga tagagtgggt aaagcagagg   120
cctggacagg gccttgagtg gattggactg attaatcctg gaagtggtgg tactaattac   180
aatgagaagt tcaagggcaa ggcaacactg actgcagaca atcctccac cactgcctac    240 atgcagctca gcagcctgac atctgatgac tctgcggttt atttctgtgc aagacggtcc   300
cctctaggga gttggatcta ctatgcttac gacggtgttg cttactgggg ccaagggact   360
ctggtcactg tctctgca                                                  378

<210> SEQ ID NO 47
<211> LENGTH: 126
<212> TYPE: PRT
<213> ORGANISM: Mus musculus
<220> FEATURE:
<221> NAME/KEY: MISC_FEATURE
<223> OTHER INFORMATION: SC27.108 Heavy Chain Variable Region

<400> SEQUENCE: 47

Gln Val Gln Met Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Leu Thr Ala Asp Lys Ser Thr Thr Ala Tyr
65                  70                  75                  80

Met Gln Leu Ser Ser Leu Thr Ser Asp Asp Ser Ala Val Tyr Phe Cys
                85                  90                  95

Ala Arg Arg Ser Pro Leu Gly Ser Trp Ile Tyr Tyr Ala Tyr Asp Gly
            100                 105                 110

Val Ala Tyr Trp Gly Gln Gly Thr Leu Val Thr Val Ser Ala
        115                 120                 125

<210> SEQ ID NO 48
<211> LENGTH: 321
<212> TYPE: DNA
<213> ORGANISM: Mus musculus
<220> FEATURE:
<221> NAME/KEY: misc_feature
<223> OTHER INFORMATION: SC27.201 Light Chain Variable Region

<400> SEQUENCE: 48
gacatccaga tgacacaatc ttcatcctcc ttttctgtct ctctgggaga cagagtcact    60
attacttgca aggcaagtga ggacatctat aatcggttag cctggtatca acagaaacca   120
ggaaatgctc ctaggctctt aatatctggt gcaaccagtt tggaagctgg ggttccttca   180

```
ggattcagtg gcagtggatc tggaaaggat tacactctca gcattaccag tcttcagact    240
gaagatgttg ctacttatta ctgtcaacag tattggagta ctcctccgac gttcggtgga    300
ggcaccaagc tggaactcaa g                                              321
```

```
<210> SEQ ID NO 49
<211> LENGTH: 107
<212> TYPE: PRT
<213> ORGANISM: Mus musculus
<220> FEATURE:
<221> NAME/KEY: MISC_FEATURE
<223> OTHER INFORMATION: SC27.201 Light Chain Variable Region

<400> SEQUENCE: 49
```

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Ala Gly Val Pro Ser Gly Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Pro
                85                  90                  95

Thr Phe Gly Gly Gly Thr Lys Leu Glu Leu Lys
            100                 105
```

```
<210> SEQ ID NO 50
<211> LENGTH: 360
<212> TYPE: DNA
<213> ORGANISM: Mus musculus
<220> FEATURE:
<221> NAME/KEY: misc_feature
<223> OTHER INFORMATION: SC27.201 Heavy Chain Variable Region

<400> SEQUENCE: 50
```

```
gaggtccagc tgcaacagtc tggacctgaa ctggtgaagc ctggggcttc agtgaagata    60
tcctgcaaga cttctggata cacattcact gaaaacatca gacactgggt gaagcagagc    120
cgaggaaaga gccttgagtg gattggtact attaatccta ataatggtga actaggtac     180 aatcagaagt tcaagggcaa ggccacattg actgtagaca gtcctccag cacagcctac    240 atggagctcc gcagcctgac atctgaggat tctgcagtct attactgtac aaggggatt    300 acaaagtccc cttatggtat ggactactgg ggtcaaggaa cctcaatcac cgtctcctca    360
```

```
<210> SEQ ID NO 51
<211> LENGTH: 120
<212> TYPE: PRT
<213> ORGANISM: Mus musculus
<220> FEATURE:
<221> NAME/KEY: MISC_FEATURE
<223> OTHER INFORMATION: SC27.201 Heavy Chain Variable Region

<400> SEQUENCE: 51
```

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Asn
            20                  25                  30
```

```
Ile Arg His Trp Val Lys Gln Ser Arg Gly Lys Ser Leu Glu Trp Ile
         35                  40                  45

Gly Thr Ile Asn Pro Asn Asn Gly Glu Thr Arg Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
             85                  90                  95

Thr Arg Gly Ile Thr Lys Ser Pro Tyr Gly Met Asp Tyr Trp Gly Gln
             100                 105                 110

Gly Thr Ser Ile Thr Val Ser Ser
         115                 120
```

<210> SEQ ID NO 52
<211> LENGTH: 321
<212> TYPE: DNA
<213> ORGANISM: Mus musculus
<220> FEATURE:
<221> NAME/KEY: misc_feature
<223> OTHER INFORMATION: SC27.203 Light Chain Variable Region

<400> SEQUENCE: 52

```
gacatccaga tgacacaatc ttcatcctcc ttttctgtat ctctaggaga cagagtcacc      60
atcacttgca aggcaagtga ggacatatat aatcggttag cctggtatca gcagaatcca     120
ggaaatactc ctaggctctt aatgtctggt gcaaccagtt tggaaactgg ggttccttca     180
agattcagtg gcagtggatc tggaaaggat tacactctca gcattaccag tcttcagatt     240
gaagatgttt ctacttatta ctgtcaacaa tattggagta ctcctccgac gttcggtgga     300
ggcaccaggc tggaaatcaa a                                                321
```

<210> SEQ ID NO 53
<211> LENGTH: 107
<212> TYPE: PRT
<213> ORGANISM: Mus musculus
<220> FEATURE:
<221> NAME/KEY: MISC_FEATURE
<223> OTHER INFORMATION: SC27.203 Light Chain Variable Region

<400> SEQUENCE: 53

```
Asp Ile Gln Met Thr Gln Ser Ser Ser Phe Ser Val Ser Leu Gly
 1               5                  10                  15

Asp Arg Val Thr Ile Thr Cys Lys Ala Ser Glu Asp Ile Tyr Asn Arg
             20                  25                  30

Leu Ala Trp Tyr Gln Gln Asn Pro Gly Asn Thr Pro Arg Leu Leu Met
         35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Ile
 65                  70                  75                  80

Glu Asp Val Ser Thr Tyr Tyr Cys Gln Gln Tyr Trp Ser Thr Pro Pro
             85                  90                  95

Thr Phe Gly Gly Gly Thr Arg Leu Glu Ile Lys
             100                 105
```

<210> SEQ ID NO 54
<211> LENGTH: 360
<212> TYPE: DNA
<213> ORGANISM: Mus musculus
<220> FEATURE:

<221> NAME/KEY: misc_feature
<223> OTHER INFORMATION: SC27.203 Heavy Chain Variable Region

<400> SEQUENCE: 54

```
gaggtccagc tgcaacagtc tggacctgag ctggtgaagc ctggggcttc agtgaagata    60
tcctgcaaga cttctggata cacattcact gaaaacatca tacactgggt gaagcagagc   120
catggaaaga gccttgagtg gattggaggt attaatccta tcaatggtgg tactagctac   180
aaccagaagt tcaagggcaa ggccacattg actgtagaca gtcctccag cacagcctac    240 atggagctcc gtagcctgac atctgaggat tctgcagtct attactgtgc aaggggatt    300 actacgtccc cttatgctat ggactactgg ggtcaaggaa cctcagtcac cgtctcctca   360
```

<210> SEQ ID NO 55
<211> LENGTH: 120
<212> TYPE: PRT
<213> ORGANISM: Mus musculus
<220> FEATURE:
<221> NAME/KEY: MISC_FEATURE
<223> OTHER INFORMATION: SC27.203 Heavy Chain Variable Region

<400> SEQUENCE: 55

```
Glu Val Gln Leu Gln Gln Ser Gly Pro Glu Leu Val Lys Pro Gly Ala
 1               5                  10                  15

Ser Val Lys Ile Ser Cys Lys Thr Ser Gly Tyr Thr Phe Thr Glu Asn
            20                  25                  30

Ile Ile His Trp Val Lys Gln Ser His Gly Lys Ser Leu Glu Trp Ile
        35                  40                  45

Gly Gly Ile Asn Pro Ile Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ile Thr Thr Ser Pro Tyr Ala Met Asp Tyr Trp Gly Gln
            100                 105                 110

Gly Thr Ser Val Thr Val Ser Ser
        115                 120
```

<210> SEQ ID NO 56
<211> LENGTH: 321
<212> TYPE: DNA
<213> ORGANISM: Mus musculus
<220> FEATURE:
<221> NAME/KEY: misc_feature
<223> OTHER INFORMATION: SC27.204 Light Chain Variable Region

<400> SEQUENCE: 56

```
gacattgtga tgacccagtc tcaaaaattc atgtccacat cagtaggaga cagggtcagc    60
gtcgcctgca aggccggtca gaatgtgggt actagtgtag cctggtatca acagaaacca   120
ggacattctc ctaaatcact gatttactcg gcatcctacc ggtacagtgg agtccctaat   180
cgcttcacag gcagtggatc tgggacagat ttcactctca ccatcagcaa tgtgcagtct   240
gaagacttgg cagactattt ctgtcagcaa tatatcacct atccgtacac gttcggaggg   300
gggaccaagc tggaaataat a                                             321
```

<210> SEQ ID NO 57
<211> LENGTH: 107
<212> TYPE: PRT

<213> ORGANISM: Mus musculus
<220> FEATURE:
<221> NAME/KEY: MISC_FEATURE
<223> OTHER INFORMATION: SC27.204 Light Chain Variable Region

<400> SEQUENCE: 57

Asp Ile Val Met Thr Gln Ser Gln Lys Phe Met Ser Thr Ser Val Gly
1               5                   10                  15

Asp Arg Val Ser Val Ala Cys Lys Ala Gly Gln Asn Val Gly Thr Ser
            20                  25                  30

Val Ala Trp Tyr Gln Gln Lys Pro Gly His Ser Pro Lys Ser Leu Ile
        35                  40                  45

Tyr Ser Ala Ser Tyr Arg Tyr Ser Gly Val Pro Asn Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ile Thr Tyr Pro Tyr
                85                  90                  95

Thr Phe Gly Gly Gly Thr Lys Leu Glu Ile Ile
            100                 105

<210> SEQ ID NO 58
<211> LENGTH: 336
<212> TYPE: DNA
<213> ORGANISM: Mus musculus
<220> FEATURE:
<221> NAME/KEY: misc_feature
<223> OTHER INFORMATION: SC27.204 Heavy Chain Variable Region

<400> SEQUENCE: 58
gaggtgaagg ttctcgagtc tggaggtggc ctggtgcagc ctggaggatc cctgaaactc      60
tcctgtgcag cctcaggatt cgattttagt agatactgga tgagttgggt ccggcaggct     120
ccagggaaag gcctagaatg gattggagaa attaatccag atagcagtac gataaactat     180
acgccatctc taaaggctaa attcatcatc tccagagaca acgccaaaaa tacgctgtac     240
ctgcaaatga gcaaagtgag atctgaggac acagcccttt attactgtac aggaccagct     300
tactggggcc aagggactct ggtcactgtc tctgca                                336

<210> SEQ ID NO 59
<211> LENGTH: 112
<212> TYPE: PRT
<213> ORGANISM: Mus musculus
<220> FEATURE:
<221> NAME/KEY: MISC_FEATURE
<223> OTHER INFORMATION: SC27.204 Heavy Chain Variable Region

<400> SEQUENCE: 59

Glu Val Lys Val Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Ala Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

```
Thr Gly Pro Ala Tyr Trp Gly Gln Gly Thr Leu Val Thr Val Ser Ala
            100                 105                 110
```

<210> SEQ ID NO 60
<211> LENGTH: 321
<212> TYPE: DNA
<213> ORGANISM: Artificial Sequence
<220> FEATURE:
<223> OTHER INFORMATION: hSC27.1 Light Chain Variable Region

<400> SEQUENCE: 60

```
gacatccaga tgacccagtc tccatcttcc gtgtctgcat ctgtaggaga cagagtcacc    60
atcacttgta aggcgagtga ggatatttac aaccggttag cctggtatca gcagaaacca   120
gggaaagccc ctaagctcct gatctatggt gcaaccagtt tggaaactgg ggtcccatca   180
aggttcagcg gcagtggatc tgggacagat tacactctca ccatcagcag cctgcagcct   240
gaagattttg caacttacta ttgtcaacag tattggagta ctccactcac gttcggtcaa   300
gggaccaagc tggagattaa a                                             321
```

<210> SEQ ID NO 61
<211> LENGTH: 107
<212> TYPE: PRT
<213> ORGANISM: Artificial Sequence
<220> FEATURE:
<223> OTHER INFORMATION: hSC27.1 Light Chain Variable Region

<400> SEQUENCE: 61

```
Asp Ile Gln Met Thr Gln Ser Pro Ser Ser Val Ser Ala Ser Val Gly
1               5                   10                  15
Asp Arg Val Thr Ile Thr Cys Lys Ala Ser Glu Asp Ile Tyr Asn Arg
            20                  25                  30
Leu Ala Trp Tyr Gln Gln Lys Pro Gly Lys Ala Pro Lys Leu Leu Ile
        35                  40                  45
Tyr Gly Ala Thr Ser Leu Glu Thr Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Tyr Trp Ser Thr Pro Leu
                85                  90                  95
Thr Phe Gly Gln Gly Thr Lys Leu Glu Ile Lys
            100                 105
```

<210> SEQ ID NO 62
<211> LENGTH: 357
<212> TYPE: DNA
<213> ORGANISM: Artificial Sequence
<220> FEATURE:
<223> OTHER INFORMATION: hSC27.1 Heavy Chain Variable Region

<400> SEQUENCE: 62

```
caggtccagc ttgtgcagtc tggggctgag gtgaagaagc ctggggcctc agtgaaggtt    60
tcctgcaagg cttctggata caccttcact gagtatactc tgcattgggt gcgccaggcc   120
cccggacaaa ggcttgagtg gatgggaggg atcaacccta caatggtga cacaatatat    180
aaccagaagt tcaagggcag agtcaccatt accagggaca catccgcgag cacagcctac   240
atggagctga gcagcctgag atctgaagac acggctgtgt attactgtgc gagaagggcg   300
attacggtct atgctatgga ctactggggt caaggtaccc tagtcaccgt ctcgagc     357
```

```
<210> SEQ ID NO 63
<211> LENGTH: 119
<212> TYPE: PRT
<213> ORGANISM: Artificial Sequence
<220> FEATURE:
<223> OTHER INFORMATION: hSC27.1 Heavy Chain Variable Region

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Leu His Trp Val Arg Gln Ala Pro Gly Gln Arg Leu Glu Trp Met
        35                  40                  45

Gly Gly Ile Asn Pro Asn Asn Gly Asp Thr Ile Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ile Thr Val Tyr Ala Met Asp Tyr Trp Gly Gln Gly
            100                 105                 110

Thr Leu Val Thr Val Ser Ser
        115

<210> SEQ ID NO 64
<211> LENGTH: 333
<212> TYPE: DNA
<213> ORGANISM: Artificial Sequence
<220> FEATURE:
<223> OTHER INFORMATION: hSC27.22 Light Chain Variable Region

<400> SEQUENCE: 64
gacattgtca tgacccagtc ccctgacagt ttggccgtta gcttggggga gcgtgccacc      60
atcaactgta gggctagtca aactgtttct acatcctcct actcttacat gcattggtat     120
cagcagaaac tggtcagcc tccaaaactg ctgatttatt tcgcatctaa cgtcgagtcc      180
ggagttcctg accggttcag cggatcagga agcggtacag attttacact taccatctca     240
tctctgcaag cagaagatgt ggccgtgtac tattgtcagc attcctggga tcccctgg       300 accttcgggc agggaaccaa gctcgagatt aaa                                   333

<210> SEQ ID NO 65
<211> LENGTH: 111
<212> TYPE: PRT
<213> ORGANISM: Artificial Sequence
<220> FEATURE:
<223> OTHER INFORMATION: hSC27.22 Light Chain Variable Region

<400> SEQUENCE: 65

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Phe Ala Ser Asn Val Glu Ser Gly Val Pro Asp
    50                  55                  60

Arg Phe Ser Gly Ser Gly Ser Gly Thr Asp Phe Thr Leu Thr Ile Ser
```

```
                65                  70                  75                  80
Ser Leu Gln Ala Glu Asp Val Ala Val Tyr Tyr Cys Gln His Ser Trp
                    85                  90                  95

Glu Ile Pro Trp Thr Phe Gly Gln Gly Thr Lys Leu Glu Ile Lys
                100                 105                 110

<210> SEQ ID NO 66
<211> LENGTH: 366
<212> TYPE: DNA
<213> ORGANISM: Artificial Sequence
<220> FEATURE:
<223> OTHER INFORMATION: hSC27.22 Heavy Chain Variable Region

<400> SEQUENCE: 66
caggtgcagt tggtgcagag cggcgccgaa gtcaagaaac caggagcttc tgtcaaagtc      60
tcctgtaaag cctccggata taccttcacc agctactgga tgaattgggt aagacaggcc     120
cccggacaga ggcttgagtg gatgggaatg atccatccct ctgacagcga gattcggctc     180
aaccagaagt ttaaagaccg agtgactatc acacgcgata ccagtgctag cacagcctac     240
atggagttga gttctcttcg tagcgaggac actgccgtgt attattgcgc ccgcatcgac     300
tcatattatg gttatctgtt ctacttcgac tattggggcc aggggaccac cgtgactgtg     360
tcttcc                                                                366

<210> SEQ ID NO 67
<211> LENGTH: 122
<212> TYPE: PRT
<213> ORGANISM: Artificial Sequence
<220> FEATURE:
<223> OTHER INFORMATION: hSC27.22 Heavy Chain Variable Region

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Arg Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
                100                 105                 110

Gly Gln Gly Thr Thr Val Thr Val Ser Ser
            115                 120

<210> SEQ ID NO 68
<211> LENGTH: 324
<212> TYPE: DNA
<213> ORGANISM: Artificial Sequence
<220> FEATURE:
<223> OTHER INFORMATION: hSC27.108 Light Chain Variable Region

<400> SEQUENCE: 68
gaaatcgtgc ttacacaatc ccctgccact ctgagccttt ctccaggcga gcagcaacc       60 ctttcctgca gtgtttcctc ttcaatcagt tccagcaatt gcactggta ccagcagaag     120
```

-continued

```
cctggtcagg cacccccgatt gttgatctat ggcacatcta acctggccag cggcatccct    180
gctcggttca gtggatctgg ctccggaaca gatttcactc tcactatcag ctcccttgag    240
cctgaagatt ttgccgtgta ctactgtcag caatggagtt cctaccccca cacctttggc    300
ggcgggacaa aggtcgagat aaaa                                            324
```

<210> SEQ ID NO 69
<211> LENGTH: 108
<212> TYPE: PRT
<213> ORGANISM: Artificial Sequence
<220> FEATURE:
<223> OTHER INFORMATION: hSC27.108 Light Chain Variable Region

<400> SEQUENCE: 69

```
Glu Ile Val Leu Thr Gln Ser Pro Ala Thr Leu Ser Leu Ser Pro Gly
1               5                   10                  15

Glu Arg Ala Thr Leu Ser Cys Ser Val Ser Ser Ile Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Trp Ser Ser Tyr Pro
                85                  90                  95

His Thr Phe Gly Gly Gly Thr Lys Val Glu Ile Lys
            100                 105
```

<210> SEQ ID NO 70
<211> LENGTH: 378
<212> TYPE: DNA
<213> ORGANISM: Artificial Sequence
<220> FEATURE:
<223> OTHER INFORMATION: hSC27.108 Heavy Chain Variable Region

<400> SEQUENCE: 70

```
caggtacagc tggtccagtc cggcgctgag gttaagaagc ccggtgcctc cgtgaaggta    60
tcttgtaagg cctcaggtta cacctttaca aattatctga tcgaatgggt gagacaggcc   120
ccaggtcagg gtctggaatg gatgggactc atcaaccctg ggagtggcgg gaccaactac   180
aacgaaaagt ttaagggag agtgacaatg accacagata ccagtacctc caccgcatat   240
atggagctgc gaagcttgag gtccgatgac actgctgtgt actattgcgc ccgtagaagc   300
ccactcgggt cttggatcta ttacgcatac gatggtgtgg cctattgggg ccagggcacc   360
ctggtgacag tcagctcc                                                  378
```

<210> SEQ ID NO 71
<211> LENGTH: 126
<212> TYPE: PRT
<213> ORGANISM: Artificial Sequence
<220> FEATURE:
<223> OTHER INFORMATION: hSC27.108 Heavy Chain Variable Region

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Ser Pro Leu Gly Ser Trp Ile Tyr Tyr Ala Tyr Asp Gly
                100                 105                 110

Val Ala Tyr Trp Gly Gln Gly Thr Leu Val Thr Val Ser Ser
            115                 120                 125

<210> SEQ ID NO 72
<211> LENGTH: 321
<212> TYPE: DNA
<213> ORGANISM: Artificial Sequence
<220> FEATURE:
<223> OTHER INFORMATION: hSC27.204 Light Chain Variable Region

<400> SEQUENCE: 72
gacatccaga tgacccagtc cccctccagc ctgtctgctt ccgtgggcga cagagtgacc    60
atcacatgca aggccggcca gaacgtgggc acctctgtgg cctggttcca gcagaagcct   120
ggcaaggccc ccaagtccct gatctactcc gcctcctaca gatactccgg cgtgccctcc   180
agattctccg gctctggctc tggcaccgac tttaccctga ccatcagctc cctgcagccc   240
gaggacttcg ccacctacta ctgccagcag tacatcacct acccctacac cttcggcgga   300
ggcaccaagg tggaaatcaa g                                             321

<210> SEQ ID NO 73
<211> LENGTH: 107
<212> TYPE: PRT
<213> ORGANISM: Artificial Sequence
<220> FEATURE:
<223> OTHER INFORMATION: hSC27.204 Light Chain Variable Region

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Lys Ala Gly Gln Asn Val Gly Thr Ser
                20                  25                  30

Val Ala Trp Phe Gln Gln Lys Pro Gly Lys Ala Pro Lys Ser Leu Ile
            35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Thr Tyr Pro Tyr
                85                  90                  95

Thr Phe Gly Gly Gly Thr Lys Val Glu Ile Lys
            100                 105

<210> SEQ ID NO 74
<211> LENGTH: 336
<212> TYPE: DNA
<213> ORGANISM: Artificial Sequence
<220> FEATURE:
<223> OTHER INFORMATION: hSC27.204 Heavy Chain Variable Region -continued

<400> SEQUENCE: 74

```
gaagtgcagc tgctggaatc tggcggcgga ctggtgcagc ctggcggatc tctgagactg      60
tcttgtgccg cctccggctt caccttctcc cggtactgga tgtcctgggt gcgacaggct     120
cctggcaagg gcctggaatg ggtgtccgag atcaaccccg actcctccac catcaactac     180
accccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                               336
```

<210> SEQ ID NO 75
<211> LENGTH: 112
<212> TYPE: PRT
<213> ORGANISM: Artificial Sequence
<220> FEATURE:
<223> OTHER INFORMATION: hSC27.204 Heavy Chain Variable Region

<400> SEQUENCE: 75

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110
```

<210> SEQ ID NO 76
<211> LENGTH: 324
<212> TYPE: DNA
<213> ORGANISM: Artificial Sequence
<220> FEATURE:
<223> OTHER INFORMATION: hSC27.108v1 Light Chain Variable Region

<400> SEQUENCE: 76

```
gaaatcgtgc tgactcagtc tcccgatttc cagtccgtca cacccaagga gaaagtcacc      60
atcacttgtt ctgtctcctc aagcatctct tctagtaacc tgcactggta tcagcagaag    120
cctgatcagt cccctaagct ttggatatac ggcacctcaa acctcgcctc cggagttcct    180
tcaaggtttt caggtagtgg atctggaacc gatttcaccc ttacaataaa cagtcttgag    240
gccgaggacg ccgccactta ctactgccag cagtggagtt cttacccccca cacatttggg    300
ggcggcacca aagtggagat caaa                                            324
```

<210> SEQ ID NO 77
<211> LENGTH: 108
<212> TYPE: PRT
<213> ORGANISM: Artificial Sequence
<220> FEATURE:
<223> OTHER INFORMATION: hSC27.108v1 Light Chain Variable Region

<400> SEQUENCE: 77

```
Glu Ile Val Leu Thr Gln Ser Pro Asp Phe Gln Ser Val Thr Pro Lys
```

```
1               5                   10                  15
Glu Lys Val Thr Ile Thr Cys Ser Val Ser Ser Ile Ser Ser Ser
                20                  25                  30

Asn Leu His Trp Tyr Gln Gln Lys Pro Asp Gln Ser Pro Lys Leu Trp
            35                  40                  45

Ile Tyr Gly Thr Ser Asn Leu Ala Ser Gly Val Pro Ser Arg Phe Ser
        50                  55                  60

Gly Ser Gly Ser Gly Thr Asp Phe Thr Leu Thr Ile Asn Ser Leu Glu
65                  70                  75                  80

Ala Glu Asp Ala Ala Thr Tyr Tyr Cys Gln Gln Trp Ser Ser Tyr Pro
                85                  90                  95

His Thr Phe Gly Gly Gly Thr Lys Val Glu Ile Lys
                100                 105
```

```
<210> SEQ ID NO 78
<211> LENGTH: 366
<212> TYPE: DNA
<213> ORGANISM: Artificial Sequence
<220> FEATURE:
<223> OTHER INFORMATION: hSC27.22-VH1-8 Heavy Chain Variable Region

<400> SEQUENCE: 78
caggtgcagc tggtgcagtc tggcgccgaa gtgaagaaac ctggcgcctc cgtgaaggtg      60
tcctgcaagg cctccggcta cacctttacc agctactgga tgaactgggt gcgacaggct    120
accggccagg gcctggaatg gatgggcatg atccacccct ccgactccga gatccggctg    180
aaccagaaat tcaaggacag agtgaccatg acccggaaca cctccatctc caccgcctac    240
atggaactgt cctccctgcg gagcgaggac accgccgtgt actactgcgc ccggatcgac    300
tcctactacg gctacctgtt ctacttcgac tactggggcc agggcaccac cgtgaccgtg    360
tcatct                                                                366
```

```
<210> SEQ ID NO 79
<211> LENGTH: 122
<212> TYPE: PRT
<213> ORGANISM: Artificial Sequence
<220> FEATURE:
<223> OTHER INFORMATION: hSC27.22-VH1-8 Heavy Chain Variable Region

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Thr Gly Gln Gly Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
                100                 105                 110

Gly Gln Gly Thr Thr Val Thr Val Ser Ser
            115                 120
```

```
<210> SEQ ID NO 80
<211> LENGTH: 366
<212> TYPE: DNA
<213> ORGANISM: Artificial Sequence
<220> FEATURE:
<223> OTHER INFORMATION: hSC27.22-VH1-46 Heavy Chain Variable Region

<400> SEQUENCE: 80
caggtgcagc tggtgcagtc tggcgccgaa gtgaagaaac ctggcgcctc cgtgaaggtg      60
tcctgcaagg cctccggcta cacctttacc agctactgga tgaactgggt gcgacaggcc     120
cctggacagg gcctggaatg gatgggcatg atccacccct ccgactccga gatccggctg     180
aaccagaaat tcaaggaccg cgtgaccatg accagagaca cctccaccag caccgtgtac     240
atggaactgt cctccctgcg gagcgaggac accgccgtgt actactgcgc ccggatcgac     300
tcctactacg gctacctgtt ctacttcgac tactggggcc agggcaccac cgtgaccgtg     360
tcatct                                                                366

<210> SEQ ID NO 81
<211> LENGTH: 122
<212> TYPE: PRT
<213> ORGANISM: Artificial Sequence
<220> FEATURE:
<223> OTHER INFORMATION: hSC27.22-VH1-46 Heavy Chain Variable Region

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser
        115                 120

<210> SEQ ID NO 82
<211> LENGTH: 366
<212> TYPE: DNA
<213> ORGANISM: Artificial Sequence
<220> FEATURE:
<223> OTHER INFORMATION: hSC27.22-VH1-69 Heavy Chain Variable Region

<400> SEQUENCE: 82
caggtgcagc tggtgcagtc tggcgccgaa gtgaagaaac ccggctcctc cgtgaaggtg      60
tcctgcaagg cttccggcgg cacctttctc agctactgga tgaactgggt gcgacaggcc     120
cctggacagg gcctggaatg gatgggcatg atccacccct ccgactccga gatccggctg     180
aaccagaaat tcaaggacag agtgaccatc accgccgacg agtccacctc caccgcctac     240
atggaactgt cctccctgcg gagcgaggac accgccgtgt actactgcgc ccggatcgac     300
tcctactacg gctacctgtt ctacttcgac tactggggcc agggcaccac cgtgaccgtg     360
``` tcatct                                                              366

<210> SEQ ID NO 83
<211> LENGTH: 122
<212> TYPE: PRT
<213> ORGANISM: Artificial Sequence
<220> FEATURE:
<223> OTHER INFORMATION: hSC27.22-VH1-69 Heavy Chain Variable Region

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Trp Met Asn Trp Val Arg Gln Ala Pro Gly Gln Gly Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
                100                 105                 110

Gly Gln Gly Thr Thr Val Thr Val Ser Ser
            115                 120

<210> SEQ ID NO 84
<211> LENGTH: 336
<212> TYPE: DNA
<213> ORGANISM: Artificial Sequence
<220> FEATURE:
<223> OTHER INFORMATION: hSC27.204v1 Heavy Chain Variable Region

<400> SEQUENCE: 84
gaagtgcagc tgctggaatc tggcggcgga ctggtgcagc ctggcggatc tctgagactg     60
tcttgtgccg cctccggctt caccttctcc cggtactgga tgtcctgggt gcgacaggct    120
cctggcaagg gcctggaatg ggtgtccgag atcaaccccg actcctccac catcaagtac    180
acccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                             336

<210> SEQ ID NO 85
<211> LENGTH: 112
<212> TYPE: PRT
<213> ORGANISM: Artificial Sequence
<220> FEATURE:
<223> OTHER INFORMATION: hSC27.204v1 Heavy Chain Variable Region

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

Ser Glu Ile Asn Pro Asp Ser Ser Thr Ile Lys Tyr Thr Pro Ser Leu
        50                  55                  60

```
Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110
```

<210> SEQ ID NO 86
<211> LENGTH: 336
<212> TYPE: DNA
<213> ORGANISM: Artificial Sequence
<220> FEATURE:
<223> OTHER INFORMATION: hSC27.204v2 Heavy Chain Variable Region

<400> SEQUENCE: 86

```
gaagtgcagc tgctggaatc tggcggcgga ctggtgcagc tggcggatc tctgagactg      60 tcttgtgccg cctccggctt caccttctcc cggtactgga tgtcctgggt gcgacaggct    120
cctggcaagg gcctggaatg ggtgtccgag atcaaccccg actcctccac catccagtac    180 accccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                              336
```

<210> SEQ ID NO 87
<211> LENGTH: 112
<212> TYPE: PRT
<213> ORGANISM: Artificial Sequence
<220> FEATURE:
<223> OTHER INFORMATION: hSC27.204v2 Heavy Chain Variable Region

<400> SEQUENCE: 87

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

Ser Glu Ile Asn Pro Asp Ser Ser Thr Ile Gln Tyr Thr Pro Ser Leu
        50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110
```

<210> SEQ ID NO 88
<211> LENGTH: 336
<212> TYPE: DNA
<213> ORGANISM: Artificial Sequence
<220> FEATURE:
<223> OTHER INFORMATION: hSC27.204v3 Heavy Chain Variable Region

<400> SEQUENCE: 88

```
gaagtgcagc tgctggaatc tggcggcgga ctggtgcagc tggcggatc tctgagactg      60 tcttgtgccg cctccggctt caccttctcc cggtactgga tgtcctgggt gcgacaggct    120
cctggcaagg gcctggaatg ggtgtccgag atcaaccccg actcctccac catcaactac    180
```

```
aaccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                              336
```

<210> SEQ ID NO 89
<211> LENGTH: 112
<212> TYPE: PRT
<213> ORGANISM: Artificial Sequence
<220> FEATURE:
<223> OTHER INFORMATION: hSC27.204v3 Heavy Chain Variable Region

<400> SEQUENCE: 89

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110
```

<210> SEQ ID NO 90
<211> LENGTH: 336
<212> TYPE: DNA
<213> ORGANISM: Artificial Sequence
<220> FEATURE:
<223> OTHER INFORMATION: hSC27.204v4 Heavy Chain Variable Region

<400> SEQUENCE: 90

```
gaagtgcagc tgctggaatc tggcggcgga ctggtgcagc ctggcggatc tctgagactg     60
tcttgtgccg cctccggctt cgacttctcc cggtactgga tgtcctgggt gcgacaggct    120
cctggcaagg gcctggaatg ggtgtccgag atcaaccccg actcctccac catcaactac    180 accccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                              336
```

<210> SEQ ID NO 91
<211> LENGTH: 112
<212> TYPE: PRT
<213> ORGANISM: Artificial Sequence
<220> FEATURE:
<223> OTHER INFORMATION: hSC27.204v4 Heavy Chain Variable Region

<400> SEQUENCE: 91

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
```

```
                   50                  55                  60
Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Gly Pro Ala Tyr Trp Gly Gln Gly Thr Leu Val Thr Val Ser Ser
            100                 105                 110
```

<210> SEQ ID NO 92
<211> LENGTH: 336
<212> TYPE: DNA
<213> ORGANISM: Artificial Sequence
<220> FEATURE:
<223> OTHER INFORMATION: hSC27.204v5 Heavy Chain Variable Region

<400> SEQUENCE: 92

```
gaagtgcagc tgctggaatc tggcggcgga ctggtgcagc ctggcggatc tctgagactg      60
tcttgtgccg cctccggctt cgacttctcc cggtactgga tgtcctgggt gcgacaggct     120
cctggcaagg gcctggaatg ggtgtccgag atcaaccccg actcctccac catcaagtac     180
acccccagcc tgaaggcccg gttcaccatc tctcgggaca actccaagaa caccctgtac     240
ctgcagatga actccctgcg ggccgaggac accgccgtgt actactgtac cggccctgct     300
tattggggcc agggcaccct cgtgaccgtg tcctct                               336
```

<210> SEQ ID NO 93
<211> LENGTH: 112
<212> TYPE: PRT
<213> ORGANISM: Artificial Sequence
<220> FEATURE:
<223> OTHER INFORMATION: hSC27.204v5 Heavy Chain Variable Region

<400> SEQUENCE: 93

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
                 20                  25                  30

Trp Met Ser Trp Val Arg Gln Ala Pro Gly Lys Gly Leu Glu Trp Val
             35                  40                  45

Ser Glu Ile Asn Pro Asp Ser Ser Thr Ile Lys Tyr Thr Pro Ser Leu
 50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Gly Pro Ala Tyr Trp Gly Gln Gly Thr Leu Val Thr Val Ser Ser
            100                 105                 110
```

<210> SEQ ID NO 94
<211> LENGTH: 336
<212> TYPE: DNA
<213> ORGANISM: Artificial Sequence
<220> FEATURE:
<223> OTHER INFORMATION: hSC27.204v6 Heavy Chain Variable Region

<400> SEQUENCE: 94

```
gaagtgcagc tgctggaatc tggcggcgga ctggtgcagc ctggcggatc tctgagactg      60
tcttgtgccg cctccggctt cgacttctcc cggtactgga tgtcctgggt gcgacaggct     120
cctggcaagg gcctggaatg ggtgtccgag atcaaccccg actcctccac catccagtac     180
```

```
accccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                              336
```

```
<210> SEQ ID NO 95
<211> LENGTH: 112
<212> TYPE: PRT
<213> ORGANISM: Artificial Sequence
<220> FEATURE:
<223> OTHER INFORMATION: hSC27.204v6 Heavy Chain Variable Region

<400> SEQUENCE: 95
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Gln Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110

```
<210> SEQ ID NO 96
<211> LENGTH: 336
<212> TYPE: DNA
<213> ORGANISM: Artificial Sequence
<220> FEATURE:
<223> OTHER INFORMATION: hSC27.204v7 Heavy Chain Variable Region

<400> SEQUENCE: 96
```

```
gaagtgcagc tgctggaatc tggcggcgga ctggtgcagc ctggcggatc tctgagactg    60
tcttgtgccg cctccggctt cgacttctcc cggtactgga tgtcctgggt gcgacaggct    120
cctggcaagg gcctggaatg ggtgtccgag atcaaccccg actcctccac catcaactac    180
aaccccagcc tgaaggcccg gttcaccatc tctcgggaca actccaagaa caccctgtac    240
ctgcagatga actccctgcg ggccgaggac accgccgtgt actactgtac cggccctgct    300
tattggggcc agggcaccct cgtgaccgtg tcctct                              336
```

```
<210> SEQ ID NO 97
<211> LENGTH: 112
<212> TYPE: PRT
<213> ORGANISM: Artificial Sequence
<220> FEATURE:
<223> OTHER INFORMATION: hSC27.204v7 Heavy Chain Variable Region

<400> SEQUENCE: 97
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
            50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Gly Pro Ala Tyr Trp Gly Gln Gly Thr Leu Val Thr Val Ser Ser
            100                 105                 110

<210> SEQ ID NO 98
<211> LENGTH: 336
<212> TYPE: DNA
<213> ORGANISM: Artificial Sequence
<220> FEATURE:
<223> OTHER INFORMATION: hSC27.204v8 Heavy Chain Variable Region

<400> SEQUENCE: 98
gaagtgcagc tgctggaatc tggcggcgga ctggtgcagc ctggcggatc tctgagactg     60
tcttgtgccg cctccggctt caccttctcc cggtactgga tgtcctgggt gcgacaggct    120
cctggcaagg gcctggaatg ggtgtccgag atcaaccccg actcctccac catcaactac    180 accccagcc tgaaggcccg gttcaccatc tctcgggaca actccaagaa cacccctgtac    240 ctgcagatga actccctgcg ggccgaggac accgccgtgt actactgtgc cggccctgct    300
tattggggcc agggcaccct cgtgaccgtg tcctct                              336

<210> SEQ ID NO 99
<211> LENGTH: 112
<212> TYPE: PRT
<213> ORGANISM: Artificial Sequence
<220> FEATURE:
<223> OTHER INFORMATION: hSC27.204v8 Heavy Chain Variable Region

<400> SEQUENCE: 99

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Arg Tyr
             20                  25                  30

Trp Met Ser Trp Val Arg Gln Ala Pro Gly Lys Gly Leu Glu Trp Val
         35                  40                  45

Ser Glu Ile Asn Pro Asp Ser Ser Thr Ile Asn Tyr Thr Pro Ser Leu
    50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110

<210> SEQ ID NO 100
<211> LENGTH: 336
<212> TYPE: DNA
<213> ORGANISM: Artificial Sequence
<220> FEATURE:
<223> OTHER INFORMATION: hSC27.204v9 Heavy Chain Variable Region

<400> SEQUENCE: 100
gaagtgcagc tgctggaatc tggcggcgga ctggtgcagc ctggcggatc tctgagactg     60
tcttgtgccg cctccggctt caccttctcc cggtactgga tgtcctgggt gcgacaggct    120

```
cctggcaagg gcctggaatg ggtgtccgag atcaaccccg actcctccac catcaagtac    180
acccccagcc tgaaggcccg gttcaccatc tctcgggaca actccaagaa caccctgtac    240
ctgcagatga actccctgcg ggccgaggac accgccgtgt actactgtgc cggccctgct    300
tattggggcc agggcaccct cgtgaccgtg tcctct                              336
```

<210> SEQ ID NO 101
<211> LENGTH: 112
<212> TYPE: PRT
<213> ORGANISM: Artificial Sequence
<220> FEATURE:
<223> OTHER INFORMATION: hSC27.204v9 Heavy Chain Variable Region

<400> SEQUENCE: 101

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Lys Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110
```

<210> SEQ ID NO 102
<211> LENGTH: 336
<212> TYPE: DNA
<213> ORGANISM: Artificial Sequence
<220> FEATURE:
<223> OTHER INFORMATION: hSC27.204v10 Heavy Chain Variable Region

<400> SEQUENCE: 102

```
gaagtgcagc tgctggaatc tggcggcgga ctggtgcagc ctggcggatc tctgagactg     60
tcttgtgccg cctccggctt cacctttctc cggtactgga tgtcctgggt gcgacaggct    120
cctggcaagg gcctggaatg ggtgtccgag atcaaccccg actcctccac catcaagtac    180
acccccagcc tgaaggcccg gttcaccatc tctcgggaca actccaagaa caccctgtac    240
ctgcagatga actccctgcg ggccgaggac accgccgtgt actactgtgc cggccctgct    300
tattggggcc agggcaccct cgtgaccgtg tcctct                              336
```

<210> SEQ ID NO 103
<211> LENGTH: 112
<212> TYPE: PRT
<213> ORGANISM: Artificial Sequence
<220> FEATURE:
<223> OTHER INFORMATION: hSC27.204v10 Heavy Chain Variable Region

<400> SEQUENCE: 103

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45
```

```
Ser Glu Ile Asn Pro Asp Ser Ser Thr Ile Gln Tyr Thr Pro Ser Leu
        50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110
```

<210> SEQ ID NO 104
<211> LENGTH: 336
<212> TYPE: DNA
<213> ORGANISM: Artificial Sequence
<220> FEATURE:
<223> OTHER INFORMATION: hSC27.204v11 Heavy Chain Variable Region

<400> SEQUENCE: 104

```
gaagtgcagc tgctggaatc tggcggcgga ctggtgcagc ctggcggatc tctgagactg      60
tcttgtgccg cctccggctt caccttctcc cggtactgga tgtcctgggt gcgacaggct     120
cctggcaagg gcctggaatg ggtgtccgag atcaaccccg actcctccac catcaactac     180
aaccccagcc tgaaggcccg gttcaccatc tctcgggaca actccaagaa caccctgtac     240
ctgcagatga actccctgcg ggccgaggac accgccgtgt actactgtgc cggccctgct     300
tattggggcc agggcaccct cgtgaccgtg tcctct                               336
```

<210> SEQ ID NO 105
<211> LENGTH: 112
<212> TYPE: PRT
<213> ORGANISM: Artificial Sequence
<220> FEATURE:
<223> OTHER INFORMATION: hSC27.204v11 Heavy Chain Variable Region

<400> SEQUENCE: 105

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Trp Met Ser Trp Val Arg Gln Ala Pro Gly Lys Gly Leu Glu Trp Val
         35                  40                  45

Ser Glu Ile Asn Pro Asp Ser Ser Thr Ile Asn Tyr Asn Pro Ser Leu
     50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110
```

<210> SEQ ID NO 106
<211> LENGTH: 336
<212> TYPE: DNA
<213> ORGANISM: Artificial Sequence
<220> FEATURE:
<223> OTHER INFORMATION: hSC27.204v12 Heavy Chain Variable Region

<400> SEQUENCE: 106

```
gaagtgcagc tgctggaatc tggcggcgga ctggtgcagc ctggcggatc tctgagactg      60
tcttgtgccg cctccggctt cgacttctcc cggtactgga tgtcctgggt gcgacaggct     120
```

```
cctggcaagg gcctggaatg ggtgtccgag atcaaccccg actcctccac catcaactac      180 accccagcc tgaaggcccg gttcaccatc tctcgggaca actccaagaa cacctgtac       240 ctgcagatga actccctgcg ggccgaggac accgccgtgt actactgtgc cggccctgct     300
tattggggcc agggcaccct cgtgaccgtg tcctct                                336

<210> SEQ ID NO 107
<211> LENGTH: 112
<212> TYPE: PRT
<213> ORGANISM: Artificial Sequence
<220> FEATURE:
<223> OTHER INFORMATION: hSC27.204v12 Heavy Chain Variable Region

<400> SEQUENCE: 107

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110

<210> SEQ ID NO 108
<211> LENGTH: 336
<212> TYPE: DNA
<213> ORGANISM: Artificial Sequence
<220> FEATURE:
<223> OTHER INFORMATION: hSC27.204v13 Heavy Chain Variable Region

<400> SEQUENCE: 108
gaagtgcagc tgctggaatc tggcggcgga ctggtgcagc ctggcggatc tctgagactg      60
tcttgtgccg cctccggctt cgacttctcc cggtactgga tgtcctgggt cgacaggct     120 cctggcaagg gcctggaatg ggtgtccgag atcaaccccg actcctccac catcaagtac     180 accccagcc tgaaggcccg gttcaccatc tctcgggaca actccaagaa cacctgtac       240 ctgcagatga actccctgcg ggccgaggac accgccgtgt actactgtgc cggccctgct     300
tattggggcc agggcaccct cgtgaccgtg tcctct                                336

<210> SEQ ID NO 109
<211> LENGTH: 112
<212> TYPE: PRT
<213> ORGANISM: Artificial Sequence
<220> FEATURE:
<223> OTHER INFORMATION: hSC27.204v13  Heavy Chain Variable Region

<400> SEQUENCE: 109

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
```

```
                35                  40                  45
Ser Glu Ile Asn Pro Asp Ser Ser Thr Ile Lys Tyr Thr Pro Ser Leu
         50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110
```

<210> SEQ ID NO 110
<211> LENGTH: 336
<212> TYPE: DNA
<213> ORGANISM: Artificial Sequence
<220> FEATURE:
<223> OTHER INFORMATION: hSC27.204v14 Heavy Chain Variable Region
      Variable Region

<400> SEQUENCE: 110

```
gaagtgcagc tgctggaatc tggcggcgga ctggtgcagc ctggcggatc tctgagactg      60
tcttgtgccg cctccggctt cgacttctcc cggtactgga tgtcctgggt gcgacaggct    120
cctggcaagg gcctggaatg ggtgtccgag atcaaccccg actcctccac catccagtac    180
acccccagcc tgaaggcccg gttcaccatc tctcgggaca actccaagaa cacctgtac     240 ctgcagatga actccctgcg ggccgaggac accgccgtgt actactgtgc cggccctgct    300
tattggggcc agggcaccct cgtgaccgtg tcctct                              336
```

<210> SEQ ID NO 111
<211> LENGTH: 112
<212> TYPE: PRT
<213> ORGANISM: Artificial Sequence
<220> FEATURE:
<223> OTHER INFORMATION: hSC27.204v14 Heavy Chain Variable Region

<400> SEQUENCE: 111

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Val
         35                  40                  45

Ser Glu Ile Asn Pro Asp Ser Ser Thr Ile Gln Tyr Thr Pro Ser Leu
     50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110
```

<210> SEQ ID NO 112
<211> LENGTH: 336
<212> TYPE: DNA
<213> ORGANISM: Artificial Sequence
<220> FEATURE:
<223> OTHER INFORMATION: hSC27.204v15 Heavy Chain Variable Region

<400> SEQUENCE: 112

```
gaagtgcagc tgctggaatc tggcggcgga ctggtgcagc ctggcggatc tctgagactg      60
```

```
tcttgtgccg cctccggctt cgacttctcc cggtactgga tgtcctgggt gcgacaggct      120
cctggcaagg gcctggaatg ggtgtccgag atcaaccccg actcctccac catcaactac      180
aaccccagcc tgaaggcccg gttcaccatc tctcgggaca actccaagaa caccctgtac      240
ctgcagatga actccctgcg ggccgaggac accgccgtgt actactgtgc cggccctgct      300
tattggggcc agggcaccct cgtgaccgtg tcctct                                336
```

```
<210> SEQ ID NO 113
<211> LENGTH: 112
<212> TYPE: PRT
<213> ORGANISM: Artificial Sequence
<220> FEATURE:
<223> OTHER INFORMATION: hSC27.204v15 Heavy Chain Variable Region

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110

<210> SEQ ID NO 114
<211> LENGTH: 214
<212> TYPE: PRT
<213> ORGANISM: Artificial Sequence
<220> FEATURE:
<223> OTHER INFORMATION: hSC27.1 Light Chain

<400> SEQUENCE: 114

Asp Ile Gln Met Thr Gln Ser Pro Ser Ser Val Ser Ala Ser Val Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 115
<211> LENGTH: 448
<212> TYPE: PRT
<213> ORGANISM: Artificial Sequence
<220> FEATURE:
<223> OTHER INFORMATION: hSC27.1 Heavy Chain

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Leu His Trp Val Arg Gln Ala Pro Gly Gln Arg Leu Glu Trp Met
        35                  40                  45

Gly Gly Ile Asn Pro Asn Asn Gly Asp Thr Ile Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ile Thr Val Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 116
<211> LENGTH: 218
<212> TYPE: PRT
<213> ORGANISM: Artificial Sequence
<220> FEATURE:
<223> OTHER INFORMATION: hSC27.22 Light Chain

<400> SEQUENCE: 116

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Phe Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215
```

<210> SEQ ID NO 117
<211> LENGTH: 451
<212> TYPE: PRT
<213> ORGANISM: Artificial Sequence
<220> FEATURE:
<223> OTHER INFORMATION: hSC27.22 Heavy Chain

<400> SEQUENCE: 117

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Arg Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 118
<211> LENGTH: 215
<212> TYPE: PRT
<213> ORGANISM: Artificial Sequence
<220> FEATURE:
<223> OTHER INFORMATION: hSC27.108 Light Chain

<400> SEQUENCE: 118

Glu Ile Val Leu Thr Gln Ser Pro Ala Thr Leu Ser Leu Ser Pro Gly
1               5                   10                  15

Glu Arg Ala Thr Leu Ser Cys Ser Val Ser Ser Ile Ser Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Trp Ser Ser Tyr Pro
                85                  90                  95

His Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 119
<211> LENGTH: 455
<212> TYPE: PRT
<213> ORGANISM: Artificial Sequence
<220> FEATURE:

<223> OTHER INFORMATION: hSC27.108 Heavy Chain

<400> SEQUENCE: 119

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Ser Pro Leu Gly Ser Trp Ile Tyr Tyr Ala Tyr Asp Gly
            100                 105                 110

Val Ala Tyr Trp Gly Gln Gly Thr Leu Val Thr Val Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400
```

```
Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455

<210> SEQ ID NO 120
<211> LENGTH: 214
<212> TYPE: PRT
<213> ORGANISM: Artificial Sequence
<220> FEATURE:
<223> OTHER INFORMATION: hSC27.204 Light Chain

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Lys Ala Gly Gln Asn Val Gly Thr Ser
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 441
<212> TYPE: PRT
<213> ORGANISM: Artificial Sequence
<220> FEATURE:
<223> OTHER INFORMATION: hSC27.204 Heavy Chain

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

```
Trp Met Ser Trp Val Arg Gln Ala Pro Gly Lys Gly Leu Glu Trp Val
        35                  40                  45
Ser Glu Ile Asn Pro Asp Ser Thr Ile Asn Tyr Thr Pro Ser Leu
 50                  55                  60
Lys Ala Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Thr Gly Pro Ala Tyr Trp Gly Gln Gly Thr Leu Val Thr Val Ser Ser
            100                 105                 110
Ala Ser Thr Lys Gly Pro Ser Val Phe Pro Leu Ala Pro Ser Ser Lys
            115                 120                 125
Ser Thr Ser Gly Gly Thr Ala Ala Leu Gly Cys Leu Val Lys Asp Tyr
            130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Gln Thr
            180                 185                 190
Tyr Ile Cys Asn Val Asn His Lys Pro Ser Asn Thr Lys Val Asp Lys
            195                 200                 205
Lys Val Glu Pro Lys Ser Cys Asp Lys Thr His Thr Cys Pro Pro Cys
            210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
            275                 280                 285
Glu Gln Tyr Asn Ser Thr Tyr Arg Val Val Ser Val Leu Thr Val Leu
            290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
            340                 345                 350
Leu Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
            370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly
            435                 440
```

```
<210> SEQ ID NO 122
<211> LENGTH: 451
<212> TYPE: PRT
<213> ORGANISM: Artificial Sequence
<220> FEATURE:
<223> OTHER INFORMATION: hSC27.22ss1 Heavy Chain

<400> SEQUENCE: 122
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Trp | Met | Asn | Trp | Val | Arg | Gln | Ala | Pro | Gly | Gln | Arg | Leu | Glu | Trp | Met |
|---|---|---|---|---|---|---|---|---|---|---|---|---|---|---|---|
| | | 35 | | | | | 40 | | | | | 45 | | | |

| Gly | Met | Ile | His | Pro | Ser | Asp | Ser | Glu | Ile | Arg | Leu | Asn | Gln | Lys | Phe |
|---|---|---|---|---|---|---|---|---|---|---|---|---|---|---|---|
| | 50 | | | | | 55 | | | | | 60 | | | | |

| Lys | Asp | Arg | Val | Thr | Ile | Thr | Arg | Asp | Thr | Ser | Ala | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Ile | Asp | Ser | Tyr | Tyr | Gly | Tyr | Leu | Phe | Tyr | Phe | Asp | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Thr | Val | Thr | Val | Ser | Ser | Ala | Ser | Thr | Lys | Gly | Pro |
|---|---|---|---|---|---|---|---|---|---|---|---|---|---|---|---|
| | | 115 | | | | | 120 | | | | | 125 | | | |

| Ser | Val | Phe | Pro | Leu | Ala | Pro | Ser | Ser | Lys | Ser | Thr | Ser | Gly | Gly | Thr |
|---|---|---|---|---|---|---|---|---|---|---|---|---|---|---|---|
| | 130 | | | | | 135 | | | | | 140 | | | | |

| Ala | Ala | Leu | Gly | Cys | Leu | Val | Lys | Asp | Tyr | Phe | Pro | Glu | Pro | Val | Thr |
|---|---|---|---|---|---|---|---|---|---|---|---|---|---|---|---|
| 145 | | | | | 150 | | | | | 155 | | | | | 160 |

| Val | Ser | Trp | Asn | Ser | Gly | Ala | Leu | Thr | Ser | Gly | Val | His | Thr | Phe | Pro |
|---|---|---|---|---|---|---|---|---|---|---|---|---|---|---|---|
| | | | | 165 | | | | | 170 | | | | | 175 | |

| Ala | Val | Leu | Gln | Ser | Ser | Gly | Leu | Tyr | Ser | Leu | Ser | Ser | Val | Val | Thr |
|---|---|---|---|---|---|---|---|---|---|---|---|---|---|---|---|
| | | | 180 | | | | | 185 | | | | | 190 | | |

| Val | Pro | Ser | Ser | Ser | Leu | Gly | Thr | Gln | Thr | Tyr | Ile | Cys | Asn | Val | Asn |
|---|---|---|---|---|---|---|---|---|---|---|---|---|---|---|---|
| | | 195 | | | | | 200 | | | | | 205 | | | |

| His | Lys | Pro | Ser | Asn | Thr | Lys | Val | Asp | Lys | Lys | Val | Glu | Pro | Lys | Ser |
|---|---|---|---|---|---|---|---|---|---|---|---|---|---|---|---|
| | 210 | | | | | 215 | | | | | 220 | | | | |

| Ser | Asp | Lys | Thr | His | Thr | Cys | Pro | Pro | Cys | Pro | Ala | Pro | Glu | Leu | Leu |
|---|---|---|---|---|---|---|---|---|---|---|---|---|---|---|---|
| 225 | | | | | 230 | | | | | 235 | | | | | 240 |

| Gly | Gly | Pro | Ser | Val | Phe | Leu | Phe | Pro | Pro | Lys | Pro | Lys | Asp | Thr | Leu |
|---|---|---|---|---|---|---|---|---|---|---|---|---|---|---|---|
| | | | | 245 | | | | | 250 | | | | | 255 | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| | | | 260 | | | | | 265 | | | | | 270 | | |

| His | Glu | Asp | Pro | Glu | Val | Lys | Phe | Asn | Trp | Tyr | Val | Asp | Gly | Val | Glu |
|---|---|---|---|---|---|---|---|---|---|---|---|---|---|---|---|
| | | 275 | | | | | 280 | | | | | 285 | | | |

| Val | His | Asn | Ala | Lys | Thr | Lys | Pro | Arg | Glu | Glu | Gln | Tyr | Asn | Ser | Thr |
|---|---|---|---|---|---|---|---|---|---|---|---|---|---|---|---|
| | 290 | | | | | 295 | | | | | 300 | | | | |

| Tyr | Arg | Val | Val | Ser | Val | Leu | Thr | Val | Leu | His | Gln | Asp | Trp | Leu | Asn |
|---|---|---|---|---|---|---|---|---|---|---|---|---|---|---|---|
| 305 | | | | | 310 | | | | | 315 | | | | | 320 |

| Gly | Lys | Glu | Tyr | Lys | Cys | Lys | Val | Ser | Asn | Lys | Ala | Leu | Pro | Ala | Pro |
|---|---|---|---|---|---|---|---|---|---|---|---|---|---|---|---|
| | | | | 325 | | | | | 330 | | | | | 335 | |

| Ile | Glu | Lys | Thr | Ile | Ser | Lys | Ala | Lys | Gly | Gln | Pro | Arg | Glu | Pro | Gln |
|---|---|---|---|---|---|---|---|---|---|---|---|---|---|---|---|
| | | | 340 | | | | | 345 | | | | | 350 | | |

| Val | Tyr | Thr | Leu | Pro | Pro | Ser | Arg | Asp | Glu | Leu | Thr | Lys | Asn | Gln | Val |
|---|---|---|---|---|---|---|---|---|---|---|---|---|---|---|---|
| | | 355 | | | | | 360 | | | | | 365 | | | |

-continued

```
Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 123
<211> LENGTH: 451
<212> TYPE: PRT
<213> ORGANISM: Artificial Sequence
<220> FEATURE:
<223> OTHER INFORMATION: hSC27.22-VH1-8 Heavy Chain

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Thr Gly Gln Gly Leu Glu Trp Met
            35                  40                  45

Gly Met Ile His Pro Ser Asp Ser Glu Ile Arg Leu Asn Gln Lys Phe
    50                  55                  60

Lys Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 124
<211> LENGTH: 451
<212> TYPE: PRT
<213> ORGANISM: Artificial Sequence
<220> FEATURE:
<223> OTHER INFORMATION: hSC27.22-VH1-46 Heavy Chain

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 125
<211> LENGTH: 451
<212> TYPE: PRT
<213> ORGANISM: Artificial Sequence
<220> FEATURE:
<223> OTHER INFORMATION: hSC27.22-VH1-69 Heavy Chain

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
435                 440                 445

Ser Pro Gly
    450

<210> SEQ ID NO 126
<211> LENGTH: 447
<212> TYPE: PRT
<213> ORGANISM: Artificial Sequence
<220> FEATURE:
<223> OTHER INFORMATION: hSC27.22 IgG2 Heavy Chain
```

<400> SEQUENCE: 126

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Met Asn Trp Val Arg Gln Ala Pro Gly Gln Arg Leu Glu Trp Met
        35                  40                  45
Gly Met Ile His Pro Ser Asp Ser Glu Ile Arg Leu Asn Gln Lys Phe
    50                  55                  60
Lys Asp Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ile Asp Ser Tyr Tyr Gly Tyr Leu Phe Tyr Phe Asp Tyr Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
```

```
                    405                 410                 415
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 127
<211> LENGTH: 448
<212> TYPE: PRT
<213> ORGANISM: Artificial Sequence
<220> FEATURE:
<223> OTHER INFORMATION: hSC27.22 IgG4 R409K Heavy Chain

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Arg Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
```

```
                    325                 330                 335
Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 128
<211> LENGTH: 448
<212> TYPE: PRT
<213> ORGANISM: Artificial Sequence
<220> FEATURE:
<223> OTHER INFORMATION: hSC27.22 IgG4 S228P Heavy Chain

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Arg Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
```

```
            245                 250                 255
Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 129
<211> LENGTH: 448
<212> TYPE: PRT
<213> ORGANISM: Artificial Sequence
<220> FEATURE:
<223> OTHER INFORMATION: hSC27.22 IgG4 S228P K370E R409K Heavy Chain

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Arg Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                    165                 170                 175
Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Glu Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 130
<211> LENGTH: 448
<212> TYPE: PRT
<213> ORGANISM: Artificial Sequence
<220> FEATURE:
<223> OTHER INFORMATION: hSC27.22 IgG4 K370E Heavy Chain

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Arg Leu Glu Trp Met
            35                  40                  45

Gly Met Ile His Pro Ser Asp Ser Glu Ile Arg Leu Asn Gln Lys Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Ile Asp Ser Tyr Tyr Gly Tyr Leu Phe Tyr Phe Asp Tyr Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
            210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Glu Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 131
<211> LENGTH: 448
<212> TYPE: PRT
<213> ORGANISM: Artificial Sequence
<220> FEATURE:
<223> OTHER INFORMATION: hSC27.22 IgG4 S228P K370E Heavy Chain

<400> SEQUENCE: 131

Gln Val Gln Leu Val Gln Ser Gly Ala Glu Val Lys Lys Pro Gly Ala
```

```
  1               5                  10                 15
Ser Val Lys Val Ser Cys Lys Ala Ser Gly Tyr Thr Phe Thr Ser Tyr
             20                 25                 30

Trp Met Asn Trp Val Arg Gln Ala Pro Gly Gln Arg Leu Glu Trp Met
             35                 40                 45

Gly Met Ile His Pro Ser Asp Ser Glu Ile Arg Leu Asn Gln Lys Phe
             50                 55                 60

Lys Asp Arg Val Thr Ile Thr Arg Asp Thr Ser Ala Ser Thr Ala Tyr
 65                 70                 75                 80

Met Glu Leu Ser Ser Leu Arg Ser Glu Asp Thr Ala Val Tyr Tyr Cys
             85                 90                 95

Ala Arg Ile Asp Ser Tyr Tyr Gly Tyr Leu Phe Tyr Phe Asp Tyr Trp
             100                105                110

Gly Gln Gly Thr Thr Val Thr Val Ser Ser Ala Ser Thr Lys Gly Pro
             115                120                125

Ser Val Phe Pro Leu Ala Pro Cys Ser Arg Ser Thr Ser Glu Ser Thr
             130                135                140

Ala Ala Leu Gly Cys Leu Val Lys Asp Tyr Phe Pro Glu Pro Val Thr
145                 150                155                160

Val Ser Trp Asn Ser Gly Ala Leu Thr Ser Gly Val His Thr Phe Pro
             165                170                175

Ala Val Leu Gln Ser Ser Gly Leu Tyr Ser Leu Ser Ser Val Val Thr
             180                185                190

Val Pro Ser Ser Ser Leu Gly Thr Lys Thr Tyr Thr Cys Asn Val Asp
             195                200                205

His Lys Pro Ser Asn Thr Lys Val Asp Lys Arg Val Glu Ser Lys Tyr
             210                215                220

Gly Pro Pro Cys Pro Pro Cys Pro Ala Pro Glu Phe Leu Gly Gly Pro
225                 230                235                240

Ser Val Phe Leu Phe Pro Pro Lys Pro Lys Asp Thr Leu Met Ile Ser
             245                250                255

Arg Thr Pro Glu Val Thr Cys Val Val Val Asp Val Ser Gln Glu Asp
             260                265                270

Pro Glu Val Gln Phe Asn Trp Tyr Val Asp Gly Val Glu Val His Asn
             275                280                285

Ala Lys Thr Lys Pro Arg Glu Glu Gln Phe Asn Ser Thr Tyr Arg Val
             290                295                300

Val Ser Val Leu Thr Val Leu His Gln Asp Trp Leu Asn Gly Lys Glu
305                 310                315                320

Tyr Lys Cys Lys Val Ser Asn Lys Gly Leu Pro Ser Ser Ile Glu Lys
             325                330                335

Thr Ile Ser Lys Ala Lys Gly Gln Pro Arg Glu Pro Gln Val Tyr Thr
             340                345                350

Leu Pro Pro Ser Gln Glu Glu Met Thr Lys Asn Gln Val Ser Leu Thr
             355                360                365

Cys Leu Val Glu Gly Phe Tyr Pro Ser Asp Ile Ala Val Glu Trp Glu
             370                375                380

Ser Asn Gly Gln Pro Glu Asn Asn Tyr Lys Thr Thr Pro Pro Val Leu
385                 390                395                400

Asp Ser Asp Gly Ser Phe Phe Leu Tyr Ser Arg Leu Thr Val Asp Lys
             405                410                415

Ser Arg Trp Gln Glu Gly Asn Val Phe Ser Cys Ser Val Met His Glu
             420                425                430
```

```
Ala Leu His Asn His Tyr Thr Gln Lys Ser Leu Ser Leu Ser Leu Gly
            435                 440                 445

<210> SEQ ID NO 132
<211> LENGTH: 448
<212> TYPE: PRT
<213> ORGANISM: Artificial Sequence
<220> FEATURE:
<223> OTHER INFORMATION: hSC27.22 IgG4 C127S S228P Heavy Chain

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Arg Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 133
<211> LENGTH: 448
<212> TYPE: PRT
<213> ORGANISM: Artificial Sequence
<220> FEATURE:
<223> OTHER INFORMATION: hSC27.22 IgG4 C127S K370E Heavy Chain

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Arg Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
         275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Glu Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 134
<211> LENGTH: 448
<212> TYPE: PRT
<213> ORGANISM: Artificial Sequence
<220> FEATURE:
<223> OTHER INFORMATION: hSC27.22 IgG4 C127S S228P K370E Heavy Chain

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Arg Leu Glu Trp Met
        35                  40                  45

Gly Met Ile His Pro Ser Asp Ser Glu Ile Arg Leu Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Ser Tyr Tyr Gly Tyr Leu Phe Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Glu Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 135
<211> LENGTH: 215
<212> TYPE: PRT
<213> ORGANISM: Artificial Sequence
<220> FEATURE:
<223> OTHER INFORMATION: hSC27.108v1 Heavy Chain

<400> SEQUENCE: 135

Glu Ile Val Leu Thr Gln Ser Pro Asp Phe Gln Ser Val Thr Pro Lys
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Pro Asp Gln Ser Pro Lys Leu Trp
            35                  40                  45

Ile Tyr Gly Thr Ser Asn Leu Ala Ser Gly Val Pro Ser Arg Phe Ser
        50                  55                  60

Gly Ser Gly Ser Gly Thr Asp Phe Thr Leu Thr Ile Asn Ser Leu Glu
65                  70                  75                  80

Ala Glu Asp Ala Ala Thr Tyr Tyr Cys Gln Gln Trp Ser Ser Tyr Pro
            85                  90                  95

His Thr Phe Gly Gly Gly Thr Lys Val Glu Ile Lys Arg Thr Val Ala
            100                 105                 110

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 136
<211> LENGTH: 441
<212> TYPE: PRT
<213> ORGANISM: Artificial Sequence
<220> FEATURE:
<223> OTHER INFORMATION: hSC27.204v1 Heavy Chain

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Lys Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255
```

Val Val Val Asp Val Ser His Glu Asp Pro Glu Val Lys Phe Asn Trp
        260             265             270

Tyr Val Asp Gly Val Glu Val His Asn Ala Lys Thr Lys Pro Arg Glu
        275             280             285

Glu Gln Tyr Asn Ser Thr Tyr Arg Val Val Ser Val Leu Thr Val Leu
    290             295             300

His Gln Asp Trp Leu Asn Gly Lys Glu Tyr Lys Cys Lys Val Ser Asn
305             310             315             320

Lys Ala Leu Pro Ala Pro Ile Glu Lys Thr Ile Ser Lys Ala Lys Gly
                325             330             335

Gln Pro Arg Glu Pro Gln Val Tyr Thr Leu Pro Pro Ser Arg Asp Glu
        340             345             350

Leu Thr Lys Asn Gln Val Ser Leu Thr Cys Leu Val Lys Gly Phe Tyr
    355             360             365

Pro Ser Asp Ile Ala Val Glu Trp Glu Ser Asn Gly Gln Pro Glu Asn
370             375             380

Asn Tyr Lys Thr Thr Pro Pro Val Leu Asp Ser Asp Gly Ser Phe Phe
385             390             395             400

Leu Tyr Ser Lys Leu Thr Val Asp Lys Ser Arg Trp Gln Gln Gly Asn
                405             410             415

Val Phe Ser Cys Ser Val Met His Glu Ala Leu His Asn His Tyr Thr
        420             425             430

Gln Lys Ser Leu Ser Leu Ser Pro Gly
            435             440

<210> SEQ ID NO 137
<211> LENGTH: 441
<212> TYPE: PRT
<213> ORGANISM: Artificial Sequence
<220> FEATURE:
<223> OTHER INFORMATION: hSC27.204v2 Heavy Chain

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Gln Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly
            435                 440

<210> SEQ ID NO 138
<211> LENGTH: 441
<212> TYPE: PRT
<213> ORGANISM: Artificial Sequence
<220> FEATURE:
<223> OTHER INFORMATION: hSC27.204v3 Heavy Chain

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Thr Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 139
<211> LENGTH: 441
<212> TYPE: PRT
<213> ORGANISM: Artificial Sequence
<220> FEATURE:
<223> OTHER INFORMATION: hSC27.204v4 Heavy Chain

<400> SEQUENCE: 139

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Val
         35                  40                  45

Ser Glu Ile Asn Pro Asp Ser Ser Thr Ile Asn Tyr Thr Pro Ser Leu
 50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Gly Pro Ala Tyr Trp Gly Gln Gly Thr Leu Val Thr Val Ser Ser
                100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430
```

<210> SEQ ID NO 140
<211> LENGTH: 441
<212> TYPE: PRT
<213> ORGANISM: Artificial Sequence
<220> FEATURE:
<223> OTHER INFORMATION: hSC27.204v5 Heavy Chain

<400> SEQUENCE: 140

```
Gln Lys Ser Leu Ser Leu Ser Pro Gly
        435                 440

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Lys Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350
```

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly
            435                 440

<210> SEQ ID NO 141
<211> LENGTH: 441
<212> TYPE: PRT
<213> ORGANISM: Artificial Sequence
<220> FEATURE:
<223> OTHER INFORMATION: hSC27.204v6 Heavy Chain

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Gln Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
            210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
        340                 345                 350

Leu Thr Lys Asn Gln Val Ser Leu Thr Cys Leu Val Lys Gly Phe Tyr
355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly
            435                 440

<210> SEQ ID NO 142
<211> LENGTH: 441
<212> TYPE: PRT
<213> ORGANISM: Artificial Sequence
<220> FEATURE:
<223> OTHER INFORMATION: hSC27.204v7 Heavy Chain

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Gly Pro Ala Tyr Trp Gly Gln Gly Thr Leu Val Thr Val Ser Ser
        100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Gln Thr
        180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly
            435                 440

<210> SEQ ID NO 143
<211> LENGTH: 441
<212> TYPE: PRT
<213> ORGANISM: Artificial Sequence
<220> FEATURE:
<223> OTHER INFORMATION: hSC27.204v8 Heavy Chain

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110

```
Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 144
<211> LENGTH: 441
<212> TYPE: PRT
<213> ORGANISM: Artificial Sequence
<220> FEATURE:
<223> OTHER INFORMATION: hSC27.204v9 Heavy Chain

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

```
Trp Met Ser Trp Val Arg Gln Ala Pro Gly Lys Gly Leu Glu Trp Val
         35                  40                  45
Ser Glu Ile Asn Pro Asp Ser Ser Thr Ile Lys Tyr Thr Pro Ser Leu
 50                  55                  60
Lys Ala Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Gly Pro Ala Tyr Trp Gly Gln Gly Thr Leu Val Thr Val Ser Ser
            100                 105                 110
Ala Ser Thr Lys Gly Pro Ser Val Phe Pro Leu Ala Pro Ser Ser Lys
            115                 120                 125
Ser Thr Ser Gly Gly Thr Ala Ala Leu Gly Cys Leu Val Lys Asp Tyr
130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Gln Thr
            180                 185                 190
Tyr Ile Cys Asn Val Asn His Lys Pro Ser Asn Thr Lys Val Asp Lys
        195                 200                 205
Lys Val Glu Pro Lys Ser Cys Asp Lys Thr His Thr Cys Pro Pro Cys
    210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
            340                 345                 350
Leu Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly
        435                 440
```

<210> SEQ ID NO 145
<211> LENGTH: 441
<212> TYPE: PRT
<213> ORGANISM: Artificial Sequence
<220> FEATURE:
<223> OTHER INFORMATION: hSC27.204v10 Heavy Chain

<400> SEQUENCE: 145

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Gln Tyr Thr Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
```

```
            370                 375                 380
Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
            435                 440

<210> SEQ ID NO 146
<211> LENGTH: 441
<212> TYPE: PRT
<213> ORGANISM: Artificial Sequence
<220> FEATURE:
<223> OTHER INFORMATION: hSC27.204v11 Heavy Chain

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Asn Pro Ser Leu
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
```

290                 295                 300
His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
                340                 345                 350

Leu Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
                435                 440

<210> SEQ ID NO 147
<211> LENGTH: 441
<212> TYPE: PRT
<213> ORGANISM: Artificial Sequence
<220> FEATURE:
<223> OTHER INFORMATION: hSC27.204v12 Heavy Chain

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Val
            35                  40                  45

Ser Glu Ile Asn Pro Asp Ser Ser Thr Ile Asn Tyr Thr Pro Ser Leu
        50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Lys Thr His Thr Cys Pro Pro Cys

```
                210                 215                 220
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
                275                 280                 285

Glu Gln Tyr Asn Ser Thr Tyr Arg Val Val Ser Val Leu Thr Val Leu
                290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
                340                 345                 350

Leu Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
                435                 440

<210> SEQ ID NO 148
<211> LENGTH: 441
<212> TYPE: PRT
<213> ORGANISM: Artificial Sequence
<220> FEATURE:
<223> OTHER INFORMATION: hSC27.204v13 Heavy Chain

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Val
                35                  40                  45

Ser Glu Ile Asn Pro Asp Ser Ser Thr Ile Lys Tyr Thr Pro Ser Leu
50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Ala Tyr Trp Gly Gln Gly Thr Leu Val Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
```

```
                130                 135                 140
Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 149
<211> LENGTH: 441
<212> TYPE: PRT
<213> ORGANISM: Artificial Sequence
<220> FEATURE:
<223> OTHER INFORMATION: hSC27.204v14 Heavy Chain

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Val
            35                  40                  45

Ser Glu Ile Asn Pro Asp Ser Ser Thr Ile Gln Tyr Thr Pro Ser Leu
```

```
            50                  55                  60
Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
            210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
            435                 440

<210> SEQ ID NO 150
<211> LENGTH: 441
<212> TYPE: PRT
<213> ORGANISM: Artificial Sequence
```

```
<220> FEATURE:
<223> OTHER INFORMATION: hSC27.204v15 Heavy Chain

<400> SEQUENCE: 150

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Val
         35                  40                  45

Ser Glu Ile Asn Pro Asp Ser Ser Thr Ile Asn Tyr Asn Pro Ser Leu
     50                  55                  60

Lys Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Pro Ala Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400
```

```
Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly
        435                 440

<210> SEQ ID NO 151
<211> LENGTH: 11
<212> TYPE: PRT
<213> ORGANISM: Artificial Sequence
<220> FEATURE:
<223> OTHER INFORMATION: hSC27.1 CDRL1

<400> SEQUENCE: 151

Lys Ala Ser Glu Asp Ile Tyr Asn Arg Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: hSC27.1 CDRL2

<400> SEQUENCE: 152

Gly Ala Thr Ser Leu Glu Thr
1               5

<210> SEQ ID NO 153
<211> LENGTH: 9
<212> TYPE: PRT
<213> ORGANISM: Artificial Sequence
<220> FEATURE:
<223> OTHER INFORMATION: hSC27.1 CDRL3

<400> SEQUENCE: 153

Gln Gln Tyr Trp Ser Thr Pro Leu Thr
1               5

<210> SEQ ID NO 154
<211> LENGTH: 5
<212> TYPE: PRT
<213> ORGANISM: Artificial Sequence
<220> FEATURE:
<223> OTHER INFORMATION: hSC27.1 CDRH1

<400> SEQUENCE: 154

Glu Tyr Thr Leu His
1               5

<210> SEQ ID NO 155
<211> LENGTH: 17
<212> TYPE: PRT
<213> ORGANISM: Artificial Sequence
<220> FEATURE:
<223> OTHER INFORMATION: hSC27.1 CDRH2

<400> SEQUENCE: 155

Gly Ile Asn Pro Asn Asn Gly Asp Thr Ile Tyr Asn Gln Lys Phe Lys
1               5                   10                  15

Gly

<210> SEQ ID NO 156
```

```
<211> LENGTH: 10
<212> TYPE: PRT
<213> ORGANISM: Artificial Sequence
<220> FEATURE:
<223> OTHER INFORMATION: hSC27.1 CDRH3

<400> SEQUENCE: 156

Arg Ala Ile Thr Val Tyr Ala Met Asp Tyr
1               5                   10

<210> SEQ ID NO 157
<211> LENGTH: 15
<212> TYPE: PRT
<213> ORGANISM: Artificial Sequence
<220> FEATURE:
<223> OTHER INFORMATION: hSC27.22 CDRL1

<400> SEQUENCE: 157

Arg Ala Ser Gln Thr Val Ser Thr Ser Ser Tyr Ser Tyr Met His
1               5                   10                  15

<210> SEQ ID NO 158
<211> LENGTH: 7
<212> TYPE: PRT
<213> ORGANISM: Artificial Sequence
<220> FEATURE:
<223> OTHER INFORMATION: hSC27.22 CDRL2

<400> SEQUENCE: 158

Phe Ala Ser Asn Val Glu Ser
1               5

<210> SEQ ID NO 159
<211> LENGTH: 9
<212> TYPE: PRT
<213> ORGANISM: Artificial Sequence
<220> FEATURE:
<223> OTHER INFORMATION: hSC27.22 CDRL3

<400> SEQUENCE: 159

Gln His Ser Trp Glu Ile Pro Trp Thr
1               5

<210> SEQ ID NO 160
<211> LENGTH: 5
<212> TYPE: PRT
<213> ORGANISM: Artificial Sequence
<220> FEATURE:
<223> OTHER INFORMATION: hSC27.22 CDRH1

<400> SEQUENCE: 160

Ser Tyr Trp Met Asn
1               5

<210> SEQ ID NO 161
<211> LENGTH: 17
<212> TYPE: PRT
<213> ORGANISM: Artificial Sequence
<220> FEATURE:
<223> OTHER INFORMATION: hSC27.22 CDRH2

<400> SEQUENCE: 161

Met Ile His Pro Ser Asp Ser Glu Ile Arg Leu Asn Gln Lys Phe Lys
1               5                   10                  15

Asp
```

```
<210> SEQ ID NO 162
<211> LENGTH: 13
<212> TYPE: PRT
<213> ORGANISM: Artificial Sequence
<220> FEATURE:
<223> OTHER INFORMATION: hSC27.22 CDRH3

<400> SEQUENCE: 162

Ile Asp Ser Tyr Tyr Gly Tyr Leu Phe Tyr Phe Asp Tyr
1               5                   10

<210> SEQ ID NO 163
<211> LENGTH: 12
<212> TYPE: PRT
<213> ORGANISM: Artificial Sequence
<220> FEATURE:
<223> OTHER INFORMATION: hSC27.108 CDRL1

<400> SEQUENCE: 163

Ser Val Ser Ser Ser Ile Ser Ser Ser Asn Leu His
1               5                   10

<210> SEQ ID NO 164
<211> LENGTH: 7
<212> TYPE: PRT
<213> ORGANISM: Artificial Sequence
<220> FEATURE:
<223> OTHER INFORMATION: hSC27.108 CDRL2

<400> SEQUENCE: 164

Gly Thr Ser Asn Leu Ala Ser
1               5

<210> SEQ ID NO 165
<211> LENGTH: 9
<212> TYPE: PRT
<213> ORGANISM: Artificial Sequence
<220> FEATURE:
<223> OTHER INFORMATION: hSC27.108 CDRL3

<400> SEQUENCE: 165

Gln Gln Trp Ser Ser Tyr Pro His Thr
1               5

<210> SEQ ID NO 166
<211> LENGTH: 5
<212> TYPE: PRT
<213> ORGANISM: Artificial Sequence
<220> FEATURE:
<223> OTHER INFORMATION: hSC27.108 CDRH1

<400> SEQUENCE: 166

Asn Tyr Leu Ile Glu
1               5

<210> SEQ ID NO 167
<211> LENGTH: 17
<212> TYPE: PRT
<213> ORGANISM: Artificial Sequence
<220> FEATURE:
<223> OTHER INFORMATION: hSC27.108 CDRH2

<400> SEQUENCE: 167

Leu Ile Asn Pro Gly Ser Gly Gly Thr Asn Tyr Asn Glu Lys Phe Lys
1               5                   10                  15

Gly
```

```
<210> SEQ ID NO 168
<211> LENGTH: 17
<212> TYPE: PRT
<213> ORGANISM: Artificial Sequence
<220> FEATURE:
<223> OTHER INFORMATION: hSC27.108 CDRH3

<400> SEQUENCE: 168

Arg Ser Pro Leu Gly Ser Trp Ile Tyr Tyr Ala Tyr Asp Gly Val Ala
1               5                   10                  15
Tyr

<210> SEQ ID NO 169
<211> LENGTH: 11
<212> TYPE: PRT
<213> ORGANISM: Artificial Sequence
<220> FEATURE:
<223> OTHER INFORMATION: hSC27.204 CDRL1

<400> SEQUENCE: 169

Lys Ala Gly Gln Asn Val Gly Thr Ser Val Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: hSC27.204 CDRL2

<400> SEQUENCE: 170

Ser Ala Ser Tyr Arg Tyr Ser
1               5

<210> SEQ ID NO 171
<211> LENGTH: 9
<212> TYPE: PRT
<213> ORGANISM: Artificial Sequence
<220> FEATURE:
<223> OTHER INFORMATION: hSC27.204 CDRL3

<400> SEQUENCE: 171

Gln Gln Tyr Ile Thr Tyr Pro Tyr Thr
1               5

<210> SEQ ID NO 172
<211> LENGTH: 5
<212> TYPE: PRT
<213> ORGANISM: Artificial Sequence
<220> FEATURE:
<223> OTHER INFORMATION: hSC27.204 CDRH1

<400> SEQUENCE: 172

Arg Tyr Trp Met Ser
1               5

<210> SEQ ID NO 173
<211> LENGTH: 17
<212> TYPE: PRT
<213> ORGANISM: Artificial Sequence
<220> FEATURE:
<223> OTHER INFORMATION: hSC27.204 CDRH2

<400> SEQUENCE: 173

Glu Ile Asn Pro Asp Ser Ser Thr Ile Asn Tyr Thr Pro Ser Leu Lys
1               5                   10                  15
```

Ala

<210> SEQ ID NO 174
<211> LENGTH: 3
<212> TYPE: PRT
<213> ORGANISM: Artificial Sequence
<220> FEATURE:
<223> OTHER INFORMATION: hSC27.204 CDRH3

<400> SEQUENCE: 174

Pro Ala Tyr
1

<210> SEQ ID NO 175
<211> LENGTH: 17
<212> TYPE: PRT
<213> ORGANISM: Artificial Sequence
<220> FEATURE:
<223> OTHER INFORMATION: hSC27.204v1, hSC27.204v5 and hSC27.405v13 CDRH2

<400> SEQUENCE: 175

Glu Ile Asn Pro Asp Ser Ser Thr Ile Lys Tyr Thr Pro Ser Leu Lys
1               5                   10                  15

Ala

<210> SEQ ID NO 176
<211> LENGTH: 17
<212> TYPE: PRT
<213> ORGANISM: Artificial Sequence
<220> FEATURE:
<223> OTHER INFORMATION: hSC27.204v2, hSC27.204v6 and hSC27.405v14 CDRH2

<400> SEQUENCE: 176

Glu Ile Asn Pro Asp Ser Ser Thr Ile Gln Tyr Thr Pro Ser Leu Lys
1               5                   10                  15

Ala

<210> SEQ ID NO 177
<211> LENGTH: 17
<212> TYPE: PRT
<213> ORGANISM: Artificial Sequence
<220> FEATURE:
<223> OTHER INFORMATION: hSC27.204v3, hSC27.204v7 and hSC27.405v15 CDRH2

<400> SEQUENCE: 177

Glu Ile Asn Pro Asp Ser Ser Thr Ile Asn Tyr Asn Pro Ser Leu Lys
1               5                   10                  15

Ala

<210> SEQ ID NO 178
<211> LENGTH: 366
<212> TYPE: DNA
<213> ORGANISM: Artificial Sequence
<220> FEATURE:
<223> OTHER INFORMATION: Codon optimized hSC27.22ss1 full length HC DNA

<400> SEQUENCE: 178
caagtgcagc tcgtccagtc cggtgccgaa gtcaagaagc cgggcgcatc agtgaaagtg      60
tcgtgcaaag cctccgggta caccttcacc tcatactgga tgaactgggt ccgccaagcc     120
ccgggacaga gactggagtg gatgggcatg attcacccat ccgattccga gatccggctg     180
aaccagaagt tcaaggaccg cgtgaccatc acccgggaca ccagcgccag cactgcctac     240

-continued

```
atggaattga gctcgctgcg gtccgaggat accgctgtgt actattgcgc gaggatcgac    300
tcctactacg gctacctttt ctacttcgac tactggggac aagggacgac cgtgactgtg    360
tcgagc                                                                366
```

UNITED STATES PATENT AND TRADEMARK OFFICE
CERTIFICATE OF CORRECTION

| | | |
|---|---|---|
| PATENT NO. | : 10,053,511 B2 | Page 1 of 1 |
| APPLICATION NO. | : 15/034992 | |
| DATED | : August 21, 2018 | |
| INVENTOR(S) | : Santaguida et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Thirtieth Day of July, 2019

Andrei Iancu
*Director of the United States Patent and Trademark Office*